US012799192B2

(12) United States Patent
Zhou

(10) Patent No.: US 12,799,192 B2

(45) Date of Patent: Nov. 17, 2026

(54) RISANKIZUMAB COMPOSITIONS

(71) Applicant: ABBVIE INC., North Chicago, IL (US)

(72) Inventor: Liqiang Zhou, Northborough, MA (US)

(73) Assignee: ABBVIE INC., North Chicago, IL (US)

( * ) Notice: Subject to any disclaimer, the term of this patent is extended or adjusted under 35 U.S.C. 154(b) by 0 days.

(21) Appl. No.: 19/190,045

(22) Filed: Apr. 25, 2025

(65) Prior Publication Data

US 2025/0313619 A1 Oct. 9, 2025

Related U.S. Application Data

(63) Continuation of application No. 18/873,298, filed as application No. PCT/US2023/025455 on Jun. 15, 2023.

(60) Provisional application No. 63/455,495, filed on Mar. 29, 2023, provisional application No. 63/444,182, filed on Feb. 8, 2023, provisional application No. 63/444,178, filed on Feb. 8, 2023, provisional application No. 63/352,459, filed on Jun. 15, 2022.

(51) Int. Cl.

| | |
|---|---|
| ***A61K 39/395*** | (2006.01) |
| ***A61K 9/00*** | (2006.01) |
| ***A61K 9/08*** | (2006.01) |
| ***A61K 38/46*** | (2006.01) |
| ***A61K 47/10*** | (2017.01) |
| ***A61K 47/12*** | (2006.01) |
| ***A61K 47/26*** | (2006.01) |
| ***C07K 16/24*** | (2006.01) |
| ***G01N 33/573*** | (2006.01) |
| *A61K 39/00* | (2006.01) |

(52) U.S. Cl.

CPC .......... *C07K 16/244* (2013.01); *A61K 9/0019* (2013.01); *A61K 9/08* (2013.01); *A61K 38/465* (2013.01); *A61K 39/3955* (2013.01); *A61K 39/39591* (2013.01); *A61K 47/10* (2013.01); *A61K 47/12* (2013.01); *A61K 47/26* (2013.01); *C12Y 301/01004* (2013.01); *G01N 33/573* (2013.01); *A61K 2039/505* (2013.01); *A61K 2039/54* (2013.01); *A61K 2039/545* (2013.01); *C07K 2317/14* (2013.01); *C07K 2317/24* (2013.01); *C07K 2317/41* (2013.01); *C07K 2317/71* (2013.01); *C07K 2317/76* (2013.01); *G01N 2333/918* (2013.01)

(58) Field of Classification Search

None

See application file for complete search history.

(56) References Cited

U.S. PATENT DOCUMENTS

| | | | |
|---|---|---|---|
| 8,187,836 | B2 | 5/2012 | Hsieh |
| 9,062,106 | B2 | 6/2015 | Bengea et al. |
| 9,550,826 | B2 | 1/2017 | Labkovsky et al. |
| 11,078,265 | B2 | 8/2021 | Nabozny et al. |
| 11,572,385 | B2 | 2/2023 | Garidel et al. |
| 2014/0178401 | A1 | 6/2014 | Nabozny et al. |
| 2021/0070852 | A1 | 3/2021 | Garidel et al. |
| 2021/0317201 | A1 | 10/2021 | Nabozny et al. |
| 2022/0251172 | A1 | 8/2022 | Frye et al. |
| 2025/0332100 | A1 | 10/2025 | Wang et al. |
| 2026/0000755 | A1 | 1/2026 | Wang et al. |

FOREIGN PATENT DOCUMENTS

| | | | |
|---|---|---|---|
| WO | WO 2013165791 | A1 | 11/2013 |
| WO | WO 2014186350 | A1 | 11/2014 |
| WO | WO 2018033482 | A1 | 2/2018 |
| WO | WO 2021048743 | A1 | 3/2021 |

OTHER PUBLICATIONS

Higel et al, European Journal of Pharmaceutics and Biopharmaceutics, vol. 100, p. 94-100 (Year: 2016).*

Bates et al., 1973, "Kinetics of hydrolysis of polyoxyethylene (20) sorbitan fatty acid ester surfactants," J. Pharm. Pharmacol., 25(6):470-477.

Bee et al., 2015, "Trace levels of the CHO host cell protease cathepsin D caused particle formation in a monoclonal antibody product," Biotechnol. Prog., 31(5):1360-1369.

Cao et al., 2015, "Free Fatty Acid Particles in Protein Formulations, Part 1: Microspectroscopic Identification," J. Pharm. Sci., 104(2):433-446.

Chiu et al., 2017, "Knockout of a Difficult-to-Remove CHO Host Cell Protein, Lipoprotein Lipase, for Improved Polysorbate Stability in Monoclonal Antibody Formulations," Biotechnol. Bioeng., 114(5):1006-1015.

Corvari et al., 2020, "Mechanisms of Surfactant Degradation: Focus on Enzymatic Hydrolysis," WCBP CMC Strategy Forum, Jan. 27, 2020, slides (21 pages).

Dorai et al., 2011, "Characterization of the proteases involved in the N-terminal clipping of glucagon-like-peptide-1-antibody fusion proteins," Biotechnol. Prog., 27(1):220-231.

Doshi et al., 2015, "Understanding particle formation: Solubility of free fatty acids as polysorbate 20 degradation byproducts in therapeutic monoclonal antibody formulations," Mol. Pharm., 12(11):3792-3804.

Fischer et al., 2017, "Specific Immune Response to Phospholipase B-Like 2 Protein, a Host Cell Impurity in Lebrikizumab Clinical Material," AAPS J., 19(1):254-263 (Epub 2016).

Gao et al., 2011, "Fragmentation of a highly purified monoclonal antibody attributed to residual CHO cell protease activity," Biotechnol. Bioeng., 108(4):977-982.

Hall et al., 2016, "Polysorbates 20 and 80 Degradation by Group XV Lysosomal Phospholipase A2 Isomer X1 in Monoclonal Antibody Formulations," J. Pharm. Sci., 105(5):1633-1642.

(Continued)

*Primary Examiner* — Yunsoo Kim

(74) *Attorney, Agent, or Firm* — JONES DAY

(57) ABSTRACT

The present disclosure relates, in part, to risankizumab compositions having a reduced level of hitchhiker protein PLA2, Poloxamer 188, and/or decreased immunogenicity.

24 Claims, 42 Drawing Sheets

Specification includes a Sequence Listing.

(56) References Cited

OTHER PUBLICATIONS

Inouye et al., 2001, “Pepsin digestion of a mouse monoclonal antibody of IgG1 class formed F(ab')(2) fragments in which the light chains as well as the heavy chains were truncated,” J. Biochem. Biophys. Methods., 48(1):23-32.
Kishore et al., 2011, “Degradation of polysorbates 20 and 80: studies on thermal autoxidation and hydrolysis,” J. Pharm. Sci., 100(2):721-731.
Kishore et al., 2011, “The degradation of polysorbates 20 and 80 and its potential impact on the stability of biotherapeutics,” Pharm. Res., 28(5):1194-1210.
Labrenz, 2014, “Ester hydrolysis of polysorbate 80 in mAb drug product: evidence in support of the hypothesized risk after the observation of visible particulate in mAb formulations,” J. Pharm. Sci., 103(8):2268-2277.
Levy et al., 2014, “Identification and characterization of host cell protein product-associated impurities in monoclonal antibody bioprocessing,” Biotechnol. Bioeng., 111(5):904-912.
Maeda et al., 2007, “Promotion of insulin aggregation by protein disulfide isomerase,” Biochim. Biophys. Acta., 1774(12):1619-1627.
Maier et al., 2024, “Illuminating a biologics development challenge: systematic characterization of CHO cell-derived hydrolases identified in monoclonal antibody formulations,” MAbs, 16(1):2375798 (15 pages).
Robert et al., 2009, “Degradation of an Fc-fusion recombinant protein by host cell proteases: Identification of a CHO cathepsin D protease,” Biotechnol. Bioeng., 104(6):1132-1141.
Saggu et al., 2015, “Identification of Subvisible Particles in Biopharmaceutical Formulations Using Raman Spectroscopy Provides Insight into Polysorbate 20 Degradation Pathway,” Pharm. Res., 32(9):2877-2888.
Shukla et al., 2008, “Host cell protein clearance during protein A chromatography: development of an improved col. wash step,” Biotechnol. Prog., 24(5):1115-1121.
Siska et al., 2015, “Free Fatty Acid Particles in Protein Formulations, Part 2: Contribution of Polysorbate Raw Material,” J. Pharm. Sci., 104(2):447-456.
Skyrizi (risankizumab), Medication Guide, AbbVie Inc., revised Sep. 2025.
Skyrizi (risankizumab), Prescribing Information, AbbVie Inc., Jun. 2022, https:/www.FDA.gov/drugsatfds.
Tomlinson et al., 2015, “Polysorbate 20 Degradation in Biopharmaceutical Formulations: Quantification of Free Fatty Acids, Characterization of Particulates, and Insights into the Degradation Mechanism,” Mol. Pharm., 12(11):3805-3815.
Tran et al., 2016, “Investigating interactions between phospholipase B-Like 2 and antibodies during Protein A chromatography,” J. Chromatogr. A., 1438:31-38.
Valente et al., 2015, “Expression of difficult-to-remove host cell protein impurities during extended Chinese hamster ovary cell culture and their impact on continuous bioprocessing,” Biotechnol. Bioeng., 112(6):1232-1242.
Wang et al., 2014, “Impact of residual impurities and contaminants on protein stability,” J. Pharm. Sci., 103(5):1315-1330.
U.S. Appl. No. 19/043,037, filed Jan. 31, 2025, Garidel et al.
U.S. Appl. No. 19/046,175, filed Feb. 5, 2025, Garidel et al.
Abe et al., 2007, “The acylation of lipophilic alcohols by lysosomal phospholipase A2,” J. Lipid Res., 48(10):2255-2263.
Ayorinde et al., 2000, “Analysis of some commercial polysorbate formulations using matrix-assisted laser desorption/ionization time-of-flight mass spectrometry,” Rapid Commun. Mass Spectrom, 14(22):2116-2124.
Bee et al., 2017, “Identification of an IgG CDR sequence contributing to co-purification of the host cell protease cathepsin D,” Biotechnol. Prog., 33(1):140-145 (Epub 2016).
Dixit et al., 2016, “Residual Host Cell Protein Promotes Polysorbate 20 Degradation in a Sulfatase Drug Product Leading to Free Fatty Acid Particles,” J. Pharm. Sci., 105(5):1657-1666.
Fisher, 2018, “The phospholipase A2 activity of peroxiredoxin 6,” J. Lipid Res., 59(7):1132-1147.
Graf et al., 2021, “Identification and Characterization of Polysorbate-Degrading Enzymes in a Monoclonal Antibody Formulation,” J. Pharm. Sci., 110(11):3558-3567.
Hinkovska-Galcheva et al., 2021, “Inhibition of lysosomal phospholipase A2 predicts drug-induced phospholipidosis,” J. Lipid Res., 62:100089 (23 pages).
Hiraoka et al., 2005, “Structure and function of lysosomal phospholipase A2: identification of the catalytic triad and the role of cysteine residues,” J. Lipid Res., 46(11):2441-2447.
International Searching Authority, International Search Report and Written Opinion for International Patent Application No. PCT/US2023/025455 (Pub No. WO 2023244746) mailed Dec. 4, 2023 (17 pages).
Khan et al., 2015, “Key interactions of surfactants in therapeutic protein formulations: A review,” Eur. J. Pharm. Biopharm., 97(Pt A):60-67.
Li et al., 2014, “Characterization and stability study of polysorbate 20 in therapeutic monoclonal antibody formulation by multidimensional ultrahigh-performance liquid chromatography-charged aerosol detection-mass spectrometry,” Anal. Chem., 86(10):5150-5157.
Li et al., 2021, “Profiling Active Enzymes for Polysorbate Degradation in Biotherapeutics by Activity-Based Protein Profiling,” Anal. Chem., 93(23):8161-8169.
Lon et al., 2021, “Pharmacokinetic Comparability of Risankizumab Formulations in Prefilled Syringe and Auto-injector for Subcutaneous Injection,” Clin. Ther., 43(3):629-636.
Martos et al., 2017, “Trends on Analytical Characterization of Polysorbates and Their Degradation Products in Biopharmaceutical Formulations,” J. Pharm. Sci., 106(7):1722-1735.
Murakami et al., 2002, “Phospholipase A2,” J. Biochem., 131(3):285-292.
Murdoch et al., 1992, “Fosinopril. A review of its pharmacodynamic and pharmacokinetic properties, and therapeutic potential in essential hypertension,” Drugs, 43(1):123-140.
Nogal et al., 2012, “Select host cell proteins coelute with monoclonal antibodies in protein A chromatography,” Biotechnol. Prog., 28(2):454-458.
Shayman et al., 2011, “Group XV phospholipase $A_2$, a lysosomal phospholipase $A_2$,” Prog. Lipid Res., 50(1):1-13 (Epub 2010).
Shayman et al., 2019, “Lysosomal phospholipase A2,” Biochim. Biophys. Acta. Mol. Cell Biol. Lipids, 1864(6):932-940 (Epub 2018).
World Health Organization (WHO), 2015, International Nonproprietary Names for Pharmaceutical Substances (INN), Recommended International Nonproprietary Names: List 113, WHO Drug Information, vol. 29, No. 2, pp. 254-255, risankizumab.
Zhang et al., 2016, “Characterization of the co-elution of host cell proteins with monoclonal antibodies during protein A purification,” Biotechnol. Prog., 32(3):708-717.
Zhang et al., 2020, “Putative Phospholipase B-Like 2 is Not Responsible for Polysorbate Degradation in Monoclonal Antibody Drug Products,” J. Pharm. Sci., 109(9):2710-2718.
Zhang et al., 2021, “Degradation of Polysorbate 20 by Sialate O-Acetylesterase in Monoclonal Antibody Formulations,” J. Pharm. Sci., 110(12):3866-3873.
Zhang et al., 2022, “Identification of the specific causes of polysorbate 20 degradation in monoclonal antibody formulations containing multiple lipases,” Pharm. Res., 39(1):75-87.
Alessandri et al., 2012, “Increased serum clearance of oligomannose species present on a human IgG1 molecule,” MAbs, 4(4):509-520.
Singh et al., 2015, “Selective targeting of the IL23 pathway: Generation and characterization of a novel high-affinity humanized anti-IL23A antibody,” MAbs, 7(4):778-791.

(56) References Cited

OTHER PUBLICATIONS

U.S. Food and Drug Administration, 2021, "Inspection of Injectable Products for Visible Particulates: Guidance for Industry; Draft Guidance," U.S. Department of Health and Human Services, Dec. 2021 (18 pages).

* cited by examiner

RISANKIZUMAB COMPOSITIONS

CROSS-REFERENCE TO RELATED APPLICATIONS

This application is a continuation of U.S. patent application Ser. No. 18/873,298, which is a U.S. National Stage Application under 35 U.S.C. § 371 of International Patent Application No. PCT/US2023/025455, filed Jun. 15, 2023, which claims the benefit of U.S. Provisional Application No. 63/352,459, filed Jun. 15, 2022, U.S. Provisional Application No. 63/455,495, filed Mar. 29, 2023, U.S. Provisional Application No. 63/444,178, filed Feb. 8, 2023, and U.S. Provisional Application No. 63/444,182, filed Feb. 8, 2023, the content of each of which is incorporated by reference herein in its entirety.

REFERENCE TO A SEQUENCE LISTING XML

This application contains an electronic Sequence Listing which has been submitted in XML file format via Patent Center, the entire content of which is incorporated by reference herein in its entirety. The Sequence Listing XML file submitted via Patent Center is entitled "13371-358-999_SEQ_LISTING.xml", was created on Apr. 24, 2025, and is 15,913 bytes in size.

BACKGROUND

Risankizumab (approved by the Food and Drug Administration (FDA) in the United States as risankizumab-rzaa and sold under the trademark name SKYRIZI©) is a humanized immunoglobulin G1 (IgG1) monoclonal antibody that is directed against the p19 subunit of IL-23. Binding of risankizumab to IL-23 p19 inhibits the action of IL-23 to induce and sustain T helper (Th) 17 type cells, innate lymphoid cells, γδT cells, and natural killer (NK) cells responsible for tissue inflammation, destruction and aberrant tissue repair. Risankizumab is especially effective in the treatment of autoimmune and inflammatory diseases, such as psoriasis. Clinical studies have revealed excellent safety and efficacy of risankizumab in, for example, the treatment of plaque psoriasis and psoriatic arthritis.

Risankizumab can be formulated at different concentrations for subcutaneous injection. For example, 60 mg/mL, 90 mg/mL and 150 mg/mL concentration risankizumab formulations have been approved by the FDA. Various risankizumab formulations have been described in the international applications PCT/US2013/038109 and PCT/IB2020/058347, the contents of which are incorporated by reference herein in their entirety.

The commercial formulations described above comprise the surfactant polysorbate 20 (PS20). It has been proposed that trace amounts of hitchhiker protein contaminants in preparations of certain recombinantly produced biologic pharmaceutical products can cause polysorbate 20 hydrolysis leading to particle formation (therapeutic protein and/or free fatty acid aggregates) and hence reduced shelf life (Khan et al. (2015) *European Journal of Pharmaceutics and Biopharmaceutics* 97:60-67).

One significant factor contributing to the presence of hitchhiker protein impurities in recombinant therapeutic monoclonal antibody formulations is their association with the product monoclonal antibodies (mAbs) (Nogal et al. (2012) Biotechnol. Prog. 28:454-458). It has been reported that mAbs may preferentially bind to select hitchhiker proteins (HPs), and the degree of interaction and/or identity of the associated HPs may vary depending on the mAb (Nogal et al. (2012) Biotechnol. Prog. 28:454-458). It has also been shown that a mAb's hitchhiker protein content in the protein A (PrA) eluate is specific for a particular antibody (Zhang et al. (2016) Biotechnol. Prog. 32:708-717), and that the primary sequence of a mAb may be responsible for the binding and consequence co-purification of the specific hitchhiker protein (Bee et al. (2016) Biotechnol. Prog. 00: 1-6). Another factor is the similar physicohemical characteristics of certain hitchhiker proteins to the particular mAb to be purified, which leads to their co-purification with the mAb. Because different hitchhiker proteins co-purify with different recombinant antibodies, it is unpredictable, prior to experimentation, whether a hitchhiker problem will be encountered during production of a new antibody, much less which hitchhiker protein will be problematic.

In addition, a major problem with protein-based therapeutics is their immunogenicity, that is, their tendency to trigger an unwanted immune response against themselves resulting in so called "anti-drug antibodies" or "ADA".

To date, there remains a need for developing risankizumab compositions with reduced levels of hitchhiker protein impurities, and with improved properties such as reduced immunogenicity.

SUMMARY

The present disclosure is based, in part, on the discovery of a particular hitchhiker protein phospholipase A2 (PLA2) which co-purifies with risankizumab, whose presence negatively impacts stability of polysorbate (e.g., polysorbate 20 and/or polysorbate 80) in risankizumab liquid pharmaceutical formulations, and that reducing the PLA2 concentration in the formulations beneficially increases the long term stability of the formulations (e.g., decreasing particle formation, increasing shelf-life of the risankizumab drug products, and the like). The increased stability of risankizumab formulations can also be achieved by using poloxamer 188 (P188) instead of PS20 or PS80. The present disclosure also describes new risankizumab compositions with a reduced level of risankizumab species modified with high mannose N-glycans (e.g., M5, M6, and/or M7) and increased purity. These risankizumab compositions exhibit decreased immunogenicity in human subjects.

Accordingly, in one aspect, the present disclosure relates to a liquid composition comprising: (1) risankizumab; and (2) PLA2 in an amount that is less than about 250 pg per mg of risankizumab.

In another aspect, the present disclosure relates to a composition comprising risankizumab, wherein the composition has one or more of the following features: (a) less than about 5.4% of total risankizumab species with N-glycosylation have a high mannose N-glycan; and/or (b) the incidence of treatment-emergent anti-drug antibody (ADA) in a human is less than about 4.7% following administration of a single subcutaneous 150 mg dose of the pharmaceutical composition to the human.

In yet another aspect, the present disclosure relates to a composition comprising: (1) risankizumab; and (2) Poloxamer 188 (P188), wherein the composition does not comprise polysorbate 20 (PS20) and/or polysorbate 80 (PS80).

BRIEF DESCRIPTION OF THE DRAWINGS

FIG. 21B is an expanded view of FIG. 21A.

DETAILED DESCRIPTION

Figure 1:
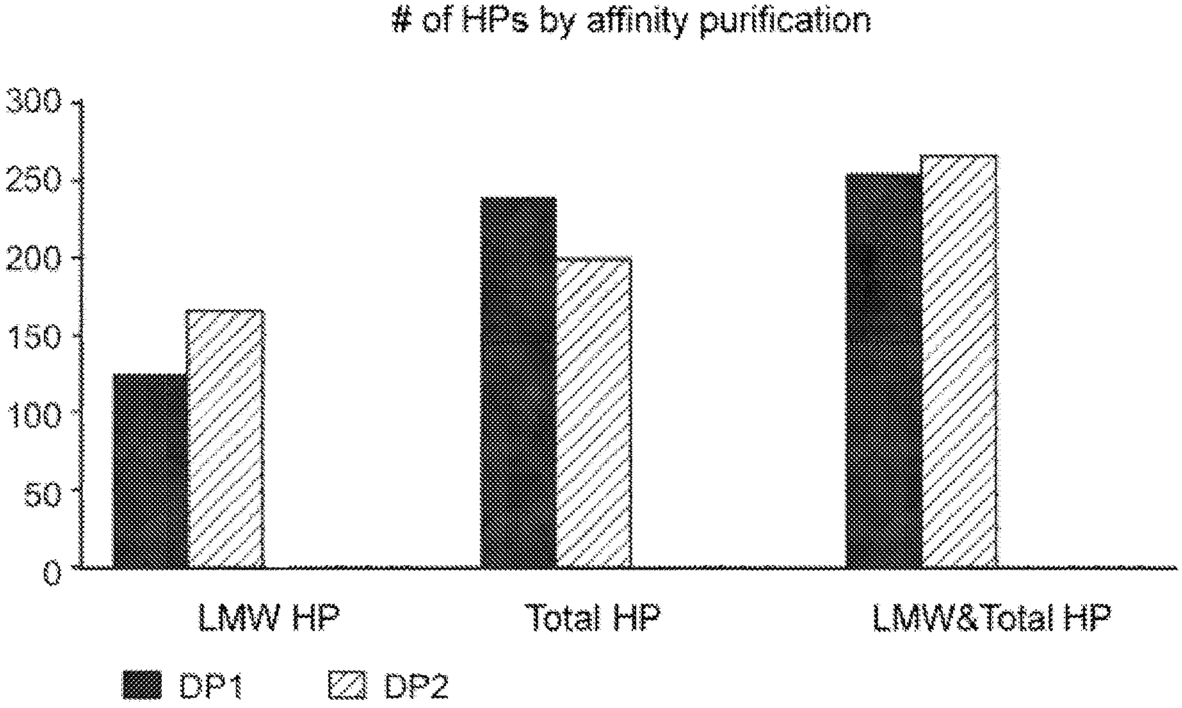
FIG. 1 shows the number of low molecular weight (LMW) hitchhiker proteins (HP), total HP, and LMW HP & total HP in DP1 and DP2 by affinity purification.

In some aspects, the present disclosure is based, in part, on the discovery of a particular hitchhiker protein PLA2, whose presence negatively impacts stability of polysorbate (e.g., PS20 and/or PS80) in risankizumab liquid pharmaceutical formulations, and that reducing PLA2 from the formulations beneficially increases the stability of the formulations (e.g., decreasing particle formation, increasing shelf-life of the risankizumab drug product, and the like). It was also found that the increased stability of risankizumab formulation can also be achieved by using poloxamer 188 instead of P20 or P80.

The initial pharmaceutical formulation developed for risankizumab had a concentration of 90 mg/ml. A 150 mg/ml formulation was subsequently approved by the U.S. FDA to enable a single subcutaneous injection of the entire 150 mg therapeutic dose. Both the commercial 75 mg/0.83 ml (90 mg/mL) and 150 mg/ml risankizumab formulations were disclosed in the FDA approved drug label and "Full Prescribing Information" of SKYRIZI® (risankizumab-rzaa) revised in December 2022, the content of each of which is incorporated by reference herein in its entirety. Both of the FDA approved risankizumab formulations comprise highly-purified, recombinantly-produced risankizumab active pharmaceutical ingredient (API). However, when the 150 mg/ml risankizumab formulation was diluted in order to explore the feasibility of developing specific product presentations, such as those used with an on-body device, unacceptable levels of particles comprised of risankizumab and/or free fatty acid aggregates were formed under certain storage conditions.

In one embodiment of the invention, this unexpected problem is believed to be caused by the residual trace levels of hitchhiker proteins co-purified with otherwise highly pure risankizumab API purified with a state-of-the-art orthogonal column chromatography process. Because the identity of hitchhiker proteins co-purified with a monoclonal antibody (mAb) varies depending on the mAb, it is unpredictable prior to experimentation whether a hitchhiker protein problem will be encountered during production of a new antibody, much less which hitchhiker protein will be problematic.

In some aspects, the present disclosure identifies PLA2 as a specific problematic hitchhiker protein co-purified with risankizumab. It is demonstrated herein that PLA2 co-purified with risankizumab causes the degradation of the surfactant polysorbate 20 (PS20), leading to particle formation in risankizumab products. An optimized purification process has been developed which specifically targets reduction of the level of PLA2 co-purified with risankizumab. In some aspects, the present disclosure therefore provides risankizumab liquid compositions with a reduced level of PLA2 and improved stability and shelf-life.

In some aspects, the present disclosure relates to new risankizumab compositions having a reduced level of risankizumab species that are modified with high mannose N-glycans (e.g., M5, M6, and/or M7), that have decreased immunogenicity.

In some aspects, the present disclosure is directed to risankizumab compositions which have a reduced level of risankizumab species having a high mannose N-glycan (M5, M6, and/or M7) and decreased immunogenicity. The decreased immunogenicity (e.g., a lower incidence of treatment-emergent anti-drug antibody following administration of a single 150 mg subcutaneous dose of the liquid composition to a human) also indicate improved product quality of the risankizumab compositions described herein.

As disclosed herein, the present disclosure relates to the following embodiments.

Embodiment 1. A liquid composition comprising: (1) either risankizumab or an anti-IL23 monoclonal antibody comprising two light chains having the amino acid sequence of SEQ ID NO: 9 and two heavy chains having the amino acid sequence of SEQ ID NO: 10; and (2) phospholipase A2 (PLA2) in an amount that is less than about 250 pg per mg of risankizumab.

Embodiment 2. The liquid composition of embodiment 1, comprising about 60 mg/ml to about 150 mg/ml risankizumab.

Embodiment 3. The liquid composition of embodiment 1 or 2, wherein the PLA2 is PLA2G15.

Embodiment 4. The liquid composition of any one of embodiments 1-3, wherein the level of PLA2 is less than about 240 pg, less than about 220 pg, less than about 200 pg, less than about 180 pg, less than about 160 pg, less than about 140 pg, less than about 120 pg, less than about 100 pg, less than about 90 pg, less than about 80 pg, less than about 70 pg, less than about 60 pg, less than about 50 pg, less than about 40 pg, less than about 30 pg, less than about 25 pg, less than about 20 pg, less than about 15 pg, less than about 10 pg, less than about 9 pg, less than about 8 pg, less than about 7 pg, less than about 6 pg, less than about 5 pg, less than about 4.4 pg, less than about 3 pg, less than about 2 pg, less than about 1 pg, less than about 0.5 pg, less than about 0.1 pg, less than about 0.05 pg, or less than about 0.01 pg per mg of risankizumab.

Embodiment 5. The liquid composition of any one of embodiments 1-3, wherein the level of PLA2 is more than about 240 pg, more than about 220 pg, more than about 200 pg, more than about 180 pg, more than about 160 pg, more than about 140 pg, more than about 120 pg, more than about 100 pg, more than about 90 pg, more than about 80 pg, more than about 70 pg, more than about 60 pg, more than about 50 pg, more than about 40 pg, more than about 30 pg, more than about 25 pg, more than about 20 pg, more than about 15 pg, more than about 10 pg, more than about 9 pg, more than about 8 pg, more than about 7 pg, more than about 6 pg, more than about 5 pg, more than about 4 pg, more than about 3 pg, more than about 2 pg, more than about 1 pg, more than about 0.5 pg, more than about 0.1 pg, more than about 0.05 pg, or more than about 0.01 pg per mg of risankizumab.

Embodiment 6. The liquid composition of any one of embodiments 1-3, wherein the level of PLA2 is from about 200 to about 249, from about 160 to about 200, from about 120 to about 160, from about 100 to about 120, from about 80 to about 100, from about 60 to about 80, from about 40 to about 60, from about 25 to about 40, from about 10 to about 25, from about 5 to about 10, from about 4 to about 10, from about 1 to about 5, from about 1 to about 4, from about 1 to about 3, from about 1 to about 2, from about 0.5 to about 1, from about 0.1 to about 0.5, from about 0.05 to about 0.1, from about 0.01 to about 0.5, or from about 70 to about 240 pg per mg of risankizumab.

Embodiment 7. The liquid composition of any one of embodiments 1-3, wherein the level of PLA2 is about 240, about 220, about 200, about 180, about 160, about 140, about 120, about 100, about 90, about 80, about 70, about 60, about 50, about 40, about 30, about 25, about 20, about 15, about 10, about 9, about 8, about 7, about 6, about 5, about 4.4, about 3, about 2, about 1, about 0.5, about 0.1, about 0.05, or about 0.01 pg per mg of risankizumab.

Embodiment 8. The liquid composition of any one of embodiments 1-7, wherein the level of PLA2 is determined by ELISA.

Embodiment 9. The liquid composition of any one of embodiments 1-8, wherein the risankizumab is produced in a CHO cell line.

Embodiment 10. The liquid composition of any one of embodiments 1-9, further comprising one or more of a surfactant, a polyol, and a buffer.

Embodiment 11. The liquid composition of embodiment 10, wherein the polyol is selected from the group consisting of trehalose, mannitol, sucrose, and sorbitol.

Embodiment 12. The liquid composition of embodiment 11, wherein the polyol is trehalose.

Embodiment 13. The liquid composition of embodiment 12, wherein the trehalose is at an amount of about 150 to about 220 mM.

Embodiment 14. The liquid composition of embodiment 13, wherein the trehalose is at an amount of about 185 mM.

Embodiment 15. The liquid composition of any one of embodiments 10-14, wherein the buffer is selected from the group consisting of acetate buffer, histidine buffer, citrate buffer, phosphate buffer, glycine buffer, and arginine buffer.

Embodiment 16. The liquid composition of embodiment 15, wherein the buffer is acetate buffer.

Embodiment 17. The liquid composition of embodiment 16, wherein the acetate buffer is at an amount of about 5 to about 50 mM.

Embodiment 18. The liquid composition of embodiment 17, wherein the acetate buffer is at an amount of about 10 mM.

Embodiment 19. The liquid composition of any one of embodiments 10-18, wherein the surfactant is selected from the group consisting of polysorbate 20 (PS20), polysorbate 80 (PS80), polysorbate 40 (PS40), polysorbate 60 (PS60), polysorbate 65 (PS65), and Poloxamer 188.

Embodiment 20. The liquid composition of embodiment 19, wherein the surfactant is PS20.

Embodiment 21. The liquid composition of embodiment 20, wherein the PS20 is at an amount of about 0.2 mg/mL.

Embodiment 22. The liquid composition of embodiment 21, comprising: 150 mg/ml risankizumab; 185 mM trehalose; 10 mM acetate; and 0.20 mg/mL polysorbate 20, wherein liquid composition has a pH of about 5.7.

Embodiment 23. The liquid composition of embodiment 21, comprising: 150 mg/ml risankizumab; 0.054 mg/mL acetic acid; 1.24 mg/mL sodium acetate trihydrate; 70 mg/mL trehalose dihydrate; 0.20 mg/mL polysorbate 20; and water for injections, wherein the liquid composition has a pH of about 5.7.

Embodiment 24. The liquid composition of any one of embodiments 20-23, wherein at least 80% of the initial concentration of PS20 is present in the composition following storage at 5° C. for 6 months.

Embodiment 25. The liquid composition of any one of embodiments 20-23, wherein at least 70% of the initial concentration of PS20 is present in the composition following storage at 5° C. for 24 months.

Embodiment 26. The liquid composition of any one of embodiments 20-23, wherein at least 60% of the initial concentration of PS20 is present in the composition following storage at 25° C. for 6 months.

Embodiment 27. The liquid composition of any one of embodiments 20-23, wherein at least 40% of the initial concentration of PS20 is present in the composition following storage at 40° C. for 6 months.

Embodiment 28. The liquid composition of any one of embodiments 20-23, wherein the total concentration of free fatty acid (FFA) present in the composition is increased no greater than 1.5-fold following storage at 5° C. for 6 months.

Embodiment 29. The liquid composition of any one of embodiments 20-23, wherein the total concentration of FFA present in the composition is no greater than 20 nmol/ml following storage at 5° C. for 6 months.

Embodiment 30. The liquid composition of any one of embodiments 20-23, wherein the total concentration of FFA present in the composition is no greater than 3.2-fold following storage at 25° C. for 6 months.

Embodiment 31. The liquid composition of any one of embodiments 20-23, wherein the total concentration of FFA present in the composition is no greater than 25 nmol/ml following storage at 25° C. for 6 months.

Embodiment 32. The liquid composition of any one of embodiments 20-23, wherein the total concentration of FFA present in the composition is no greater than 3-fold following storage at 40° C. for 6 months.

Embodiment 33. The liquid composition of any one of embodiments 20-23, wherein the total concentration of FFA present in the composition is no greater than 35 nmol/ml following storage at 40° C. for 6 months.

Embodiment 34. The liquid composition of embodiment 19, wherein the surfactant is PS80.

Embodiment 35. The liquid composition of embodiment 34, wherein at least 80% of the initial concentration of PS80 is present in the composition following storage at 5° C. for 6 months.

Embodiment 36. The liquid composition of embodiment 34, wherein at least 60% of the initial concentration of PS80 is present in the composition following storage at 25° C. for 6 months.

Embodiment 37. The liquid composition of embodiment 34, wherein at least 60% of the initial concentration of PS80 is present in the composition following storage at 40° C. for 6 months.

Embodiment 38. The liquid composition of embodiment 34, wherein the total concentration of FFA present in the composition is increased no greater than 8-fold following storage at 5° C. for 6 months.

Embodiment 39. The liquid composition of embodiment 34, wherein the total concentration of FFA present in the composition is no greater than 40 nmol/ml following storage at 5° C. for 6 months.

Embodiment 40. The liquid composition of embodiment 34, wherein the total concentration of FFA present in the composition is increased no greater than 12-fold following storage at 25° C. for 6 months.

Embodiment 41. The liquid composition of embodiment 34, wherein the total concentration of FFA present in the composition is no greater than 60 nmol/ml following storage at 25° C. for 6 months.

Embodiment 42. The liquid composition of embodiment 34, wherein the total concentration of FFA present in the composition is increased no greater than 2.5 fold following storage at 40° C. for 6 months.

Embodiment 43. The liquid composition of embodiment 34, wherein the total concentration of FFA present in the composition is no greater than 15 nmol/ml following storage at 40° C. for 6 months.

Embodiment 44. The liquid composition of any one of embodiments 24-43, wherein the PS20 or PS80 is measured using HPLC-CAD.

Embodiment 45. The liquid composition of any one of embodiments 24-43, wherein the FFA is measured using LC-FFA assay.

Embodiment 46. The liquid composition of any one of embodiments 1-45, wherein no visible or glittering particles are observed over 24 months at 4° C.

Embodiment 47. The liquid composition of any one of embodiments 1-46, wherein the liquid composition is packaged in a vial, a pre-filled syringe, or an on-body device.

Embodiment 48. The liquid composition of any one of embodiments 1-47, wherein the liquid composition is a pharmaceutical composition and is suitable for subcutaneous injection.

Embodiment 49. The liquid composition of any one of embodiments 1-47, wherein the liquid composition is a pharmaceutical composition and is suitable for intravenous injection.

Embodiment 50. A method of treating an immunological disease with the composition of any one of embodiments 1-49.

Embodiment 51. A composition comprising risankizumab, wherein the composition has one or more of the following features: (a) less than about 5.4% of total risankizumab species with N-glycosylation have a high mannose N-glycan; (b) at least about 99.1% of risankizumab is present as a monomer and/or no more than about 0.4% of risankizumab is present as high molecular weight (HMW) species as measured by ultra-performance size exclusion chromatography (UP-SEC); (c) more than about 97.5% of risankizumab is present as a main peak and/or less than about 2.2% of risankizumab is present as low molecular weight (LMW) species as measured by capillary gel electrophoresis under non-reducing conditions (CGE-NR); and/or (d) the incidence of treatment-emergent anti-drug antibody (ADA) is less than about 4.7% following administration of a single subcutaneous dose of the composition to a human.

Embodiment 52. The composition of embodiment 51, comprising about 60 mg/ml to about 150 mg/ml risankizumab.

Embodiment 53. The composition of embodiment 51 or 52, wherein the pharmaceutical composition has at least feature (a): less than about 5.4% of total risankizumab species with N-glycosylation have a high mannose N-glycan.

Embodiment 54. The composition of embodiment 53, wherein the high mannose N-glycan comprises one or more high mannose N-glycans selected from mannose 5 N-glycan (M5), mannose 6 N-glycan (M6), and mannose 7 N-glycan (M7).

Embodiment 55. The composition of embodiment 54, wherein the high mannose N-glycan is M5, M6, and M7.

Embodiment 56. The composition of any one of embodiments 51-55, wherein the level of risankizumab with the high mannose N-glycan is less than 5.3%, less than about 5.2%, less than about 5.1%, less than about 5.0%, less than about 4.9%, less than about 4.8%, less than about 4.7%, less than about 4.6%, less than about 4.5%, less than about 4.4%, less than about 4.3%, less than about 4.2%, less than about 4.1%, less than about 4.0%, less than about 3.9%, less than about 3.8%, or less than about 3.7% of total risankizumab species with N-glycosylation.

Embodiment 57. The composition of any one of embodiments 51-56, wherein the level of risankizumab with the high mannose N-glycan is more than about 5.3%, more than about 5.2%, more than about 5.1%, more than about 5.0%, more than about 4.9%, more than about 4.8%, more than about 4.7%, more than about 4.6%, more than about 4.5%, more than about 4.4%, more than about 4.3%, more than about 4.2%, more than about 4.1%, more than about 4.0%, more than about 3.9%, more than about 3.8%, more than about 3.7%, or more than about 3.6% of total risankizumab species with N-glycosylation.

Embodiment 58. The composition of any one of embodiments 51-57, wherein the level of risankizumab with the high mannose N-glycan is from about 3.6% to about 5.3%, from about 3.6% to about 5.0%, from about 3.6% to about 4.8%, from about 3.6% to about 4.5%, from about 3.6% to about 4.1%, from about 3.6% to about 3.8%, from about 3.8% to about 5.3%, from about 4.1% to about 5.3%, from about 4.5% to about 5.3%, from about 4.8% to about 5.3%, from about 5.0% to about 5.3%, from about 4.3% to about 4.9%, or from about 3.6% to about 4.9% of total risankizumab species with N-glycosylation.

Embodiment 59. The composition of any one of embodiments 51-58, wherein the level of risankizumab with the high mannose N-glycan is about 5.3%, about 5.2%, about 5.1%, about 5.0%, about 4.9%, about 4.8%, about 4.7%, about 4.6%, about 4.5%, about 4.4%, about 4.3%, about 4.2%, about 4.1%, about 4.0%, about 3.9%, about 3.8%, about 3.7%, or about 3.6% of total risankizumab species with N-glycosylation.

Embodiment 60. The composition of embodiment 54, wherein the high mannose N-glycan is M5.

Embodiment 61. The composition of embodiment 60, wherein the level of risankizumab with M5 is less than 5.3%, less than about 5.2%, less than about 5.1%, less than about 5.0%, less than about 4.9%, less than about 4.8%, less than about 4.7%, less than about 4.6%, less than about 4.5%, less than about 4.4%, less than about 4.3%, less than about 4.2%, less than about 4.1%, less than about 4.0%, less than about 3.9%, less than about 3.8%, less than about 3.7%, less than about 3.6%, less than about 3.5%, less than about 3.4%, less than about 3.3%, less than about 3.2%, less than about 3.1%, less than about 3.0%, less than about 2.9%, or less than about 2.8% of total risankizumab species with N-glycosylation.

Embodiment 62. The composition of embodiment 60 or 61, wherein the level of risankizumab with M5 is more than about 5.2%, more than about 5.1%, more than about 5.0%, more than about 4.9%, more than about 4.8%, more than about 4.7%, more than about 4.6%, more than about 4.5%, more than about 4.4%, more than about 4.3%, more than about 4.2%, more than about 4.1%, more than about 4.0%, more than about 3.9%, more than about 3.8%, more than about 3.7%, more than about 3.6%, more than about 3.5%, more than about 3.4%, more than about 3.3%, more than about 3.2%, more than about 3.1%, more than about 3.0%, more than about 2.9%, or more than about 2.8%, or more than about 2.7% of total risankizumab species with N-glycosylation.

Embodiment 63. The composition of any one of embodiments 60-62, wherein the level of risankizumab with M5 is from about 2.7% to about 5.2%, about 3.1% to about 5.2%, about 3.5% to about 5.2%, about 4.0% to about 5.2%, about 4.5% to about 5.2%, from about 5% to about 5.2%, from about 2.7% to about 5.0%, about 2.7% to about 4.5%, about 2.7% to about 4.0%, about 2.7% to about 3.5%, about 2.7% to about 3.1%, from about 3.2% to about 3.7%, or from about 2.7% to about 3.7% of total risankizumab species with N-glycosylation.

Embodiment 64. The composition of any one of embodiments 60-63, wherein the level of risankizumab with M5 is about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, or about 5.2% of total risankizumab species with N-glycosylation.

Embodiment 65. The composition of embodiment 54, wherein the high mannose glycan is M6.

Embodiment 66. The composition of embodiment 65, wherein the level of risankizumab with M6 is less than about 2.6%, less than about 2.5%, less than about 2.4%, less than about 2.3%, less than about 2.2%, less than about 2.1%, less than about 2.0%, less than about 1.9%, less than about 1.8%, less than about 1.7%, less than about 1.6%, less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, or less than about 0.5% of total risankizumab species with N-glycosylation.

Embodiment 67. The composition of embodiment 65 or 66, wherein the level of risankizumab with M6 is more than about 2.5%, more than about 2.4%, more than about 2.3%, more than about 2.2%, more than about 2.1%, more than about 2.0%, more than about 1.9%, more than about 1.8%, more than about 1.7%, more than about 1.6%, more than about 1.5%, more than about 1.4%, more than about 1.3%, more than about 1.2%, more than about 1.1%, more than about 1.0%, more than about 0.9%, more than about 0.8%, more than about 0.7%, more than about 0.6%, more than about 0.5%, or more than about 0.4% of total risankizumab species with N-glycosylation.

Embodiment 68. The composition of any one of embodiments 65-67, wherein the level of risankizumab with M6 is from about 0.4% to about 2.5%, from about 0.4% to about 2.4%, from about 0.4% to about 2.2%, from about 0.4% to about 2.0%, from about 0.4% to about 1.8%, from about 0.4% to about 1.6%, from about 0.4% to about 1.4%, from about 0.4% to about 1.2%, from about 0.4% to about 1.0%, from about 0.4% to about 0.9%, from about 0.4% to about 0.8%, from about 0.4% to about 0.7%, from about 0.4% to about 0.6%, from about 0.4% to about 0.5%, or from about 0.6% to about 0.7% of total risankizumab species with N-glycosylation.

Embodiment 69. The composition of any one of embodiments 65-68, wherein the level of risankizumab with M6 is about 2.5%, about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, or about 0.4% of total risankizumab species with N-glycosylation.

Embodiment 70. The composition of embodiment 54, wherein the high mannose glycan is M7.

Embodiment 71. The composition of embodiment 70 wherein the level of risankizumab with M7 is less than about 2.0%, less than about 1.9%, less than about 1.8%, less than about 1.7%, less than about 1.6%, less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, or more than about 0.4% of total risankizumab species with N-glycosylation.

Embodiment 72. The composition of embodiment 70 or 71, wherein the level of risankizumab with M7 is more than about 1.9%, more than about 1.8%, more than about 1.7%, more than about 1.6%, more than about 1.5%, more than about 1.4%, more than about 1.3%, more than about 1.2%, more than about 1.1%, more than about 1.0%, more than about 0.9%, more than about 0.8%, more than about 0.7%, more than about 0.6%, more than about 0.5%, or more than about 0.4% of total risankizumab species with N-glycosylation.

Embodiment 73. The composition of any one of embodiments 70-72, wherein the level of risankizumab with M7 is from about 0.4% to about 1.9%, from about 0.4% to about 1.8%, from about 0.4% to about 1.6%, from about 0.4% to about 1.4%, from about 0.4% to about 1.2%, from about 0.4% to about 1.0%, from about 0.4% to about 0.9%, from about 0.4% to about 0.8%, from about 0.4% to about 0.7%, from about 0.4% to about 0.6%, from about 0.4% to about 0.5%, or from about 0.5% to about 0.6% of total risankizumab species with N-glycosylation.

Embodiment 74. The composition of any one of embodiments 70-73, wherein the level of risankizumab with M7 is about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, or about 0.4% of total risankizumab species with N-glycosylation.

Embodiment 75. The composition of any one of embodiments 51-74, wherein the level of risankizumab with the high mannose N-glycan is determined by 2-AB and HILIC-FL Chromatography.

Embodiment 76. The composition of any one of embodiments 51-74, wherein the level of risankizumab with the high mannose N-glycan is determined by RapiFluor HILIC-FL Chromatography.

Embodiment 77. The composition of any one of embodiments 51-76, wherein greater than about 84.4% of total risankizumab species with N-glycosylation have fucosylated complex oligosaccharides.

Embodiment 78. The composition of embodiment 77, wherein from about 88.0% to about 90.9% of total risankizumab species with N-glycosylation have fucosylated complex oligosaccharides.

Embodiment 79. The composition of embodiment 77 or 78, wherein the level of risankizumab with fucosylated complex oligosaccharides is determined by 2-AB and HILIC-FL Chromatography.

Embodiment 80. The composition of embodiment 77 or 78, wherein the level of risankizumab with the high mannose N-glycan is determined by RapiFluor HILIC-FL Chromatography.

Embodiment 81. The composition of any one of embodiments 51-80, wherein the composition comprises from about 0.8% to about 1.4% aglycosylated risankizumab.

Embodiment 82. The composition of embodiment 81, wherein the aglycosylated risankizumab is determined by Tryptic peptide mapping.

Embodiment 83. The composition of embodiment 51 or 52, wherein the composition has at least feature (b): at least about 99.1% of risankizumab is present as a monomer and/or no more than about 0.4% of risankizumab is present as high molecular weight (HMW) species as measured by ultra-performance size exclusion chromatography (UP-SEC).

Embodiment 84. The composition of embodiment 83, wherein at least about 99.1% of risankizumab is present as a monomer and no more than about 0.4% of risankizumab is present as high molecular weight (HMW) species as measured by ultra-performance size exclusion chromatography (UP-SEC).

Embodiment 85. The composition of embodiment 83 or 84, wherein at least about 99.2%, at least about 99.3%, at least about 99.4%, at least about 99.5%, at least about 99.6%, or at least about 99.7% of risankizumab is present as a monomer.

Embodiment 86. The composition of any one of embodiments 83-85, wherein from about 99.1% to about 99.7%, 99.1% to about 99.6%, from about 99.2% to about 99.7%, or from about 99.2% to about 99.6% of risankizumab is present as a monomer.

Embodiment 87. The composition of any one of embodiments 83-86, wherein no more than about 0.35%, no more than about 0.3%, no more than about 0.25%, no more than about 0.2%, no more than about 0.15%, or no more than about 0.1% of risankizumab is present as high molecular weight (HMW) species.

Embodiment 88. The composition of any one of embodiments 83-87, wherein from about 0.1% to about 0.4%, from about 0.1 to about 0.3%, from about 0.1 to about 0.2%, from about 0.2% to about 0.4%, or from about 0.2% to about 0.3% of risankizumab is present as high molecular weight (HMW) species.

Embodiment 89. The composition of embodiment 51 or 52, wherein the composition has at least feature (c): more than about 97.5% of risankizumab is present as a main peak and/or less than about 2.2% of risankizumab is present as low molecular weight (LMW) species as measured by capillary gel electrophoresis under non-reducing conditions (CGE-NR).

Embodiment 90. The composition of embodiment 89, more than about 97.5% of risankizumab is present as a main peak and less than about 2.2% of risankizumab is present as low molecular weight (LMW) species.

Embodiment 91. The composition of embodiment 89 or 90, wherein more than about 97.6%, more than about 97.7%, more than about 97.8%, more than about 97.9%, more than about 98.0%, more than about 98.1%, more than about 98.2%, more than about 98.3%, or more than about 98.4% of risankizumab is present as a main peak.

Embodiment 92. The composition of any one of embodiments 89-91, wherein from about 97.6% to about 98.4%, from about 97.6% to about 98.3%, from about 97.6% to about 98.2%, from about 97.7% to about 98.4%, from about 97.7% to about 98.3%, from about 97.7% to about 98.2%, from about 97.8% to about 98.4%, from about 97.8% to about 98.3%, or from about 97.8% to about 98.2% of risankizumab is present as a main peak.

Embodiment 93. The composition of any one of embodiments 89-92, wherein less than about 2.1%, less than 2.0%, less than 1.9%, less than 1.8%, less than 1.7%, less than 1.6%, or less than 1.5% of risankizumab is present as low molecular weight (LMW) species.

Embodiment 94. The composition of any one of embodiments 89-93, wherein from about 1.5% to about 2.1%, from about 1.6% to about 2.1%, from about 1.7% to about 2.1%, from about 1.5% to about 2.0%, from about 1.6% to about 2.0%, or from about 1.7% to about 2.0% of risankizumab is present as low molecular weight (LMW) species.

Embodiment 95. The composition of embodiment 51 or 52, wherein the composition has at least feature (d): the incidence of treatment-emergent anti-drug antibody (ADA) in a human is less than about 4.7% following administration of a single subcutaneous 150 mg dose of the composition to the human.

Embodiment 96. The composition of embodiment 95, wherein the incidence of treatment-emergent ADA is less than about 4.5%, less than about 4.0%, less than about 3.5%, less than about 3.0%, less than about 2.5%, less than about 2.0%, less than about 1.5%, less than about 1.0%, less than about 0.5%, less than about 0.4%, less than about 0.3%, less than about 0.2%, less than about 0.1%, less than about 0.01%, less than about 0.001%, or less than about 0.0001%.

Embodiment 97. The composition of embodiment 95 or 96, wherein the incidence of treatment-emergent ADA is 0.0%.

Embodiment 98. The composition of any one of embodiments 95-97, wherein the incidence of treatment-emergent ADA is measured following administration of a single subcutaneous injection of 150 mg dose of the composition to a human.

Embodiment 99. The composition of any one of embodiments 95-98, wherein the presence of ADA is determined using a bridging electrochemiluminescence immunoassay.

Embodiment 100. The composition of any one of embodiments 51-99, wherein the risankizumab is produced in a CHO cell line.

Embodiment 101. The composition of any one of embodiments 51-100, further comprising a pharmaceutically acceptable excipient.

Embodiment 102. The pharmaceutical composition of embodiment 101, wherein the excipient is selected from the group consisting of surfactant, polyol, and buffer.

Embodiment 103. The pharmaceutical composition of embodiment 102, wherein the polyol is trehalose.

Embodiment 104. The pharmaceutical composition of embodiment 103, wherein the trehalose is at an amount of about 150 to about 220 mM.

Embodiment 105. The pharmaceutical composition of embodiment 104, wherein the trehalose is at an amount of about 185 mM.

Embodiment 106. The pharmaceutical composition of any one of embodiments 101-105, wherein the buffer is selected from the group consisting of acetate buffer, and succinate buffer.

Embodiment 107. The pharmaceutical composition of embodiment 106, wherein the buffer is acetate buffer.

Embodiment 108. The pharmaceutical composition of embodiment 107, wherein the acetate buffer is at an amount of about 5 to about 50 mM.

Embodiment 109. The pharmaceutical composition of embodiment 108, wherein the acetate buffer is at an amount of about 10 mM.

Embodiment 110. The pharmaceutical composition of any one of embodiments 101-109, wherein the surfactant is polysorbate 20 (PS20).

Embodiment 111. The pharmaceutical composition of embodiment 110, wherein the PS20 is at an amount of about 0.02 mg/ml.

Embodiment 112. The pharmaceutical composition of embodiment 111, wherein the PS20 is at an amount of about 0.2 mg/mL.

Embodiment 113. The pharmaceutical composition of embodiment 112, comprising: 150 mg/ml risankizumab; 185 mM trehalose; 10 mM acetate; and 0.20 mg/mL polysorbate 20, wherein pharmaceutical composition has a pH of about 5.7.

Embodiment 114. The pharmaceutical composition of embodiment 112, comprising: 150 mg/ml risankizumab; 0.054 mg/mL acetic acid; 1.24 mg/mL sodium acetate trihydrate; 70 mg/mL trehalose dihydrate; 0.20 mg/mL polysorbate 20; and Water for injection, USP; wherein the pharmaceutical composition has a pH of about 5.7.

Embodiment 115. The pharmaceutical composition of embodiment 110, wherein the risankizumab is present in a concentration of 150 mg/ml.

Embodiment 116. The pharmaceutical composition of any one of embodiments 101-115, wherein the pharmaceutical composition is packaged in a vial, a pre-filled syringe, or an on-body device.

Embodiment 117. The pharmaceutical composition of any one of embodiments 101-116, wherein the pharmaceutical composition is suitable for subcutaneous injection.

Embodiment 118. The pharmaceutical composition of any one of embodiments 101-117, wherein the pharmaceutical composition is suitable for intravenous injection.

Embodiment 119. The pharmaceutical composition of any of the embodiments 101-118, wherein the pharmaceutical composition is a liquid composition.

Embodiment 120. The pharmaceutical composition of any of the embodiments 101-118, wherein the pharmaceutical composition is an aqueous liquid composition.

Embodiment 121. A method of treating an immunological disease with the pharmaceutical composition of any one of embodiments 101-120.

Embodiment 122. A process for producing a risankizumab drug product having PLA2 in an amount that is less than about 250 pg per mg of risankizumab, the process comprising: (1) culturing a host cell line expressing risankizumab in a growth medium under conditions that permit production of risankizumab; (2) clarifying the growth medium by centrifugation and depth filtration; (3) contacting the clarified medium containing risankizumab with a Protein A resin; (4) eluting risankizumab from the protein A resin to obtain a first eluate; (5) filtering the first eluate through a depth filter; (6) contacting the filtered first eluate to a mixed-mode resin to obtain a first flowthrough containing risankizumab; (7) contacting the first flow-through to a cation exchange resin; (8) eluting risankizumab from the cation exchange resin to obtain a second eluate; (9) processing the second eluate by ultrafiltration and diafiltration, thereby obtaining a risankizumab drug product having PLA2 in an amount that is less than about 250 pg per mg of risankizumab.

Embodiment 123. The process of embodiment 122 further comprising subjecting the first eluate to a viral inactivation step prior to the step (5).

Embodiment 124. The process of embodiment 122 or 123 further comprising subjecting the second eluate to viral filtration prior to the step (9).

Embodiment 125. A process for producing a risankizumab drug product having risankizumab with a high mannose N-glycan in an amount that is less than about 5.4% of total risankizumab species with N-glycosylation, the process comprising: (1) culturing a host cell line expressing risankizumab in a growth medium under conditions that permit production of risankizumab; (2) clarifying the growth medium by centrifugation and depth filtration; (3) contacting the clarified medium containing risankizumab with a Protein A resin; (4) eluting risankizumab from the protein A resin to obtain a first eluate; (5) filtering the first eluate through a depth filter; (6) contacting the filtered first eluate to a mixed-mode resin to obtain a first flowthrough containing risankizumab; (7) contacting the first flow-through to a cation exchange resin; (8) eluting risankizumab from the cation exchange resin to obtain a second eluate; (9) processing the second eluate by ultrafiltration and diafiltration, thereby obtaining a risankizumab drug product having risankizumab with a high mannose N-glycan in an amount that is less than about 5.4% of total risankizumab species with N-glycosylation.

Embodiment 126. The process of embodiment 125, further comprising subjecting the first eluate to a viral inactivation step prior to the step (5).

Embodiment 127. The process of embodiment 125 or 126, further comprising subjecting the second eluate to viral filtration prior to the step (9).

Embodiment 128. A composition comprising: (1) risankizumab; and (2) Poloxamer 188 (P188), wherein the composition optionally does not comprise polysorbate 20 (PS20) and/or polysorbate 80 (PS80).

Embodiment 129. The composition of embodiment 128, comprising about 60 mg/ml to about 150 mg/ml risankizumab.

Embodiment 130. The composition of embodiment 128 or 129, further comprising phospholipase A2 (PLA2).

Embodiment 131. The composition of any one of embodiments 128-130, wherein the PLA2 is PLA2G15.

Embodiment 132. The composition of any one of embodiments 128-131, wherein the level of PLA2 is greater than about 250 pg, wherein the level of PLA2 is greater than about 260 pg, greater than about 270 pg, greater than about 280 pg, greater than about 290 pg, greater than about 300 pg, greater than about 310 pg, greater than about 320 pg, greater than about 330 pg, greater than about 340 pg, greater than about 350 pg, greater than about 360 pg, greater than about 380 pg, greater than about 400 pg, greater than about 450 pg, greater than about 500 pg, greater than about 550 pg, greater than about 600 pg, greater than about 650 pg, greater than about 700 pg, greater than about 750 pg, greater than about 800 pg, greater than about 900 pg, or greater than about 1000 pg, per mg of risankizumab.

Embodiment 133. The composition of any one of embodiments 128-131, wherein the level of PLA2 is from about 250 pg to about 1100 pg, from about 260 pg to about 1100 pg, from about 270 pg to about 1100 pg, from about 280 pg to about 1100 pg, from about 290 pg to about 1100 pg, from about 300 pg to about 1100 pg, from about 310 pg to about 1100 pg, from about 320 pg to about 1100 pg, from about 340 pg to about 1100 pg, from about 360 pg to about 1100 pg, from about 250 pg to about 1000 pg, from about 250 pg to about 900 pg, from about 250 pg to about 800 pg, from about 250 pg to about 700 pg, from about 250 pg to about 600 pg, from about 250 pg to about 500 pg, from about 250 pg to about 400 pg, from about 250 pg to about 1030 pg, from about 290 pg to about 1090 pg, from about 360 pg to about 450 pg, or from about 310 pg to about 920 pg, per mg of risankizumab.

Embodiment 134. The composition of any one of embodiments 128-131, wherein the level of PLA2 is about 260 pg, about 270 pg, about 280 pg, about 290 pg, about 300 pg, about 310 pg, gr about 320 pg, about 330 pg, about 340 pg, about 350 pg, about 360 pg, about 380 pg, about 400 pg, about 450 pg, about 500 pg, about 550 pg, about 600 pg, about 650 pg, about 700 pg, about 750 pg, about 800 pg, about 900 pg, about 1000 pg, or about 1100 pg, per mg of risankizumab.

Embodiment 135. The composition of any one of embodiments 130-134, wherein the level of PLA2 is determined by ELISA.

Embodiment 136. The composition of any one of embodiments 128-135, wherein at least 85% of the initial amount of P118 is retained following storage at 5° C. for 6 months.

Embodiment 137. The composition of any one of embodiments 128-135, wherein at least 80% of the initial amount of P118 is retained following storage at 5° C. for 6 months.

Embodiment 138. The composition of any one of embodiments 128-135, wherein at least 65% of the initial amount of P118 is retained following storage at 25° C. for 3 months.

Embodiment 139. The composition of any one of embodiments 128-135, wherein at least 60% of the initial amount of P118 is retained following storage at 25° C. for 6 months.

Embodiment 140. The composition of any one of embodiments 128-135, wherein at least 60% of the initial amount of P118 is retained following storage at 40° C. for 3 months.

Embodiment 141. The composition of any one of embodiments 128-135, wherein at least 60% of the initial amount of P118 is retained following storage at 40° C. for 6 months.

Embodiment 142. The composition of any one of embodiments 136-141, wherein the P188 is measured using a Pluronic F-68 colorimetric assay.

Further benefits of the present disclosure will be apparent to one skilled in the art from reading this patent application. The embodiments of the disclosure described in the following paragraphs are intended to illustrate the invention and should not be deemed to narrow the scope of the invention.

Definitions

The singular forms "a," "an" and "the" include plural referents unless the context clearly dictates otherwise.

The term "and/or" as used in a phrase such as "A and/or B" herein is intended to mean "A and B", "A or B", "A", or "B".

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, such that they indicate the inclusion of the recited feature but without excluding one or more other such features.

The term "carrier" used in connection with a pharmaceutical excipient refers to any and all solvents, dispersion media, preservatives, coatings, isotonic and absorption delaying agents, and the like, that are compatible with pharmaceutical administration.

The term "patient", "subject", "individual" and the like refers to humans.

Risankizumab

According to USAN, risankizumab has the following chemical names:

1. Immunoglobulin G1, anti-(human interleukin 23 subunit p19) (human-*Mus musculus* heavy chain), disulfide with human-*Mus musculus* κ-chain, dimer
2. Immunoglobulin G1-kappa, anti-(human interleukin-23 subunit alpha (IL-23-A, interleukin-23 subunit p19, IL-23p19)); humanized monoclonal antibody; γ1 heavy chain (1-449) [humanized VH (*Homo sapiens* IGHV1-69*08 (79%)-(IGHD)-IGHJ6*01 (91%)) [8.8.13](1-120)-*Homo sapiens* IGHG1*03 {CH2 $L^4$>A(237), L5>A(238), CH3 $K^{107}$>-(450)}(121-449)], (223-214')-disulfide with kappa light chain (1'-214') [humanized V-KAPPA (*Homo sapiens* IGKV1-27*01 (80%)-IGKJ2*02 (91%)) [6.3.9](1'-107')-*Homo sapiens* IGKC*01 (108'-214')]; dimer (229-229":232-232")-bisdisulfide According to INN (see WHO Drug Information, 29 (2), 254-255), risankizumab has the chemical name:

Immunoglobulin G1-kappa, anti-[*Homo sapiens* IL23A (interleukin 23 subunit alpha, IL-23A, IL23 subunit p19 IL23p19)], humanized monoclonal antibody; gamma1 heavy chain (1-449) [humanized VH (*Homo sapiens* IGHV1-69*02 (79.40%)-(IGHD)-IGHJ5*01) [8.8.13](1-120)-*Homo sapiens* IGHG1*01, G1m17,1 (CH1 (121-218), hinge (219-233), CH2 L1.3>A (237), L1.2>A(238) (234-343), CH3 (344-448), CHS K2>del (449)) (121-449)], (223-214')-disulfide with kappa light chain (1'-214') [humanized V-KAPPA (*Homo sapiens* IGKV1-27*01 (80.00%)-IGKJ2*01) [6.3.9](1'-107')-*Homo sapiens* IGKC*01, Km3 (108'-214')]; dimer (229-229":232-232")-bisdisulfide Risankizumab binds with high affinity to human IL-23 and inhibits IL-23 stimulated IL-17 production at inhibitory concentration (IC) 50 concentrations below 10 pM, as compared with 167 pM for ustekinumab in the same system. Risankizumab does not affect IL-12 at a maximum tested concentration (33 nM) and it does not inhibit IL-12 stimulated IFN-γ production.

Risankizumab Amino Acid Sequences

Risankizumab has the CDRs shown in Tables 1 and 2. The variable regions of risankizumab are shown in Table 3.

TABLE 1

| Light Chain CDR Sequences | | |
|---|---|---|
| L-CDR1 | L-CDR2 | L-CDR3 |
| KASRDVAIAVA (SEQ ID NO: 1) | WASTRHT (SEQ ID NO: 2) | HQYSSYPFT (SEQ ID NO: 3) |

TABLE 2

| Heavy Chain CDR Sequences | | |
|---|---|---|
| H-CDR1 | H-CDR2 | H-CDR3 |
| GYTFT DQTIH (SEQ ID NO: 4) | YIYPRDDSP KYNENFKG (SEQ ID NO: 5) | PDRSGY AWFIY (SEQ ID NO: 6) |

TABLE 3

| | |
|---|---|
| Humanized VL Sequence | DIQMTQSPSSLSASVGDRVTITCKASRD VAIAVAWYQQKPGKVPKLLIYWASTRHT GVPSRFSGSGSRTDFTLTISSLQPEDVA DYFCHQYSSYPFTFGSGTKLEIK (SEQ ID NO: 7) |
| Humanized VH Sequence | QVQLVQSGAEVKKPGSSVKVSCKASGYT FTDQTIHWMRQAPGQGLEWIGYIYPRDD SPKYNENFKGKVTITADKSTSTAYMELS SLRSEDTAVYYCAIPDRSGYAWFIYWGQ GTLVTVSS (SEQ ID NO: 8) |

Risankizumab comprises the heavy and light chain sequences shown in Table 4.

TABLE 4

```
risankizumab light chain sequence (SEQ ID NO: 9)
DIQMTQSPSS LSASVGDRVT ITCKASRDVA IAVAWYQQKP GKVPKLLIYW  50
ASTRHTGVPS RFSGSGSRTD FTLTISSLQP EDVADYFCHQ YSSYPFTFGS 100
GTKLEIKRTV AAPSVFIFPP SDEQLKSGTA SVVCLLNNFY PREAKVOWKV 150
DNALQSGNSQ ESVTEQDSKD STYSLSSTLT LSKADYEKHK VYACEVTHQG 200
LSSPVTKSEN RGEC                                        214

risankizumab heavy chain sequence (SEQ ID NO: 10)
QVOLVOSGAE VKKPGSSVKV SCKASGYTFT DQTIHWMRQA PGQGLEWIGY  50
IYPRDDSPKY NENFKGKVTI TADKSTSTAY MELSSLRSED TAVYYCAIPD 100
RSGYAWFIYW GQGTLVTVSS ASTKGPSVFP LAPSSKSTSG GTAALGCLVK 150
DYFPEPVTVS WNSGALTSGV HTFPAVLQSS GLYSLSSVVT VPSSSLGTQT 200
YICNVNHKPS NTKVDKRVEP KSCDKTHTCP PCPAPEAAGG PSVFLFPPKP 250
KDTLMISRTP EVTCVVVDVS HEDPEVKENW YVDGVEVHNA KTKPREEQYN 300
STYRVVSVLT VLHQDWLNGK EYKCKVSNKA LPAPIEKTIS KAKGQPREPQ 350
VYTLPPSREE MTKNQVSLTC LVKGFYPSDI AVEWESNGQP ENNYKTTPPV 400
LDSDGSFFLY SKLTVDKSRW QQGNVFSCSV MHEALHNHYT QKSLSLSPG  449
```

Risankizumab Compositions with Reduced Hitchhiker Proteins

In one aspect, the present disclosure relates to a liquid composition comprising: (1) risankizumab; and (2) PLA2 in an amount that is less than about 250 pg per mg of risankizumab.

In one embodiment, the liquid composition described herein comprises about 60 mg/ml to about 150 mg/ml risankizumab. For example, and without limitation, the liquid composition described herein comprises about 70 mg/ml to about 150 mg/ml, about 80 mg/ml to about 150 mg/ml, about 90 mg/ml to about 150 mg/ml, about 100 mg/ml to about 150 mg/ml, about 110 mg/ml to about 150 mg/ml, about 120 mg/ml to about 150 mg/ml, about 130 mg/ml to about 150 mg/ml, about 140 mg/ml to about 150 mg/ml, 60 mg/ml to about 70 mg/ml, 60 mg/ml to about 80 mg/ml, 60 mg/ml to about 90 mg/ml, 60 mg/ml to about 100 mg/ml, 60 mg/ml to about 110 mg/ml, 60 mg/ml to about 120 mg/ml, 60 mg/ml to about 130 mg/ml, or 60 mg/ml to about 140 mg/ml risankizumab, and ranges and amounts between any of these aforementioned concentrations.

In one embodiment, the liquid composition described herein comprises about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, or about 150 mg/ml risankizumab.

As used herein, the term "Phospholipase A2" or "PLA2" refers to a well-known family of enzymes that catalyze the hydrolysis of membrane phospholipids. PLA2 catalyzes the hydrolysis of the sn-2 position of membrane glycerophospholipids to liberate arachidonic acid (AA), a precursor of eicosanoids including prostaglandins (PGs) and leukotrienes (LTs). The same reaction also produces lysophosholipids, which represent another class of lipid mediators (Murakami and Kudo (2002) J. Biochem 131:285-292). There are at least sixteen groups of phospholipase A2s. Dennis and coworkers have categorized these into six groups based on their properties: secreted phospholipase A2 (sPLA2 Groups I, II, III, V, IX, X, XI, XII, XIII, and XIV); cytosolic phospholipase A2 (Group IV cPLA2); calcium-independent phospholipase A2 (Group VI iPLA2); PAF acetylhydrolases (GVII and GVIII PAF-AH PLA2s); lysosomal phospholipase A2 (Group XV LPLA2); and adipose-specific phospholipase A2 (GXVI AdPLA) (Shayman and Tesmer (2019) Molecular and Cell Biology of Lipids 1864:932-940). In some embodiments, PLA2 according to the present disclosure is able to catalyze the hydrolysis of a surfactant, such as polysorbate 20 (PS20), polysorbate 80 (PS80), polysorbate 40 (PS40), polysorbate 60 (PS60), polysorbate 65 (PS65), or Poloxamer 188, etc. Exemplary PLA2 according to the present disclosure include, but are not limited to, PLA2G15, PLA2G7, and PLA2G2.

As used herein, the term "PLA2G15", also known as "PLA2 group XV", refers to a unique member of the PLA2 family (Shayman et al. (2011) *Prog. Lipid Res.* 50:1-13). PLA2G15 is localized within cells to lysosomes and late endosomes, has an acid pH optimum and acts as a PLA2 (Abe and Shayman (2007) *J. Lipid Res.* 48:2255-2263). The primary structure of PLA2G15 is highly conserved between mouse, bovine and human. Six exons are present in the gene. The primary structure of the human and mouse enzyme consists of 412 amino acids (407 for the bovine enzyme). The enzymes contain consensus sequences that include a signal peptide cleavage site and a lipase motif, AXSXG that is characteristic of serine hydrolases. The serine is part of a catalytic triad that also includes aspartic acid and histidine. An amino terminal 33 amino acid signal peptide is present with a cleavage site between proline 33 and alanine 34 on the mouse and human peptide. In addition, four N-linked glycosylation sites are present in the mouse and human protein (three in the bovine protein) (Hiraoka and Shayman (2005) J. Lipid Res. 46:2441-2447). The structure and function of PLA2G15 is further described in Shayman and Tesmer, Molecular and Cell Biology of Lipids (2019) 1864: 932-940, the content of which is incorporated by reference herein in its entirety.

Representative human PLA2G15 cDNA and human PLA2G15 protein sequences are well-known in the art and are publicly available from the National Center for Biotechnology Information (NCBI). For example, two different human PLA2G15 isoforms are known. Human PLA2G15 isoform 1 (NP_036452.1) is encodable by the transcript variant 1 (NM_012320.4), which is the longer transcript. Human PLA2G15 isoform 2 (NP_001350480.1) is encodable by the transcript variant 2 (NM_001363551.2), which has a shorter and distinct C-terminus, compared to isoform 1. Nucleic acid and polypeptide sequences of PLA2G15 orthologs in organisms other than humans are well-known and include, for example, chimpanzee PLA2G15 (XM_001167383.5 and XP_001167383.1), Rhesus monkey PLA2G15 (NM_001265818.1 and NP_001252747.1), cattle PLA2G15 (NM_174560.2 and NP_776985.2), dog PLA2G15 (NM_001002940.1 and NP_001002940.1), rat PLA2G15 (NM_001004277.2 and NP_001004277.1), mouse PLA2G15 (NM_001357319.1 and NP_001344248.1; NM_133792.3 and NP_598553.1), Chinese hamster PLA2G15 (XM_003504311.5 and XP_003504359.1; XM_027437910.2 and XP_027293711.1), chicken PLA2G15 (XM_001231518.7 and XP_001231519.1), tropical clawed frog PLA2G15 (XM_012962222.3 and XP_012817676.2; XM_031900713.1 and XP_031756573.1), and zebrafish PLA2G15 (NM_001386706.1 and NP_001373635.1). Representative sequences of PLA2G15 orthologs are presented in Table 5.

Anti-PLA2G15 antibodies suitable for detecting PLA2G15 protein are well-known in the art and include, for example, antibodies catalog Nos. NBP1-92089, H00023659-M01, and NBP2-17193, NBP1-92088, and NBP2-17192 (Novus Biologicals, Littleton, CO), antibody orb185108 (biorbyt, St. Louis, MO), antibodies catalog Nos. ABIN7004525, ABIN2580837, ABIN2580838, and ABIN2580836 (available on the World Wide Web at antibodies-online.com), antibodies catalog Nos. sc-376078, sc-529817, sc-543705, sc-522840, sc-376078 AC, sc-376078 HRP, sc-376078 FITC, sc-376078 PE, and sc-376078 AF488 (Santa Cruz Biotechnology, Dallas, TX), etc. In addition, reagents are well-known for detecting PLA2G15 expression. Multiple clinical tests of PLA2G15 are available in NIH Genetic Testing Registry (GTR®) (e.g., GTR Test ID: GTR000543805.3, offered by Fulgent Clinical Diagnostics Lab (Temple City, CA)).

TABLE 5

```
SEQ ID NO: 11
Mouse PLA2G15 isoform 1, Amino Acid Sequence (NP_598553.1)
  1 mdrhlctcre tqlrsglllp lfllmmladl tlpaqrhppv vlvpgdlgnq leakldkpkv
 61 vhylcskktd syftlwinle lllpviidcw idnirlvynr tsratqfpdg vdvrvpgfge
121 tfsmefldps krnvgsyfyt mveslvgwgy trgedvrgap ydwrrapnen gpyflalrem
181 ieemyqmygg pvvlvahsmg nvymlyflqr qpqvwkdkyi hafvslgapw ggvaktlrvl
241 asgdnnripv igplkireqq rsavstswll pynhtwshek vfvytpttny tlrdyhrffr
301 digfedgwfm rqdteglvea mtppgvelhc lygtgvptpn sfyyesfpdr dpkicfgdgd
361 gtvnlesvlq cqawqsrqeh rvslqelpgs ehiemlanat tlaylkrvll ep

SEQ ID NO: 12
Mouse PLA2G15 isoform 2 Amino Acid Sequence, (NP_001344248.1)
  1 mdrhlctcre tqlrsglllp lfllmmladl tlpaqrhppv vlvpgdlgnq leakldkpkv
 61 vhylcskktd syftlwinle lllpviidcw idnirlvynr tsratqfpdg vdvrvpgfge
121 tfsmefldps krnvgsyfyt mveslvgwgy trgedvrgap ydwrraptaa tslegqiypc
181 lrltggalgg rgqdaacpgl rrqqshsrhw atedpgtaai crlyqlatai qphlvt

SEQ ID NO: 13
Chinese hamster PLA2G15 isoform X1 Amino Acid Sequence
(XP_003504359.1)
  1 mdrhhltcra tqlrsgllvp llllmmladl alsvqrhppv vlvpgdlgnq leakldkpkv
 61 vhylcskrtd syftlwinle lllpviidcw idnirlvynr tsratqfpdg vdvrvpgfge
121 tfslefldps krtvgsyfht mveslvgwgy trgedlrgap ydwrrapnen gpyflalrem
181 ieemyqmygg pvvlvahsmg nmytlyflqr qpqawkdkyi hafislgapw ggvaktlrvl
241 asgdnnripv igplkireqq rsavstswll pynhtwshdk vfvhtpttny tlrdyhqffq
301 dirfedgwfm rqdteglvea mmppgvelhc lygtgvptpd sfyyesfpdr dpkicfgdgd
361 gtvnlesvlq cqawqsrqeh kvslqelpgs ehiemlanat tlaylkrvlf ep

SEQ ID NO: 14
Chinese hamster PLA2G15 isoform X2 Amino Acid Sequence
(XP_027293711.1)
  1 mdrhhltcra tqlrsgllvp llllmmladl alsvqrhppv vlvpgdlgnq leakldkpkv
 61 vhylcskrtd syftlwinle lllpviidcw idnirlvynr tsratqfpdg vdvrvpgfge
121 tfslefldps krtvgsyfht mveslvgwgy trgedlrgap ydwrraptat tglegqvypr
181 1hftgcalgg rgqdparpgl rrqqshpcyw at
```

Included in Table 5 are polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 5, or a portion thereof. Such polypeptides can have a function of the full-length polypeptide as described further herein. Polypeptides with or without signal peptides, and/or including or only the proprotein, and/or including or only the mature protein are further included.

In one embodiment, the liquid composition described herein comprises PLA2 in a detectable amount that is less than 250 pg per mg of risankizumab. For example, and without limitation, PLA2 in the liquid compositions described herein is in an amount that is less than about 240, less than about 220, less than about 200, less than about 180, less than about 160, less than about 140, less than about 120, less than about 100, less than about 90, less than about 80, less than about 70, less than about 60, less than about 50, less than about 40, less than about 30, less than about 25, less than about 20, less than about 15, less than about 10, less than about 9, less than about 8, less than about 7, less than about 6, less than about 5, less than about 4.4, less than about 3, less than about 2, less than about 1, less than about 0.5, less than about 0.1, less than about 0.05, or less than about 0.01 pg per mg of risankizumab, or any range in between, inclusive, such as from about 200 to about 249, from about 160 to about 200, from about 120 to about 160, from about 100 to about 120, from about 80 to about 100, from about 60 to about 80, from about 40 to about 60, from about 25 to about 40, from about 10 to about 25, from about 5 to about 10, from about 4 to about 10, from about 1 to about 5, from about 1 to about 4, from about 1 to about 3, from about 1 to about 2, from about 0.5 to about 1, from about 0.1 to about 0.5, from about 0.05 to about 0.1, or from about 0.01 to about 0.5 pg per mg of risankizumab. In some embodiments, the PLA2 is in an amount that is less than or at the limit of detection of a PLA2 detection assay, e.g., less than or at about 9 pg per mg of risankizumab; or less than or at about 4.4 pg per mg of risankizumab. In one embodiment, PLA2 is in an amount that is from about 70 to about 240 pg per mg of risankizumab.

In one embodiment, the liquid composition described herein comprises PLA2 in an amount that is about 240, about 220, about 200, about 180, about 160, about 140, about 120, about 100, about 90, about 80, about 70, about 60, about 50, about 40, about 30, about 25, about 20, about 15, about 10, about 9, about 8, about 7, about 6, about 5, about 4.4, about 3, about 2, about 1, about 0.5, about 0.1, about 0.05, or about 0.01 pg per mg of risankizumab.

In one embodiment, the liquid composition described herein comprises PLA2 in an amount that is less than about 250 pg, but more than about 240 pg, more than about 220 pg, more than about 200 pg, more than about 180 pg, more than about 160 pg, more than about 140 pg, more than about 120 pg, more than about 100 pg, more than about 90 pg, more than about 80 pg, more than about 70 pg, more than about 60 pg, more than about 50 pg, more than about 40 pg, more than about 30 pg, more than about 25 pg, more than about 20 pg, more than about 15 pg, more than about 10 pg, more than about 9 pg, more than about 8 pg, more than about 7 pg, more than about 6 pg, more than about 5 pg, more than about 4 pg, more than about 3 pg, more than about 2 pg, more than about 1 pg, more than about 0.5 pg, more than about 0.1 pg, more than about 0.05 pg, or more than about 0.01 pg per mg of risankizumab.

In one embodiment, the present disclosure relates to a liquid composition comprising: (1) about 150 mg/ml risankizumab comprising a light chain having the amino acid sequence of SEQ ID NO: 9 and a heavy chain having the amino acid sequence of SEQ ID NO: 10; and (2) PLA2 in an amount that is less than about 250 (e.g., no greater than 240, from about 70 to about 240, less than about 9, or less than about 4.4) pg per mg of risankizumab.

The PLA2 in the liquid compositions described herein may be PLA2G2, PLA2G15, or a combination thereof. In one embodiment, the PLA2 is PLA2G15.

The amount of PLA2 in the liquid compositions described herein can be determined using methods known in the art, e.g., by mass spectrometry, or by ELISA. In one embodiment, the amount of PLA2 in the liquid compositions described herein is determined by ELISA, e.g., using the ELISA method described in Example 9.

In one embodiment, PLA2 in the liquid compositions described herein is derived from a CHO cell line.

In one embodiment, the liquid composition described herein further comprises one or more of a surfactant, a polyol, and a buffer.

The polyol may be selected from the group consisting of trehalose, mannitol, sucrose, and sorbitol. In one embodiment, the polyol is trehalose, and the trehalose is at an amount of about 150 to about 220 mM (e.g., about 185 mM).

The buffer may be selected from the group consisting of acetate buffer, histidine buffer, citrate buffer, phosphate buffer, glycine buffer, and arginine buffer. In one embodiment, the buffer is acetate buffer, and the acetate buffer is at an amount of about 5 to about 100 mM (e.g., about 10 mM).

The surfactant may be selected from the group consisting of polysorbate 20 (PS20), polysorbate 80 (PS80), polysorbate 40 (PS40), polysorbate 60 (PS60), polysorbate 65 (PS65), and Poloxamer 188. In one embodiment, the surfactant is PS20, and the PS20 is at an amount of up to 1.0 mg/ml (e.g., about 1.0 mg/ml, about 0.8 mg/ml, about 0.6 mg/ml, about 0.4 mg/ml, about 0.2 mg/mL, or about 0.1 mg/ml). In another embodiment, the surfactant is PS80, and the PS80 is at an amount of up to 1.0 mg/ml (e.g., about 1.0 mg/ml, about 0.8 mg/ml, about 0.6 mg/ml, about 0.4 mg/ml, about 0.2 mg/ml, or about 0.1 mg/ml).

In one embodiment, the liquid composition described herein has a pH of about 5.0 to about 6.5 (e.g., about 5.7).

In one embodiment, the liquid composition described herein comprises (1) 150 mg/mL risankizumab comprising a light chain having the amino acid sequence of SEQ ID NO: 9 and a heavy chain having the amino acid sequence of SEQ ID NO: 10; 185 mM trehalose; 10 mM acetate; and 0.20 mg/mL polysorbate 20, wherein liquid composition has a pH of about 5.7; and (2) PLA2 (e.g., PLA2G15) in an amount that is less than about 250 pg per mg of risankizumab.

In one embodiment, the liquid composition described herein comprises (1) 150 mg/ml risankizumab comprising a light chain having the amino acid sequence of SEQ ID NO: 9 and a heavy chain having the amino acid sequence of SEQ ID NO: 10; 0.054 mg/mL acetic acid; 1.24 mg/mL sodium acetate trihydrate; 70 mg/mL trehalose dihydrate; 0.20 mg/mL polysorbate 20; and, wherein the liquid composition has a pH of about 5.7; and (2) PLA2 (e.g., PLA2G15) in an amount that is less than about 250 pg per mg of risankizumab.

In one embodiment, the liquid composition described herein comprises (1) 150 mg/ml risankizumab comprising a light chain having the amino acid sequence of SEQ ID NO: 9 and a heavy chain having an amino acid sequence of SEQ ID NO: 10; 0.054 mg/mL acetic acid; 1.24 mg/mL sodium acetate trihydrate; 70 mg/mL trehalose dihydrate; 0.20 mg/mL polysorbate 20; and, wherein the liquid composition has a pH of about 5.7; and (2) PLA2 (e.g., PLA2G15) in an amount that is less than about 250 (e.g. no greater than 240, from about 70 to about 240, less than about 9, or less than about 4.4) pg per mg of risankizumab.

In one embodiment, the liquid composition described herein comprises (1) 150 mg/ml risankizumab comprising a light chain having the amino acid sequence of SEQ ID NO: 9 and a heavy chain having an amino acid sequence of SEQ ID NO: 10; 0.054 mg/mL acetic acid; 1.24 mg/mL sodium acetate trihydrate; 70 mg/mL trehalose dihydrate; 0.20 mg/mL polysorbate 20; and, wherein the liquid composition has a pH of about 5.7; and (2) PLA2 (e.g., PLA2G15) in an amount that is less than about 250 (e.g. no greater than 240, from about 70 to about 240, less than about 9, or less than about 4.4) pg per mg of risankizumab, wherein the amount of PLA2 is determined by ELISA (e.g., the ELISA method described in Example 9).

Liquid formulations encompassed by the present disclosure may comprise added water, such as USP grade water.

In some embodiments, the liquid pharmaceutical formulation described herein is packaged in a vial, a pre-filled syringe, or an on-body device.

In some embodiments, the liquid pharmaceutical formulation described herein is suitable for parenteral administration. Parenteral administration includes e.g., subcutaneous, intramuscular, intradermal, intramedullary injections, as well as intrathecal, direct intraventricular, intravenous, intraperitoneal and intravitreal. In one embodiment, the disclosed liquid formulation is an injectable formulation. In one embodiment, the liquid formulation disclosed herein is suitable for subcutaneous injection or intravenous injection.

Risankizumab Compositions with Reduced High Mannose N-Glycans, Increased Purity, and/or Reduced Immunogenicity In another aspect, the present disclosure relates to a composition comprising risankizumab, wherein the composition has one or more of the following features: (a) less than about 5.4% of total risankizumab species with N-glycosylation have a high mannose N-glycan; (b) at least about 99.1% of risankizumab is present as a monomer and/or no more than about 0.4% of risankizumab is present as high molecular weight (HMW) species as measured by ultra-performance size exclusion chromatography (UP-SEC); (c) more than about 97.5% of risankizumab is present as a main peak and/or less than about 2.2% of risankizumab is present as low molecular weight (LMW) species as measured by capillary gel electrophoresis under non-reducing conditions (CGE-NR); and/or (d) the incidence of treatment-emergent anti-drug antibody (ADA) is less than about 4.7% following administration of a single subcutaneous 150 mg dose of the composition to a human.

In one embodiment, the composition is a pharmaceutical composition.

In one embodiment, the pharmaceutical composition is a liquid composition.

In one embodiment, the pharmaceutical composition is an aqueous composition.

In one embodiment, the present disclosure relates to a composition comprising risankizumab, wherein the composition has feature (a): less than about 5.4% of total risankizumab species with N-glycosylation have a high mannose N-glycan.

In one embodiment, the present disclosure relates to a composition comprising risankizumab, wherein the composition has feature (b): at least about 99.1% of risankizumab is present as a monomer and/or no more than about 0.4% of risankizumab is present as high molecular weight (HMW) species as measured by ultra-performance size exclusion chromatography (UP-SEC).

In one embodiment, the present disclosure relates to a composition comprising risankizumab, wherein the composition has feature (c) more than about 97.5% of risankizumab is present as a main peak and/or less than about 2.2% of risankizumab is present as low molecular weight (LMW) species as measured by capillary gel electrophoresis under non-reducing conditions (CGE-NR).

In one embodiment, the present disclosure relates to a composition comprising risankizumab, wherein the composition has feature (d) the incidence of treatment-emergent anti-drug antibody (ADA) is less than about 4.7% following administration of a single subcutaneous 150 mg dose of the composition to a human.

In one embodiment, the present disclosure relates to a composition comprising risankizumab, wherein the composition has feature (a) less than about 5.4% of total risankizumab species with N-glycosylation have a high mannose N-glycan; and (b) at least about 99.1% of risankizumab is present as a monomer and/or no more than about 0.4% of risankizumab is present as high molecular weight (HMW) species as measured by ultra-performance size exclusion chromatography (UP-SEC).

In one embodiment, the present disclosure relates to a composition comprising risankizumab, wherein the pharmaceutical composition has feature (a) less than about 5.4% of total risankizumab species with N-glycosylation have a high mannose N-glycan; and (c) more than about 97.5% of risankizumab is present as a main peak and/or less than about 2.2% of risankizumab is present as low molecular weight (LMW) species as measured by capillary gel electrophoresis under non-reducing conditions (CGE-NR).

In one embodiment, the present disclosure relates to a composition comprising risankizumab, wherein the composition has feature (a) less than about 5.4% of total risankizumab species with N-glycosylation have a high mannose N-glycan; and (d) the incidence of treatment-emergent anti-drug antibody (ADA) is less than about 4.7% following administration of a single subcutaneous 150 mg dose of the composition.

In one embodiment, the present disclosure relates to a composition comprising risankizumab, wherein the composition has feature (b) at least about 99.1% of risankizumab is present as a monomer and/or no more than about 0.4% of risankizumab is present as high molecular weight (HMW) species as measured by ultra-performance size exclusion chromatography (UP-SEC); and (c) more than about 97.5% of risankizumab is present as a main peak and/or less than about 2.2% of risankizumab is present as low molecular weight (LMW) species as measured by capillary gel electrophoresis under non-reducing conditions (CGE-NR).

In one embodiment, the present disclosure relates to a composition comprising risankizumab, wherein the composition has feature (b) at least about 99.1% of risankizumab is present as a monomer and/or no more than about 0.4% of risankizumab is present as high molecular weight (HMW) species as measured by ultra-performance size exclusion chromatography (UP-SEC); and (d) the incidence of treatment-emergent anti-drug antibody (ADA) is less than about 4.7% following a single subcutaneous dose of the composition.

In one embodiment, the present disclosure relates to a composition comprising risankizumab, wherein the composition has feature (c) more than about 97.5% of risankizumab is present as a main peak and/or less than about 2.2% of risankizumab is present as low molecular weight (LMW) species as measured by capillary gel electrophoresis under non-reducing conditions (CGE-NR); and (d) the incidence of treatment-emergent anti-drug antibody (ADA) is less than about 4.7% following a single subcutaneous dose of the composition.

In one embodiment, the present disclosure relates to a composition comprising risankizumab, wherein the composition has feature (a) less than about 5.4% of total risankizumab species with N-glycosylation have a high mannose N-glycan; (b) at least about 99.1% of risankizumab is present as a monomer and/or no more than about 0.4% of risankizumab is present as high molecular weight (HMW)

species as measured by ultra-performance size exclusion chromatography (UP-SEC); and (c) more than about 97.5% of risankizumab is present as a main peak and/or less than about 2.2% of risankizumab is present as low molecular weight (LMW) species as measured by capillary gel electrophoresis under non-reducing conditions (CGE-NR).

In one embodiment, the present disclosure relates to a composition comprising risankizumab, wherein the composition has feature (a) less than about 5.4% of total risankizumab species with N-glycosylation have a high mannose N-glycan; (b) at least about 99.1% of risankizumab is present as a monomer and/or no more than about 0.4% of risankizumab is present as high molecular weight (HMW) species as measured by ultra-performance size exclusion chromatography (UP-SEC); and (d) the incidence of treatment-emergent anti-drug antibody (ADA) is less than about 4.7% following administration of a single subcutaneous 150 mg dose of the composition to a human.

In one embodiment, the present disclosure relates to a composition comprising risankizumab, wherein the composition has feature (b) at least about 99.1% of risankizumab is present as a monomer and/or no more than about 0.4% of risankizumab is present as high molecular weight (HMW) species as measured by ultra-performance size exclusion chromatography (UP-SEC); (c) more than about 97.5% of risankizumab is present as a main peak and/or less than about 2.2% of risankizumab is present as low molecular weight (LMW) species as measured by capillary gel electrophoresis under non-reducing conditions (CGE-NR); and (d) the incidence of treatment-emergent anti-drug antibody (ADA) is less than about 4.7% following administration of a single subcutaneous dose of the composition to a human.

In one embodiment, the present disclosure relates to a composition comprising risankizumab, wherein the composition has feature (a) less than about 5.4% of total risankizumab species with N-glycosylation have a high mannose N-glycan; (b) at least about 99.1% of risankizumab is present as a monomer and/or no more than about 0.4% of risankizumab is present as high molecular weight (HMW) species as measured by ultra-performance size exclusion chromatography (UP-SEC); (c) more than about 97.5% of risankizumab is present as a main peak and/or less than about 2.2% of risankizumab is present as low molecular weight (LMW) species as measured by capillary gel electrophoresis under non-reducing conditions (CGE-NR); and (d) the incidence of treatment-emergent anti-drug antibody (ADA) is less than about 4.7% following administration of a single subcutaneous dose of the composition to a human.

In one embodiment, the composition described herein comprises about 60 mg/ml to about 150 mg/ml risankizumab. For example, and without limitation, the composition described herein comprises about 70 mg/ml to about 150 mg/ml, about 80 mg/ml to about 150 mg/ml, about 90 mg/ml to about 150 mg/ml, about 100 mg/ml to about 150 mg/ml, about 110 mg/ml to about 150 mg/ml, about 120 mg/ml to about 150 mg/ml, about 130 mg/ml to about 150 mg/ml, about 140 mg/ml to about 150 mg/ml, 60 mg/ml to about 70 mg/ml, 60 mg/ml to about 80 mg/ml, 60 mg/ml to about 90 mg/ml, 60 mg/ml to about 100 mg/ml, 60 mg/ml to about 110 mg/ml, 60 mg/ml to about 120 mg/ml, 60 mg/ml to about 130 mg/ml, or 60 mg/ml to about 140 mg/ml risankizumab, and ranges and amounts between any of these aforementioned concentrations.

In one embodiment, the composition described herein comprises about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, or about 150 mg/ml risankizumab.

In one embodiment, the risankizumab is produced in a CHO cell line.

In one embodiment, the composition described herein further comprises a pharmaceutically acceptable excipient.

In one embodiment, the pharmaceutical composition described herein comprises 150 mg/ml risankizumab; 185 mM trehalose; 10 mM acetate; and 0.20 mg/mL polysorbate 20, wherein pharmaceutical composition has a pH of about 5.7.

In one embodiment, the pharmaceutical composition described herein comprises 150 mg/ml risankizumab; 0.054 mg/mL acetic acid; 1.24 mg/mL sodium acetate trihydrate; 70 mg/mL trehalose dihydrate; 0.20 mg/mL polysorbate 20; and Water for injection, USP; wherein the pharmaceutical composition has a pH of about 5.7.

In one embodiment, the pharmaceutical composition described herein has a pH of about 5.0 to about 6.5 (e.g., about 5.7).

In some embodiments, the pharmaceutical composition described herein is packaged in a vial, a pre-filled syringe, or an on-body device.

In some embodiments, the pharmaceutical composition described herein is suitable for parenteral administration. Parenteral administration includes e.g., subcutaneous, intramuscular, intradermal, intramedullary injections, as well as intrathecal, direct intraventricular, intravenous, intraperitoneal and intravitreal. In one embodiment, the disclosed liquid formulation is an injectable formulation. In one embodiment, the liquid formulation disclosed herein is suitable for subcutaneous injection or intravenous injection.

In some aspects, provided herein is a method of treating an immunological disease with the composition described herein. The immunological disease includes but is not limited to autoimmune and inflammatory diseases (e.g., psoriasis, inflammatory bowel disease, ulcerative colitis, psoriatic arthritis, and Crohn's disease).

a. Risankizumab Pharmaceutical Compositions with Reduced High Mannose N-Glycans

In one embodiment, the compositions provided herein have at least feature (a): less than about 5.4% of total risankizumab species with N-glycosylation have a high mannose N-glycan.

In one embodiment, the high mannose N-glycan comprises one or more high mannose N-glycans selected from mannose 5 N-glycan (M5), mannose 6 N-glycan (M6), and mannose 7 N-glycan (M7). For example, in one embodiment, the high mannose N-glycan is M5, M6, and M7.

In one embodiment, the composition described herein comprises a plurality of risankizumab species with or without N-glycosylation, wherein the sum of risankizumab with M5, risankizumab with M6, and risankizumab with M7 is less than 5.4% of total risankizumab species with N-glycosylation. For example, and without limitation, the sum of risankizumab with M5, risankizumab with M6, and risankizumab with M7 in the compositions described herein is in a detectable amount that is less than 5.3%, less than about 5.2%, less than about 5.1%, less than about 5.0%, less than about 4.9%, less than about 4.8%, less than about 4.7%, less than about 4.6%, less than about 4.5%, less than about 4.4%, less than about 4.3%, less than about 4.2%, less than about 4.1%, less than about 4.0%, less than about 3.9%, less than about 3.8%, or less than about 3.7% of total risankizumab species with N-glycosylation, or any range in between, inclusive, such as from about 3.6% to about 5.3%, from about 3.6% to about 5.0%, from about 3.6% to about 4.8%, from about 3.6% to about 4.5%, from about 3.6% to about 4.1%, from about 3.6% to about 3.8%, from about 3.8% to about 5.3%, from about 4.1% to about 5.3%, from about 4.5% to about 5.3%, from about 4.8% to about 5.3%, from about 5.0% to about 5.3%, from about 4.3% to about 4.9%, or from about 3.6% to about 4.9% of total risankizumab species with N-glycosylation.

In one embodiment, the composition described herein comprises the sum of risankizumab with M5, risankizumab with M6, and risankizumab with M7 in an amount that is less than about 5.4%, but more than about 5.3%, more than about 5.2%, more than about 5.1%, more than about 5.0%, more than about 4.9%, more than about 4.8%, more than about 4.7%, more than about 4.6%, more than about 4.5%, more than about 4.4%, more than about 4.3%, more than about 4.2%, more than about 4.1%, more than about 4.0%, more than about 3.9%, more than about 3.8%, more than about 3.7%, or more than about 3.6% of total risankizumab species with N-glycosylation.

In one embodiment, the composition described herein comprises the sum of risankizumab with M5, risankizumab with M6, and risankizumab with M7 in an amount that is about 5.3%, about 5.2%, about 5.1%, about 5.0%, about 4.9%, about 4.8%, about 4.7%, about 4.6%, about 4.5%, about 4.4%, about 4.3%, about 4.2%, about 4.1%, about 4.0%, about 3.9%, about 3.8%, about 3.7%, or about 3.6% of total risankizumab species with N-glycosylation.

In one embodiment, the present disclosure relates to a composition comprising about 150 mg/ml of an antibody comprising a light chain having the amino acid sequence of SEQ ID NO: 9 and a heavy chain having the amino acid sequence of SEQ ID NO: 10 with or without N-glycosylation, wherein less than about 5.4% (e.g., from about 3.6% to about 4.1%, from about 4.3% to about 4.9%, or from about 3.6% to about 4.9%) of total antibody species with N-glycosylation have a high mannose N-glycan (e.g., M5, M6, and M7).

In one embodiment, the high mannose N-glycan is M5.

In one embodiment, the composition described herein comprises a plurality of risankizumab species with or without N-glycosylation, wherein the level of risankizumab with M5 is less than 5.3% of total risankizumab species with N-glycosylation. For example, and without limitation, the level of risankizumab with M5 in the compositions described herein is in a detectable amount that is less than about 5.2%, less than about 5.1%, less than about 5.0%, less than about 4.9%, less than about 4.8%, less than about 4.7%, less than about 4.6%, less than about 4.5%, less than about 4.4%, less than about 4.3%, less than about 4.2%, less than about 4.1%, less than about 4.0%, less than about 3.9%, less than about 3.8%, less than about 3.7%, less than about 3.6%, less than about 3.5%, less than about 3.4%, less than about 3.3%, less than about 3.2%, less than about 3.1%, less than about 3.0%, less than about 2.9%, or less than about 2.8% of total risankizumab species with N-glycosylation, or any range in between, inclusive, such as from about 2.7% to about 5.2%, about 3.1% to about 5.2%, about 3.5% to about 5.2%, about 4.0% to about 5.2%, about 4.5% to about 5.2%, from about 5% to about 5.2%, from about 2.7% to about 5.0%, about 2.7% to about 4.5%, about 2.7% to about 4.0%, about 2.7% to about 3.5%, about 2.7% to about 3.1%, from about 3.2% to about 3.7%, or from about 2.7% to about 3.7% of total risankizumab species with N-glycosylation.

In one embodiment, the composition described herein comprises the risankizumab with M5 in a detectable amount that is less than about 5.3%, but more than about 5.2%, more than about 5.1%, more than about 5.0%, more than about 4.9%, more than about 4.8%, more than about 4.7%, more than about 4.6%, more than about 4.5%, more than about 4.4%, more than about 4.3%, more than about 4.2%, more than about 4.1%, more than about 4.0%, more than about 3.9%, more than about 3.8%, more than about 3.7%, more than about 3.6%, more than about 3.5%, more than about 3.4%, more than about 3.3%, more than about 3.2%, more than about 3.1%, more than about 3.0%, more than about 2.9%, or more than about 2.8%, or more than about 2.7% of total risankizumab species with N-glycosylation.

In one embodiment, the composition described herein comprises the risankizumab with M5 in an amount that is about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, or about 5.2% of total risankizumab species with N-glycosylation.

In one embodiment, the present disclosure relates to a composition comprising about 150 mg/ml risankizumab with or without N-glycosylation, wherein less than about 5.3% (e.g., from about 2.7% to about 3.1%, from about 3.2% to about 3.7%, or from about 2.7% to about 3.7%) of total risankizumab species with N-glycosylation have M5.

In one embodiment, the high mannose N-glycan is M6.

In one embodiment, the composition described herein comprises a plurality of risankizumab species with or without N-glycosylation, wherein the level of risankizumab with M6 is less than 2.6% of total risankizumab species with N-glycosylation. For example, and without limitation, the level of risankizumab with M6 in the compositions described herein is in a detectable amount that is less than about 2.5%, less than about 2.4%, less than about 2.3%, less than about 2.2%, less than about 2.1%, less than about 2.0%, less than about 1.9%, less than about 1.8%, less than about 1.7%, less than about 1.6%, less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, or less than about 0.5% of total risankizumab species with N-glycosylation, or any range in between, inclusive, such as from about 0.4% to about 2.5%, from about 0.4% to about 2.4%, from about 0.4% to about 2.2%, from about 0.4% to about 2.0%, from about 0.4% to about 1.8%, from about 0.4% to about 1.6%, from about 0.4% to about 1.4%, from about 0.4% to about 1.2%, from about 0.4% to about 1.0%, from about 0.4% to about 0.9%, from about 0.4% to about 0.8%, from about 0.4% to about 0.7%, from about 0.4% to about 0.6%, from about 0.4% to about 0.5%, or from about 0.6% to about 0.7% of total risankizumab species with N-glycosylation.

In one embodiment, the composition described herein comprises risankizumab with M6 in a detectable amount that is less than about 2.6%, but more than about 2.5%, more than about 2.4%, more than about 2.3%, more than about 2.2%, more than about 2.1%, more than about 2.0%, more than about 1.9%, more than about 1.8%, more than about 1.7%, more than about 1.6%, more than about 1.5%, more than about 1.4%, more than about 1.3%, more than about 1.2%, more than about 1.1%, more than about 1.0%, more than about 0.9%, more than about 0.8%, more than about 0.7%, more than about 0.6%, more than about 0.5%, or more than about 0.4% of total risankizumab species with N-glycosylation.

In one embodiment, the composition described herein comprises risankizumab with M6 in an amount that is about 2.5%, about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, or about 0.4% of total risankizumab species with N-glycosylation.

In one embodiment, the present disclosure relates to a composition comprising about 150 mg/ml risankizumab with or without N-glycosylation, wherein less than about 2.6% (e.g., from about 0.4% to about 0.5%, from about 0.6% to about 0.7%, or from about 0.4% to about 0.7%) of total risankizumab species with N-glycosylation have M6.

In one embodiment, the high mannose N-glycan is M7.

In one embodiment, the composition described herein comprises a plurality of risankizumab species with or without N-glycosylation, wherein the level of risankizumab with M7 is less than 2.0% of total risankizumab species with N-glycosylation. For example, and without limitation, the level of risankizumab with M6 in the compositions described herein is in a detectable amount that less than about 1.9%, less than about 1.8%, less than about 1.7%, less than about 1.6%, less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, or more than about 0.4% of total risankizumab species with N-glycosylation, or any range in between, inclusive, such as from about 0.4% to about 1.9%, from about 0.4% to about 1.8%, from about 0.4% to about 1.6%, from about 0.4% to about 1.4%, from about 0.4% to about 1.2%, from about 0.4% to about 1.0%, from about 0.4% to about 0.9%, from about 0.4% to about 0.8%, from about 0.4% to about 0.7%, from about 0.4% to about 0.6%, from about 0.4% to about 0.5%, or from about 0.5% to about 0.6% of total risankizumab species with N-glycosylation.

In one embodiment, the composition described herein comprises risankizumab with M7 in a detectable amount that is less than about 2.0%, but more than about 1.9%, more than about 1.8%, more than about 1.7%, more than about 1.6%, more than about 1.5%, more than about 1.4%, more than about 1.3%, more than about 1.2%, more than about 1.1%, more than about 1.0%, more than about 0.9%, more than about 0.8%, more than about 0.7%, more than about 0.6%, more than about 0.5%, or more than about 0.4% of total risankizumab species with N-glycosylation.

In one embodiment, the composition described herein comprises risankizumab with M7 in an amount that is about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, or about 0.4% of total risankizumab species with N-glycosylation.

In one embodiment, the present disclosure relates to a composition comprising about 150 mg/ml risankizumab with or without N-glycosylation, wherein less than about 2.0% (e.g., from about 0.4% to about 0.5%, from about 0.5% to about 0.6%, or from about 0.4% to about 0.6%) of total risankizumab species with N-glycosylation have M7.

In one embodiment, the amount of risankizumab with the high mannose N-glycan in the compositions described herein can be determined using methods known in the art, e.g., by 2-AB and HILIC-FL Chromatography (e.g., using the 2-AB and HILIC-FL Chromatography method described in Example 12), or by RapiFluor HILIC-FL Chromatography (using the RapiFluor HILIC-FL Chromatography method described in Example 13).

In one embodiment, the pharmaceutical composition described herein comprises about 150 mg/mL risankizumab; 185 mM trehalose; 10 mM acetate; and 0.20 mg/mL polysorbate 20, wherein pharmaceutical composition has a pH of about 5.7; and wherein less than about 5.4% of total risankizumab species with N-glycosylation have a high mannose N-glycan (e.g., M5, M6 and/or M7).

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein less than about 5.4% of total risankizumab species with N-glycosylation have a high mannose N-glycan (e.g., M5, M6 and/or M7).

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein less than about 5.4% of total risankizumab species with N-glycosylation have a high mannose N-glycan (e.g., M5, M6 and/or M7); wherein the amount of risankizumab with the high mannose N-glycan is determined by 2-AB and HILIC-FL Chromatography (e.g., using the 2-AB and HILIC-FL Chromatography method described in Example 12), or by RapiFluor HILIC-FL Chromatography (e.g., using the RapiFluor HILIC-FL Chromatography method described in Example 13).

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein the sum of risankizumab with M5, risankizumab with M6, and risankizumab with M7 is less than about 5.4% (e.g., from about 3.6% to about 4.1%, from about 4.3% to 4.9%, or from about 3.6% to about 4.9%) of total risankizumab species with N-glycosylation.

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein the sum of risankizumab with M5, risankizumab with M6, and risankizumab with M7 is less than about 5.4% (e.g., from about 3.6% to about 4.1%, from about 4.3% to 4.9%, or from about 3.6% to about 4.9%) of total risankizumab species with N-glycosylation, wherein the amount of risankizumab with the high mannose N-glycan is determined by 2-AB and HILIC-FL Chromatography (e.g., using the 2-AB and HILIC-FL Chromatography method described in Example 12), or by RapiFluor HILIC-FL Chromatography (e.g., using the RapiFluor HILIC-FL Chromatography method described in Example 13).

Liquid formulations encompassed by the present disclosure may comprise added water, such as USP grade water.

In some embodiments, greater than about 84.4% of total risankizumab species with N-glycosylation have fucosylated complex oligosaccharides. For example, and without limitation, the level of risankizumab with fucosylated complex oligosaccharides in the compositions described herein is in an amount that is greater than about 85%, greater than about 85.5%, greater than about 86%, greater than about 86.5%, greater than about 87%, greater than about 87.5%, greater than about 88%, greater than about 88.5%, greater than about 89%, greater than about 89.5%, greater than about 90%, or greater than about 90.5% of total risankizumab species with N-glycosylation.

In some embodiments, the level of risankizumab with fucosylated complex oligosaccharides in the compositions described herein is in an amount that is from about 85% to about 91%, from about 88.0% to about 88.9%, from about 89.8% to about 90.9%, or from 88.0% to 90.9% of total risankizumab species with N-glycosylation. In some embodiments, the level of risankizumab with fucosylated complex oligosaccharides in the compositions described herein is in an amount that is about 88.0%, about 88.3%, about 88.4%, about 88.9%, about 89.8%, about 90.2%, or about 90.9% of total risankizumab species with N-glycosylation.

In some embodiments, the level of risankizumab with fucosylated complex oligosaccharides is determined by 2-AB and HILIC-FL Chromatography or by RapiFluor HILIC-FL Chromatography.

In some embodiments, the composition comprises from about 0.8% to about 1.4% (e.g., about 0.8%, about 0.9%, about 1.0%, about 1.1%, about 1.2%, about 1.3%, or about 1.4%) aglycosylated risankizumab.

In some embodiments, the aglycosylated risankizumab is determined by Tryptic peptide mapping (e.g., using the Tryptic peptide mapping analysis described in Example 14).

b. Risankizumab Compositions with Increased Purity

In one embodiment, the composition provided herein has at least feature (b): at least about 99.1% of risankizumab is present as a monomer and/or no more than about 0.4% of risankizumab is present as high molecular weight (HMW) species as measured by ultra-performance size exclusion chromatography (UP-SEC). For example, the composition described herein comprises risankizumab, wherein at least about 99.1% of risankizumab is present as a monomer and no more than about 0.4% of risankizumab is present as high molecular weight (HMW) species as measured by UP-SEC.

In one embodiment, at least about 99.1% of risankizumab is present as a monomer in the compositions provided herein as measured by UP-SEC. For example, and without limitation, at least about 99.2%, at least about 99.3%, at least about 99.4%, at least about 99.5%, at least about 99.6%, or at least about 99.7% of risankizumab is present as a monomer as measured by UP-SEC, or any range in between, inclusive, such as from about 99.1% to about 99.7%, 99.1% to about 99.6%, from about 99.2% to about 99.7%, or from about 99.2% to about 99.6% of risankizumab is present as a monomer as measured by UP-SEC.

In one embodiment, no more than about 0.4% of risankizumab is present as high molecular weight (HMW) species in the compositions provided herein as measured by UP-SEC. For example, and without limitation, no more than about 0.35%, no more than about 0.3%, no more than about 0.25%, no more than about 0.2%, no more than about 0.15%, or no more than about 0.1% of risankizumab is present as high molecular weight (HMW) species as measured by UP-SEC, or any range in between, inclusive, such as from about 0.1% to about 0.4%, from about 0.1 to about 0.3%, from about 0.1 to about 0.2%, from about 0.2% to about 0.4%, or from about 0.2% to about 0.3% of risankizumab is present as high molecular weight (HMW) species as measured by UP-SEC.

In one embodiment, the present disclosure relates to a composition comprising about 150 mg/ml risankizumab, and wherein at least about 99.1% (from about 99.1% to about 99.7%, 99.1% to about 99.6%, from about 99.2% to about 99.7%, or from about 99.2% to about 99.6%) of risankizumab is present as a monomer and/or no more than about 0.4% (from about 0.1% to about 0.4%, from about 0.1 to about 0.3%, from about 0.1 to about 0.2%, from about 0.2% to about 0.4%, or from about 0.2% to about 0.3%) of risankizumab is present as high molecular weight (HMW) species as measured by ultra-performance size exclusion chromatography (UP-SEC).

In one embodiment, the pharmaceutical composition described herein comprises about 150 mg/mL risankizumab; 185 mM trehalose; 10 mM acetate; and 0.20 mg/mL polysorbate 20, wherein pharmaceutical composition has a pH of about 5.7; and wherein at least about 99.1% (from about 99.1% to about 99.7%, 99.1% to about 99.6%, from about 99.2% to about 99.7%, or from about 99.2% to about 99.6%) of risankizumab is present as a monomer and/or no more than about 0.4% (from about 0.1% to about 0.4%, from about 0.1 to about 0.3%, from about 0.1 to about 0.2%, from about 0.2% to about 0.4%, or from about 0.2% to about 0.3%) of risankizumab is present as high molecular weight (HMW) species as measured by ultra-performance size exclusion chromatography (UP-SEC) (e.g., using the UP-SEC method described in Example 15).

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein at least about 99.1% (from about 99.1% to about 99.7%, 99.1% to about 99.6%, from about 99.2% to about 99.7%, or from about 99.2% to about 99.6%) of risankizumab is present as a monomer and/or no more than about 0.4% (from about 0.1% to about 0.4%, from about 0.1 to about 0.3%, from about 0.1 to about 0.2%, from about 0.2% to about 0.4%, or from about 0.2% to about 0.3%) of risankizumab is present as high molecular weight (HMW) species as measured by ultra-performance size exclusion chromatography (UP-SEC) (e.g., using the UP-SEC method described in Example 15).

Liquid formulations encompassed by the present disclosure may comprise added water, such as USP grade water.

In one embodiment, the composition described herein has at least feature (c): more than about 97.5% of risankizumab is present as a main peak and/or less than about 2.2% of risankizumab is present as low molecular weight (LMW) species as measured by capillary gel electrophoresis under non-reducing conditions (CGE-NR). For example, the composition described herein comprises risankizumab, wherein more than about 97.5% of risankizumab is present as a main peak and less than about 2.2% of risankizumab is present as low molecular weight (LMW) species as measured by CGE-NR.

In one embodiment, more than about 97.5% of risankizumab is present as a main peak as measured by CGE-NR. For example, and without limitation, more than about 97.6%, more than about 97.7%, more than about 97.8%, more than about 97.9%, more than about 98.0%, more than about 98.1%, more than about 98.2%, more than about 98.3%, or more than about 98.4% of risankizumab is present as a main peak as measured by CGE-NR, or any range in between, inclusive, such as from about 97.6% to about 98.4%, from about 97.6% to about 98.3%, from about 97.6% to about 98.2%, from about 97.7% to about 98.4%, from about 97.7% to about 98.3%, from about 97.7% to about 98.2%, from about 97.8% to about 98.4%, from about 97.8% to about 98.3%, or from about 97.8% to about 98.2% of risankizumab is present as a main peak as measured by CGE-NR.

In one embodiment, less than about 2.2% of risankizumab is present as low molecular weight (LMW) species as measured by CGE-NR. For example, and without limitation, less than about 2.1%, less than 2.0%, less than 1.9%, less than 1.8%, less than 1.7%, less than 1.6%, or less than 1.5% of risankizumab is present as low molecular weight (LMW) species as measured by CGE-NR, or any range in between, inclusive, such as from about 1.5% to about 2.1%, from about 1.6% to about 2.1%, from about 1.7% to about 2.1%, from about 1.5% to about 2.0%, from about 1.6% to about 2.0%, or from about 1.7% to about 2.0% of risankizumab is present as low molecular weight (LMW) species as measured by CGE-NR.

In one embodiment, the present disclosure relates to a composition comprising about 150 mg/ml risankizumab, and wherein more than about 97.5% (e.g., from about 97.6% to about 98.4%, from about 97.6% to about 98.3%, from about 97.6% to about 98.2%, from about 97.7% to about 98.4%, from about 97.7% to about 98.3%, from about 97.7% to about 98.2%, from about 97.8% to about 98.4%, from about 97.8% to about 98.3%, or from about 97.8% to about 98.2%) of risankizumab is present as a main peak and/or less than about 2.2% (e.g., from about 1.5% to about 2.1%, from about 1.6% to about 2.1%, from about 1.7% to about 2.1%, from about 1.5% to about 2.0%, from about 1.6% to about 2.0%, or from about 1.7% to about 2.0%) of risankizumab is present as low molecular weight (LMW) species as measured by capillary gel electrophoresis under non-reducing conditions (CGE-NR).

In one embodiment, the pharmaceutical composition described herein comprises about 150 mg/mL risankizumab; 185 mM trehalose; 10 mM acetate; and 0.20 mg/mL polysorbate 20, wherein pharmaceutical composition has a pH of about 5.7; and wherein more than about 97.5% (e.g., from about 97.6% to about 98.4%, from about 97.6% to about 98.3%, from about 97.6% to about 98.2%, from about 97.7% to about 98.4%, from about 97.7% to about 98.3%, from about 97.7% to about 98.2%, from about 97.8% to about 98.4%, from about 97.8% to about 98.3%, or from about 97.8% to about 98.2%) of risankizumab is present as a main peak and/or less than about 2.2% (e.g., from about 1.5% to about 2.1%, from about 1.6% to about 2.1%, from about 1.7% to about 2.1%, from about 1.5% to about 2.0%, from about 1.6% to about 2.0%, or from about 1.7% to about 2.0%) of risankizumab is present as low molecular weight (LMW) species as measured by capillary gel electrophoresis under non-reducing conditions (CGE-NR) (e.g., using the CGE-NR method described in Example 15).

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein more than about 97.5% (e.g., from about 97.6% to about 98.4%, from about 97.6% to about 98.3%, from about 97.6% to about 98.2%, from about 97.7% to about 98.4%, from about 97.7% to about 98.3%, from about 97.7% to about 98.2%, from about 97.8% to about 98.4%, from about 97.8% to about 98.3%, or from about 97.8% to about 98.2%) of risankizumab is present as a main peak and/or less than about 2.2% (e.g., from about 1.5% to about 2.1%, from about 1.6% to about 2.1%, from about 1.7% to about 2.1%, from about 1.5% to about 2.0%, from about 1.6% to about 2.0%, or from about 1.7% to about 2.0%) of risankizumab is present as low molecular weight (LMW) species as measured by capillary gel electrophoresis under non-reducing conditions (CGE-NR) (e.g., using the CGE-NR method described in Example 15).

Liquid formulations encompassed by the present disclosure may comprise added water, such as USP grade water.

c. Risankizumab Compositions with Reduced Immunogenicity

In one embodiment, the composition described herein has at least feature (d): the incidence of treatment-emergent anti-drug antibody (ADA) is less than about 4.7% following administration of a single subcutaneous dose of the pharmaceutical composition to a human.

For example, and without limitation, the incidence of treatment-emergent ADA is less than about 4.5%, less than about 4.0%, less than about 3.5%, less than about 3.0%, less than about 2.5%, less than about 2.0%, less than about 1.5%, less than about 1.0%, less than about 0.5%, less than about 0.4%, less than about 0.3%, less than about 0.2%, less than about 0.1%, less than about 0.01%, less than about 0.001%, or less than about 0.0001%.

In one embodiment, the incidence of treatment-emergent ADA is about 0.0%.

In one embodiment, the incidence of treatment-emergent ADA is measured following administration of a single subcutaneous injection of 150 mg dose of the pharmaceutical composition to a human.

In one embodiment, the presence of ADA is determined by using a validated bridging electrochemiluminescence immunoassay.

In one embodiment, the incidence of treatment-emergent ADA is less than about 4.7%, e.g., is about 0.0%, following administration of a single subcutaneous injection of a 150 mg dose of the pharmaceutical composition as measured by using a bridging electrochemiluminescence immunoassay (e.g., by using the bridging electrochemiluminescence immunoassay described in Example 16).

In one embodiment, the present disclosure relates to a composition comprising about 150 mg/ml risankizumab, and wherein the incidence of treatment-emergent anti-drug antibody (ADA) is less than about 4.7% (e.g., about 0.0%) following administration of a single subcutaneous injection of a 150 mg dose of the composition to a human.

In one embodiment, the pharmaceutical composition described herein comprises about 150 mg/mL risankizumab; 185 mM trehalose; 10 mM acetate; and 0.20 mg/mL polysorbate 20, wherein pharmaceutical composition has a pH of about 5.7; and wherein the incidence of treatment-emergent anti-drug antibody (ADA) is less than about 4.7% (e.g., about 0.0%) following administration of a single subcutaneous injection of 150 mg dose of the pharmaceutical composition to a human.

In one embodiment, the pharmaceutical composition described herein comprises about 150 mg/mL risankizumab; 185 mM trehalose; 10 mM acetate; and 0.20 mg/mL polysorbate 20, wherein pharmaceutical composition has a pH of about 5.7; and wherein the incidence of treatment-emergent anti-drug antibody (ADA) is less than about 4.7% (e.g., about 0.0%) following administration of a single subcutaneous injection of a 150 mg dose of the pharmaceutical composition as determined by using a bridging electrochemiluminescence immunoassay (e.g., by using the bridging electrochemiluminescence immunoassay described in Example 16).

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein the incidence of treatment-emergent anti-drug antibody (ADA) is less than about 4.7% (e.g., about 0.0%) following administration of a single subcutaneous injection of 150 mg dose of the pharmaceutical composition to a human.

In one embodiment, the pharmaceutical composition described herein comprises about 150 mg/ml risankizumab; 0.054 mg/mL acetic acid; 1.24 mg/mL sodium acetate trihydrate; 70 mg/mL trehalose dihydrate; 0.20 mg/mL polysorbate 20; and, wherein the pharmaceutical composition has a pH of about 5.7; and wherein the incidence of treatment-emergent anti-drug antibody (ADA) is less than about 4.7% (e.g., about 0.0%) following administration of a single subcutaneous injection of a 150 mg dose of the pharmaceutical composition to a human as determined by using a bridging electrochemiluminescence immunoassay (e.g., by using the bridging electrochemiluminescence immunoassay described in Example 16).

Liquid formulations encompassed by the present disclosure may comprise added water, such as USP grade water.

Risankizumab Compositions with Poloxamer 188

In one aspect, the present disclosure relates to a composition comprising: (1) risankizumab; and (2) Poloxamer 188 (P188), wherein the composition does not comprise polysorbate 20 (PS20) and/or polysorbate 80 (PS80).

In one embodiment, the composition described herein comprises about 60 mg/ml to about 150 mg/ml risankizumab. For example, and without limitation, the composition described herein comprises about 70 mg/ml to about 150 mg/ml, about 80 mg/ml to about 150 mg/ml, about 90 mg/ml to about 150 mg/ml, about 100 mg/ml to about 150 mg/ml, about 110 mg/ml to about 150 mg/ml, about 120 mg/ml to about 150 mg/ml, about 130 mg/ml to about 150 mg/ml, about 140 mg/ml to about 150 mg/ml, 60 mg/ml to about 70 mg/ml, 60 mg/ml to about 80 mg/ml, 60 mg/ml to about 90 mg/ml, 60 mg/ml to about 100 mg/ml, 60 mg/ml to about 110 mg/ml, 60 mg/ml to about 120 mg/ml, 60 mg/ml to about 130 mg/ml, or 60 mg/ml to about 140 mg/ml risankizumab, and ranges and amounts between any of these aforementioned concentrations.

In one embodiment, the composition described herein comprises about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, or about 150 mg/ml risankizumab.

In one embodiment, the composition described herein further comprises phospholipase A2 (PLA2) in an amount that is greater than about 250 pg per mg of risankizumab.

In one embodiment, the composition described herein comprises PLA2 in an amount that is greater than about 260 pg, greater than about 270 pg, greater than about 280 pg, greater than about 290 pg, greater than about 300 pg, greater than about 310 pg, greater than about 320 pg, greater than about 330 pg, greater than about 340 pg, greater than about 350 pg, greater than about 360 pg, greater than about 380 pg, greater than about 400 pg, greater than about 450 pg, greater than about 500 pg, greater than about 550 pg, greater than about 600 pg, greater than about 650 pg, greater than about 700 pg, greater than about 750 pg, greater than about 800 pg, greater than about 900 pg, or greater than about 1000 pg, per mg of risankizumab, or any range in between, inclusive, such as from about 250 pg to about 1100 pg, from about 260 pg to about 1100 pg, from about 270 pg to about 1100 pg, from about 280 pg to about 1100 pg, from about 290 pg to about 1100 pg, from about 300 pg to about 1100 pg, from about 310 pg to about 1100 pg, from about 320 pg to about 1100 pg, from about 340 pg to about 1100 pg, from about 360 pg to about 1100 pg, from about 250 pg to about 1000 pg, from about 250 pg to about 900 pg, from about 250 pg to about 800 pg, from about 250 pg to about 700 pg, from about 250 pg to about 600 pg, from about 250 pg to about 500 pg, from about 250 pg to about 400 pg, from about 250 pg to about 1030 pg, from about 290 pg to about 1090 pg, from about 360 pg to about 450 pg, or from about 310 pg to about 920 pg, per mg of risankizumab.

In one embodiment, the composition described herein comprises PLA2 in an amount that is about 260 pg, about 270 pg, about 280 pg, about 290 pg, about 300 pg, about 310 pg, gr about 320 pg, about 330 pg, about 340 pg, about 350 pg, about 360 pg, about 380 pg, about 400 pg, about 450 pg, about 500 pg, about 550 pg, about 600 pg, about 650 pg, about 700 pg, about 750 pg, about 800 pg, about 900 pg, about 1000 pg, or about 1100 pg, per mg of risankizumab.

The PLA2 in the compositions described herein may be PLA2G2, PLA2G15, or a combination thereof. In one embodiment, the PLA2 is PLA2G15.

The amount of PLA2 in the compositions described herein can be determined using methods known in the art, e.g., by mass spectrometry, or by ELISA. In one embodiment, the amount of PLA2 in the compositions described herein is determined by ELISA, e.g., using the ELISA method described in Example 9.

In some embodiments, the composition does not comprise PS80.

Risankizumab Purification

In one embodiment, risankizumab may be recombinantly produced in various host cells (e.g., a CHO cell or a NS0 cell) using methods described in the Examples (e.g., Example 3) or using methods known in the art, e.g., cell culture method using hydrolysate-based or a chemically defined medium containing particular ranges of manganese and/or galactose (see e.g., U.S. Pat. No. 9,062,106) or by using recombinant host cells overexpressing p31, 4 galatosyl-transferase or with host cells having a beta galactosidase knock down (U.S. Pat. No. 9,550,826). U.S. Pat. Nos. 9,062,106 and 9,550,826 are incorporated by reference herein in their entireties.

Figure 14:
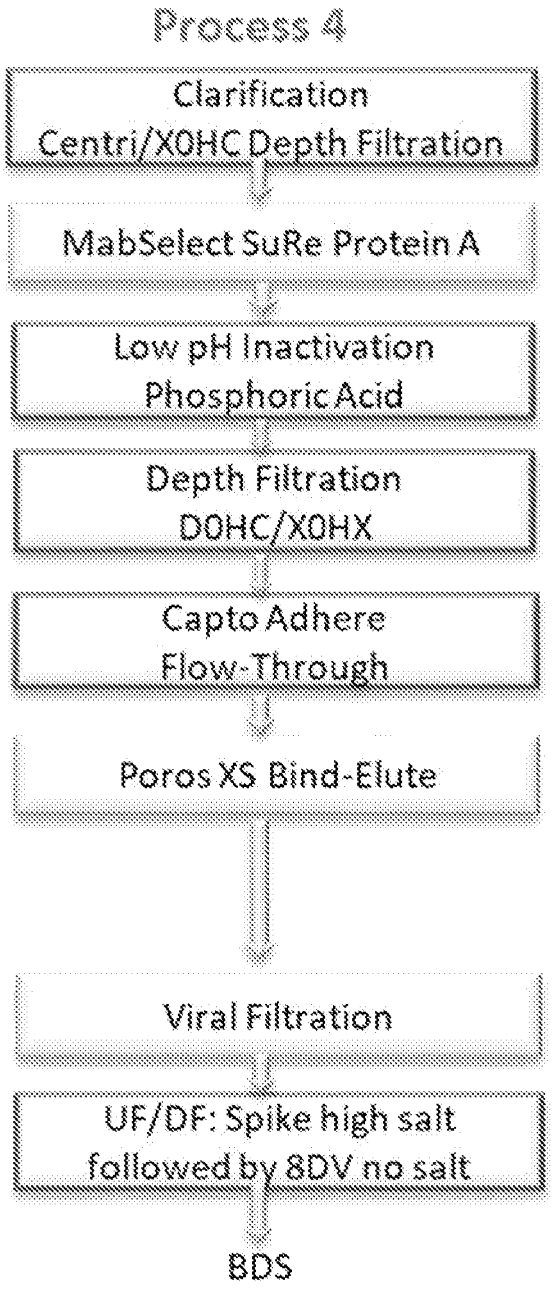
FIG. 14 shows a general overview of the newly developed purification process for risankizumab drug substance (referred to herein as the Process 4 development).
Figure 15A:
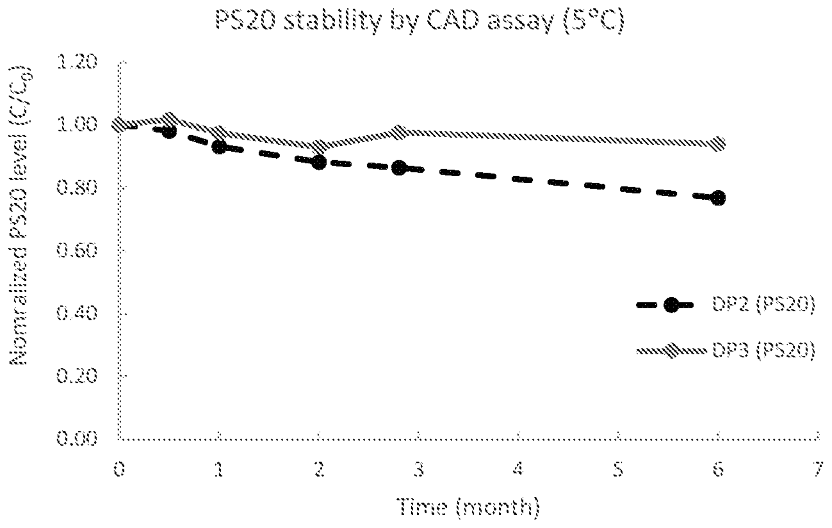
FIG. 15A shows PS20 stability in DP2 (PS20) and DP3 (PS20) measured by CAD assay at 5° C.
Figure 15B:
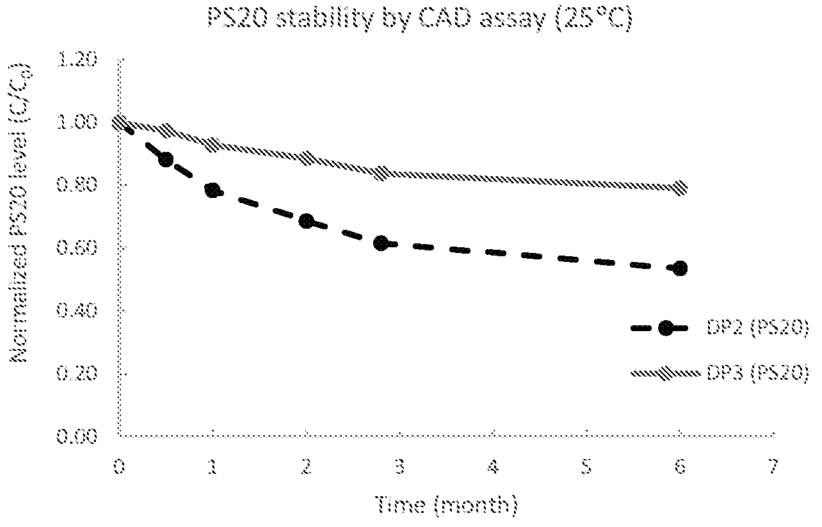
FIG. 15B shows PS20 stability in DP2 (PS20) and DP3 (PS20) measured by CAD assay at 25° C.
Figure 15C:
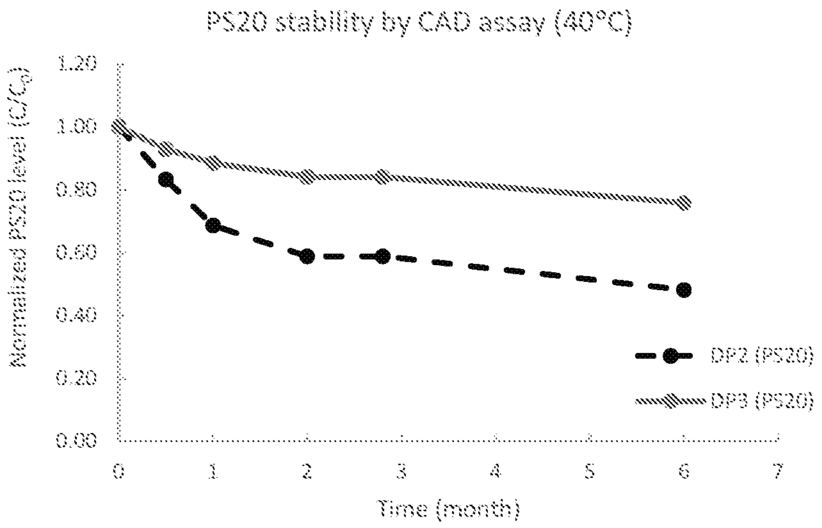
FIG. 15C shows PS20 stability in DP2 (PS20) and DP3 (PS20) measured by CAD assay at 40° C.
Figure 16A:
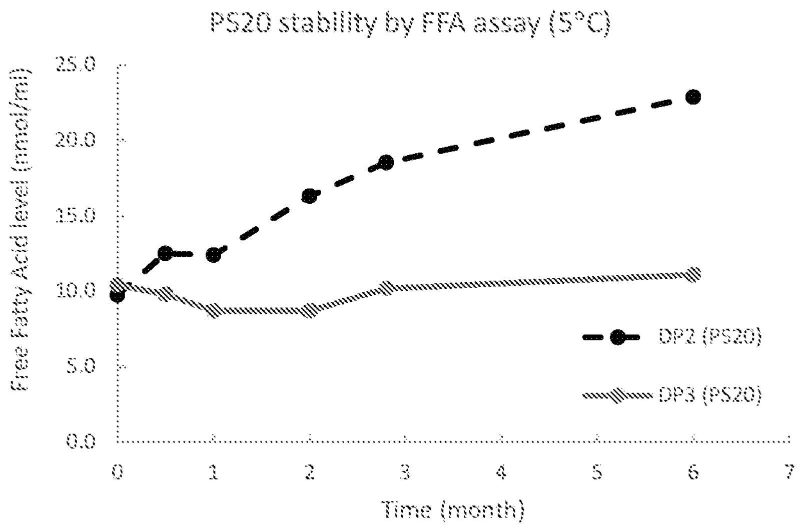
FIG. 16A shows PS20 stability in DP2 (PS20) and DP3 (PS20) measured by FFA assay at 5° C.
Figure 16B:
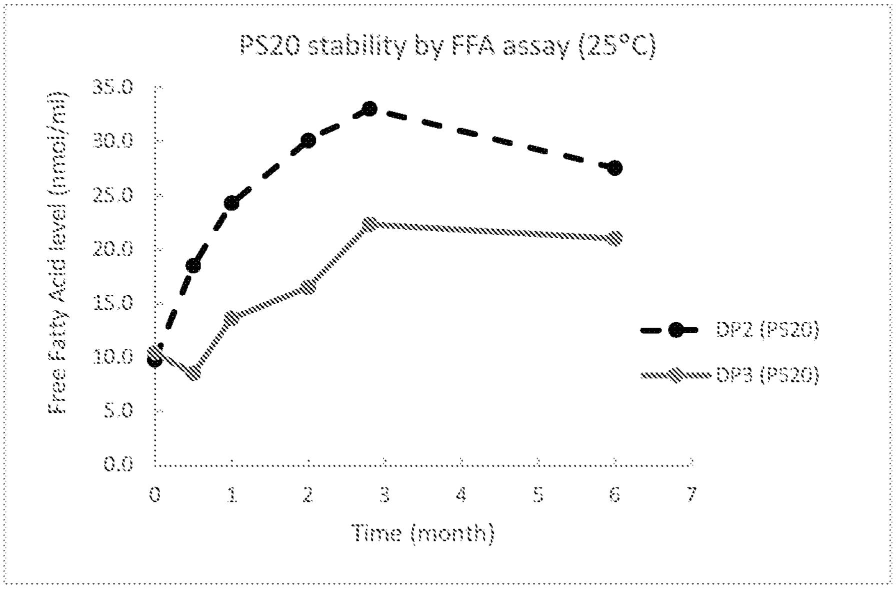
FIG. 16B shows PS20 stability in DP2 (PS20) and DP3 (PS20) measured by FFA assay at 25° C.
Figure 17A:
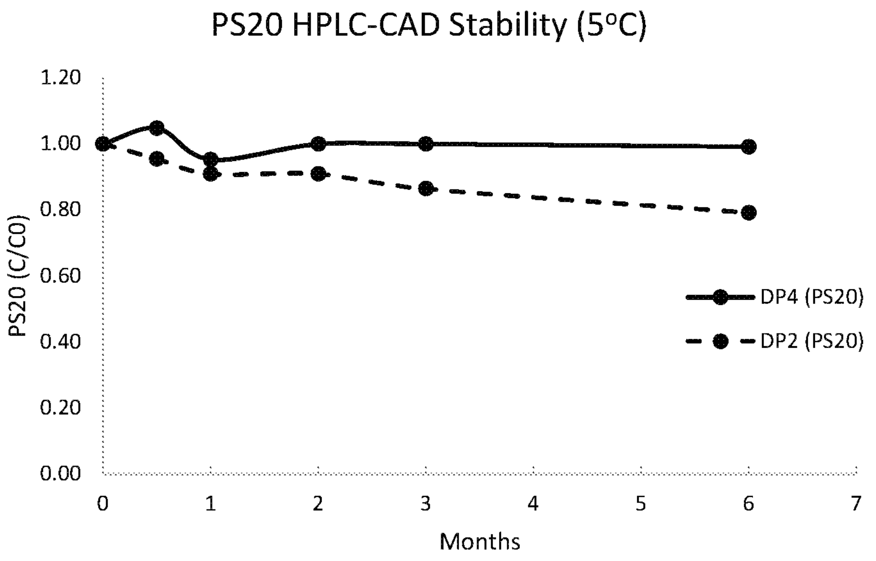
FIG. 17A shows PS20 stability in DP2 (PS20) and DP4 (PS20) measured by CAD assay at 5° C.
Figure 17B:
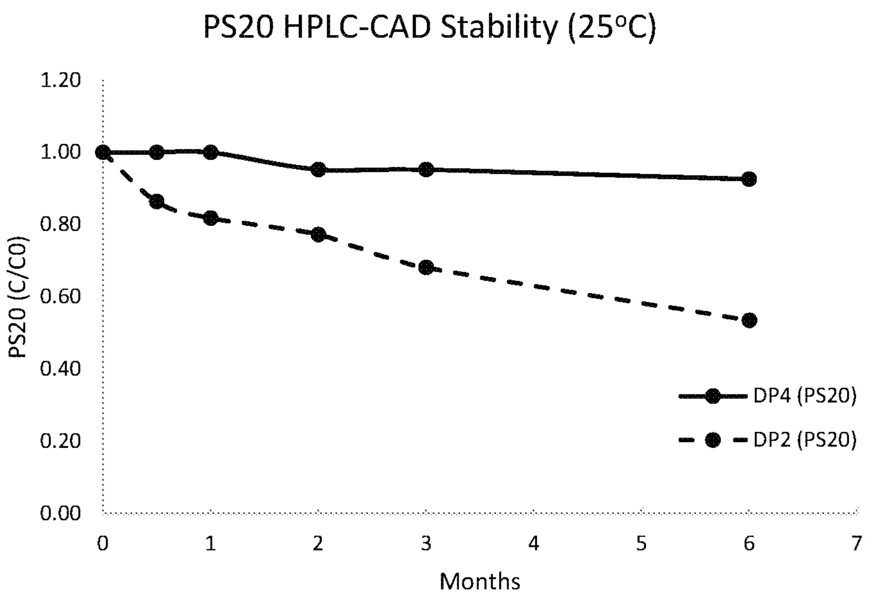
FIG. 17B shows PS20 stability in DP2 (PS20) and DP4 (PS20) measured by CAD assay at 25° C.
Figure 17C:
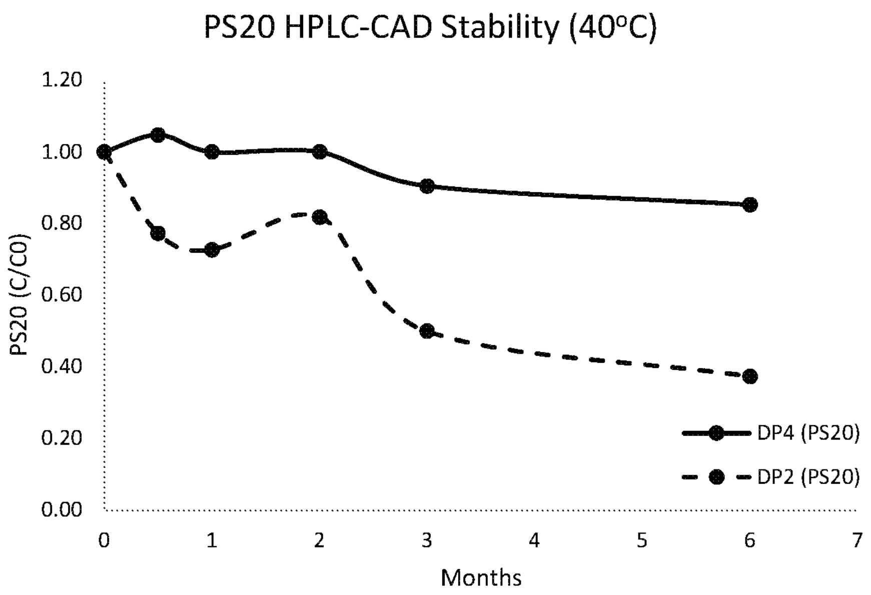
FIG. 17C shows PS20 stability in DP2 (PS20) and DP4 (PS20) measured by CAD assay at 40° C.
Figure 18A:
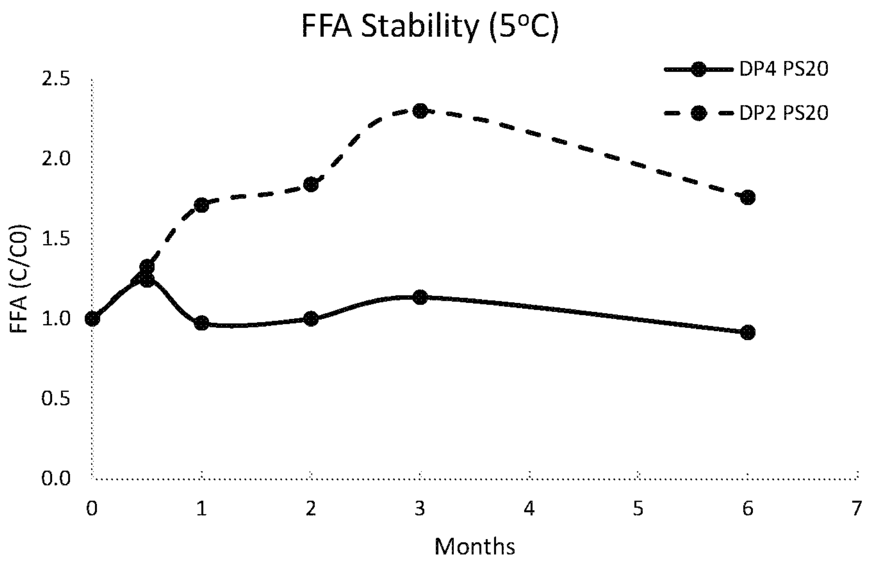
FIG. 18A and FIG. 18B show PS20 stability in DP2 (PS20) and DP4 (PS20) measured by FFA assay at 5° C.
Figure 18B:
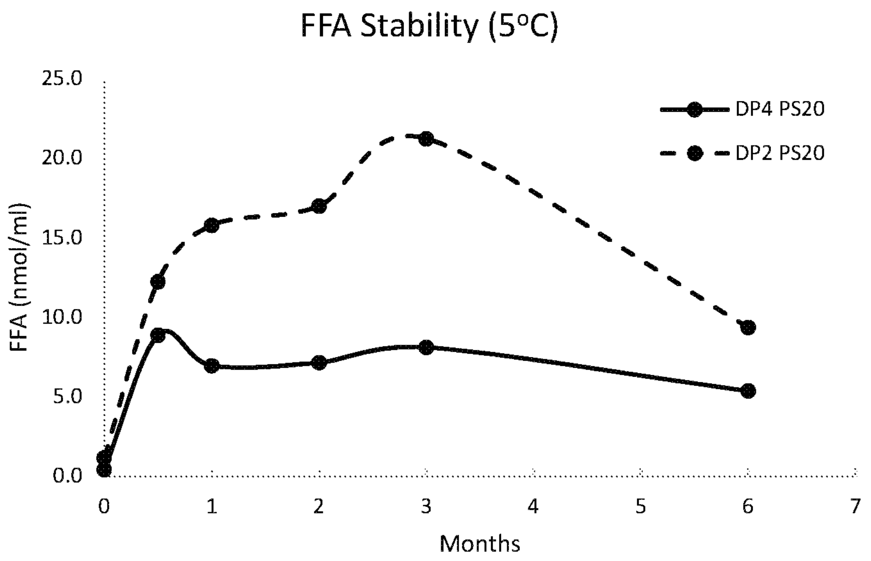
Figure 18C:
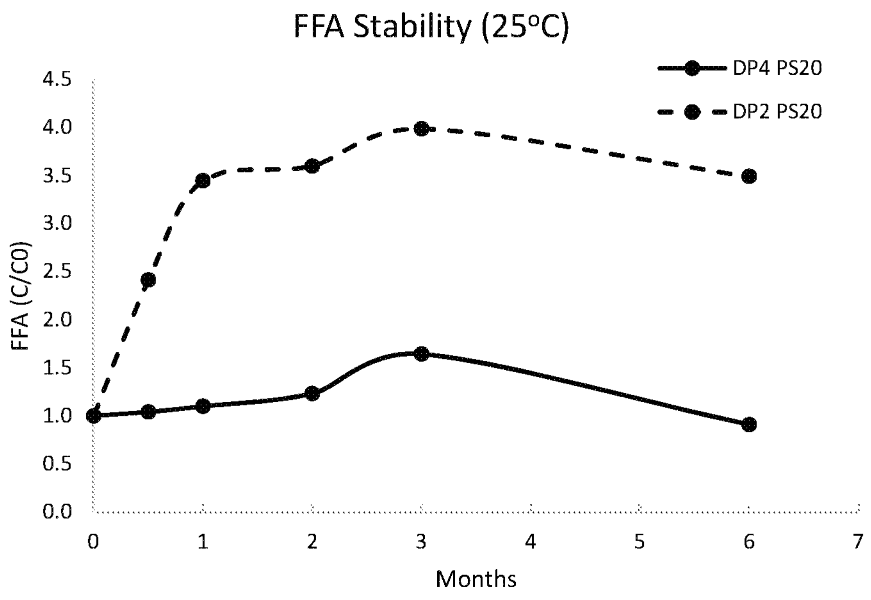
FIG. 18C and FIG. 18D show PS20 stability in DP2 (PS20) and DP4 (PS20) measured by FFA assay at 25° C.
Figure 18D:
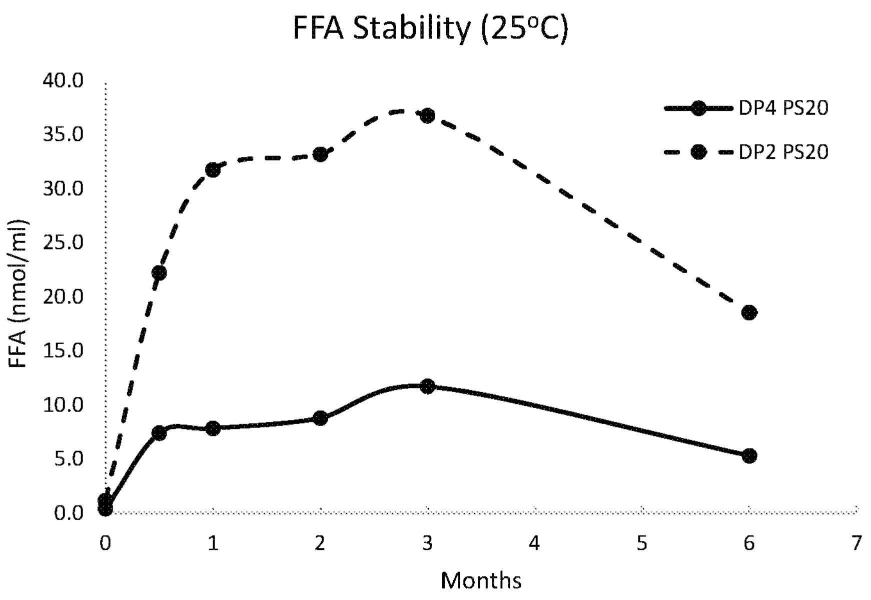
Figure 19A:
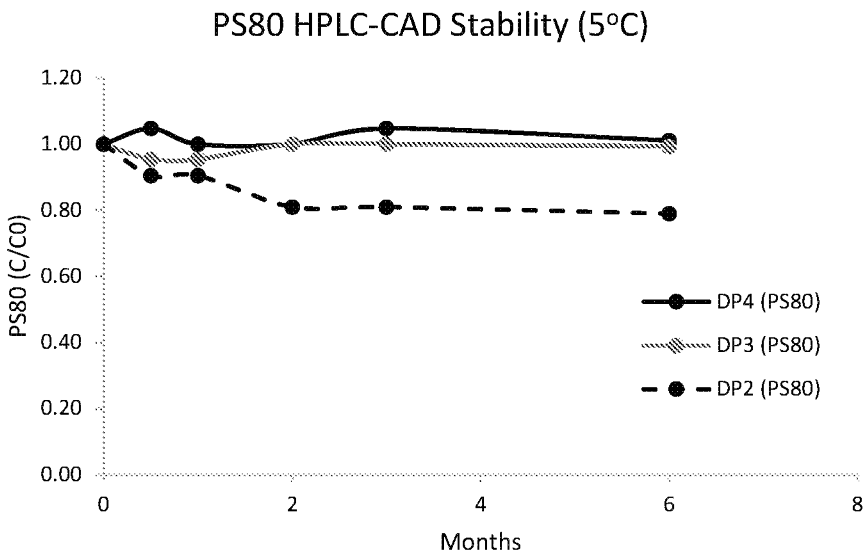
FIG. 19A shows PS80 stability in DP2 (PS80), DP3 (PS80), and DP4 (PS80) measured by CAD assay at 5° C.
Figure 19B:
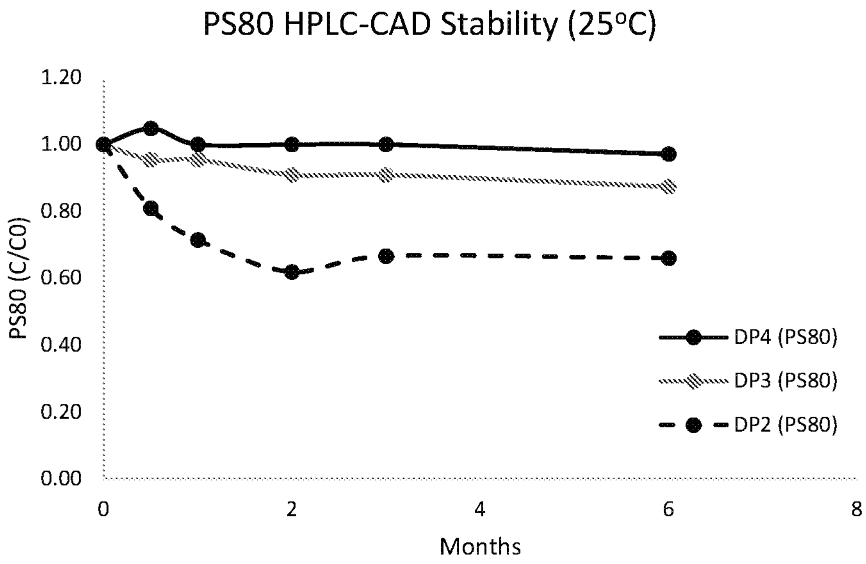
FIG. 19B shows PS80 stability in DP2 (PS80), DP3 (PS80), and DP4 (PS80) measured by CAD assay at 25° C.
Figure 19C:
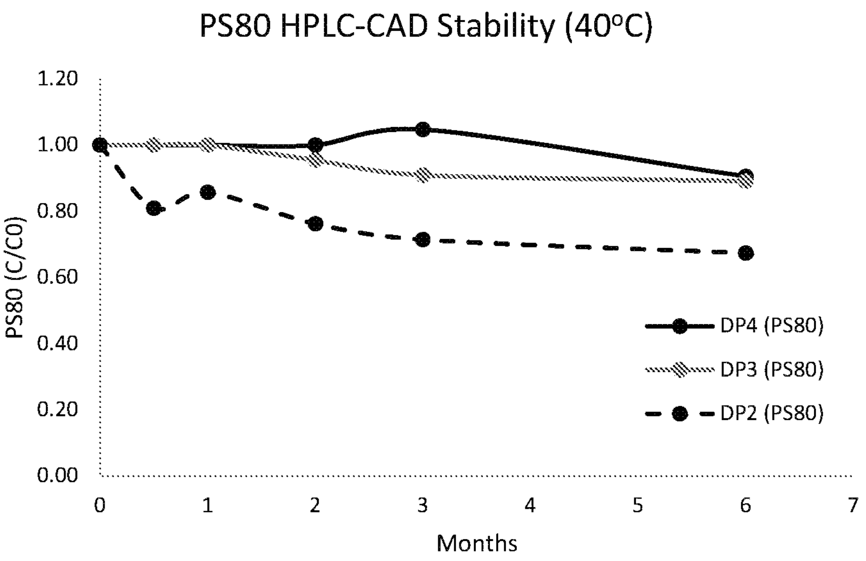
FIG. 19C shows PS80 stability in DP2 (PS80), DP3 (PS80), and DP4 (PS80) measured by CAD assay at 40° C.
Figure 20A:
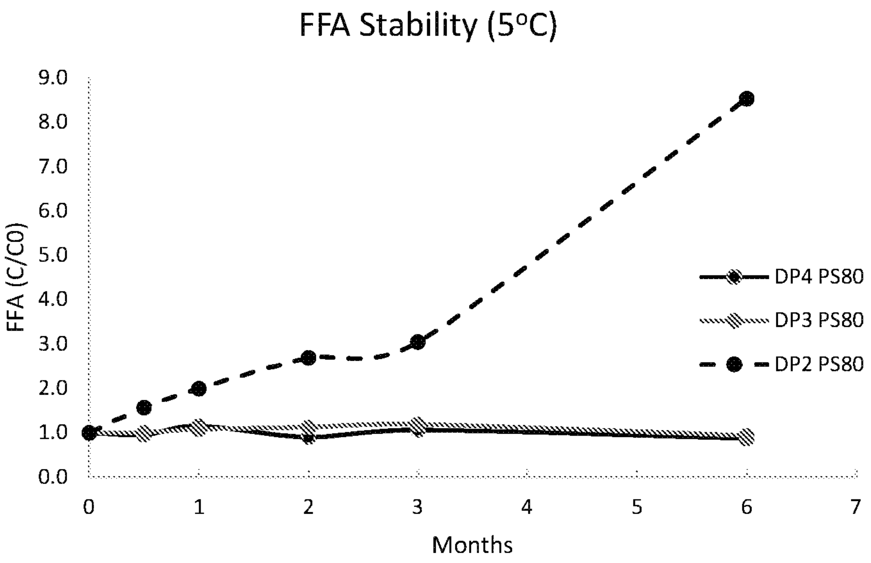
FIG. 20A and FIG. 20B show PS80 stability in DP2 (PS80), DP3 (PS80), and DP4 (PS80) measured by FFA assay at 5° C.
Figure 20B:
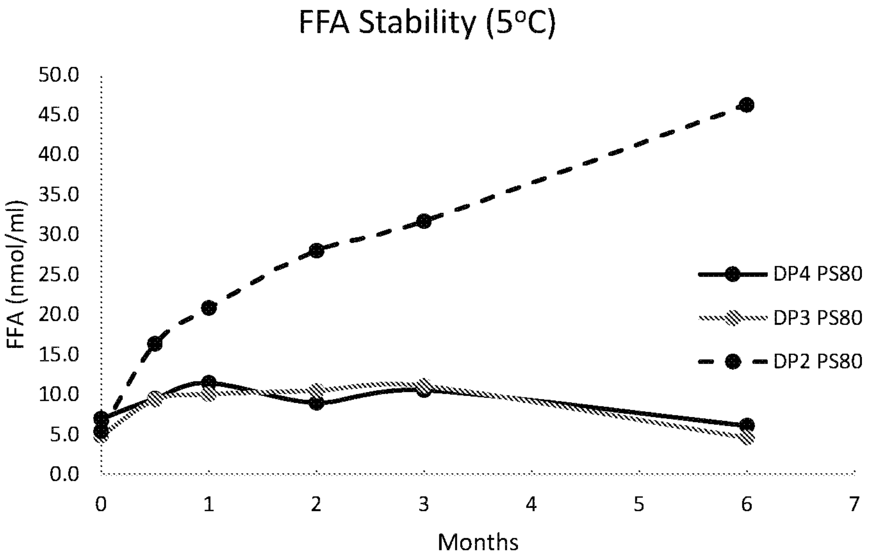
Figure 20C:
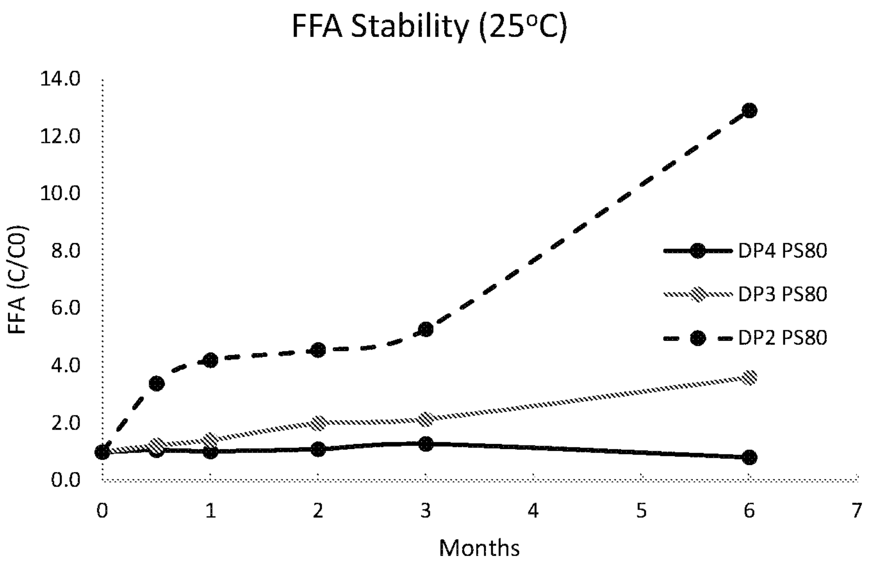
FIG. 20C and FIG. 20D show PS80 stability in DP2 (PS80), DP3 (PS80), and DP4 (PS80) measured by FFA assay at 25° C.
Figure 20D:
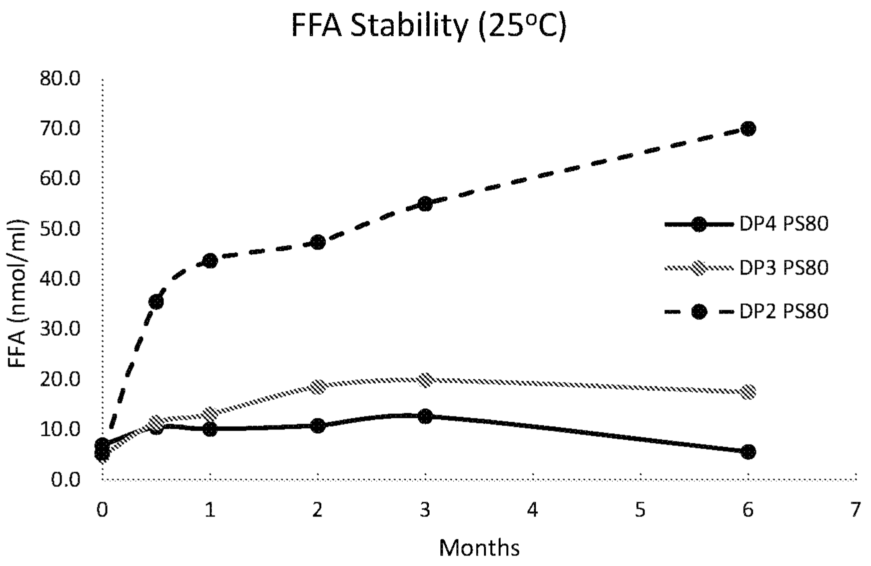
Figure 20E:
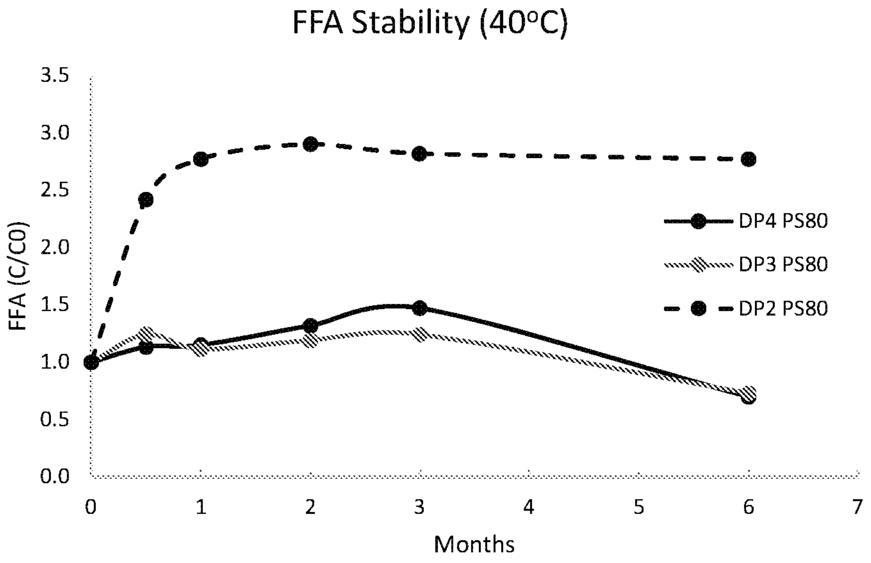
FIG. 20E and FIG. 20F show PS80 stability in DP2 (PS80), DP3 (PS80), and DP4 (PS80) measured by FFA assay at 40° C.
Figure 20F:
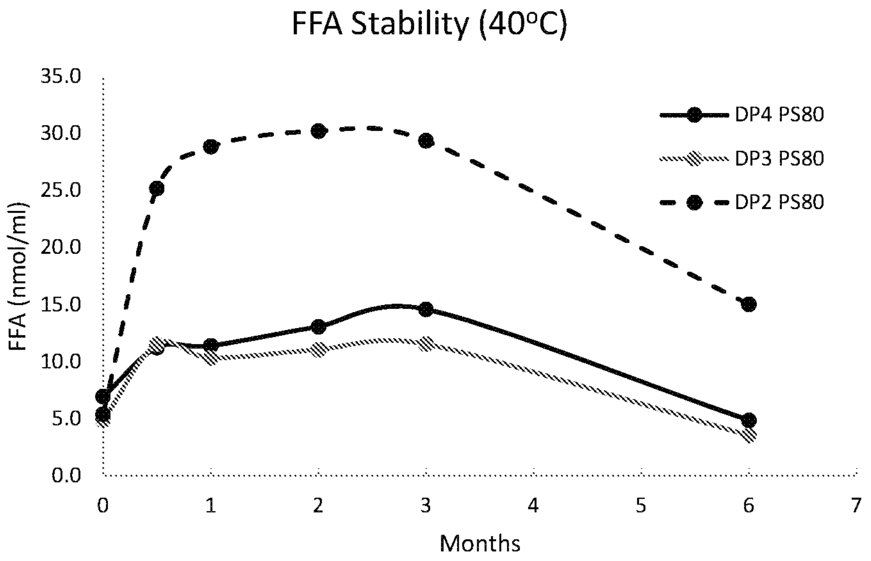

Risankizumab compositions described herein may be produced using exemplary optimized purification processes described in Example 3 and FIG. 14 herein and described below.

Once a clarified solution or mixture comprising the antibody has been obtained, separation of the antibody from the other proteins produced by the cell, such as HPs, may be performed using a combination of different purification techniques, including, but not limited to, affinity separation steps, ion exchange separation steps, mixed mode separation steps, and hydrophobic interaction separation steps, singly or in combination. The separation steps separate mixtures of proteins based on biophysical characteristics, such as, without limitation, charge, degree of hydrophobicity, and/or size depending upon the particular form of separation, including chromatographic separation. In one aspect of the present disclosure, separation may be performed using chromatography, including, without limitation, cationic, anionic, hydrophobic interaction, and/or mixed mode chromatography. Several different chromatography resins are commercially available for each of these techniques, allowing accurate tailoring of the purification scheme to the particular protein involved. The essence of each described separation method is that proteins can be caused either to traverse at different rates through a chromatographic medium, such as resin in a column, achieving a physical separation that increases as they pass further through the chromatographic medium, or to adhere selectively to a chromatographic medium, such as a column's separation resin, and then differentially eluted using different eluents. In some cases, the antibody is separated from HPs when the HPs specifically adhere to the chromatographic medium, such as a column's resin and the antibody does not, i.e., the antibody is contained in the eluent, while in other cases the antibody of interest may adhere to the chromatographic medium, such as the column's resin, while HPs are extruded from the column during a wash cycle.

a. Primary Recovery

In certain embodiments, it may be advantageous to subject a sample produced according to the present disclosure to at least a first phase of clarification and primary recovery.

The primary recovery may include one or more centrifugation steps to further clarify the sample mixture and thereby aid in purifying the protein of interest. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification.

In certain embodiments, the primary recovery may also include the use of one or more depth filtration steps to further clarify the sample matrix and thereby aid in purifying the antibodies produced using the cell culture techniques of the present disclosure. Depth filters contain filtration media having a graded density. Such graded density allows larger particles to be trapped near the surface of the filter while smaller particles penetrate the larger open areas at the surface of the filter, only to be trapped in the smaller openings nearer to the center of the filter. In certain embodiments, the depth filtration step can be a delipid depth filtration step. Although certain embodiments employ depth filtration steps only during the primary recovery phase, other embodiments may employ depth filters, including delipid depth filters, during one or more additional phases of purification. Non-limiting examples of depth filters that can be used in the context of the present disclosure include the XOHC depth filter, DOHC depth filter, Cuno™ model 30/60ZA depth filters (3M Corp.), and 0.45/0.2 μm Sartopore™ bi-layer filter cartridges.

b. Affinity Chromatography

In certain embodiments, it may be advantageous to subject risankizumab produced according to the present disclosure to affinity chromatography to further purify antibody away from HPs (e.g., lipase). In certain embodiments the chromatographic material may be capable of selectively or specifically binding to risankizumab. Non-limiting examples of such chromatographic material include: Protein A, Protein G, chromatographic material comprising, for example, an antigen bound by an antibody of interest, and chromatographic material comprising an Fc binding protein. In some embodiments, the affinity chromatography step may involve subjecting the primary recovery sample to a column comprising a suitable Protein A resin. In certain embodiments, Protein A resin may be useful for affinity purification and isolation of a variety of antibody isotypes, particularly IgG1, IgG2, and IgG4. Protein A is a bacterial cell wall protein that binds to mammalian IgGs primarily through their Fc regions. In its native state, Protein A has five IgG binding domains as well as other domains of unknown function.

There are several commercial sources for Protein A resin. One suitable resin may be MabSelect™ from GE Healthcare. Another suitable resin may be MabSelect SuRe™. A non-limiting example of a suitable column packed with MabSelect™ is an about 1.0 cm diameter×about 21.6 cm long column (~17 ml bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™ or MabSelect SuRe™.

c. Ion Exchange Chromatography

In certain embodiments, it may be advantageous to subject risankizumab produced according to the present disclosure to ion exchange chromatography in order to purify risankizumab away from HPs (e.g., lipase). Ion exchange separation includes any method by which two substances are separated based on the difference in their respective ionic charges, and can employ either cationic exchange material or anionic exchange material. For example, the use of a cationic exchange material versus an anionic exchange material is based on the localized charges of the protein. Therefore, it is encompassed by the present disclosure to employ an anionic exchange step prior to the use of a cationic exchange step, or a cationic exchange step prior to the use of an anionic exchange step. Furthermore, it is encompassed by the present disclosure to employ only a cationic exchange step, only an anionic exchange step, or any serial combination of the two.

In performing the separation, the initial protein mixture can be contacted with the ion exchange material by using any of a variety of techniques, e.g., using a batch purification technique or a chromatographic technique.

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange resins such as DE23™, DE32™ DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Fe all available from Pharmacia AB. Further, both DEAE and CM derivitized ethylene glycol-methacrylate copolymer such as TOYOPEARL™ DEAE-6505 or M and TOYOPEARL™ CM-650S or M are available from Toso Haas Co., Philadelphia, Pa. In some embodiments, cation exchange chromatography with Poros™ XS Resin is used.

d. Ultrafiltration/Diafiltration

In certain embodiments, it may be advantageous to subject risankizumab produced according to the present disclosure to ultrafiltration and/or diafiltration in order to purify risankizumab away from HPs (e.g., lipase). Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 μm. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultrafiltration rate. This washes microspecies from the solution at a constant volume, effectively purifying the retained protein. In certain embodiments of the present disclosure, a diafiltration step may be employed to exchange the various buffers used in connection with the present disclosure, optionally prior to further chromatography or other purification steps, as well as to remove impurities from the protein preparations.

e. Hydrophobic Interaction Chromatography

In certain embodiments, it may be advantageous to subject risankizumab produced according to the present disclosure to hydrophobic interaction chromatography in order to purify risankizumab away from HPs (lipase). For example, a first eluate obtained from an ion exchange column can be subjected to a hydrophobic interaction material such that a second eluate having a reduced level of HPs is obtained. Hydrophobic interaction chromatography (HIC) steps, such as those disclosed herein, are generally performed to purify proteins, including removal of HPs.

In performing an HIC-based separation, the sample mixture is contacted with the HIC material, e.g., using a batch purification technique or using a column. Prior to HIC purification it may be desirable to remove any chaotropic agents or very hydrophobic substances, e.g., by passing the mixture through a pre-column.

Whereas ion exchange chromatography relies on the charges of the protein to isolate them, hydrophobic interaction chromatography uses the hydrophobic properties of the protein. Hydrophobic groups on the protein interact with hydrophobic groups on the column. The more hydrophobic a protein is the stronger it will interact with the column. Thus, the HIC step removes host cell derived impurities (e.g., DNA and other high and low molecular weight product-related species).

HIC columns normally comprise a base matrix (e.g., cross-linked agarose or synthetic copolymer material) to which hydrophobic ligands (e.g., alkyl or aryl groups) are coupled. A suitable HIC column comprises an agarose resin substituted with phenyl groups (e.g., a Phenyl Sepharose™ column). Many HIC columns are available commercially. Examples include, but are not limited to, Phenyl Sepharose™ 6 Fast Flow column with low or high substitution (Pharmacia LKB Biotechnology, AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany); Macro-Prep™ Mehyl or Macro-Prep™ t-Butyl Supports (Bio-Rad, California); WP HI-Propyl (C3)™ column (J. T. Baker, New Jersey); and Toyopearl™ ether, phenyl or butyl columns (TosoHaas, Pa.).

F. Multimodal (Mixed-Mode) Chromatography

In certain embodiments, it may be advantageous to subject risankizumab produced according to the present disclosure to multimodal chromatography in order to purify risankizumab away from HPs (e.g., lipase). Multimodal chromatography is chromatography that utilizes a multimodal media resin. Such a resin comprises a multimodal chromatography ligand. In certain embodiments, such a ligand refers to a ligand that is capable of providing at least two different, but co-operative, sites which interact with the substance to be bound. One of these sites gives an attractive type of charge-charge interaction between the ligand and the substance of interest. The other site typically gives electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. Multimodal chromatography ligands are also known as "mixed mode" chromatography ligands.

In certain embodiments, the multimodal chromatography resin may be comprised of multimodal ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support may be prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g., styrene or styrene derivatives, divinylbenzene, acrylamides, acrylate esters, methacrylate esters, vinyl esters, vinyl amides etc. Such synthetic polymers can be produced according to standard methods, see e.g., "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden. In some embodiments, the mixed-mode chromatography combines anion exchange (AEX) and hydrophobic interaction (HIC) functionality. One non-limiting example of such mixed-mode chromatography suitable for the present disclosure is Capto™ Adhere mixed mode chromatography.

Characterization of Risankizumab Compositions

Reducing hitchhiker proteins from risankizumab formulations beneficially increases the stability of the formulations (e.g., decreasing particle formation, increasing shelf life of the risankizumab drug product, and the like). In one embodiment, no visible or glittering particles are observed in the liquid risankizumab compositions described herein over at least 3 months (e.g., at least 6 months, at least 9 months, at least 12 months, at least 15 months, at least 18 months, at least 21 months, at least 24 months, at least 27 months, at least 30 months, at least 33 months, or at least 36 month) at 2° to 40° C. (e.g., 4° C. to 35° C., 4° C. to 25° C., 4° C. to 15° C., 4° C. to 10° C., 2° C. to 8° C., or any temperature within the aforementioned ranges, such as about 2° C., about 4° C., about 5° C., about 8° C., about 25° C., about 40° C., etc.). In one embodiment, no visible or glittering particles are observed in the liquid risankizumab compositions described herein over 24 months at about 4° C.

In some embodiments, the liquid risankizumab compositions described herein comprises a surfactant with increased stability. The surfactant may be selected from the group consisting of polysorbate 20 (PS20), polysorbate 80 (PS80), polysorbate 40 (PS40), polysorbate 60 (PS60), polysorbate 65 (PS65), and Poloxamer 188.

The stability of the surfactant in the liquid risankizumab compositions described herein can be assessed by directly measuring the amount of surfactant in the liquid risankizumab compositions after storage at a certain temperature (e.g., 2° C., 4° C., 5° C., 8° C., 10° C., 12° C., 25° C., 30° C., 35° C., or 40° C.) for a period of time (e.g., 3 months, 6 months, 9 months, 12 months, 18 months, 24 months, 30 months, 36 months, etc.). Alternatively, the stability of the surfactant in the liquid risankizumab compositions described herein can be assessed by measuring the amount of the degradation products of the surfactant (e.g., the amount of the free fatty acids), in the risankizumab compositions after storage at a certain temperature (e.g., 2° C., 4° C., 5° C., 8° C., 10° C., 12° C., 25° C., 30° C., 35° C., or 40° C.) for a period of time (e.g., 3 months, 6 months, 9 months, 12 months, 18 months, 24 months, 30 months, 36 months, etc.). In some embodiments, the period of time is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more months, or any range in between, inclusive, such as 3 months to 36 months, 12 months to 24 months, etc.

In some embodiments, the liquid risankizumab compositions described herein comprises PS20, e.g., at a concentration of 0.20 mg/mL, and the stability of PS20 in such liquid risankizumab compositions is increased.

In one embodiment, the stability of PS20 is assessed by directly measuring the amount of PS20 in the risankizumab compositions after storage at a certain temperature (e.g., 2° C., 4° C., 5° C., 8° C., 10° C., 12° C., 25° C., 30° C., 35° C., or 40° C.) for a period of time (e.g., 3 months, 6 months, 9 months, 12 months, 18 months, 24 months, 30 months, 36 months, etc.). The amount of PS20 may be measured using any method known in the art, e.g., using High Performance Liquid Chromatography Charged Aerosol Detector (HPLC-CAD), such as the HPLC-CAD described in Example 10. In some embodiments, the period of time is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more months, or any range in between, inclusive, such as 3 months to 36 months, 12 months to 24 months, etc.

For example, in some embodiments, at least 80% (e.g., at least 85%, at least 90%, at least 95%, at least 98%, at least 99%, or about 100%) of the initial amount of PS20 is retained following storage at 5° C. for 6 months. In some embodiments, at least 70% (e.g., at least 75%, at least 80%, at least 85%, at least 90%, at least 95%, at least 98%, at least 99%, or about 100%) of the initial amount of PS20 is retained following storage at 5° C. for 24 months. In some embodiments, at least 60% (e.g., at least 65%, at least 70%, at least 75%, at least 80%, at least 85%, at least 90%, at least 95%, at least 98%, at least 99%, or about 100%) of the initial amount of PS20 is retained following storage at 25° C. for 6 months. In some embodiments, at least 40% (e.g., at least 45%, at least 50%, at least 55%, at least 60%, at least 65%, at least 70%, at least 75%, at least 80%, at least 85%, at least 90%, at least 95%, at least 98%, at least 99%, or about 100%) of the initial amount of PS20 is retained following storage at 40° C. for 6 months.

In one embodiment, the stability of PS20 is assessed by measuring the amount of free fatty acid (FFA), the degradation products of PS20, in the risankizumab compositions formulated with PS20 after storage at a certain temperature (e.g., 2° C., 4° C., 5° C., 8° C., 10° C., 12° C., 25° C., 30° C., 35° C., or 40° C.) for a period of time (e.g., 3 months, 6 months, 9 months, 12 months, 18 months, 24 months, 30 months, 36 months, etc.). The amount of FFA may be measured using any method known in the art, e.g., using enzymatic FFA or LC-FFA assay, such as the reversed-phase high performance liquid chromatography UV (RP-HPLC-UV) method described in Example 10. In some embodiments, the period of time is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more months, or any range in between, inclusive, such as 3 months to 36 months, 12 months to 24 months, etc.

For example, in some embodiments, the total amount of FFA in the liquid compositions formulated with PS20 described herein is increased no greater than 1.75-fold (e.g., no greater than 1.5-fold, no greater than 1.25-fold, or no greater than 1.1-fold), or is not increased following storage at 5° C. for 6 months. In some embodiments, the total amount of FFA in the liquid compositions formulated with PS20 described herein is no greater than 20 nmol/ml (e.g., no greater than 18 nmol/ml, no greater than 15 nmol/ml, no greater than 12 nmol/ml, no greater than 10 nmol/ml, no greater than 8 nmol/ml, or no greater than 5 nmol/ml, or any range in between, inclusive, such as 5 nmol/ml to 10 nmol/ml) following storage at 5° C. for 6 months. In some embodiments, the FFA is in an amount that is less than or at the limit of detection of an FFA detection assay.

In some embodiments, the total amount of FFA in the liquid compositions formulated with PS20 described herein is increased no greater than 3.5-fold (e.g., no greater than 3.2-fold, no greater than 3.0-fold, no greater than 2.5-fold, no greater than 2.0-fold, no greater than 1.8-fold, no greater than 1.6-fold, no greater than 1.4-fold, no greater than 1.2-fold, or no greater than 1.1-fold), or is not increased following storage at 25° C. for 6 months. In some embodiments, the total amount of FFA in the liquid compositions formulated with PS20 described herein is no greater than 25 nmol/ml (e.g., no greater than 20 nmol/ml, no greater than 18 nmol/ml, no greater than 15 nmol/ml, no greater than 12 nmol/ml, no greater than 10 nmol/ml, no greater than 8 nmol/ml, or no greater than 5 nmol/ml, or any range in between, inclusive, such as 5 nmol/ml to 10 nmol/ml) following storage at 25° C. for 6 months. In some embodiments, the FFA is in an amount that is less than or at the limit of detection of an FFA detection assay.

In some embodiments, the total amount of FFA in the liquid compositions formulated with PS20 described herein is increased no greater than 3-fold (e.g., no greater than 2.8-fold, no greater than 2.5-fold, no greater than 2.0-fold, no greater than 1.8-fold, no greater than 1.6-fold, no greater than 1.4-fold, no greater than 1.2-fold, or no greater than 1.1-fold), or is not increased following storage at 40° C. for 6 months. In some embodiments, the total amount of FFA in the liquid compositions formulated with PS20 described herein is no greater than 35 nmol/ml (e.g., no greater than 30 nmol/ml, no greater than 25 nmol/ml, no greater than 20 nmol/ml, no greater than 18 nmol/ml, no greater than 15 nmol/ml, no greater than 12 nmol/ml, no greater than 10 nmol/ml, no greater than 8 nmol/ml, or no greater than 5 nmol/ml, or any range in between, inclusive, such as 5 nmol/ml to 10 nmol/ml) following storage at 40° C. for 6 months. In some embodiments, the FFA is in an amount that is less than or at the limit of detection of an FFA detection assay, e.g., less than or at 1 nmol/ml.

In some embodiments, the liquid risankizumab compositions described herein comprises PS80, and the stability of PS80 in such liquid risankizumab compositions is increased.

In one embodiment, the stability of PS80 is assessed by directly measuring the amount of PS80 in the risankizumab compositions after storage at a certain temperature (e.g., 2° C., 4° C., 5° C., 8° C., 10° C., 12° C., 25° C., 30° C., 35° C., or 40° C.) for a period of time (e.g., 3 months, 6 months, 9 months, 12 months, 18 months, 24 months, 30 months, 36 months, etc.). The amount of PS80 may be measured using any method known in the art, e.g., using HPLC-CAD, such as the HPLC-CAD described in Example 10. In some embodiments, the period of time is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more months, or any range in between, inclusive, such as 3 months to 36 months, 12 months to 24 months, etc.

For example, in some embodiments, at least 80% (e.g., at least 85%, at least 90%, at least 95%, at least 98%, at least 99%, or about 100%) of the initial amount of PS80 is retained following storage at 5° C. for 6 months. In some embodiments, at least 60% (e.g., at least 65%, at least 70%, at least 75%, at least 80%, at least 85%, at least 90%, at least 95%, at least 98%, at least 99%, or about 100%) of the initial amount of PS80 is retained following storage at 25° C. for 6 months. In some embodiments, at least 60% (e.g., at least 65%, at least 70%, at least 75%, at least 80%, at least 85%, at least 90%, at least 95%, at least 98%, at least 99%, or about 100%) of the initial amount of PS80 is retained following storage at 40° C. for 6 months.

In one embodiment, the stability of PS80 is assessed by measuring the amount of free fatty acid (FFA), the degradation products of PS80, in the risankizumab compositions formulated with PS80 after storage at a certain temperature (e.g., 2° C., 4° C., 5° C., 8° C., 10° C., 12° C., 25° C., 30° C., 35° C., or 40° C.) for a period of time (e.g., 3 months, 6 months, 9 months, 12 months, 18 months, 24 months, 30 months, 36 months, etc.). The amount of FFA may be measured using any method known in the art, e.g., using enzymatic FFA or LC-FFA assay, such as the RP-HPLC-UV method described in Example 10. In some embodiments, the period of time is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more months, or any range in between, inclusive, such as 3 months to 36 months, 12 months to 24 months, etc.

For example, in some embodiments, the total amount of FFA in the liquid compositions formulated with PS80 described herein is increased no greater than 8-fold (e.g., no greater than 7-fold, no greater than 6-fold, no greater than 5-fold, no greater than 4-fold, no greater than 3-fold, no greater than 2-fold, no greater than 1.5-fold, no greater than 1.2-fold, or no greater than 1.1-fold), or is not increased following storage at 5° C. for 6 months. In some embodiments, the total amount of FFA in the liquid compositions formulated with PS80 described herein is no greater than 45 nmol/ml (e.g., no greater than 40 nmol/ml, no greater than 35 nmol/ml, no greater than 30 nmol/ml, no greater than 25 nmol/ml, no greater than 20 nmol/ml, no greater than 18 nmol/ml, no greater than 15 nmol/ml, no greater than 12 nmol/ml, no greater than 10 nmol/ml, no greater than 8 nmol/ml, or no greater than 5 nmol/ml, or any range in between, inclusive, such as 5 nmol/ml to 10 nmol/ml, 5 nmol/ml to 20 nmol/ml, 5 nmol/ml to 30 nmol/ml, or 5 nmol/ml to 45 nmol/ml) following storage at 5° C. for 6 months. In some embodiments, the FFA is in an amount that is less than or at the limit of detection of an FFA detection assay, e.g., less than or at 1 nmol/ml.

In some embodiments, the total amount of FFA in the liquid compositions formulated with PS80 described herein is increased no greater than 12-fold (e.g., no greater than 11-fold, no greater than 10-fold, no greater than 9-fold, no greater than 8-fold, no greater than 7-fold, no greater than 6-fold, no greater than 5-fold, no greater than 4-fold, no greater than 3-fold, no greater than 2-fold, no greater than 1.5-fold, no greater than 1.2-fold, or no greater than 1.1-fold) following storage at 25° C. for 6 months. In some embodiments, the total amount of FFA in the liquid compositions formulated with PS80 described herein is no greater than 65 nmol/ml (e.g., no greater than 60 nmol/ml, no greater than 55 nmol/ml, no greater than 50 nmol/ml, no greater than 45 nmol/ml, no greater than 40 nmol/ml, no greater than 35 nmol/ml, no greater than 30 nmol/ml, no greater than 25 nmol/ml, no greater than 20 nmol/ml, no greater than 18 nmol/ml, no greater than 15 nmol/ml, no greater than 12 nmol/ml, no greater than 10 nmol/ml, no greater than 8 nmol/ml, or no greater than 5 nmol/ml, or any range in between, inclusive, such as 5 nmol/ml to 10 nmol/ml, 5 nmol/ml to 20 nmol/ml, 5 nmol/ml to 30 nmol/ml, or 5 nmol/ml to 65 nmol/ml) following storage at 25° C. for 6 months. In some embodiments, the FFA is in an amount that is less than or at the limit of detection of an FFA detection assay, e.g., less than or at 1 nmol/ml.

In some embodiments, the total amount of FFA in the liquid compositions formulated with PS80 described herein is no greater than 2.5-fold (e.g., no greater than 2-fold, no greater than 1.5-fold, no greater than 1.2-fold, or no greater than 1.1-fold), or is not increased following storage at 40° C. for 6 months. In some embodiments, the total amount of FFA in the liquid compositions formulated with PS80 described herein is no greater than 15 nmol/ml (e.g., no greater than 12 nmol/ml, no greater than 10 nmol/ml, no greater than 8 nmol/ml, no greater than 5 nmol/ml, or no greater than 3 nmol/ml, or any range in between, inclusive, such as 3 nmol/ml to 5 nmol/ml, 3 nmol/ml to 10 nmol/ml, 5 nmol/ml to 10 nmol/ml, or 3 nmol/ml to 15 nmol/ml) following storage at 40° C. for 6 months. In some embodiments, the FFA is in an amount that is less than or at the limit of detection of an FFA detection assay.

In some aspects, the risankizumab composition described herein comprises Poloxamer 188. In some embodiments, the P188 containing risankizumab composition does not comprise PS20 and/or PS80. In some embodiments, the stability of P188 in the risankizumab composition is increased compared to the stability PS20 or PS80.

In some embodiments, the stability of P188 is assessed by directly measuring the amount of P188 in the risankizumab compositions after storage at a certain temperature (e.g., 2° C., 4° C., 5° C., 8° C., 10° C., 12° C., 25° C., 30° C., 35° C., or 40° C.) for a period of time (e.g., 3 months, 6 months, 9 months, 12 months, 18 months, 24 months, 30 months, 36 months, etc.). The amount of P188 may be measured using any method known in the art, e.g., using a Pluronic F-68 colorimetric assay, such as the Pluronic F-68 colorimetric assay described in Example 17. In some embodiments, the period of time is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more months, or any range in between, inclusive, such as 3 months to 36 months, 12 months to 24 months, 3 months to 6 months, etc.

For example, in some embodiments, at least 85% (e.g., at least 90%, at least 95%, at least 98%, at least 99%, or about 100%) of the initial amount of P188 is retained following storage at 5° C. for 3 months. In some embodiments, at least 65% (e.g., at least 70%, at least 75%, at least 80%, at least 85%, at least 90%, at least 95%, at least 98%, at least 99%, or about 100%) of the initial amount of P188 is retained following storage at 25° C. for 3 months. In some embodiments, at least 60% (e.g., at least 65%, at least 70%, at least 75%, at least 80%, at least 85%, at least 90%, at least 95%, at least 98%, at least 99%, or about 100%) of the initial amount of P188 is retained following storage at 40° C. for 3 months.

For example, in some embodiments, at least 80% (e.g., at least 85%, at least 90%, at least 95%, at least 98%, at least 99%, or about 100%) of the initial amount of P188 is retained following storage at 5° C. for 6 months. In some embodiments, at least 60% (e.g., at least 65%, at least 70%, at least 75%, at least 80%, at least 85%, at least 90%, at least 95%, at least 98%, at least 99%, or about 100%) of the initial amount of P188 is retained following storage at 25° C. for 6 months. In some embodiments, at least 60% (e.g., at least 65%, at least 70%, at least 75%, at least 80%, at least 85%, at least 90%, at least 95%, at least 98%, at least 99%, or about 100%) of the initial amount of P188 is retained following storage at 40° C. for 6 months.

Example 1: Particles were Observed Upon Dilution of Risankizumab Drug Products DP1 and DP2

Risankizumab drug product 1 (DP1) at 90 mg/ml was developed using the process and formulation as described in international application PCT/US2013/038109. Risankizumab drug product 2 (DP2) at a concentration of 150 mg/ml was subsequently developed and approved by FDA. The formulations of DP1 and DP2 are shown in Table 6 below.

TABLE 6

| Drug products | Risankizumab purification processes | Formulations |
|---|---|---|
| Drug Product 1 (DP1) | Process 1 | Risankizumab 90.0 mg/mL;<br>Disodium succinate hexahydrate 1.054 mg/mL;<br>Succinic acid 0.059 mg/mL;<br>Sorbitol 41.0 mg/mL;<br>Polysorbate 20 0.20 mg/mL;<br>Water for Injections (WFI);<br>pH 6.2 |
| Drug Product 2 (DP2) | Process 2 | Risankizumab 150 mg/ml<br>Sodium acetate trihydrate 1.24 mg/mL<br>Acetic acid 0.054 mg/mL<br>Trehalose dihydrate 70.0 mg/mL<br>Polysorbate 20 0.20 mg/ml<br>Water for Injections (WFI)<br>pH 5.7 |

Risankizumab formulations DP1 and DP2 comprise highly purified risankizumab API and are stable. However, particles comprising free fatty acids (FFAs) were unexpectedly observed in DP1 and DP2, especially when DP2 was diluted (e.g., 51 mg/ml and 60 mg/ml) and used for researching the feasibility of on-body device presentations and placed under certain storage conditions, as shown in Table 7 below.

TABLE 7

| Formulation | Particle morphology | 1st observed under stability testing | Particle type |
|---|---|---|---|
| 90 mg/mL DP1 | Small, cannot re-disperse | 5° C./12M | Protein and FFA |
| 150 mg/mL DP2 diluted to 60 mg/mL | Small flake like particles, FFA like | 5° C./6M | Protein and/or FFA |
| 150 mg/mL DP2 diluted to 51 mg/mL | Many FFA like dispersed particles | all temp/3M | FFA particles |

Example 2: Proteomic Analysis Identified Candidate Hitchhiker Proteins

It was hypothesized by the inventors that formation of particles in the risankizumab products was due to degradation of the surfactant polysorbate 20 (PS20), which may lead to antibody aggregation. The degradation of PS20 was hypothesized to be caused by a residual CHO cell esterase that had co-purified with risankizumab drug substance. To identify putative hitchhiker proteins (HPs) that may have led to the degradation of polysorbate-20 in risankizumab drug product, host cell proteins (HCPs) from DP1 and DP2 bulk drug substance (BDS) samples were enriched followed by LC-MS/MS analysis.

Multiple risankizumab BDS samples from each DS process were pooled to generate the representative BDS material for HCP enrichment and identification. In total, six BDS batches from the Process 1 were pooled to generate the representative DP1 BDS sample, four DP2 BDS batches were mixed to make the DP2 BDS sample for the HCP enrichment and identification study.

The protein concentration of each representative risankizumab BDS sample was measured and shown in Table 8.

TABLE 8

| Risankizumab concentration in the pooled samples risankizumab concentration mg/mL | |
|---|---|
| DP1 BDS | DP2 BDS |
| 91.12 | 153.83 |

Method

Immunoaffinity Purification for HCP Enrichment from Risankizumab

1. Anti-HCP Antibody Coupling to Sepharose Bead a. Buffer Preparation:

Acidification buffer: 1 mM HCl;

Coupling buffer: 200 mM $NaHCO_3$, 500 mM NaCl, pH 9.0;

Blocking buffer: 1 M ethanolamine; pH 8.0;

Wash buffer: 100 mM Sodium Acetate; 500 mM NaCl, pH 4.0.

B. Buffer Exchange of Anti-HCP AntiBodies

Anti-total HCP antibody (CRO: Biogenes®): 1.99 mg/mL;

Anti-LMW HCP antibody (CRO: Covance®): 5.19 mg/ml;

Dialysis device: Thermo Scientific Pro #66810.

3 mL of Anti-total HCP antibody and 3 mL anti-LMW HCP antibody were buffer exchanged in 4 L of coupling buffer (described above) respectively by dialysis over night at cold room using low speed mixing (around 60 rpm).

C. Conditioning of Cyanogen Bromide (CNBR) Activated Sepharose Bead (Cytiva Catalog #71-5000-15 AF)

0.5 g of CNBR Sepharose bead was weighed into a poly-Prep chromatography column (Bio-Rad catalog #731-1550). Sepharose beads were suspended in 5 mL of 1 mM ice-cold HCl. The column was inverted to make sure the sepharose bead fully wet (about 10 min); the column was placed into a 15 mL centrifuge tube and centrifuged at 200 g for 7 min to dry the bead (Beckman Avanti J-15R); CNBR sepharose bead was washed additional 3 times using 1 mM ice-cold HCl.

D. Anti-HCP Antibody Coupling, Wash 4 mL of buffer-exchanged anti-total HCP antibody and anti-LMW HCP antibody were added to two separate poly-prep chromatography columns containing conditioned CNBR activated sepharose bead obtained in c. The two columns were kept at cold room for overnight in a rocker with low-speed mixing to couple anti-LMW or anti-total HCP antibodies to the CNBR activated sepharose bead. The poly-prep chromatography columns were centrifuged to remove the unbound anti-HCP antibody from sepharose bead by centrifuging for 7 min at 200 g (Beckman Avanti J-15R).

5 mL blocking buffer was added to each column and mixed on a bench rocker at low speed for overnight in a cold room for blocking of the antibody immobilized sepharose bead. The blocking buffer was removed by centrifugation (the same as described in step c). The columns were washed by alternating coupling buffer and wash buffer (4 times each, 5 mL per wash). Finally, the columns were conditioned in 1×PBS buffer by adding and eluting 5 mL of 1×PBS twice. The sepharose bead (antibody-coupled) was stored suspended in the PBS buffer in the column at 4° C. until use.

2. Packing the Immunoaffinity Columns for HCP Purification/Enrichment

The suspended sepharose bead (antibody-coupled) was transferred from the poly-prep chromatography column to Tricorn 5/50 column (Cytiva product code: 28406409; ~1 mL column volume (CV)). The agitation was minimized to avoid introduction of air bubbles in the sepharose bead packings in the Tricorn column. The Tricorn column was connected with peristaltic pump P1 (Cytiva) to set up the immunoaffinity purification system. The Tricorn column was conditioned by running 20 mL (20 CV) PBS buffer using P1 pump to drive the liquid flow at flow rate 0.5 mL/min. The sepharose bead packed Tricorn column was stored at 4° C.

3. HCP Coupling, Wash and Elution from Purification Column

Two Tricorn immunoaffinity columns (Anti-total HCP and Anti-LMW HCP columns) packed as described above working with two separate P1 pumps were used to sequentially purify the pooled risankizumab BDS samples (DP1 and DP2). For each risankizumab BDS sample, the following procedures and materials were used for HCP coupling, wash, and elution from the immunoaffinity column.

A. Buffer Preparation

Protein binding buffer: 1×PBS (pH 7.4);

Washing buffer: 1×PBS, 0.05% Tween 20 (pH 7.4);

Elution buffer: 100 mM Glycine, 400 mM Arginine (HCl) (pH 2.7);

Neutralization buffer: 1 M Tris-HCl (pH 8.5).

A total of 4.5 g risankizumab BDS sample was prepared (depending on the risankizumab concentration in the pooled BDS samples, 50 mL of 90 mg/mL, 30 mL of 150 mg/mL) for the purification at each Tricorn immunoaffinity column (total two columns). 50 (30) mL of DP1 or DP2 pooled BDS samples were aliquoted into 5 aliquots (each 10 or 6 mL) for each cycle of risankizumab BDS samples loading, and washed on the immunoaffinity columns (total 5 cycles, each aliquot is for one cycle). At each cycle 10 mL (or 6 mL) risankizumab BDS samples were circulated through Tricorn immunoaffinity column at flow rate around 0.5 mL/min for 40 min. The Tricorn column was washed with about 20 CV wash buffer delivered by the P1 pump. The circulation and wash steps were repeated for the other 4 aliquots of risankizumab BDS samples in each Tricorn immunoaffinity column. Each column was washed with an additional 10 CV wash buffer after 5 cycles of loading and washing of risankizumab BDS samples at each Tricorn column. Bound proteins (HCPs as well as risankizumab molecules) were eluted from each Tricorn column using 15 mL (CV) elution buffer delivered by P1 pump at the same flow rate around 0.5 mL/min. The eluate was neutralized with neutralization buffer (1 mL eluate mix with 200 μL neutralization buffer) to around pH 7 (measured with pH probe). Neutralization should occur after purification eluate come out from the column. The protein concentration was measured in each neutralized eluate from the Tricorn immunoaffinity column for each risankizumab BDS sample by Lunatic spectrophotometer. Concentration should be below detection of limit.

4. Concentrate Purification Eluate from Immunoaffinity Column

The purification eluate (about 15 mL) was concentrated using 15 mL 3k MWCO (Millipore, Catalog number UFC900324) to a total volume of about 0.5 mL. The 0.5 mL eluate was further concentrated using 0.5 mL size, 3K MWCO (Millipore, Catalog number, UFC500324) to a final volume about 100 μL. Lunatic spectrophotometer was used to measure the concentration of total protein in each 100 μL concentrated eluate. Total protein concentration should be around 1 mg/mL. Similar purification and concentrating procedures were used for all the 4 representative risankizumab BDS samples using the same immunoaffinity purification columns (Anti-LMW and Anti-Total HCP columns). The total 8 elute samples were collected from purification and concentration of all four pooled risankizumab BDS samples for LC-MS/MS analysis.

LC-MS/MS Method for HP Identification

1. Sample Denaturation and Reduction

60 μL of 8 M urea and 8.8 μL of 1 M DTT were added to 20 μL of each eluate sample. Each sample was incubated at 37° C. for 30 min with 450 rpm shaking.

2. Sample Alkylation and Digestion

200 μL of 8 M urea was added to 0.5 mL 30 kDa MWCO centrifugal filter (Millipore, Catalog number, MRCFOR030). The reduced sample was then added to the filter and centrifuged at 14,000×g for 15 min. 400 μL of 8 M urea was added to the filter and centrifuged at 14,000×g for 15 min. The flow-through from the collection tube was discarded. 100 μL of 50 mM iodoacetamide solution was added and mixed at 600 rpm in a thermo-mixer for 1 min and incubated without mixing for 20 min at room temperature. The filter was centrifuged at 14,000×g for 10 min. 100 μL of 8 M urea was added to the filter and centrifuged at 14,000×g for 15 min. This step was repeated once. 100 μL of 50 mM ammonium bicarbonate was added to the filter unit and centrifuged at 14,000×g for 10 min. This step was repeated once. The filter was transferred to new collection tubes.

35 μL of 50 mM ammonium bicarbonate was added and then 1 μL of 0.4 μg/uL trypsin (Thermo Scientific, Catalog number, 90057, enzyme to protein ratio 1:50) was added and mixed at 600 rpm in thermo-mixer for 1 min. The filter was incubated in a thermo-mix at 37° C. overnight. The tube was wrapped with parafilm to avoid evaporation. The filter was then centrifuged next day at 14,000×g for 10 min. 40 μL of 50 mM ammonium bicarbonate was added and the filter was centrifuged at 14,000×g for 10 min. The sample was acidified with formic acid to make sure pH<1. Peptide concentration was measured by Bradford colorimetric assay (Thermo Scientific, Catalog number, 23250).

3. LC-MS/MS Analysis

For each digested sample, 800 ng was injected onto a Bruker nanoElute™ ultra high-pressure liquid chromatography (UHPLC) system with an Aurora Series UHPLC C18 column, 120 Å, 25 cm×75 μm ID, 1.6 μm (Ionopticks, Catalog number, AUR2-25075C18A-CSI) maintained at 50° C. A gradient of mobile phase A (0.1% formic acid in water) and mobile phase B (0.1% formic acid in acetonitrile), shown in Table 9 at a flow rate of 250 nL/min was used to elute the peptides into the mass spectrometer.

TABLE 9

Gradient for LC-MS/MS analysis

| Time (min) | Mobile Phase A (%) | Mobile Phase B (%) |
|---|---|---|
| 0 | 98 | 2 |
| 60 | 87 | 13 |
| 90 | 80 | 20 |
| 100 | 70 | 30 |
| 110 | 15 | 85 |
| 120 | 15 | 85 |

A Bruker timsTOF pro QTOF mass spectrometer was used to acquire data operating in positive ion mode, scanning 100 to 1700 m/z in PASEF mode. Ion mobility resolution was set to 0.60-1.35 V·s/cm2 over a ramp time of 100 ns. For each cycle 10 PASEF MS/MS scans were performed towards precursors with 14,500 intensity units to reach a near 100% duty cycle. A polygon filter was applied in the m/z and ion mobility to exclude low m/z, single charged ions from MS/MS fragmentation. Collisional energy was ramped stepwise as a function of ion mobility. The data were searched against a CHO proteome database by MSFragger V17.1.

Results

TABLE 10

Potential hitchhiker proteins (HPs) identified in pooled risankizumab BDS samples.

| Protein Name |
|---|
| putative phospholipase B-like 2 |
| acid ceramidase-like |
| isoamyl acetate-hydrolyzing esterase 1 homolog |
| sphingomyelin phosphodiesterase |
| sialate O-acetylesterase-like |
| liver carboxylesterase-like isoform 1 |
| liver carboxylesterase 4-like |
| ester hydrolase C11orf54 homolog isoform 1 |
| lipoprotein lipase |
| calcineurin-like phosphoesterase domain-containing protein 1-like |
| peroxiredoxin-6-like, partial |

By affinity purification, various hitchhiker proteins, including putative phospholipase B-like 2 (PLBL2), acid ceramidase, isoamyl acetate-hydrolyzing esterase 1, sphingomyelin phosphodiesterase, liver carboxylesterase-like isoform 1 (CES1), liver carboxylesterase 4, ester hydrolase C11orf54 homolog isoform 1, sialate O-acetylesterase-like (SIAE), calcineurin-like phosphoesterase domain-containing protein 1, and peroxiredoxin-6-like, partial, (Prdx6), were identified in pooled risankizumab BDS samples (FIG. 1 and Table 10). Some of these proteins, such as PLBL2 and acid ceramidase, have also been reported to be present in another antibody drug substance previously (Graf et al. (2021) *J. Pharm. Sci.* 110:3358-3567).

Example 3: Development of Risankizumab Drug Products with Improved Stability

It was hypothesized by the inventors that the presence of certain types of hitchhiker proteins from host cells (e.g., host cell lipases) caused the particle formation in diluted risankizumab drug product. To solve this problem and improve stability and shelf-life of risankizumab products, as well as to further improve their quality, new risankizumab drug substance, Process 4 DS was developed. An exemplary purification process for producing Process 4 DS is described below.

CHO cells expressing risankizumab were thawed and cultured at increasing volumes in shake flasks, cell bags and seed bioreactor phases to provide sufficient cells to inoculate the production bioreactor. The cell culture broth was harvested by centrifugation and filtration to efficiently remove cells, providing the clarified harvest for further purification of the product. The clarified harvest was subsequently processed through a series of chromatography steps, virus inactivation, virus filtration, concentration and buffer exchange by tangential flow filtration, and final formulation. The purification process was developed to reduce host cell lipases by screening various reagents and conditions, including but not limited to, for example, the protein A chromatography wash scheme and wash buffers, depth filters, chromatography column resins (e.g., AEX resins, CEX resins, MM resins, and/or HIC resins), and/or conditions for ultrafiltration & diafiltration (UF/DF) process. The reagents and conditions that effectively reduced the certain host cell lipase levels in the purified risankizumab drug substance (DS) as measured by ELISA at acceptable yield tradeoff were adapted to establish two optimized purification processes, referred to herein as Process 3 and Process 4. Besides the purification process, the upstream cell culturing process of Process 4 was further modified to enhance culture longevity, productivity, and robustness.

The general overview of the purification process of Process 4 is shown in FIG. 14A. Specifically, the cell culture broth was harvested and clarified by centrifugation and depth filtration with a X0HC depth filter. The clarified harvest was first purified with affinity chromatography using MabSelect SuRe™ Protein A Resin. The eluate was subjected to low pH inactivation using phosphoric acid and then to depth filtration with X0HC and DOHC depth filters. The risankizumab antibody sample was then purified with Capto™ Adhere mixed mode chromatography. The flow-through was further purified by cation exchange chromatography with Poros™ XS Resin. The eluate was subjected to viral filtration. Ultrafiltration/diafiltration (UF/DF) was then performed by directly spiking the load with high-salt solution followed by 8DV with no salt. The purified bulk drug substance (BDS) was then formulated and properly stored.

Detailed parameters of the different steps of Process 4 are described below.

Primary Recovery

Primary recovery by centrifugation and depth filtration was used to remove cells and cell debris from the production bioreactor tank. The 3000 L production bioreactor served as the feed tank to a 710 Alpha Laval centrifuge. The centrifuge was run at a setpoint of 5555 rpm with a feed rate of 30 L/min and discharge interval, 215 seconds for GMP1 to GMP3, and 252 seconds for GMP4, respectively. The centrate was subsequently passed through a filter train of eighteen 1.1 $m^2$ Millipore XOHC media Pod units followed by two Sartopore 2 30-inch (1.8 $m^2$ each) 0.45 μm/0.2 μm capsule filters.

After the bioreactor harvest was centrifuged and depth filtered, the filters were flushed with a target weight of 396 kg of 50 mM Sodium Acetate, pH 5.5 buffer. Centrifugation and filtration of the harvest were performed as a single unit operation. The filtration was performed at ambient temperature (18-25° C.) in a fermentation suite. The harvest temperature was chilled to 18-22° C. with set point of 20° C. prior to filtration. The filtrate was collected in a 3000 L harvest tank, chilled to 2-8° C., and can be held up to 3 days.

MabSelect SuRe Protein A Chromatography

MabSelect SuRe Protein A chromatography was used to capture risankizumab Process 4 DS from the clarified harvest and to reduce the amount of process-related impurities. The MabSelect SuRe self-pack column (GE Healthcare) was 60 cm in diameter with a target volume of ~62.0 L (bed height of 21 to 23 cm). Operations were performed at ambient temperature (18-25° C.) in a fermentation suite with the process parameters shown below in Table 11A.

The MabSelect SuRe column was operated in bind and elute mode. Three cycles of MabSelect SuRe chromatography were required to process each batch. The column was equilibrated with 50 mM sodium acetate pH 5.5, then loaded to a 13 to 35 g of risankizumab per L of resin. There were three wash steps following loading. Wash 1 was 50 mM sodium acetate pH 5.5. Wash 2 was 50 mM Tris, 1 M arginine, pH 8.0, and Wash 3 was 50 mM sodium acetate pH 5.5. Elution was performed with 50 mM sodium acetate pH 3.5. The column was then regenerated with 0.2 M Sodium Hydroxide, and re-equilibrated with equilibration buffer prior to next cycle loading.

The load material (2-8° C.) was not warmed prior to being loaded onto the column. The eluate peak collection started at 0.2 OD ascending to 0.2 OD descending (280 nm wavelength, 1 mm path length). Eluate was entered into a 300 L portable stainless-steel tank or a 500 L single use mixing (SUM) system and then passed through a 0.45/0.2 μm filter offline and entered the collection vessel. One Sartopore 2 30-inch (1.8 $m^2$ each) 0.45 μm/0.2 μm capsule filter was used for eluate filtration. Each eluate filter was used for 3 cycles of daily MabSelect SuRe chromatography. The MabSelect SuRe eluate was collected in a 700 L portable stainless-steel tank or 1000 L single use mixing (SUM) system and can be held up to 1 day at 9-25° C. or up to 3 days chilled to 2-8° C. before proceeding to low pH Inactivation.

TABLE 11A

Summary of MabSelect SuRe Protein A Capture Parameters

| Process Step | Buffer Description | CV's CV = 62.0 L | Flow Rate (cm/hr) |
|---|---|---|---|
| Equilibration 1 | 50 mM Sodium Acetate pH 5.5 | 4.0 | 264 |
| Equilibration 1 | 50 mM Sodium Acetate pH 5.5 | 1.0 | 264 |
| Load | Clarified Harvest to 13-35 g/L | As calculated | 264 |
| Wash 1 | 50 mM Sodium Acetate pH 5.5 | 3.0 | 264 |
| Wash 2 | 50 mM Tris, 1M Arginine, pH 8.0 | 8.0 | 264 |
| Wash 3 | 50 mM Sodium Acetate pH 5.5 | 5.0 | 264 |
| Elution | 50 mM Sodium Acetate pH 3.5 | 5.0 | 264 |
| Regeneration | 0.2M NaOH | 5.0 | 264 |
| Post Regen Rinse | 50 mM Sodium Acetate pH 5.5 | 3.0 | 264 |
| Interim Storage | 50 mM Sodium Acetate, 2% Benzyl Alcohol, pH 5.0 | 5.0 | 264 |
| CIP | 0.5M NaOH | 3.0 | 264 |
| Storage | 50 mM Sodium Acetate, 2% Benzyl Alcohol, pH 5.0 | 5.0 | 264 |

pH Inactivation and POD Filtration

The purpose of the pH inactivation step was to inactivate adventitious viruses that may be present. The pH inactivation step was carried out at ambient temperature (18-25° C.) in a fermentation suite.

The pH of the Protein A eluate was adjusted to 3.5±0.1 (measured at 18-25° C.) with 0.5 M phosphoric acid. After a hold period of 60-90 minutes, the inactivated material was neutralized to pH 8.0±0.1 (measured at 18-25° C.) using 2.0 M Tris. The conductivity of the material should be in the range of 3.8 to 4.8 mS/cm (measured at 24-26° C.) for the subsequent filtration, thus dilution was not needed prior to POD filtration.

Depth filtration was used to remove particles and reduce impurity levels in the process stream. The filter train was comprised of two 1.1 $m^2$ Millipore DOHC media Pod units followed by five 1.1 $m^2$ Millipore XOHC media Pod units and a Sartopore 2 30-inch (1.8 $m^2$ each) 0.45 μm/0.2 μm capsule filter in GMP1 and GMP2. The quantity of DOHC filters and XOHC filters were reduced to one and four, respectively in GMP3 and GMP4 in order to increase the step yield. The filter train was equilibrated with approximately 37.5 L/$m^2$ of 25 mM Tris, 25 mM sodium chloride, pH 8.0, and then the contents of the feed tank were filtered. The filter train was subsequently rinsed with approximately 20.0 L/$m^2$ of 25 mM Tris, 25 mM sodium chloride, pH 8.0. The filtrate was collected in a 700 L portable stainless-steel tank or 1000 L SUM system and proceed to Capto Adhere chromatography on the same day.

Capto Adhere Chromatography

The Capto Adhere chromatography step was used to reduce impurity levels in the process stream. The column packed with Capto Adhere resin was 45 cm in diameter with a target volume of 19.1 L (bed height of 12 cm). Operations were performed at ambient temperature (18-25° C.) in a purification suite with the process parameters shown below in Table 11B.

The Capto Adhere column was operated in flow through mode. One cycle of Capto Adhere chromatography was required to process each batch. The column was first pre-equilibrated with 2 M sodium chloride, then equilibrated with 25 mM Tris, 25 mM sodium chloride, pH 8.0. The column was loaded from 150 to 300 g of risankizumab/L of resin and then washed with 260 mM Tris, pH 8.0. The column was regenerated with 0.1 M acetic acid, pH 2.9, and 2 M sodium chloride. The column was sanitized with 1 M sodium hydroxide after each batch and was stored in 0.1 M sodium hydroxide.

The load material was kept at 18-25° C. prior to being loaded onto the column. During the load, the product flow through was collected starting from 1OD on the peak front and ended collection at 5OD on the peak tail during Wash (280 nm wavelength, 1 mm path length). The Capto Adhere flowthrough was collected in a 1000 L portable stainless-steel tank or 1000 L SUM system.

The Capto Adhere FTW was adjusted to target pH 5.25 on the day of Capto Adhere chromatography. To prepare the Poros XS load, the Capto Adhere FTW material is titrated to pH 5.25+0.1 (measured at 18-25° C.) using 2 M acetic acid and the conductivity adjusted to 4.5 to 7.5 mS/cm with WFI if needed. The adjusted Capto Adhere FTW was filtered by one Sartopore 2 30-inch (1.8 $m^2$) 0.45 μm/0.2 μm capsule filter. The filtered adjusted Capto Adhere FTW can be held up to 1 day at 9-25° C. or up to 3 days chilled to 2-8° C. before proceeding to Poros XS chromatography.

TABLE 11B

| Summary of Capto Adhere Chromatography Parameters | | | |
|---|---|---|---|
| Process Step | Buffer Description | CV's CV = 19.1 L | Flow Rate (cm/hr) |
| Pre-Equilibration | 2M Sodium Chloride | 2.0 | 160 |
| Equilibration | 25 mM Tris, 40 mM NaCl, pH8.0 | 6.0 | 160 |
| Load | Capto Adhere Load (150-300 g/L) | As calculated | 160 |
| Wash | 260 mM Tris, pH8.0 | 8.0 | 160 |
| Regen 1 | 0.1M Acetic Acid, pH2.9 | 5.0 | 160 |
| Rinse 1 | WFI | 1.0 | 160 |
| Regen 2 | 2M Sodium Chloride | 8.0 | 160 |
| Rinse | WFI | 1.0 | 160 |
| Sanitization | 1.0M NaOH Hold 60-90 Minutes | 5.0 | 160 |
| Storage | 0.1M NaOH | 5.0 | 160 |

Poros XS Chromatography

The Poros XS chromatography step was used to reduce basic species and process related impurities such as host cell proteins and leached Protein A. The column packed with Poros XS resin was 60 cm in diameter with a target volume of 56.5 L (bed height of 20 cm). Operations were performed at ambient temperature (18-25° C.) in a purification suite with the process parameters shown below in Table 11C.

The Poros XS column was operated in bind and eluate mode. Two cycle of Poros XS chromatography was required to process each batch. The column was equilibrated with 50 mM sodium acetate, 31 mM sodium chloride, pH 5.25. The loading range for the column was 25 to 50 g of risankizumab/L of resin. The wash step was 50 mM sodium acetate, 31 mM sodium chloride, pH 5.25. Elution was performed with 50 mM sodium acetate, 181 mM sodium chloride, pH 5.25. While the elution buffer pH for GMP1 to GMP3 was close to the target, the elution buffer pH for GMP4 was adjusted to 5.34, the higher end of the elution pH batch record range (5.15-5.35) using 5 M sodium hydroxide to improve the Poros XS step yield. The column was regenerated with 25 mM Tris, 3 M sodium chloride, pH 8.5 prior to next cycle. Lastly, the column was sanitized with 1.0 M sodium hydroxide, and stored in 0.1 M sodium hydroxide. The column was sanitized and stored at the end of the last cycle for each batch run.

The Poros XS load was filtered with one Sartopore 2 30-inch (1.8 $m^2$ each) 0.45 μm/0.2 μm capsule filter on the day of Poros XS chromatography. The eluate peak collection started from 1OD on the peak front and ended collection at 5OD on the peak tail during elution (280 nm wavelength, 1 mm path length). Eluate was passed through a 0.45/0.2 μm filter as it exited the chromatography skid and entered the collection vessel using two Sartopore 2 30-inch (1.8 $m^2$ each) 0.45 μm/0.2 μm capsule filter for eluate filtration. The filter was used for 2 cycles of Poros XS chromatography on the same process day. The Poros XS eluate was collected in a 500 L portable stainless-steel tank or 1000 L SUM system and can be held at 2-25° C. for up to 5 days before proceeding to Nanofiltration.

TABLE 11C

| Summary of Poros XS Chromatography Parameters | | | |
|---|---|---|---|
| Process Step | Buffer Description | CV's CV=56.5 L | Flow Rate (cm/hr) |
| Equilibration | 50 mM Sodium Acetate, 31 mM Sodium Chloride, pH 5.25 | 5.0 | 300 |
| Load | Poros XS Load (25-50 g/L) | As calculated | 218 |
| Wash | 50 mM Sodium Acetate, 31 mM Sodium Chloride, pH 5.25 | 5.0 | 218 |
| Elution | 50 mM Sodium Acetate, 181 mM Sodium Chloride, pH 5.25 | 5.0 | 218 |
| Regeneration | 25 mM Tris, 3M Sodium Chloride, pH 8.5 | 3.0 | 300 |
| Sanitization | 1.0M NaOH Hold 60 Minutes | 5.0 | 300 |
| Storage | 0.1M NaOH | 5.0 | 300 |

Viral Filtration

The viral filtration provided the capability to remove adventitious viruses that were greater than 20 nm in size. The process was carried out at ambient temperature (18-25° C.) in a purification suite.

The viral filtration filter train consisted of two Millipore Virosolve Pro Magnus 2.1 Shield (0.51 $m^2$ each) 0.1 μm capsule filters in parallel, two Millipore Virosolve Pro Magnus 2.1 filters (0.51 $m^2$ each) in parallel, and a single Sartopore 2 30-inch (1.8 $m^2$) 0.45 μm/0.2 μm capsule filter. Prior to product filtration, each pre-filter and Virosolve nanofilter were flushed with ≥102 L of WFI, and then flushed with ≥26 L with 50 mM sodium acetate, 181 mM sodium chloride, pH 5.25. Filtration of the product was performed utilizing a quattroflow pump, with a target nanofilter pressure of 23 psig, and an upper limit of 32 psig. The post filtration flush was 20 L of 50 mM sodium acetate, 181 mM sodium chloride, pH 5.25. The viral filtrate can be held for up to 5 days at 2-25° C.

UF/DF

The UF/DF step was used to concentrate the product and diafilter it into the final formulation buffer. The process utilized 30 kD Millipore Pellicon3 Biomax UF Modules, D Screen and was performed at ambient temperature (18-25° C.) in a purification suite with the process parameters shown below in Table 11 D.

The load material was diluted with 5 M sodium chloride in 10× dilution (9 part of nanofiltrate to 1 part of 5 M sodium chloride), and then the pH of the load material was adjusted to 5.45±0.1 (measured at 18-25° C.) with 2 M sodium acetate. The adjusted load material was filtered by a single Sartopore 2 30-inch (1.8 $m^2$) 0.45 μm/0.2 μm capsule filter into the recirculation tank prior to loading to the UF/DF membranes.

UF/DF was carried out on Skid Z-2300 with eight 1.14 $m^2$ membranes, for a total of 9.12 $m^2$ of membrane area. The UF/DF load was concentrated to a target of 50 g/L, then diafiltered with 0.002% (w/v) sodium chloride followed with concentration to 235 g/L. The retentate was passed through a single Sartopore 2 10-inch 0.45/0.2 μm (0.45 $m^2$) sterile filter as it was removed from the ultrafiltration membranes and system and entered the collection vessel, 100 L Impulse Mixer system. The ultrafiltration system was rinsed with approximately 5 kg of 0.002% sodium chloride to recover product held up in the system. Both rinse 1 and rinse 2 were transferred through the same Sartopore 2

10-inch 0.45/0.2 μm (0.45 $m^2$) sterile filter into the Rinse 1 collection bag and Rinse 2 collection bag separately. After rinsate recovery, the retentate was diluted with the appropriate amount of Rinse 1 and Rinse 2 to achieve the concentration target of 200 g/L.

The retentate pool was formulated with the addition of 5× formulation buffer, 50 mM acetate, 925 mM Trehalose, 0.1% Tween 20, pH 5.70. Final bulk drug substance was diluted to 150 g/L Risakizumab in 1× formulation buffer, 10 mM acetate 185 mM Trehalose, 0.02% Tween 20, pH 5.70. The formulated UF/DF retentate was then filtered through 0.22 μm Millipak 200 sterile filter (0.1 $m^2$). The final formulated UF/DF retentate may be held up to 1 day at 9-25° C., and up to 5 days chilled at 2-8° C. before proceeding to the final bagging step.

TABLE 11D

Process Description for Ultrafiltration/Diafiltration

| Process Step | Concentrate Target (g/L) | Volume | TMP (psig) | Feed Flow Rate Target (L/min/$m^2$) |
|---|---|---|---|---|
| UF1 | 50 | | 10-20 (Target 15) | 6 |
| DF1 | | 8 DVs | | 6 |
| UF2 | 235 | | 10-20 (Target 15) | 6 [a] |
| Rinse 1 | | 2 kg | 10-20 (Target 15) | |
| Rinse 2 | | 2 kg | 10-20 (Target 15) | |
| UF/DF Retentate with Rinse | 200 | | 10-20 (Target 15) | |
| Formulation and Dilution | 150 | | | |

[a] UF2 flow rate needs to decrease over the course in order to keep TMP in range.

Bagging

The purpose of Bagging was to package and store the final bulk drug substance. Operation was performed at ambient temperature (18-25° C.) in a purification suite. The filtered formulated UF/OF retentate was pumped into sterile 6 L Celsius FFT bags. The bags were filled to a volume of approximately 6 kg.

Process 4 parameter targets are summarized in Table 11E below.

TABLE 11E

Process 4 Parameter Targets

| Unit Operation | Operational Parameters | Parameter Targets |
|---|---|---|
| Primary Recovery | Harvest Batch Size | 3000 L |
| | Centrifuge g-force | 7024 g |
| | X0HC POD Area | 19.8 $m^2$ |
| | Sartopore 2 0.45 μm/0.2 μm Filter Area | 3.6 $m^2$ |
| | Rinse Buffer | 50 mM Sodium Acetate pH 5.5 |
| | Clarified Harvest Protein Concentration | 2.0 g/L |
| Protein A Chromatography | Resin | MabSelect SuRe Protein A |
| | Column Size | 60 cm (ID) × 22 cm (L) |
| | Equilibration and Wash 1 Buffer | 50 mM Sodium Acetate pH 5.5 |
| | Wash 2 Buffer | 50 mM Tris, 1M Arginine, pH 8.0 |
| | Elution Buffer | 50 mM Sodium Acetate pH 3.5 |
| | Resin Loading | 15-35 g/L |
| | Load, Wash1, Elution Flow Rate | 264 cm/hr |
| | Protein A Eluate Concentration | ~20 g/L |
| Low pH Viral Inactivation | Low pH Buffer | 0.5M Phosphoric Acid |
| | Protein A Eluate Inactivation pH | 3.4-3.6 |
| | Low pH Hold Time | 60-90 minutes |
| | Neutralization Buffer | 2M Tris |
| | Neutralization pH | pH 8.0 |
| | D0HC Area | 1.1 $m^2$/2.2 $m^2$ |
| | XOHC POD Area | 5.5 $m^2$/4.4 $m^2$ |
| Mixed Mode Chromatography | Load Protein Concentration | ~15 g/L |
| | Resin | Capto Adhere |
| | Column Size | 45 cm (ID) × 12 cm (L) |
| | Equilibration | 25 mM Tris, 25 mM NaCl, pH 8.0 |
| | Wash Buffer | 260 mM Tris, pH 8.0 |
| | Resin Loading | 150-300 g/L |
| | Load and Wash1a Flow Rate | 160 cm/h |
| | Capto Ahdere Flow Through Concentration | ~13.5 g/L |
| Cation Exchange Chromatography | Resin | Poros XS column |
| | Column Size | 60 cm (ID) × 20 cm (L) |
| | Load pH | pH 5.25 |
| | Load Conductivity | 4.5-7.5 mS/cm |
| | Equilibration/Wash Buffer | 50 mM NaAc, 31 mM NaCl, pH 5.25 |
| | Resin Loading | 25-50 g/L |
| | Elution Buffer | 50 mM NaAcetate, 181 mM NaCl, pH 5.25 |
| | Load, Wash and Elution Flow Rate | 218 cm/h |
| Viral Filtration | Load Protein Concentration | ~13.0 g/L |
| | Loading Throughput (g/L) | ≤7800 g/$m^2$ |
| | Loading Throughput (L/$m^2$) | ≤600 L/$m^2$ |
| | Virosolve Magnus Shield Pre-filter Area | 1.02 $m^2$ |
| | Virosolve Magnus Shield Pre-filter Pressure | ≤60 psi |
| | Virosolve Magnus Area | 1.02 $m^2$ |
| | Virosolve Magnus filter Pressure | ≤32 psi (Target 23 psi) |
| | Rinse Buffer | 50 mM NaAcetate, 181 mM NaCl, pH 5.25 |
| | Viral Filtrate Protein Concentration | ~12 g/L |
| Ultrafiltration/Diafiltration | UF Membrane | 30 kD Pellicon 3 Biomax membranes, D Screen (Millipore) |
| | 30 kD Pellicon 3 Biomax Membranes Area | 9.12 $m^2$ |
| | Membrane Loading (g/$m^2$) | 200-500 |
| | Protein Concentration at Diafiltration | 50 g/L |
| | Diafiltration Buffer | 0.002% NaCl |
| | Diafiltration Volume | 8 diavolumes |
| | Formulated Bulk Drug Substance | 150 g/L |
| | Bagging: Millipak 200 Sterile Filter | Bagging: 0.1 $m^2$ |
| Filling, Storage, and Transportation | Storage Container | Bagging: 6 L Celsius FFT Bags |
| | Target Fill Volume | Bagging: 6 L |

Risankizumab produced with Process 3 and Process 4 were formulated to generate drug product 3 (DP3) and drug product 4 (DP4), respectively, according to the Table 12 shown below.

TABLE 12

| Drug products | Risankizumab purification processes | Formulations |
|---|---|---|
| Drug Product 3 (DP3) | Process 3 | Risankizumab 150 mg/mL<br>Sodium acetate trihydrate 1.24 mg/mL<br>Acetic acid 0.054 mg/mL<br>Trehalose dihydrate 70.0 mg/mL<br>Polysorbate 20 0.20 mg/mL<br>Water for Injections (WFI)<br>pH 5.7 |
| Drug Product 4 (DP4) | Process 4 | Risankizumab 150 mg/mL<br>Sodium acetate trihydrate 1.24 mg/mL<br>Acetic acid 0.054 mg/mL<br>Trehalose dihydrate 70.0 mg/mL<br>Polysorbate 20 0.20 mg/mL<br>Water for Injections (WFI)<br>pH 5.7 |

No visible or glittering particles were observed for the 60 mg/ml presentation of DP3 over 24-month stability at 4° C. The 51 mg/ml presentation further confirmed the increased stability of DP3 compared to DP2.

Glittering particles were observed at 3 months in the 51 mg/mL presentation of DP2 (Table 7), whereas no visible product-related particles were observed in the 51 mg/mL presentation of DP3 at 6 months.

Similarly, no visible or glittering particles were observed for the 60 mg/mL presentation of DP4 vial over 18-month stability at 4° C.

Example 4: PLA2 Identification by LC-MS Proteomics

Several types of phospholipases, including phospholipase A2 Group XV (PLA2 G15), have been identified as potential factors contributing to polysorbate 20 degradation. These lipases can occur in very low abundance in DS, complicating detection by LC-MS/MS. Enriching lipase levels with immunoaffinity purification, using immobilized antibodies to specific lipases, can increase the abundance levels needed for detection by LC-MS/MS. In this study, immunoaffinity purification was utilized to enrich PLA2 in DP1, DP2, DP3, and DP4 DS. The enriched DS was analyzed by enzyme-linked immunoassay (ELISA) and LC-MS/MS.

Multiple batches of DS were pooled to generate material for the PLA2 enrichment. The protein concentrations of each DS pool are shown in Table 13.

TABLE 13

| Risankizumab concentration in the DS Pools<br>Risankizumab concentration, mg/mL | | | |
|---|---|---|---|
| DP1 | DP2 | DP3 | DP4 |
| 91.12 | 153.83 | 152.73 | 151.73 |

1. Immunoaffinity Purification (Chromatography) for PLA2 a. Buffer Exchange for PLA2 Antibody (a) Buffers:

(1) Acidification buffer: 1 mM HCl;

(2) Coupling buffer: 200 mM $NaHCO_3$; 500 mM NaCl, pH=9.0;

(3) Blocking buffer: 1 M ethanolamine; pH=8.0;

(4) Wash buffer: 100 mM sodium acetate; 500 mM NaCl, pH=4.0;

(5) PLA2 antibody: 1 mg/mL.

(b) Buffer Exchange for PLA2 Antibody.

3.5 μg of PLA2 antibody was thawed at room temperature. The Slide-A-Lyzer™ dialysis cassette 10K MWCO (Thermo Fisher Scientific, catalog #66810) was used to exchange PLA2 antibody buffer with coupling buffer. The dialysis cassette was floated in 4 L coupling buffer over night at 4° C. at 60 rpm. Buffer exchanged PLA2 antibodies were collected into a clean microtube and proceed to section B described below.

B. Conditioning Cyanogen Bromide (CNBR) Activated Sepharose Beads 0.5 g of CNBR activated Sepharose beads (Cytiva, catalog #71-5000-15 AF) were weighed and the beads were filled into a poly-Prep chromatography column (Bio-Rad, catalog #731-1550). The beads were suspended in 5 mL ice-cold 1 mM HCl solution. The column was inverted to ensure the beads were fully hydrated (approximately 10 minutes). The column was placed into a 15 mL conical tube and centrifuged at 200 g (Beckman Avanti J-15R) for 7 minutes to dry the beads. The preceding two steps were repeated to wash the beads three additional times in the ice-cold 1 mM HCl solution. The beads were kept dry after the wash step.

C. PLA2 Antibody Coupling

The concentration of buffer exchanged PLA2 antibodies was determined from section A using Lunatic UV/Vis polychromatic spectrophotometer with the extinction coefficient of 1.0 M-1 cm-1 (E1%=10). The concentration of PLA2 antibody was 0.78 mg/mL before coupling with CNBR Sepharose beads. 4 mL PLA2 antibody was added to the column filled with CNBR Sepharose beads. Coupling buffer was used to increase the volume of PLA2 antibody up to 4 mL if needed. The column was placed on a bench rocker and rocked at low speed overnight at 4° C. to complete coupling antibodies with beads. The column was centrifuged to remove unbound antibodies at 200 g for 7 minutes. The concentration of PLA2 antibody remaining in the column filtrate was determined. The concentration of PLA2 antibody remaining in the filtrate was 0.01 mg/mL. 5 mL blocking buffer was added in the column and the column was rocked at low speed overnight at 4° C. The column was centrifuged to remove the blocking buffer at 200 g for 7 minutes. 5 mL coupling buffer was added in the column and the column was centrifuged at 200 g for 7 minutes to remove the buffer, and this step was repeated three additional times. 5 mL wash buffer I was added in the column and the column was centrifuged at 200 g for 7 minutes to remove the buffer. This step was repeated three additional times for further washing. 5 mL PBS buffer was added to condition the column and the column was centrifuged at 200 g for 7 minutes to remove the buffer, and this step was repeated and the beads were kept suspended in 5 mL PBS buffer. The column was kept at 4° C. if not proceeding to the next step.

D. Packing the Immunoaffinity Column for PLA2 Enrichment

A Tricorn 5/50 column (Cytiva, catalog #28406409) was rinsed in 20% ethanol for at least 1 minute at room temperature. The column volume (CV) is approximately 1 mL. The beads (coupled with PLA2 antibodies) were transferred from the poly-Prep chromatography column to the Tricorn 5/50 column. Agitation was minimized to avoid the introduction of air bubbles while packing the Tricorn column with the beads. The immunoaffinity column was equilibrated with 20 CV PBS, pH 7.4, at 0.5 mL/minute. The immunoaffinity column was used in the next steps described below or stored at 4° C. until use.

E. PLA2 Elution for DS Samples a. PLA2 Enrichment 4.5 g of each DS sample in 5 aliquots were prepared to load onto the immunoaffinity column. One aliquot was used per circulation. DP1: 10 mL per aliquot, 50 mL in total; DP2: 6 mL per aliquot, 30 mL in total; DP3: 6 mL per aliquot, 30 mL in total; DP4: 6 mL per aliquot, 30 mL in total. The column was equilibrated with 10 CV PBS, pH 7.4. One aliquot of DP1 BDS sample was recirculated through the immunoaffinity column at 0.5 mL/minute for 40 minutes. The column was washed with 20 CV PBS, 0.05% Tween 20, pH 7.4 at 0.5 mL/minute. The recirculating and washing steps were repeated in this section for the additional 4 aliquots of DS. The column was eluted with 10 CV 100 mM glycine, 400 mM arginine-HCl, pH 2.7 at 0.5 mL/minute into a 10 mL conical tube. The elute was immediately neutralized with 1.5 mL 1 M Tris-HCl, pH 8.5. The enriched sample was kept on ice through this procedure. The neutralized eluate was confirmed to be approximately pH 7.0 using a pH strip. The eluting and neutralizing steps were repeated for each DS pool.

F. Concentration of the Enriched Samples

Each eluate was transferred to an Amicon concentrator (3K MWCO, 15 mL; Millipore, catalog #UFC900324), and centrifuged at 4,000 g for an hour at 4° C. The protein concentration in the concentrated, neutralized eluates was measured by A280 using a Lunatic UV/Vis polychromatic spectrophotometer (E1%=15.2).

2. PLA2 ELISA

PLA2 concentration was measured by ELISA as described in other embodiments described herein.

A. Analysis of ELISA Results

The results show that PLA2 was enriched by 92-fold in DP1, 57-fold in DP2, and 80-fold in DP3. No PLA2 was detected in DP4 samples (Table 14).

TABLE 14

PLA2 concentrations and enrichment fold

| Sample | Initial PLA2 (ng/mg) | Final PLA2 (ng/mg) | Fold Enrichment |
|---|---|---|---|
| DP1 DS | 0.54 | 49.41 | 92 |
| DP2 DS | 0.59 | 33.68 | 57 |
| DP3 DS | 0.27 | 21.52 | 80 |
| DP4 DS | N/A* | N/A* | N/A** |

*The lower limit of quantitation of the assay is 0.328 ng/mL. Samples were diluted at minimum required dilution (2-fold) which was included in the LOQ calculation.
**Protein concentration (absorbance280) was not provided, therefore normalized PLA2 concentration cannot be reported (ng/mg).

3. LC-MS/MS Method for PLA2 Identification

A. Sample Denaturation and Reduction

8 M urea was added to 20 μg of each eluate sample to reach a urea concentration of 6 M. 1 M DTT was added to reach 10 mM. Each eluate sample was incubated at 37° C. for 30 minutes with 450 rpm shaking.

B. Sample Alkylation and Digestion

200 μL 8 M urea was added to 0.5 mL 30 kDa MWCO centrifugal filter (Millipore, catalog #MRCFOR030). The reduced sample was then added to the filter and centrifuged at 14,000×g for 15 minutes. 400 μL 8 M urea was added to the filter and the filter was centrifuged at 14,000×g for 15 minutes. The flow-through was discarded from the collection tube. 100 μL 50 mM iodoacetamide solution was added and mixed at 600 rpm in a thermo-mixer for 1 minute and incubated without mixing for 20 minutes at room temperature. The filter was centrifuged at 14,000×g for 10 minutes. 100 μL 8 M urea was added to the filter and centrifuged at 14,000×g for 15 minutes. This step was repeated once. 100 μL 50 mM ammonium bicarbonate was added to the filter unit and centrifuged at 14,000×g for 10 minutes. This step was repeated once. The filter was transferred to new collection tubes. 35 μL 50 mM ammonium bicarbonate was added and then 1 μL 0.4 μg/uL trypsin (Thermo Scientific, catalog #90057, enzyme to protein ratio 1:50) was added and mixed at 600 rpm in thermo-mixer for 1 minute. The filter was incubated in a thermo-mix at 37° C. overnight. The tube was wrapped with parafilm to avoid evaporation. The filter was centrifuged the next day at 14,000×g for 10 minutes. 40 μL 50 mM ammonium bicarbonate was added, and the filter was centrifuged at 14,000×g for 10 minutes. The sample was acidified with formic acid to make sure pH<1. Peptide concentration was measured by Bradford colorimetric assay (Thermo Scientific, Catalog #23250).

C. LC-MS/MS Analysis

For each digested sample, 400 ng was injected onto a Waters AQCUITY UPLC M-class system with a Double nanoViper™ PepMap™ Neo column, 2 μm, C18, 75 μm×500 mm (Thermo Scientific, catalog #DNV75500PN) maintained at 50° C. A gradient of mobile phase A (0.1% formic acid in water) and mobile phase B (0.1% formic acid in acetonitrile), shown in Table 15 at a flow rate of 200 nL/minute was used to elute the peptides into the mass spectrometer.

TABLE 15

Gradient for LC-MS/MS analysis

| Time (minute) | Mobile Phase A (%) | Mobile Phase B (%) |
|---|---|---|
| 0 | 98 | 2 |
| 5 | 95 | 5 |
| 10 | 95 | 5 |
| 180 | 65 | 35 |
| 200 | 30 | 70 |
| 201 | 0 | 100 |
| 210 | 0 | 100 |

A Thermo Scientific Orbitrap™ Fusion™ Lumos™ mass spectrometer was used to acquire data operating in positive ion mode. The survey scan was performed with 240,000 resolutions from 400 to 1500 m/z with an Automatic Gain Control (AGC) target of 4e6 and max injection time of 50 ms. The monoisotopic masses with 2 to 7 plus charges were selected with a minimum intensity threshold of 2.5e4, then fragmented by higher-energy collisional dissociation (HCD). The cycle time is ~3 s. The data were searched against a CHO proteome database by Proteome Discoverer 3.0.

The nanoLC-MS/MS analysis identified PLA2G15 (UniProt ID: G3HKV9) in the eluate of enriched DS of DP1 and DP2 (≥2 unique peptides for protein identification) as shown in Table 16.

TABLE 16

PLA2G15 identification by IP-MS in the risankizumab BDS of Processes DP1, DP2, DP3, and DP4

| Process | Unique Peptides to PLA2G15 |
|---|---|
| DP1 | 8 |
| DP2 | 6 |
| DP3 | 1 |
| DP4 | 0 |

Conclusion

In this study, PLA2G15 proteins were successfully enriched by immunoaffinity purification and subsequently detected in DP1 and DP2 DS using LC-MS/MS. A single PLA2G15 unique peptide was detected in DP3, which is below the criterion required to identify a protein, and no PLA2G15 unique peptides were detected in DP4 DS. These findings align with the observed PS20 degradation during long term storage or at accelerated stability conditions in DP1 and DP2 DS, while PS20 degradation was not observed in DP3 and DP4.

Example 5: PLA2 Identification by Western Blot Analysis

The phospholipase A2 group XV (PLA2G15) levels in different risankizumab DS samples were also evaluated by Western Blot.

Risankizumab BDS samples were obtained by pooling batches of risankizumab DS produced by the same risankizumab processes. The samples were fairly depleted of risankizumab by ultrafiltration using an Amicon filter with a one hundred kDa molecular weight cut off. Two hundred microliters of pooled BDS sample was added to an Amicon filter and spun until one hundred microliters of filtrate was obtained. The filtrate, containing proteins of molecular weight below one hundred kDa, as well as some residual risankizumab were evaluated by Western Blot Analysis.

TABLE 17

| Risankizumab BDS Pooled Sample | Pooled Sample Concentration (mg/ml) |
|---|---|
| DP1 | 91.12 |
| DP2 #1 | 153.83 |
| DP2 #2 | 150.02 |
| DP3 | 152.73 |
| DP4 | 151.73 |

SDS-PAGE and Western Blot

Risankizumab samples and CHO PLA2G15 protein were run on a 4-12% SDS-PAGE. The proteins were transferred to a PVDF membrane and probed with a rabbit anti-PLA2G15 antibody. An anti-rabbit antibody conjugated to horseradish peroxidase was used as the detection reagent. The development was completed with a chromogenic TMB substrate.

Results

Figure 2:
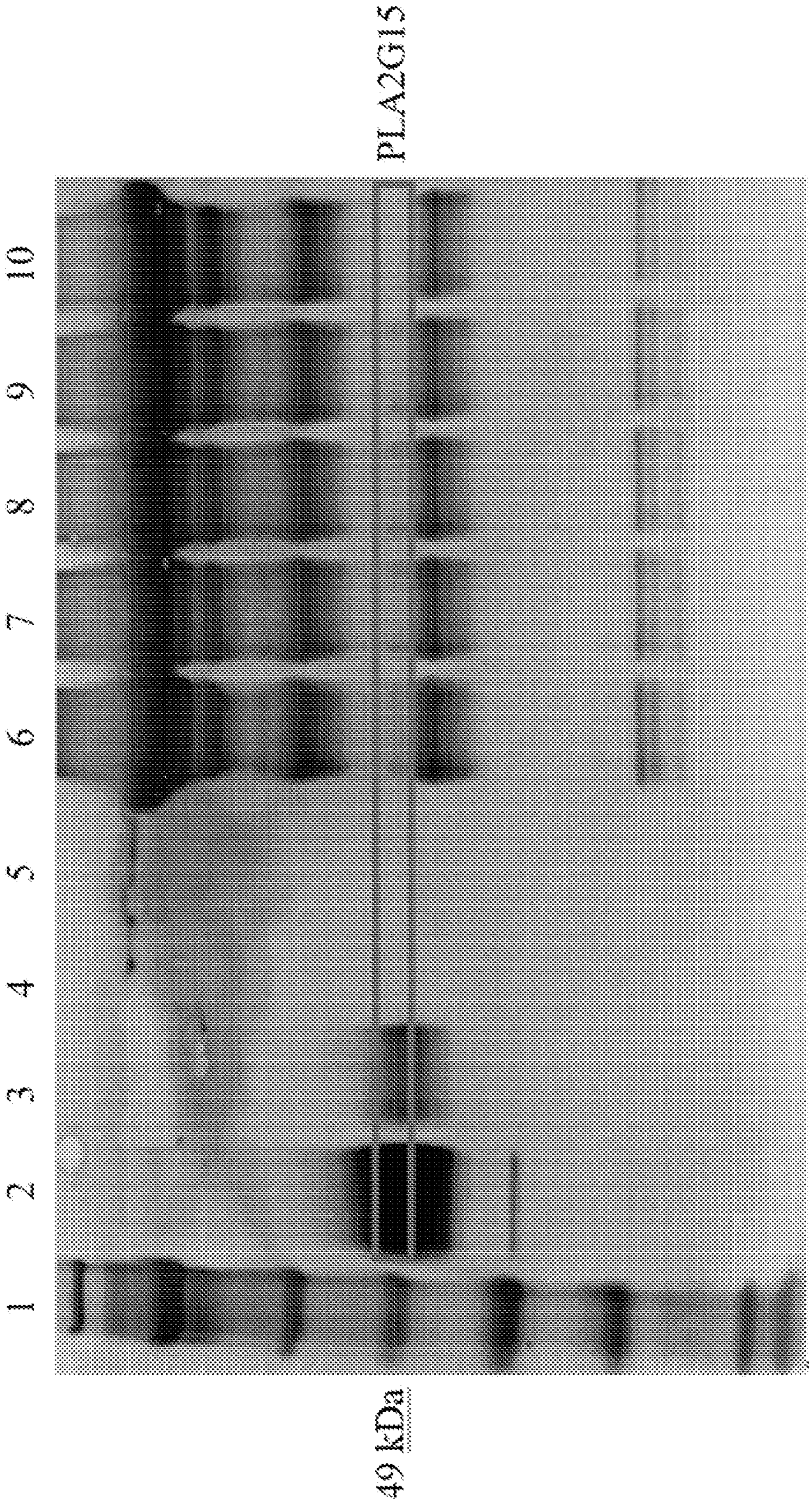
FIG. 2 shows Western Blot probed with anti-PLA2G15 antibody: Lane 1, MW standards; Lane 2, 1 ng PLA2G15 (MW: 47 kDa); Lane 3, 0.1 ng PLA2G15; Lane 6, DP1; Lane 7, DP2_#1; Lane 8, DP2_#2; Lane 9, DP3; and Lane 10, DP4.
Figure 3A:
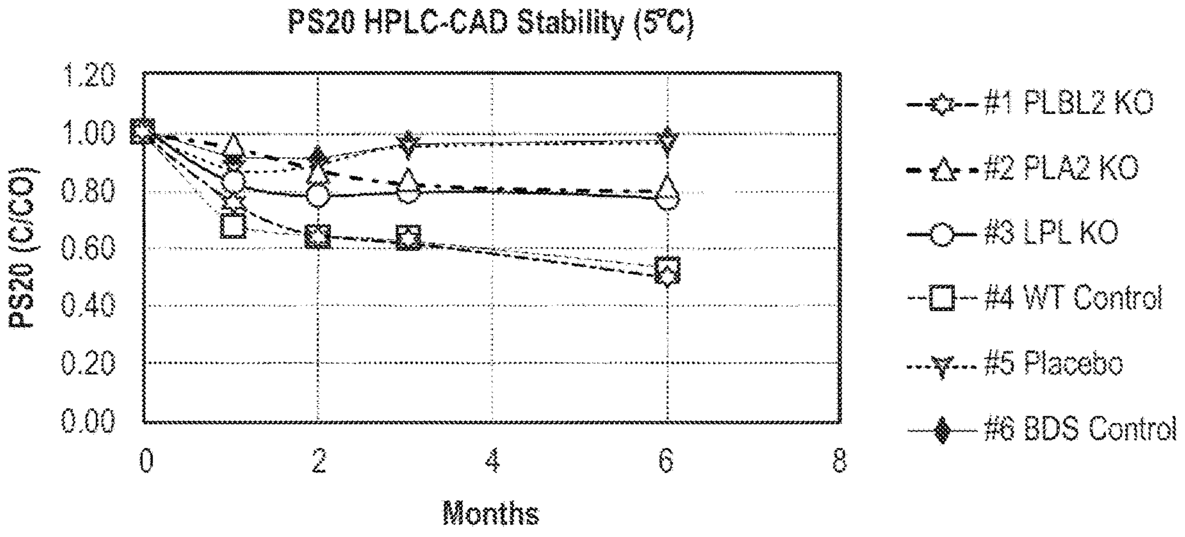
FIG. 3A shows PS20 stability at 5° C. in samples made from various control cell lines and knockout cell lines measured by CAD assay.
Figure 3B:
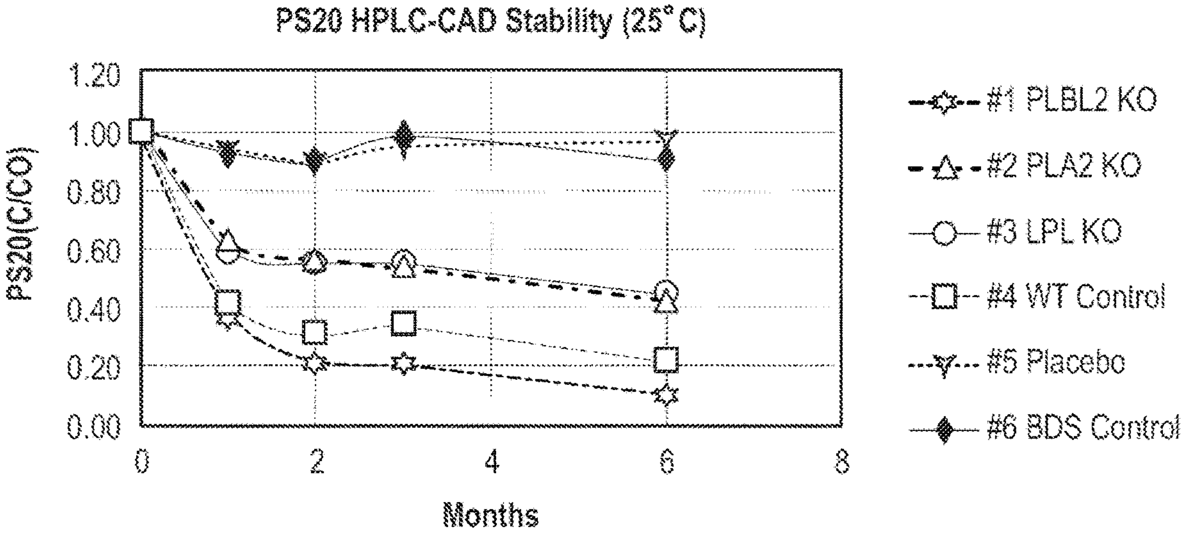
FIG. 3B shows PS20 stability at 25° C. in samples made from various control cell lines and knockout cell lines measured by CAD assay. #5 Placebo: PS20 control. #6: BDS Control: DP4 BDS.
Figure 3C:
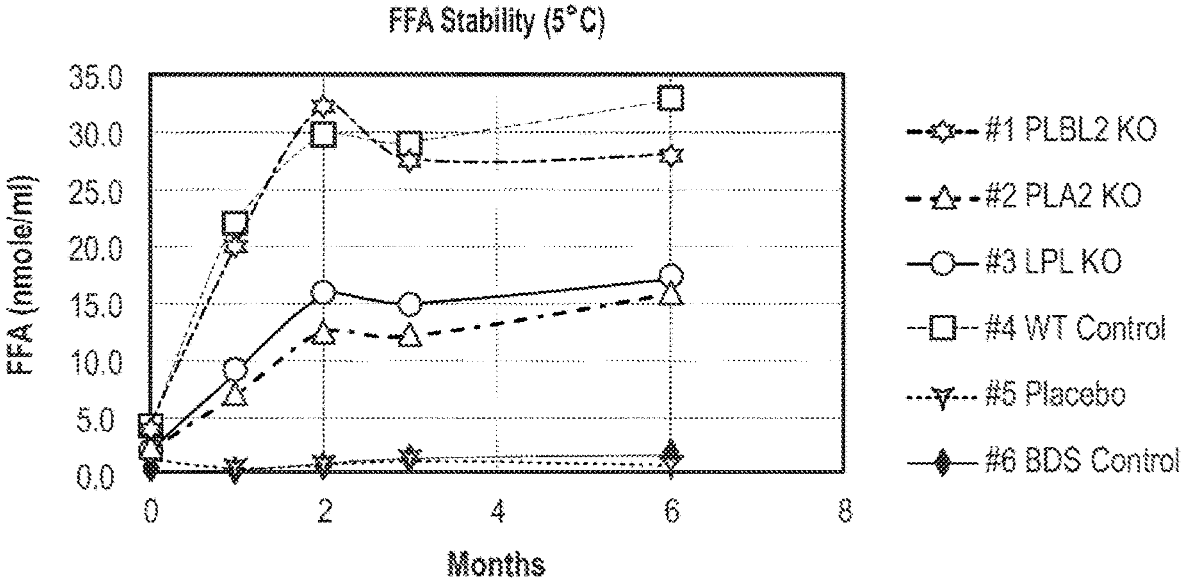
FIG. 3C shows PS20 stability at 5° C. in samples made from various control cell lines and knockout cell lines measured by FFA assay. #5 Placebo: PS20 control. #6: BDS Control: DP4 BDS.
Figure 3D:
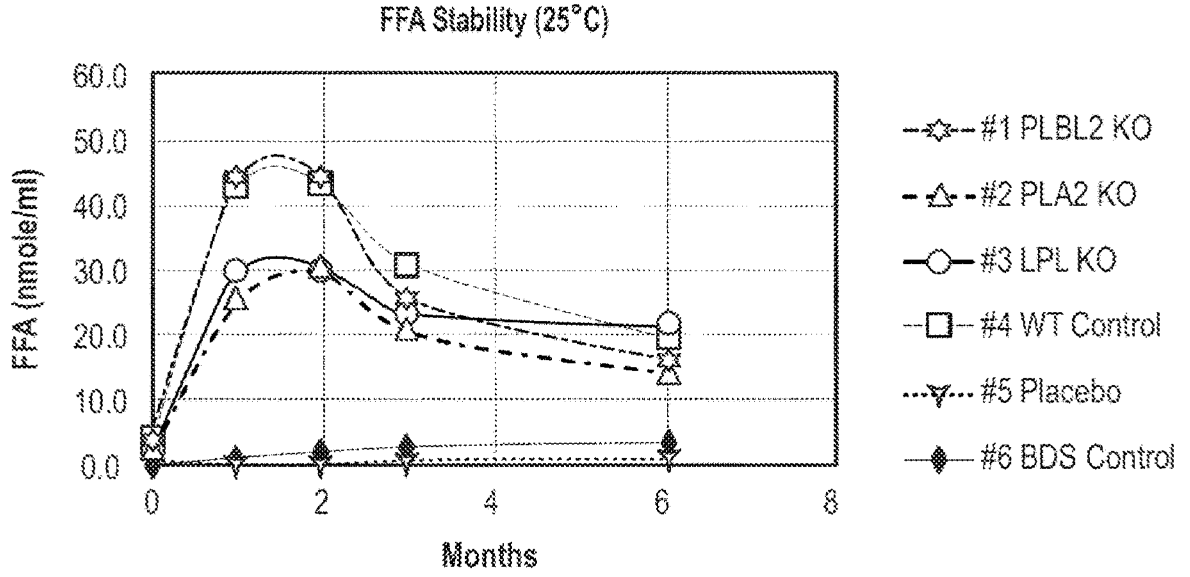
FIG. 3D shows PS20 stability at 25° C. in samples made from various control cell lines and knockout cell lines measured by FFA assay. #5 Placebo: PS20 control. #6: BDS Control: DP4 BDS.

The PLA2G15 band on the Western Blot at molecular weight 47 kDa were observed in all risankizumab BDS batches, except DP4, with slightly less observed in the DP3 batch (FIG. 2).

Example 6: Knockout Cell-Line Data Indicate that PLBL2 is not the Problematic Hitchhiker Protein To identify the specific hitchhiker proteins that led to the degradation of PS20, CHO cell lines with specific hitchhiker protein PLBL2, PLA2, or LPL depleted were generated and characterized.

Cell Line Development and Cell Culture Material Generation

CHO clones expressing risankizumab were established. Top two clones were pooled in equal parts and used as a starting cell source for CRISPR/Cas9 mediated gene knockout (KO) experiments, using a Ribonucleoprotein (RNP) based approach. In parallel work streams, three proteins of interest were targeted individually, with unique guides designed against their respective genes in the CHO genome: Phospsolipase B-Like 2 Protein (PLBL2; NCBI: 100769512), Phospholipase A2 Group XV (PLA2G15; NCBI: 100760699) and Lipoprotein Lipase (LPL; NCBI: 100689191). The respective KO pools were allowed to recover after CRISPR/cas9 RNP transfection and were then single cell cloned via limiting dilution plating method. Top clones, one per knock-out target, were selected based on phenotype (growth and productivity) and Next Generation Sequencing (NGS) data. Results from NGS analysis indicated the top PLBL2, LPL, and PLA2G15 knock-out clones had 0%, 0.13% and 20% wild-type sequence, respectively, present in the NGS preparations. Clones were then used for antibody production. The parental cell line (referred to as wild-type, wt), was used in parallel to generate relevant control material. Cell culture harvests were clarified by centrifugation, frozen on dry ice (for all conditions).

Purification Development

The PLBL2 KO, PLA2G15 KO, LPL KO and wild-type process control materials were thawed and purified using Process 1 (see Example 1), while ultrafiltration/diafiltration (UF/DF) followed Process 4 (see Example 3). The materials from each process stream were clarified through depth filtration, followed by protein-A affinity chromatography, depth filtration, anion exchange (AEX) chromatography, cation exchange (CEX) chromatography, UF/DF and formulation with PS20 addition at a target risankizumab protein concentration of 150 g/L. The in-process intermediates were submitted for product quality assessment. In addition to the four preparations from the purification process (3 KOs and wild-type control), a placebo control (negative control; 10 mM Acetate, 185 mM Trehalose, 0.02% Tween20, pH 5.70) and a DP4 BDS control (positive control that was purified by the Process 4, see Example 3) were also included in the PS20 stability study for up to 12-months that was set up at storage temperatures of 5° C., 25° C., and 40° C., respectively. High molecular weight (HMW) by size exclusion chromatography (SEC), charge variants by weak cation exchange chromatography (WCX), low molecular weight (LMW) by non-reduced capillary electrophoresis sodium dodecyl sulfate (CE-SDS), free fatty acids (FFA) and PS20 levels were monitored during the stability study at various time points.

Analytical Development

Antibody preparations derived from the knock-out samples and controls were tested for the presence of the three lipases by specific ELISA methods: PLBL2 and PLA2G15 were measured using CHO-specific in-house methods and LPL was measured using a commercial anti-mouse ELISA kit. PS20 stability was measured in samples that were incubated for different lengths of time (several time points over a 12-month period) and different temperatures (5° C., 25° C., 40° C.) using two different methods. One method measured the total amount of PS20 present in the sample; PS20 was quantified directly by using a RP-HPLC-CAD method. The other method assessed the breakdown of PS20 by measuring the amount of free fatty acid, mainly lauric acid that was released by hydrolysis. This was done using a RP-HPLC method with UV detection. The free fatty acids (FFAs) were labeled with PDAM (1-Pyrenyldiazomethane) for detection prior to analysis. The generated signal is directly proportional to the quantity of FFAs released. Risankizumab product quality was also assessed on the samples that were incubated at different time points and temperatures using SEC to measure % HMW, non-reduced CE-SDS to measure % LMW, and CEX to measure charge variants.

Results

The in-process mapping results have demonstrated that there were no impacts on the process performance and product quality across all the conditions tested. The observation at the 3-month (5° C., 25° C., and 40° C.) and 6-month time points (5° C., 25° C., and 40° C. storage conditions) versus study start (0-month) indicated that the absence of PLBL2 in BDS did not improve PS20 stability when compared to relevant process control conditions (FIGS. 3A-3D). These trends were observed in both the CAD and FFA assay results reported by the analytical development group (FIGS. 3A-3D). These data indicate that PLBL2 is unlikely the key hitchhiker protein responsible for PS20 degradation in risankizumab formulations.

TABLE 18

| Sample Description | | PLBL2 (pg/mg) | LPL (pg/mg) | PLA2 (pg/mg) | CAD @t0 (mg/mL) | FFA @ to (nmole/mL) |
|---|---|---|---|---|---|---|
| Lipase KO BDS Samples | #1 PLBL2 KO | 8.4 | 90 | 215 | 0.18 | 3.3 |
| | #2 PLA2G15 (80%) | 39503.1 | 70 | 218 | 0.17 | 0.5 |
| | #3 LPL | 25307.3* | 80 | 267 | 0.17 | 1.1 |
| | #4 CHOZN WT CTRL | 46889.3 | 90 | 184 | 0.18 | 2.7 |
| | #5 PS20 Control | N/A | N/A | N/A | 0.18 | <LOQ |
| | #6 DP4 BDS | N/A | N/A | N/A | 0.19 | <LOQ |

*Results from Poros XS eluate

Enzymes are among the hitchhiker proteins (HPs) present in drug substance, such as lipases, esterases, etc. The active site of an enzyme is composed of combination of amino acid residues with a certain structure, which varies among the different types of enzymes. As a result, enzymes usually have different activities and specificities towards different substrates. Since PS20 is a chemical mixture, different enzymes may have different degradation rates for the various components in PS20. The different enzymes, therefore, may lead to different PS20 degradation patterns (profiles). The degradation pattern analysis can therefore provide useful information in identifying certain groups of enzymes as potential root causes of PS20 degradation.

PLA2G15 Spiking Study in DP3 Material and Risankizumab Buffer

1. Methods

PS20-CAD subspecies method was used. This method was originally developed to qualitatively determine subspecies composition and to quantify the PS20 subspecies relative to a PS20 manufacturing standard. The HPLC system used in this study was an Agilent 1260 II infinity HPLC equipped with a quaternary pump, mobile phase degassing unit, refrigerated auto sampler, temperature controlled column compartment, and a Thermo Scientific charged aerosol detector (CAD). Data was collected by Waters Empower acquisition system. Methods for detecting PS20 using Charged Aerosol Detector (CAD) are also described in Example 10.

2. Study Design

Study design for PLA2G15 spiking study is shown in Table 19 below.

TABLE 19

| PLA2G15 spiking study at 25° C. | | | | | | | |
|---|---|---|---|---|---|---|---|
| Study Arms (vials; solution volume 1 mL) | Sample Type | $1^{st}$ injection | $2^{nd}$ injection | $3^{rd}$ injection | $4^{th}$ injection | $5^{th}$ injection | $6^{th}$ injection* |
| A1: DP3 (150 mg/ml + 1 μg/mL* PLA2G15) | A1 | Yes | Yes | Yes | Yes | Yes | Yes |
| B1: Risankizumab buffer for 150 mg/ml + 1 μg/mL PLA2G15 | B1 | Yes | Yes | Yes | Yes | Yes | Yes |
| C1: Expired DP2 material (150 mg/ml; PS20 degradation fingerprints reference) | C1 | Yes | No | No | No | No | Yes |
| D1: DP3 (150 mg/ml) (without spiking) | D1 | Yes | No | No | No | No | Yes |

*1 μg/mL was the final PLA2G15 concentration in solutions.

Example 7: Hitchhiker Protein Spiking Studies Indicate PLA2 as the Problematic Hitchhiker Protein PS20 consists primarily of polyoxyethylene sorbitan laurate acid esters. However, due to the nature of the manufacturing process, commercial PS20 is a mixture of oligomers that includes polyethylene glycols, polyethylene glycol esters, isosorbide polyethoxlates, sorbitan polyethoxylates, polysorbate monoesters, polysorbate diesters, and sorbitol polyethoxylate ester, etc. (Ayorinde et al. (2000) *Rapid Commun. Mass Spectrom* 14:2116-2124; Li et al. (2014) *Anal. Chem.* 86:5150-5157; Martos et al. (2017) *J. Pharm. Sci.,* 106:1722-1735). A commercial PS20 lot typically contains more than 3000 different chemical components.

Since the system takes 70 minutes to finish each injection (labeled as "injection" in Table 19), repeated injections measured the degradation patterns (profiles) at different incubation times. All samples were kept in a 25° C. autosampler during the entire test.

3. Result

Figure 4A:
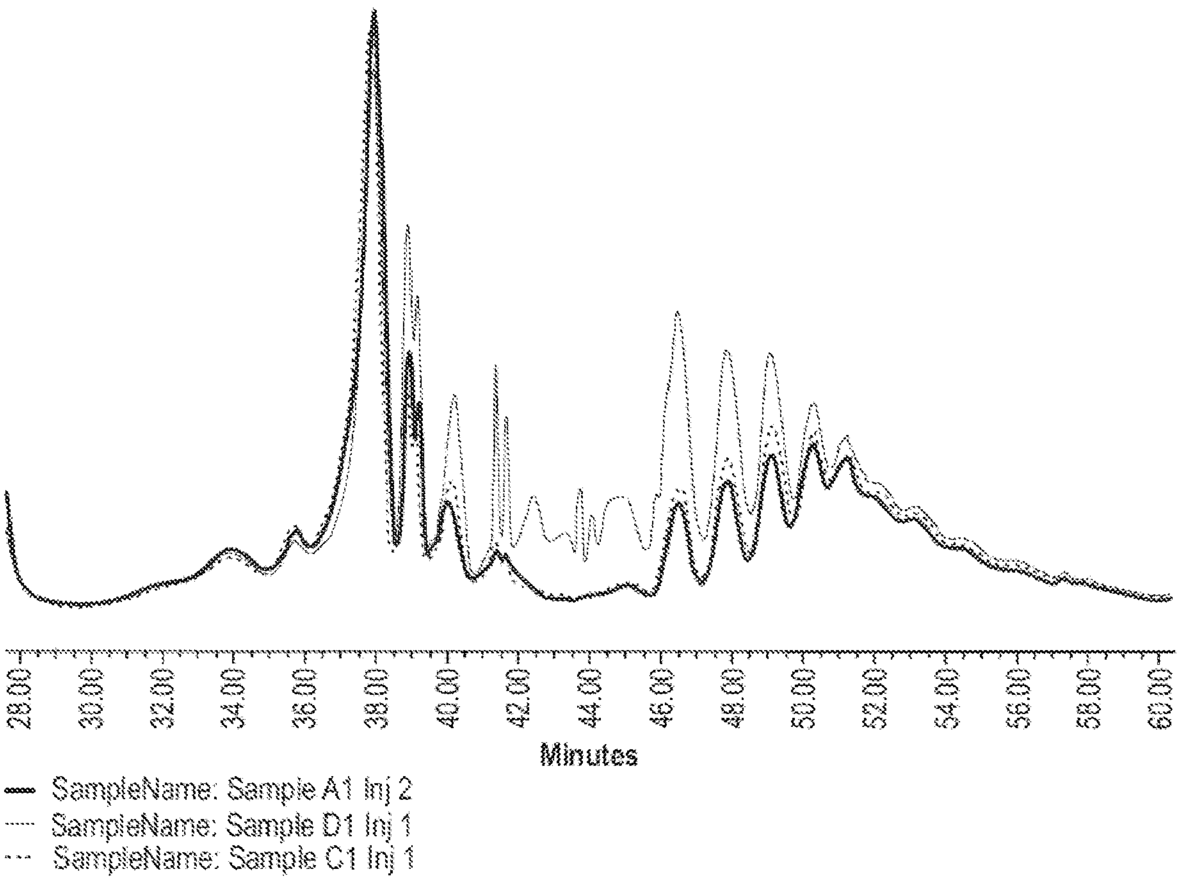
FIG. 4A shows PS20 subspecies chromatogram overlay of Sample C1 Injection 1 (DP2 after 30 months at 2-8° C.), Sample A1 Injection 2 (DP3 spiked with 1 μg/mL PLA2G15 after ~9 hours of incubation at room temperature and 25° C.), and sample D1 Injection 1 (DP3 material without spiking, no meaningful PS20 degradation).

The degradation profile of PS20 in DP3 spiked with PLA2G15 matched the PS20 degradation patterns (profiles) observed in diluted DP2 materials (FIG. 4A).

PLA2G15 Spiking Study at Various Spiking Levels in DP4 Material

1. Methods

PS20-CAD subspecies method described above was used.

2. Study Design

Study design for PLA2G15 spiking study is shown in Table 20 below.

TABLE 20

Study design for 8 Arms Spiked with Different Levels of PLA2G15

| | **PLA2G15 Spiking level in DP4 (ng/mg) | **PLA2G15 Spiking level in DP4 (μg/mL) |
|---|---|---|
| Arm1 | 0 | 0 |
| Arm2 | 0.01875 | 0.002813 |
| Arm3 | 0.0375 | 0.005625 |
| Arm4 | 0.075 | 0.01125 |
| Arm5 | 0.15 | 0.0225 |
| Arm6 | 0.3 | 0.045 |
| Arm7 | 0.6 | 0.09 |
| Arm8 | DP2 | |

**Different ways to label the PLA2G15 spiking levels (e.g., 0.3 ng/mg × 150 mg/mL risankizumab = 0.9 μg/mL final PLA2G15 concentration in the DP4 solution); Two types of labels were used here to compare ELISA data with spiking levels in this study.
All samples were incubated at 25°C.

3. Result

Figure 4B:
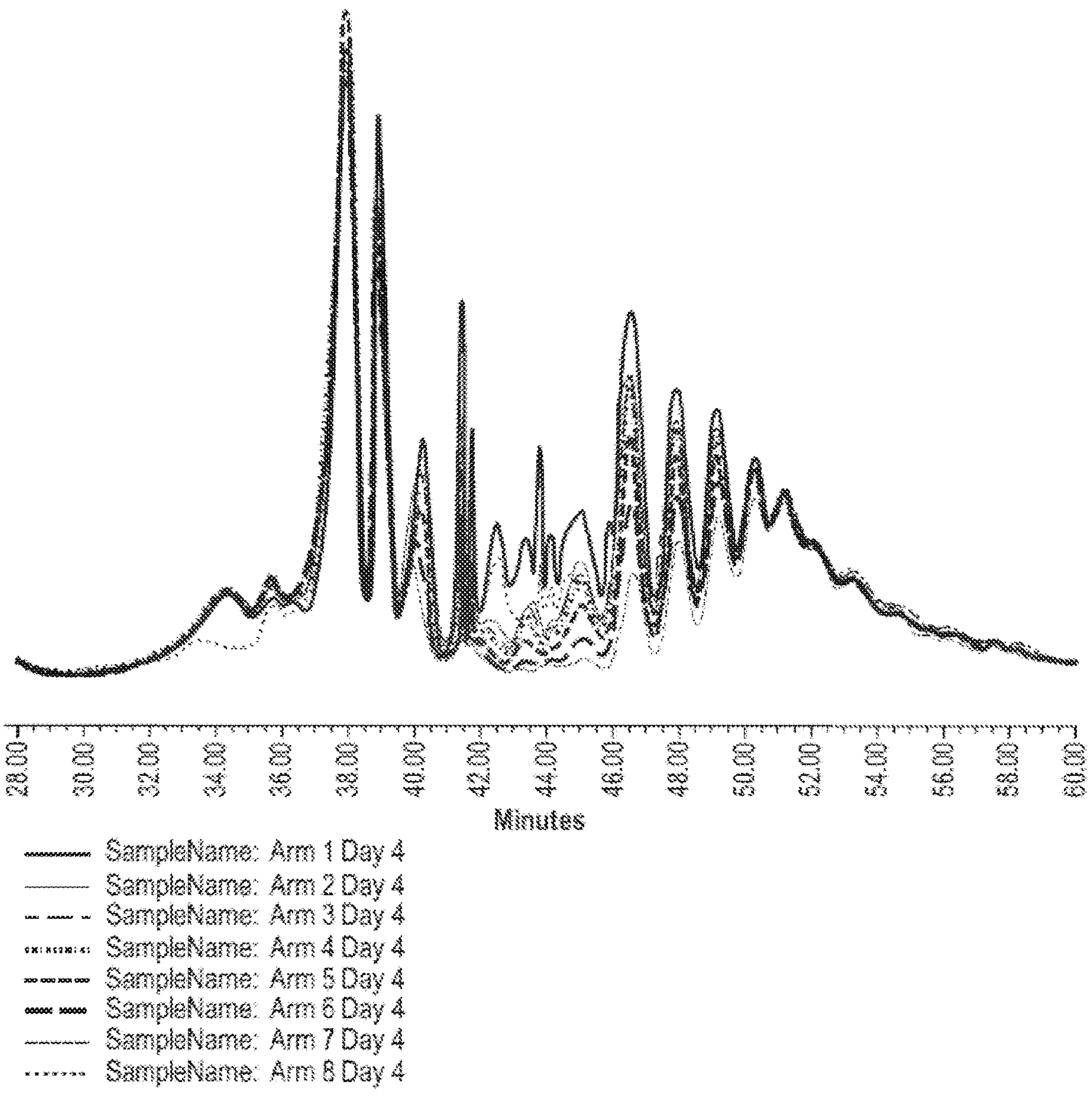
FIG. 4B shows PS20 subspecies chromatogram overlay of PS20 degradation in DP4 solutions at different PLA2G15 spiking levels (more sample information can be found in Table 20) after 4 days' incubation at 25° C. Arm 8 was a DP2 control sample. A small difference near 42 minutes in Arm 8 could be caused by leachables from a syringe filter used in this lab filling for this arm, since this peak was not observed in historical data.

PS20 subspecies data from T0, day 1, day 4 and day 11 25° C. incubated samples have been collected. All samples were kept at 5° C. in the autosampler during data collection. T0 to one month (1 M) PS20 concentration data have also been collected. The PLA2G15 spiking concentration dependent PS20 degradation rates were observed. PLA2G15 induced PS20 degradation patterns were very similar at all PLA2G15 spiking levels (FIG. 4B).

PLBL2 Spiking Study

1. Background

Phospholipase B-Like 2 protein (PLBL2) was detected in DP2 materials. Early literature reported that PLBL2 could induce PS20 degradation in antibody formulations. However, a very high concentration was used in the study (Dixit, et al, *Journal of pharmaceutical science,* 2016, 105:1657-1666). A recent publication suggested that it is very unlikely that PLBL2 is responsible for the PS20 degradation in antibody formulations due to its low activity (Zhang et al. *Journal of pharmaceutical science,* 2020, 109: 2710-2718).

2. Methods

PS20-CAD subspecies method described above was used.

3. Study Design

DP3 drug solution was spiked with 5 μg/mL PLBL2 enzyme. The solution was mixed and tested. All samples were studied at 25° C. The study design was similar to PLA2G15 spiking study in DP3 material as described above. More information regarding the study design is shown in Table 21A below.

TABLE 21A

Study design for PLBL2, CES and SIAE spiking studies

| Study Arms (vials; solution volume 1 mL) | Sample Type | $1^{st}$ injection | $2^{nd}$ injection | $3^{rd}$ injection | $4^{th}$ injection | $5^{th}$ injection | $6^{th}$ injection* |
|---|---|---|---|---|---|---|---|
| Arm 1: DP3/DP4 (150 mg/ml + 5 μg/mL PLBL2) | A3 | Yes | Yes | Yes | Yes | Yes | Yes |
| Arm 2: DP3/DP4 (150 mg/ml + 5 μg/mL CES | B3 | Yes | Yes | Yes | Yes | Yes | Yes |
| Arm3: DP3/DP4 (150 mg/ml+ 5 μg/mL Sialate O-acetylesterase) | C3 | Yes | Yes | Yes | Yes | Yes | Yes |
| Arm 4: Expired DP2 material (150 mg/ml; PS20 degradation fingerprints reference) | D3 | Yes | No | No | No | No | Yes |
| Arm 5: DP3/DP4 (150 mg/ml) (without spiking) | E3 | Yes | No | No | No | No | Yes |

4. Result

Figure 5:
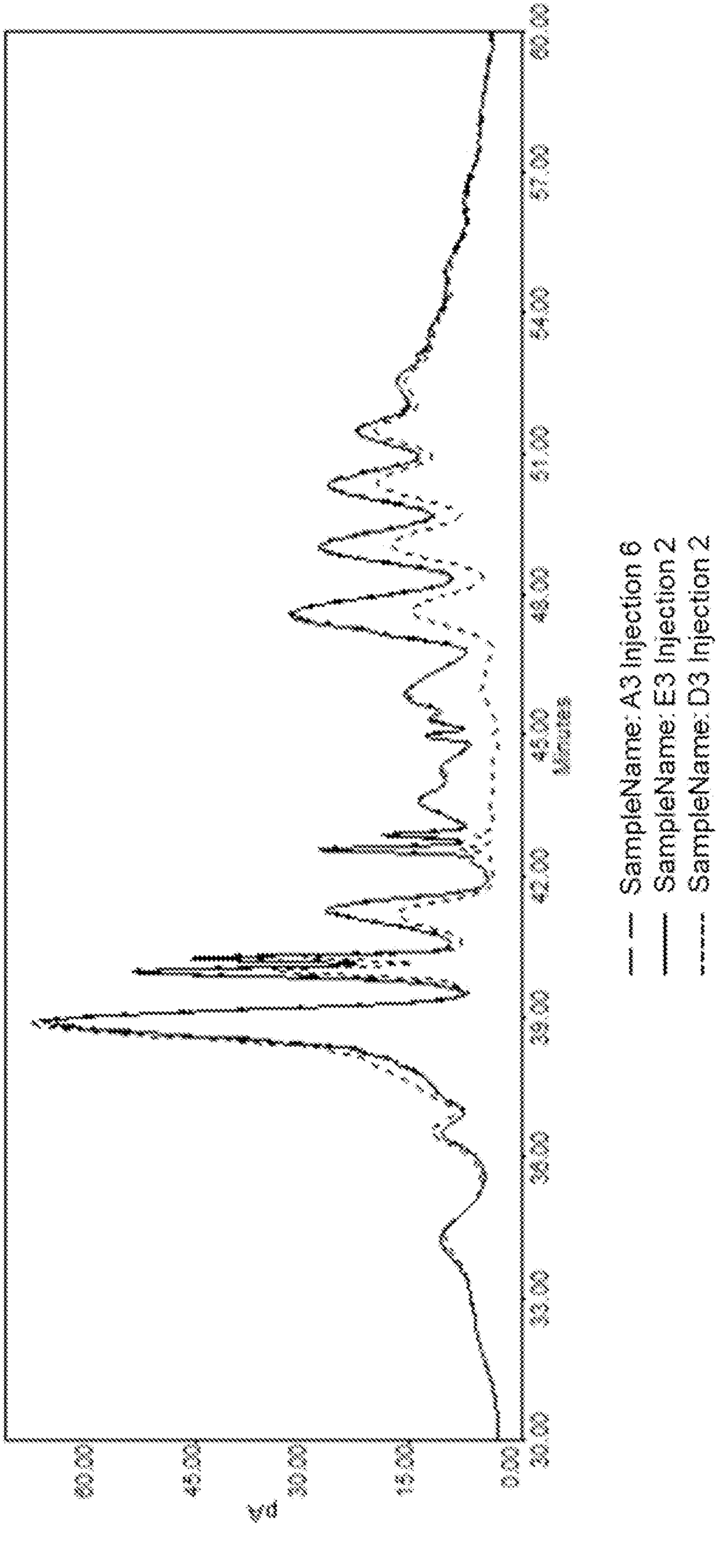
FIG. 5 shows PS20 subspecies chromatogram overlay of Sample E3 Injection 2 (DP3; no meaningful PS20 degradation), Sample A3 Injection 6 (DP3 spiked with 5 μg/mL PLBL2 after ~30 hours of incubation at 25° C.; total incubation time after spiking was about 20 hours at 2~8° C. plus 26 hours at 25° C.), and Sample D3 Injection 2 (PS20 in DP2 after ~30 months of storage at 2-8° C.).

No detectable PS20 degradation was observed after ~30 hours of incubation at 25° C. A typical result is shown in FIG. 5. This result confirmed the low activity of PLBL2 to PS20 degradation. The spiking level (5 μg/mL) was much higher than the PLBL2 concentration detected in DP2 material by the PLBL2 ELISA method. The lack of detectable PS20 degradation after ~30 hours incubation at 25° C. indicates that PLBL2 is unlikely the main root cause for the PS20 degradation in DP2 materials.

CES Spiking Study

1. Background

Carboxylesterase 1 (CES 1) was detected in DP2 materials. Literature reported that CES 1 could induce PS20 degradation in antibody formulations (Zhang et al. *Pharmaceutical Research,* 2022, 39:75-87).

2. Methods

PS20-CAD subspecies method described above was used.

3. Study Design for CES Spiking Study

DP3 drug solution was spiked with 5 μg/mL CES 1 enzyme. The solution was mixed and tested. All samples were studied at 25° C. The study design was similar to PLA2G15 spiking study in risankizumab DP3 material. More information can be found in Table 21A.

4. Result

Figure 6A:
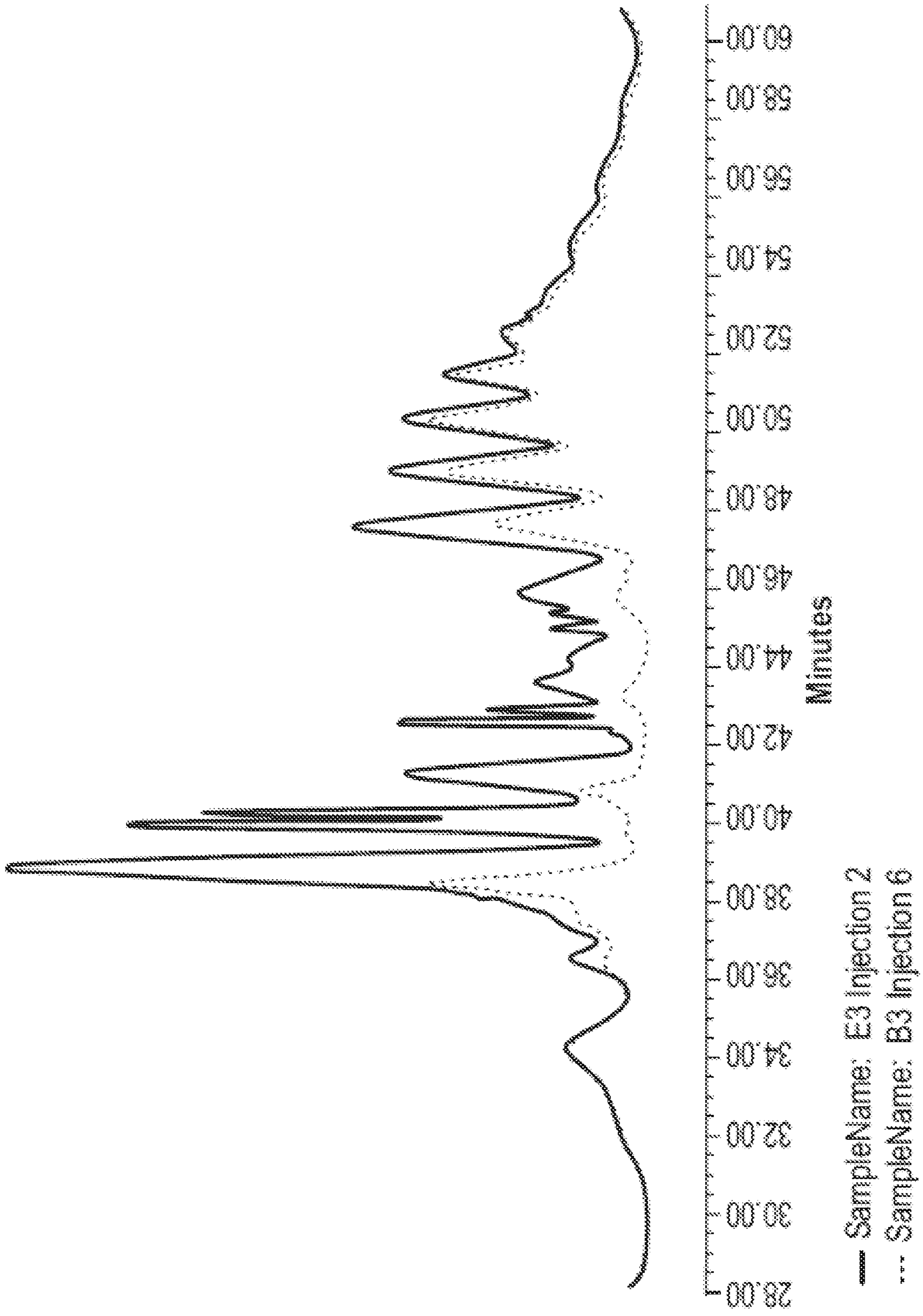
FIG. 6A shows PS20 subspecies chromatogram overlay of Sample E3 Injection 2 (DP3; no meaningful PS20 degradation) and Sample B3 Injection 6 (DP3 spiked with 5 μg/mL CES 1 after ~30 hours of incubation at 25° C.; total incubation time after spiking was about 20 hours at 2~8° C. plus 27 hours at 25° C.).
Figure 6B:
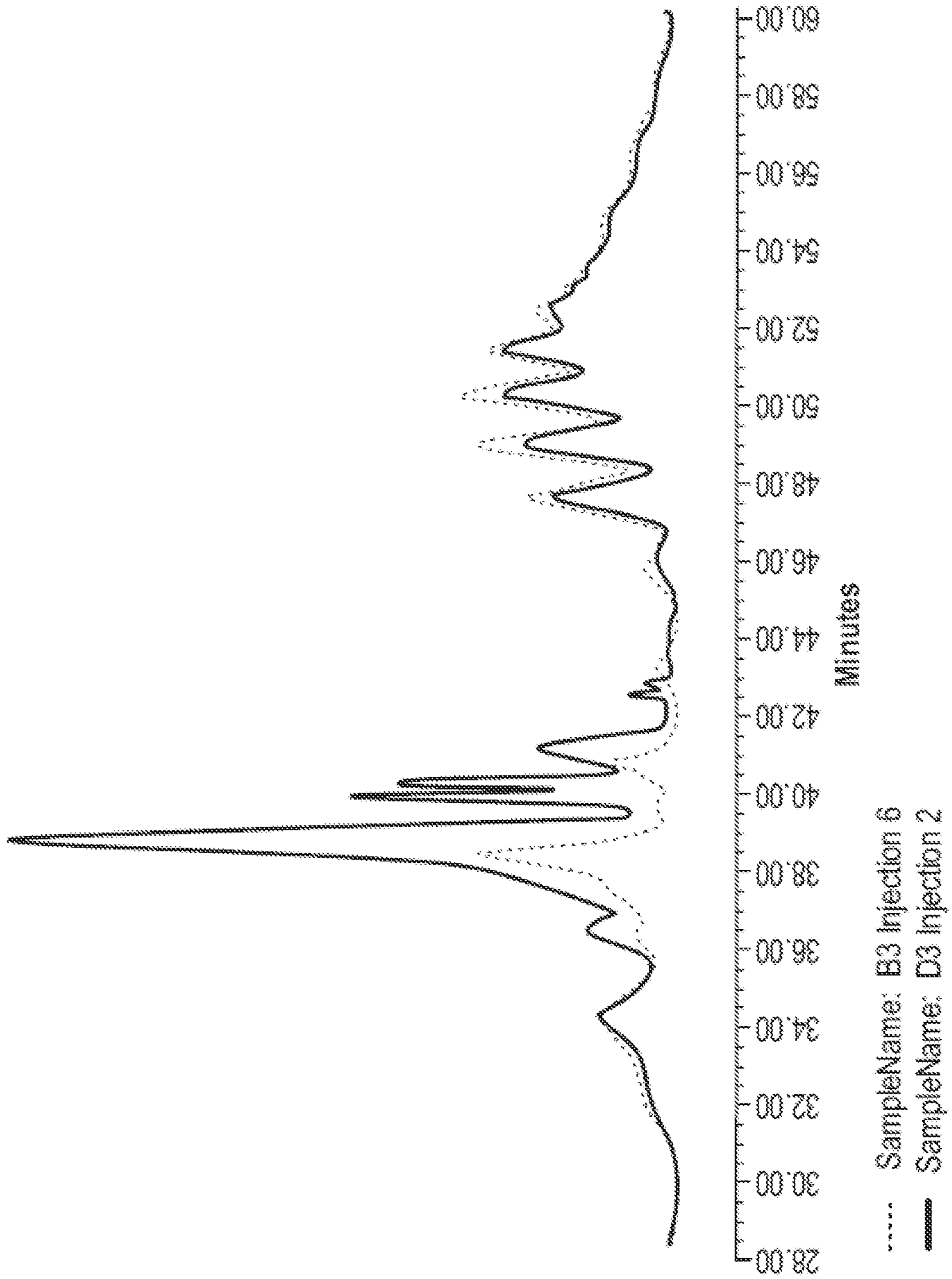
FIG. 6B shows PS20 subspecies chromatogram overlay of Sample D3 Injection 2 (PS20 degradation in DP2, after ~30 months of storage at 2-8° C.) and Sample B3 Injection 6 (DP3 spiked with 5 μg/mL CES 1 after ~30 hours of incubation at 25° C.; total incubation time after spiking was about 20 hours at 2~8° C. plus 27 hours at 25° C.).

Significant PS20 degradation was observed after only a few hours of incubation at 25° C. PS20 degradation patterns (profiles) at different incubation time were similar (degradation levels were different). CES 1 can cause significant degradation of PS20 in risankizumab formulations. However, the PS20 degradation pattern by CES 1 in the risankizumab formulation was very different from the observed PS20 degradation pattern/profile in DP2 materials. The main PS20 peak (polyoxyethylene sorbitan mono-laurate) degraded significantly by CES 1, but retention time>50 minutes PS20 subspecies region only showed little degradation. A typical result is shown in FIG. 6A. An overlay of a PS20 degradation pattern (profile) observed in DP2 and caused by CES 1 is shown in FIG. 6B and they are very different. Therefore, CES 1 is unlikely to be the main contributor of PS20 degradation in DP2 materials.

Sialate O-Acetylesterase Spiking Study

1. Background

Sialate O-acetylesterase (SIAE) was detected in DP2 materials. Literature reported that SIAE could induce PS20 degradation in antibody formulations, and a moderate level of PS20 degradation was observed after 5 days of incubation at 45° C., but a high enzyme concentration was used (5 μg/mL) in the study (Zhang et al. *Journal of pharmaceutical sciences,* 2021, 110:3899-3873). The reported PS20 degradation pattern was different from the pattern observed in DP2 materials. In the literature, SIAE caused a significant decrease of the main PS20 peak (polyoxyethylene sorbitan mono-laurate) (Zhang et al. *Journal of pharmaceutical sciences,* 2021, 110:3899-3873), while this peak is stable in DP2 materials tested herein.

2. Methods

PS20-CAD subspecies method described above was used.

3. Study Design for Sialate O-Acetylesterase Spiking Study

DP3 drug solution was spiked with 5 μg/mL SIAE enzyme. The solution was mixed and tested. More information regarding the study design can be found in Table 21A.

4. Result

Figure 7:
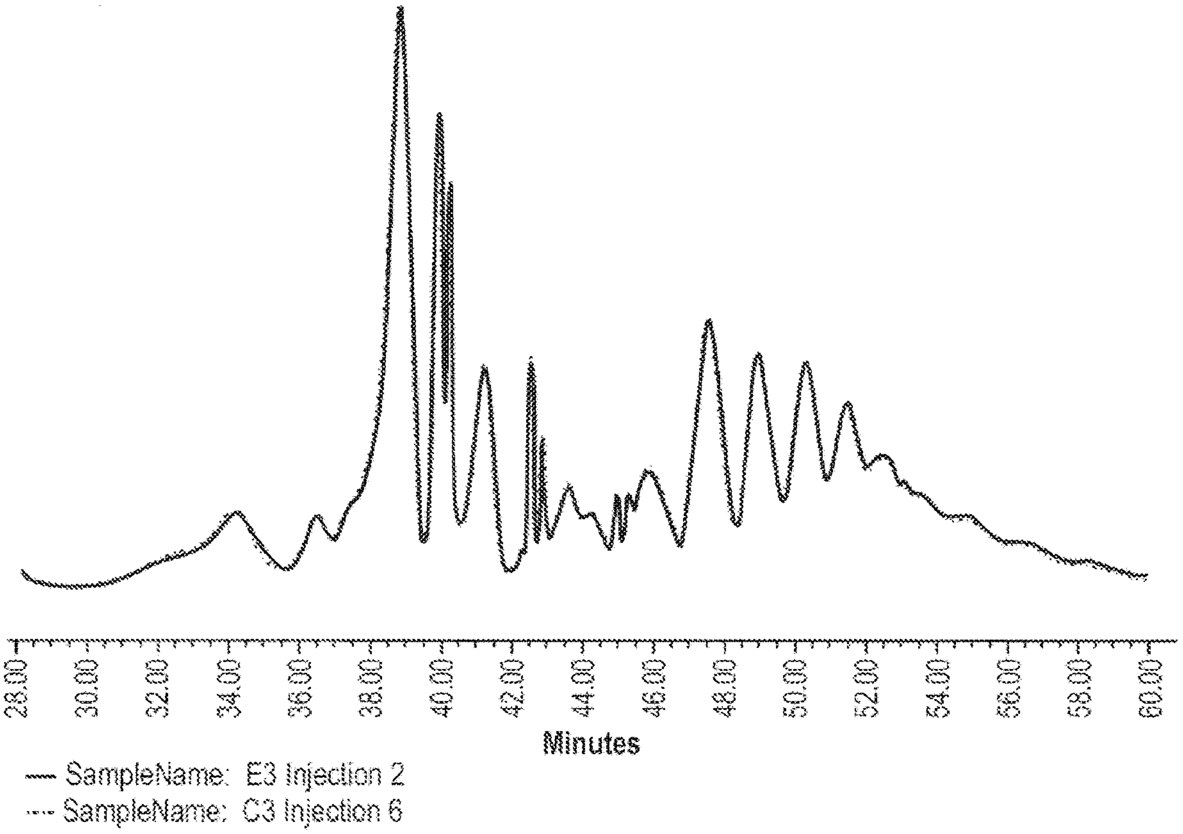
FIG. 7 shows PS20 subspecies chromatogram overlay of Sample E3 Injection 2 (DP3, no meaningful PS20 degradation) and Sample C3 Injection 6 (DP3 spiked with 5 μg/mL SIAE after ~30 hours of incubation at 25° C.; total incubation time after spiking was about 20 hours at 2~8° C. plus 28 hours at 25° C.).

A typical result is shown in FIG. 7. This result confirmed the low activity of SIAE to PS20 degradation. At the spiking level at 5 μg/mL, no detectable PS20 degradation was observed after ~30 hours incubation at 25° C. The lack of detectable PS20 degradation after ~30 hours incubation at 25° C. suggests that it is unlikely SIAE is the main contributor for the PS20 degradation in DP2 materials.

Peroxiredoxin 6 (PRDX6) Spiking Study

1. Background

Peroxiredoxin 6 (PRDX6) has been detected in DP2 materials using LC-MS. Literature reported that PRDX6 can have PLA2 like activity. However, the PLA2 like activity of native protein is limited at neutral pH. The activity is greater at acid environment and at neutral pH with oxidized phospholipids (Fisher (2018) *Journal of lipid research* 59:1132-1147).

2. Materials

Recombinant human Peroxiredoxin 6 protein (PRDX6) (ab87631, AB87631-100UG, 1 mg/ml. Abcam, kept at −80° C. before use)

3. Methods

PS20-CAD subspecies method described above was used.

4. Study Design for PRDX6 Spiking Study

Risankizumab DP3 was spiked with 5 μg/mL PRDX6 enzyme. The solution was mixed and tested. More information regarding the study design can be found in Table 21B below.

TABLE 21B

Study design for PRDX6 and PLA2G7 spiking studies

| Study Arms (vials; solution volume 1 mL) | Sample Type | 1st injection | 2nd injection | 3rd injection | 4th injection | 5th injection | 6th injection | 7th injection | 8th injection* |
|---|---|---|---|---|---|---|---|---|---|
| Arm 1: DP3/DP4 (150 mg/mL + 5 μg/mL PRDX6) | A4 | Yes | Yes | Yes | Yes | Yes | Yes | Yes | Yes |
| Arm 2: DP3/DP4 150 mg/mL + 5 μg/mL PLA2G7) | B4 | Yes | Yes | Yes | Yes | Yes | Yes | Yes | Yes |
| Arm 3: Expired DP2 material (150 mg/mL; PS20 degradation fingerprints reference) | C4 | Yes | No | No | No | No | No | No | Yes |
| Arm 4: DP3/DP4 (150 mg/mL) (without spiking) | D4 | Yes | No | No | No | No | No | No | Yes |

*Note:
Data from 8th injections was collected, but 7th injections were plotted in the summary due to the concern of low remaining solution volume in vials at 8th injection.

5. Results

Figure 8:
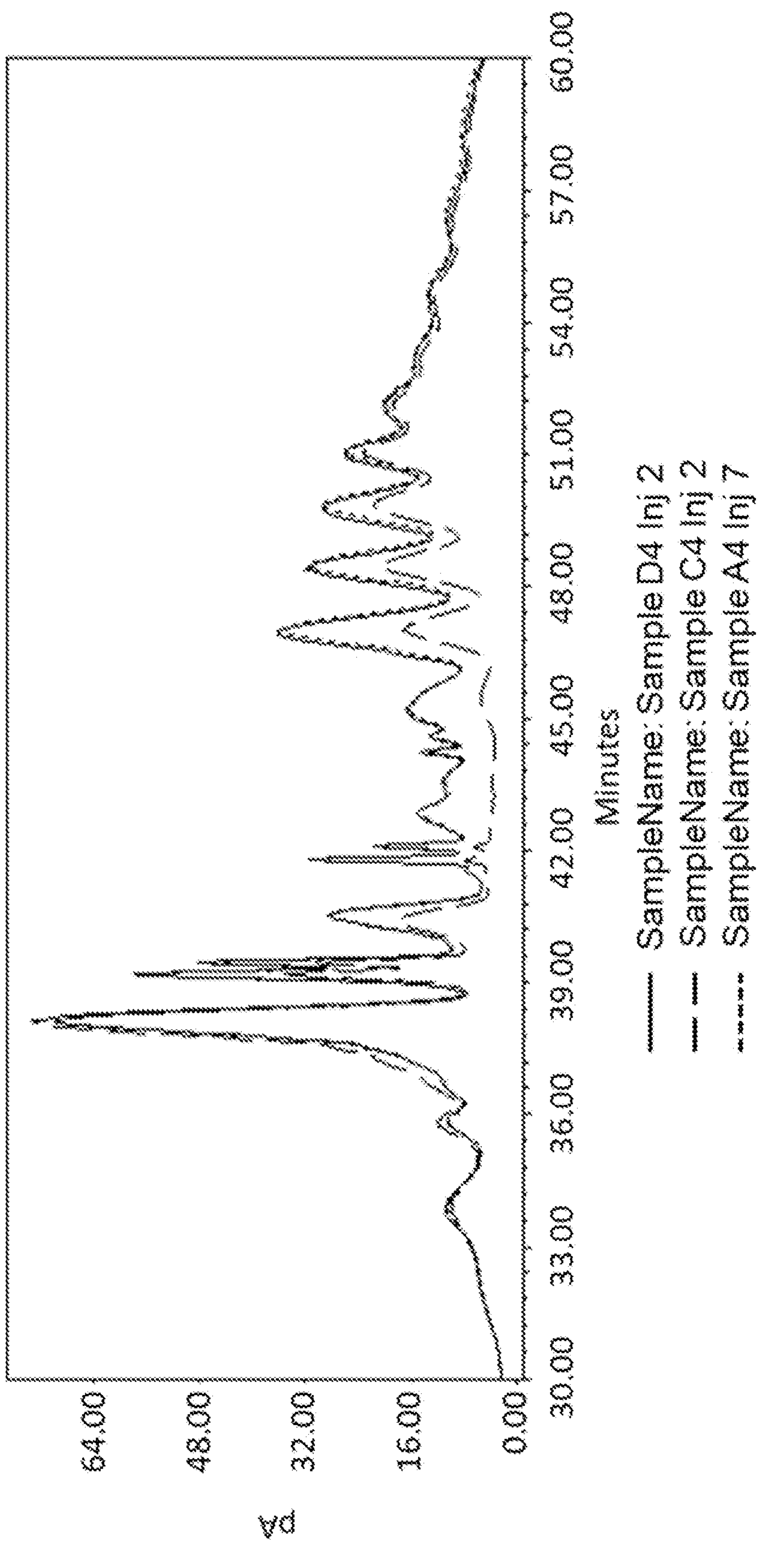
FIG. 8 shows PS20 subspecies chromatogram overlay of Sample D4 Injection 2 (DP3, no meaningful PS20 degradation), Sample A4 Injection 7 (DP3 spiked with 5 μg/mL PRDX6 after ~30 hours of incubation at 25° C.; total incubation time after spiking was about 27 hours at 25° C.), and Sample C4 Injection 2 (PS20 in DP2 after ~30 months of storage at 2-8° C.).

A typical result is shown in FIG. 8. The result showed the low activity of PRDX6 to PS20 degradation. At the spiking level at 5 μg/mL, no detectable PS20 degradation were observed after ~30 hours incubation at 25° C. The lack of detectable PS20 degradation after ~30 hours incubation at 25° C. indicates that it is unlikely PRDX6 is the main contributor for the PS20 degradation in DP2 materials.

PLA2G7 Spiking Study

1. Background

Phospholipase A2 Group VII (PLA2G7) has been detected in DP2 materials using LC-MS. Literature reported that PLA2G7 can degrade PS20 in antibody formulation solutions (Li et al. (2021) *Analytical chemistry* 93:8161-8169).

2. Materials

Recombinant human PLA2G7/PAF-AH/LP-PLA2 protein, (5106-PL-010; 0.44 mg/mL, Bio-techne, kept at −80° C. before use)

3. Methods

PS20-CAD subspecies method described above was used.

4. Study Design for PLA2G7 Spiking Study

Risankizumab DP3 was spiked with 5 μg/mL PLA2G7 enzyme. The solution was mixed and tested. More information regarding the study design can be found in Table 21B.

5. Results

Figure 9:
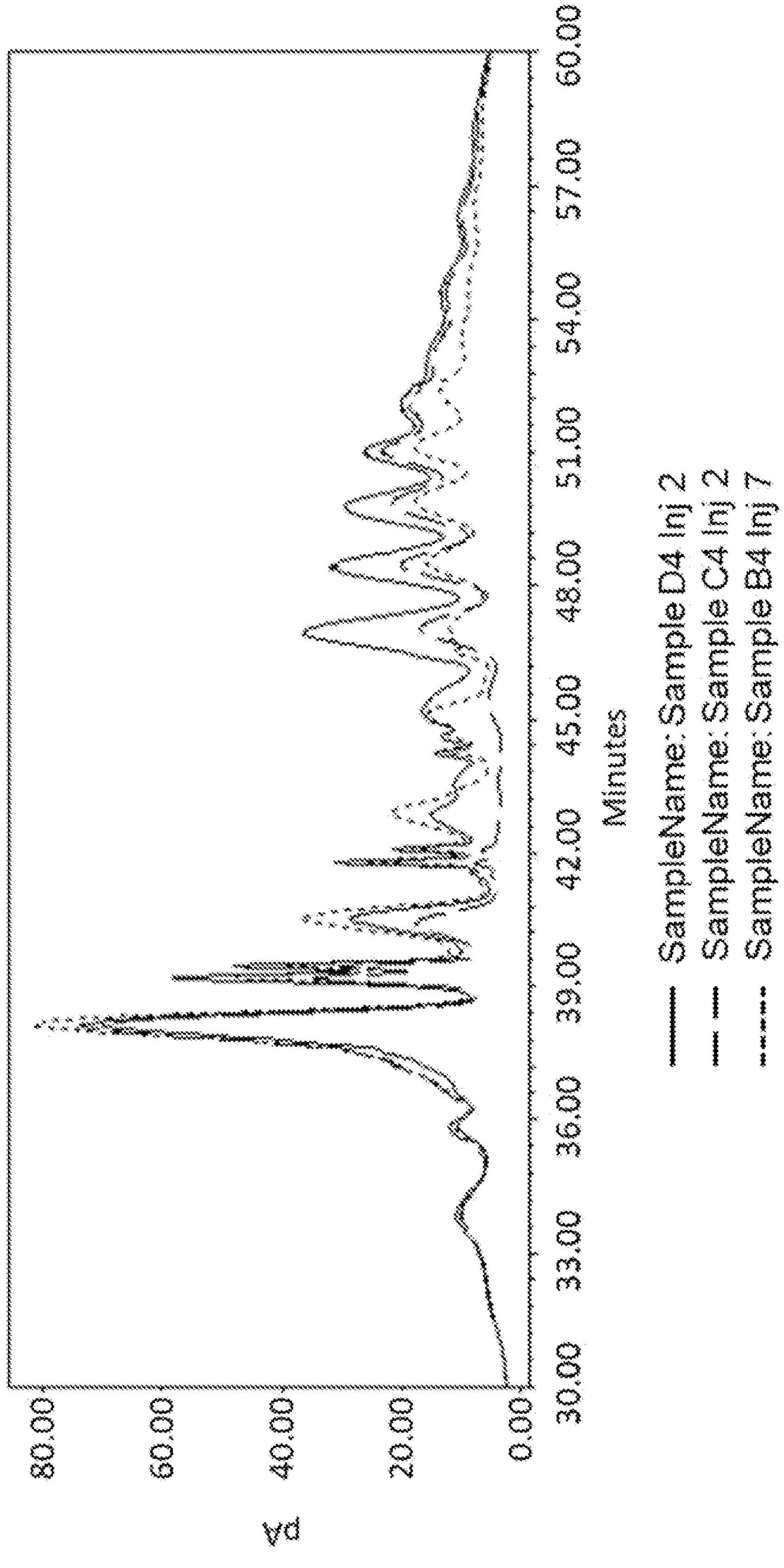
FIG. 9 shows PS20 subspecies chromatogram overlay of Sample D4 Injection 2 (DP3, no meaningful PS20 degradation), Sample B4 Injection 7 (DP3 spiked with 5 μg/mL PLA2G7 after ~30 hours of incubation at 25° C.; total incubation time after spiking was about 28 hours at 25° C.), and Sample C4 Injection 2 (PS20 in DP2 after ~30 months of storage at 2-8° C.).

A typical result is shown in FIG. 9. The result confirmed that PLA2G7 caused PS20 degradation with a relatively high activity. However, the PS20 degradation profile caused by PLA2G7 was very different from the PS20 degradation profile observed in DP2 materials. The spiking study result indicates that it is unlikely PLA2G7 is the main contributor for the PS20 degradation in DP2 materials.

Summary

PS20 degradation patterns (profiles) in DP3 and DP4 materials spiked with six enzymes have been studied. These six enzymes have been detected in DP2 materials (four by LC-MS and two by an ELISA assay). Three enzymes (PLBL2, PRDX6, and SIAE) showed very low activities to PS20 degradation even at very high concentration. Therefore, these three enzymes are unlikely to be the main root causes of PS20 degradation in DP2 materials. Enzymes CES and PLA2G7 showed moderate activities to PS20 degradation. But the PS20 degradation patterns (profiles) caused by CES and PLA2G7 were very different from the pattern (profile) observed in DP2 materials. Therefore, CES and PLA2G7 are also unlikely the main root cause of PS20 degradation in DP2 materials. PS20 degradation pattern (profile) caused by PLA2G15 matches the PS20 degradation pattern in DP2 materials well. This study indicates that PLA2G15 is the key responsible enzyme that causes PS20 degradation in DP2 drug product.

Example 8: PLA2G15 Inhibition Studies Confirm PLA2 as the Problematic Hitchhiker Protein It has been reported that a small molecule drug fosinopril can inhibit the activity of PLA2G15 (Phospholipase A2 Group XV) with an IC50 around 0.18 uM (Hinkovska-Galcheva et al. (2021) J. Lipid. Res. 62:100089). Fosinopril is an angiotensin converting enzyme (ACE) inhibitor, which is been used to treat hypertension and some types of chronic heart failure (Murdoch et al. (1992) Drugs 43:123-140). It has been further suggested that fosinopril inhibits the PLA2G15 activity through the interference of PLA2G15 binding to liposomes surfaces as the result of a liposome PLA2G15 cosedimentation assay (Hinkovska-Galcheva et al. (2021) J. Lipid. Res. 62:100089). In order to further confirm that PLA2G15 is mainly responsible for polysorbate 20 (PS20) degradation in the DP2 material, a series of PLA2G15 inhibition studies were performed by spiking of different levels of fosinopril in the DP2 material. In this study, DP2 samples were aseptically spiked with different levels of fosinopril. All samples (including non-spiked samples) were incubated at room temperature in the dark for two weeks. PS20 degradation levels in those samples were tested with a PS20 subspecies method. PS20 degradation levels in those samples were compared with negative controls (non-spiked samples kept at room temperature in dark for two weeks) and positive controls (non-spiked samples kept at −80° C. before testing). Fosinopril dose dependent protection (inhibition) of PS20 degradation in the DP2 material has been observed. The protection (inhibition) has been observed even at a sub ug/mL spiking level. This result combined with other studies further confirmed that PLA2G15 is the root cause of PS20 degradation in the DP2 material. The chemical structure of fosinopril is shown below.

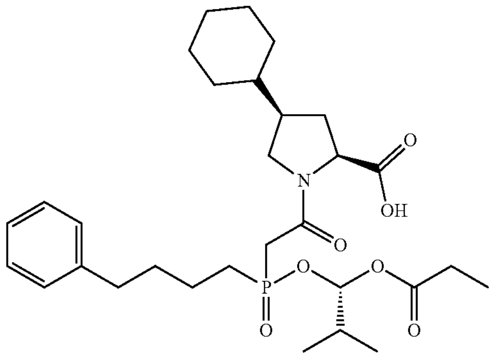 [SMILES: CCC(=O)O[C@@H](OP(=O)(CCCCc1ccccc1)CC(=O)N1C[C@@H](C2CCCCC2)C[C@H]1C(=O)O)C(C)C]

Materials

DP2 material (kept at −80° C.)
Fosinopril sodium (F13085MG) (from Sigma Aldrich)

Sample Preparation

Fosinopril sodium was dissolved in Mill-Q water at a concentration of 0.5 mg/mL. The solution was aseptically filtered with a 0.22 syringe filter before use. During the filtration, the syringe filter was flushed with Mill-Q water and then with the 0.5 mg/mL fosinopril water solution. Lower concentrations of fosinopril water solutions were aseptically diluted with Mill-Q water. More detailed sample preparation can be found in Table 22. All vials were glass vials, and solutions were well mixed before incubation. Samples were incubated at room temperature in dark for two weeks before testing.

TABLE 22

| Samples preparation | | | | | | | | |
|---|---|---|---|---|---|---|---|---|
| Steps | Vial 1 | Vial 2 | Vial 3 | Vial 4 | Vial 5 | Vial 6 | Vial 7 | Vial 8 |
| Fosinopril sodium water stock solution concentration (mg/mL) used in spiking | 0.5 | 0.5 | 0.167 | 0.167 | 0.042 | 0.042 | 0.01 | 0 |
| Spiked Forsinopril sodium stock solution volume (uL) | 50 | 25 | 50 | 25 | 50 | 25 | 25 | 0 |
| DP2 volume in vial (uL) | 250 | 250 | 250 | 250 | 250 | 250 | 250 | 250 |
| Total volume in vial after spiking (uL) | 300 | 275 | 300 | 275 | 300 | 275 | 275 | 250 |
| Calculated final Fosinopril sodium concentration in vials (ug/mL) | 83.3 | 45.5 | 27.8 | 15.2 | 6.9 | 3.8 | 0.9 | 0 |

Test Method

A PS20 HPLC-CAD subspecies method was used to test the PS20 levels qualitatively as well as profiles in all samples. Solutions were transferred to HPLC vials and diluted with Milli-Q water (1:1 dilution). All HPLC vials were mixed well before placed in an HPLC autosampler for testing. Sample descriptions and labels can be found in Table 23.

TABLE 23

| Sample information | |
|---|---|
| Study Arms | Sample ID |
| Arm 1: DP2 (spiked with 83.3 ug/mL fosinopril sodium; kept at room temperature in dark for two weeks) (1:1 diluted with water before test) | H7-1 |
| Arm 2: DP2 (spiked with 45.5 ug/mL fosinopril sodium; kept at room temperature in dark for two weeks) (1:1 diluted with water before test) | H7-2 |
| Arm 3: DP2 (spiked with 27.8 ug/mL fosinopril sodium; kept at room temperature in dark for two weeks) (1:1 diluted with water before test) | H7-3 |
| Arm 4: DP2 (spiked with 15.2 ug/mL fosinopril sodium; kept at room temperature in dark for two weeks) (1:1 diluted with water before test) | H7-4 |
| Arm 5: DP2 (spiked with 6.9 ug/mL fosinopril sodium; kept at room temperature in dark for two weeks) (1:1 diluted with water before test) | H7-5 |
| Arm 6: DP2 (spiked with 3.8 ug/mL fosinopril sodium; kept at room temperature in dark for two weeks) (1:1 diluted with water before test) | H7-6 |
| Arm 7: DP2 (spiked with 0.9 ug/mL fosinopril sodium; kept at room temperature in dark for two weeks) (1:1 diluted with water before test) | H7-7 |
| Arm 8: DP2 kept at room temperature in dark for two weeks) (1:1 diluted with water before test) | H7-8 |
| Arm 9: DP2 (Kept at −80° C.; 1:1 diluted with water before test) | H7-9 |

Results

Figure 10:
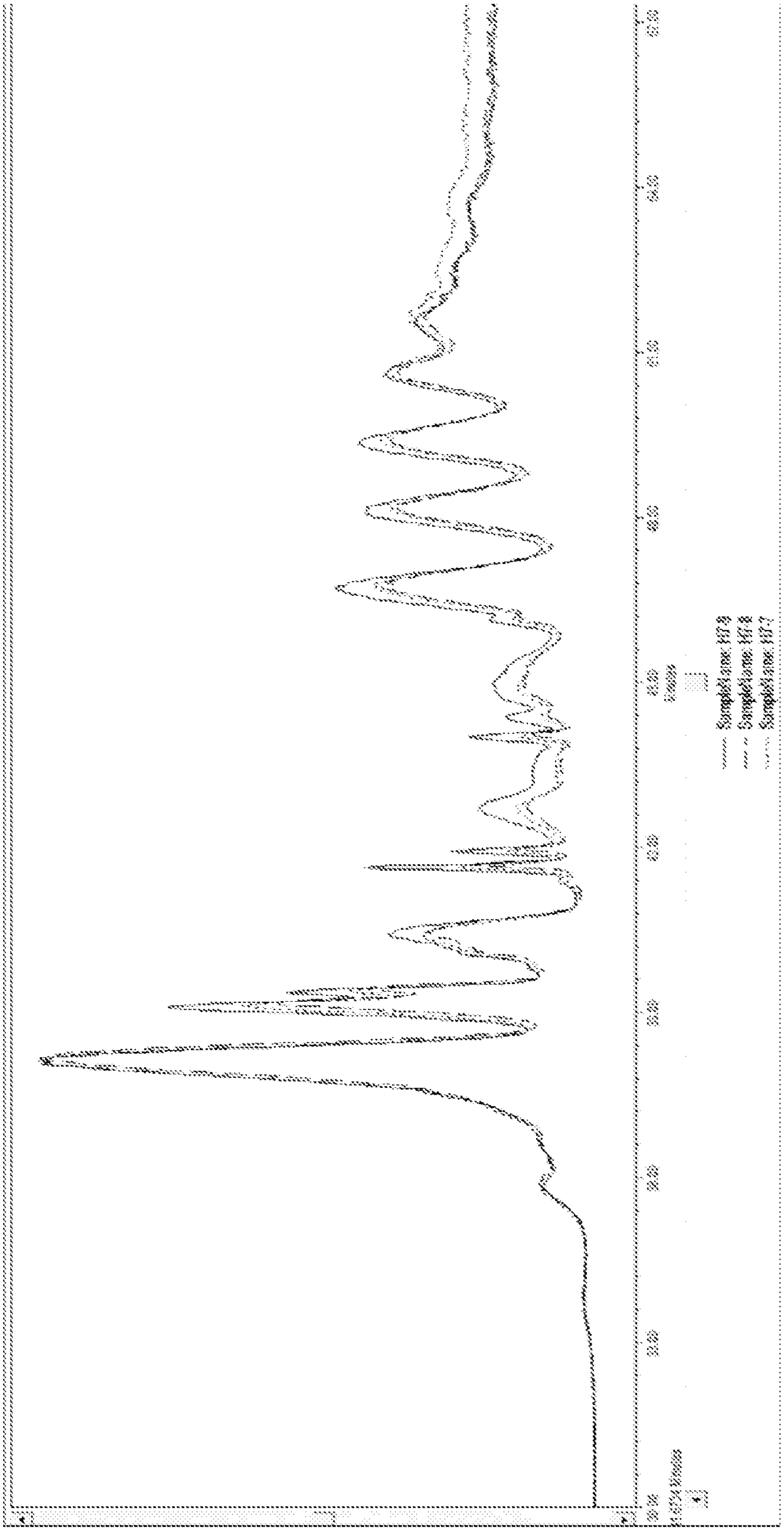
FIG. 10 shows PS20 subspecies chromatogram overlay of sample H7-9, H7-8, and H7-7. H7-9: DP2 (kept at −80° C.); H7-8: DP2 (kept at RT for two weeks); H7-7: DP2 spiked with 0.9 ug/mL fosinopril (kept at RT for two weeks). Signals were normalized to correct the concentration change due to the spiking (normalized with the peak at the 37 minutes, which is stable in the DP2 material based on historical data).
Figure 11:
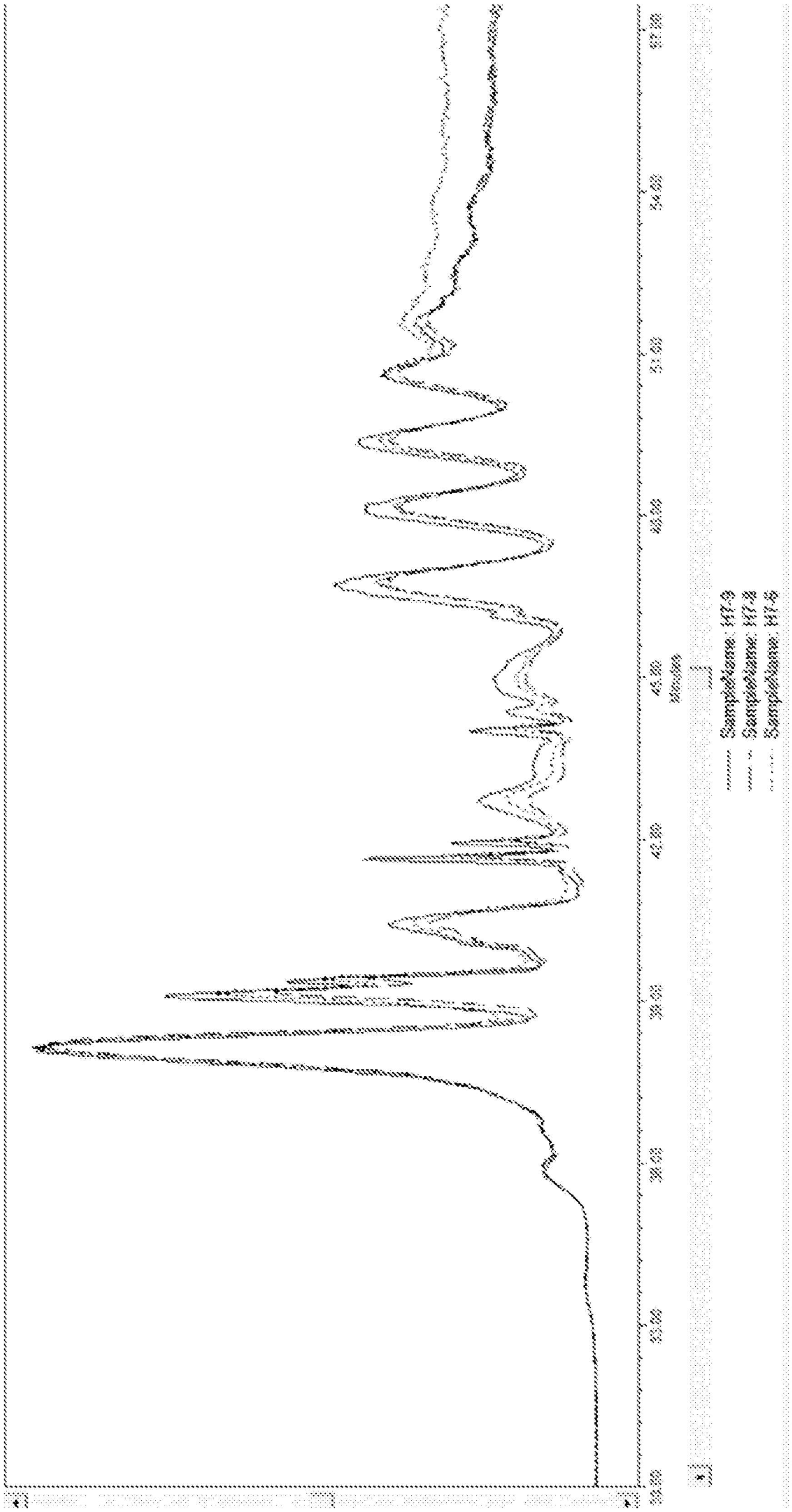
FIG. 11 shows PS20 subspecies chromatogram overlay of sample H7-9, H7-8, and H7-6. H7-9: DP2 (kept at −80° C.); H7-8: DP2 (kept at RT for two weeks); H7-6: DP2 spiked with 3.8 ug/mL fosinopril (kept at RT for two weeks). Signals were normalized to correct the concentration change due to the spiking (normalized with the peak at the 37 minutes, which is stable in the DP2 material based on historical data).
Figure 12:
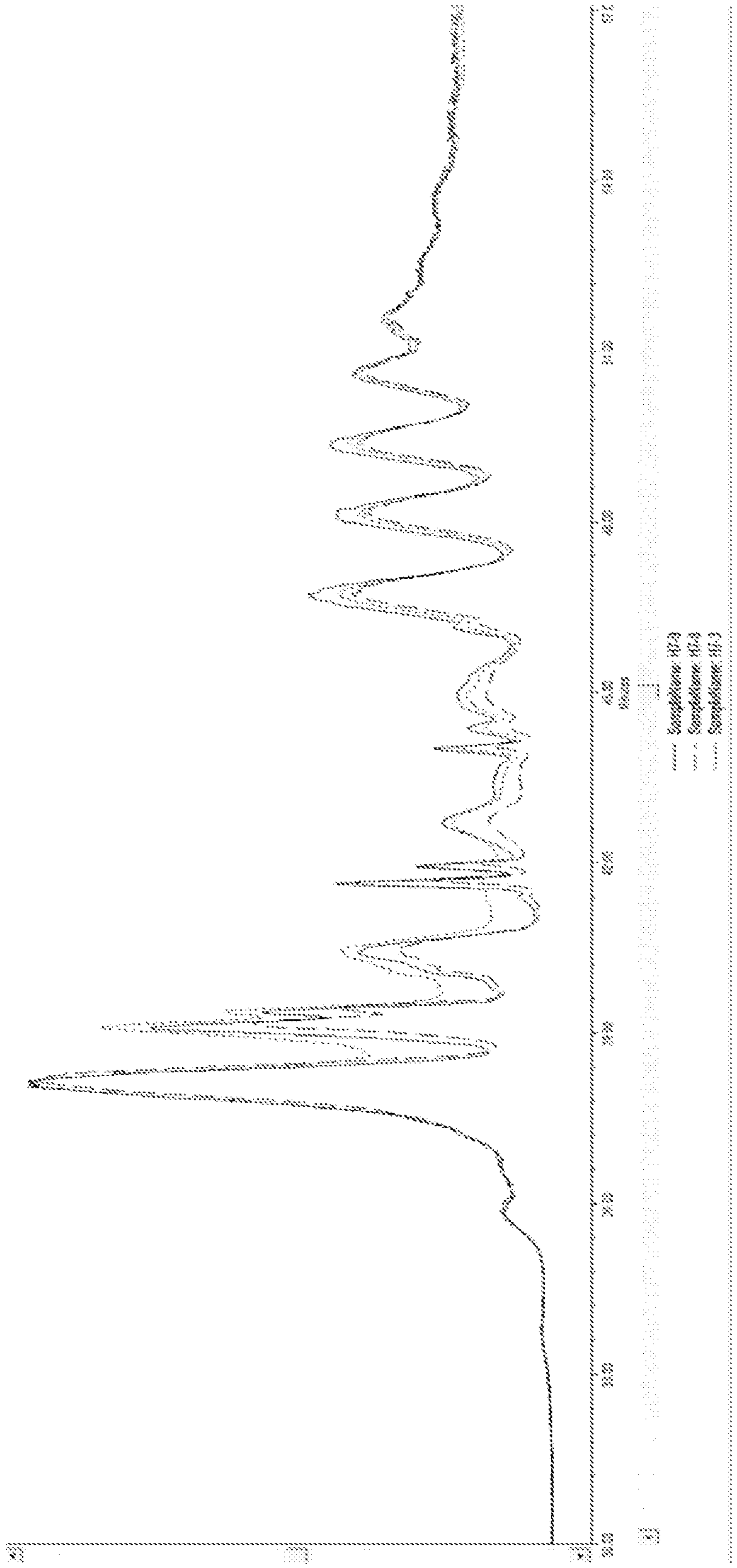
FIG. 12 shows PS20 subspecies chromatogram overlay of sample H7-9, H7-8, and H7-3. H7-9: DP2 (kept at −80° C.); H7-8: DP2 (kept at RT for two weeks); H7-3: DP2 spiked with 27.8 ug/mL fosinopril (kept at RT for two weeks). Signals were normalized to correct the concentration change due to the spiking (normalized with the peak at the 37 minutes, which is stable in the DP2 material based on historical data). The higher background in spiked sample around 39 to 42 minutes should come from co-elution of fosinopril.

Dose (concentration) dependent protection (inhibition) of PS20 degradation by fosinopril in the DP2 material solutions were observed during the study. For example, even at the lowest fosinopril spiking level (0.9 μg/mL), reduction of PS20 degradation has been observed compared to the non-spiked control sample. FIG. 10 shows the result with a fosinopril spiking level at 0.9 μg/mL. FIG. 11 shows the result with a fosinopril spiking level at 3.8 μg/mL. FIG. 12 shows the result with a fosinopril spiking level at 27.8 g/mL.

Figure 13:
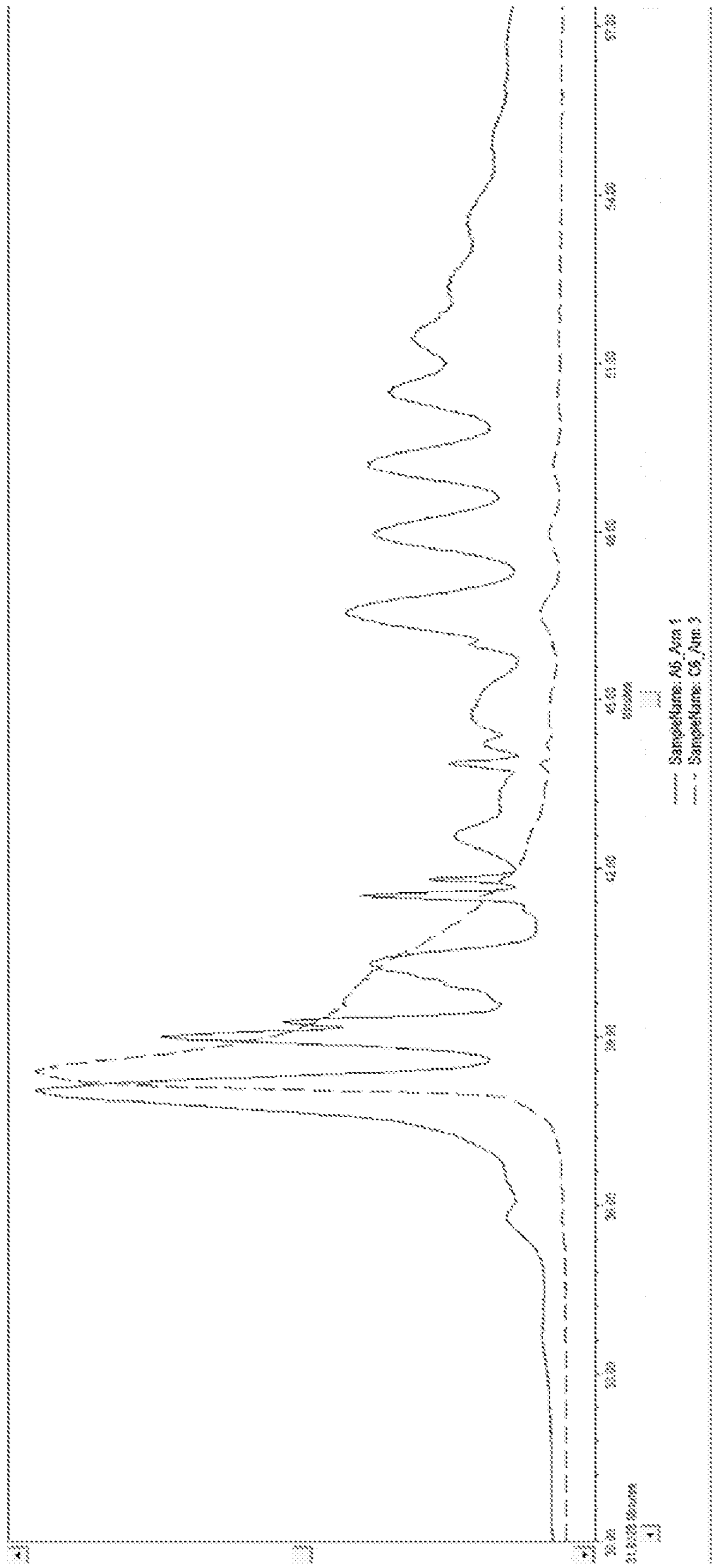
FIG. 13 shows PS20 subspecies chromatogram overlay of sample A6 and C6. A6 DP2 material (kept at −80° C., 1:1 diluted with water before test); C6: DP2 material (spiked with 930 ug/mL fosinopril; kept at room temperature for two weeks; 1:1 diluted with water before test). Signal from C6 was normalized for a better comparison with A5.

Since fosinopril could co-elute with PS20 in the chromatograms (the peak is around retention time of 39.5 minutes), it can be detected at high spiking levels (e.g., 39 to 42 minutes in FIG. 12). Further analysis was done to evaluate the potential impact on the observed PS20 signal. FIG. 13 shows a normalized result with a very high fosinopril spiking level (930 ug/mL). It shows that fosinopril peak is around 39.5 minutes. Due to relatively low fosinopril spiking levels in FIGS. 10-12, the impact on retention time>42 minutes can be ignored.

Summary

Dose dependent protection (inhibition) of PS20 degradation by fosinopril spiking in the DP2 material has been observed. Fosinopril showed protection (inhibition) even at 0.9 μg/mL spiking level. Since fosinopril is a potent PLA2G15 inhibitor, the study results combined with other studies further confirmed that PLA2G15 should be the root cause of PS20 degradation in the DP2 material.

Example 9: Risankizumab Drug Products DP3 and DP4 have Lower Hitchhiker Protein Levels Residual hitchhiker proteins in the drug substance concentrate samples were determined by Enzyme Linked Immunosorbent Assay (ELISA) as described below.

PLA2 ELISA

1. Principle 96-well microtiter plates (Nunc Maxisorp Cat. #439454; VWR Cat. #62409-002) were coated with polyclonal rabbit-anti-CHO-PLA2 antibodies (1 mg/mL), and then incubated with SuperBlock in TBS (Thermo Scientific Cat #37535) to block non-specific sites. Recombinant PLA2 standards ([PLA-2G15 (cg) (34-412)]-6His, 1.05 mg/mL) and drug substance were then added to the plates. Plates were incubated to allow for the residual PLA2 present in the standards and samples to bind to the polyclonal anti-PLA2 antibodies. Plates were washed to remove unbound material, and biotinylated rabbit-anti-CHO PLA2 polyclonal antibodies (1 mg/mL) were added to the plates. Plates were incubated to allow for the biotinylated antibodies to bind to the residual PLA2 antigens bound to the anti-PLA2 antibodies. Plates were washed to remove unbound material and neutravidin-HRP (enzyme labeled horse radish peroxidase; Thermo Scientific Cat. #31030) was added to the plates. Plates were incubated to allow for the neutravidin-HRP to bind to the bound biotinylated antibodies. Plates were washed to remove unbound material and K-Blue TMB substrate (Neogen Cat. #308177) was added to the plates. The chromogenic substrate was oxidized by the bound enzyme conjugated antibody, producing a blue color. Reaction was stopped with 4N (2M) Sulfuric Acid (Ricca Cat. #8322-32), changing color to yellow. Color intensity was directly proportional to the amount of residual PLA2 antigen bound in the wells. Plates were read at 450 nanometers using the plate reader.

2. Safety

3. Equipment

Molecular Devices Plate Reader or equivalent
BioTek ELx405's 96 W Plate Washer or equivalent
Adjustable pipettes with tips, Rainin or equivalent
8 or 12 channel pipette with tips, Rainin or equivalent
Titer plate shaker, Lab-line or equivalent, room temperature
Incubator/Shaker, Lab-line Environ plate shaker or equivalent, 37° C.
pH Meter
Balance 4. Materials 96-well microtiter plates, Nunc Maxisorp Cat. #439454 (VWR Cat. #62409-002) or equivalent
ELISA plate sealing tape—Corning Cat. #430454 or equivalent
Polypropylene tubes
Milli-Q Water, MPS-66 or equivalent
Sodium Bicarbonate, $NaHCO_3$FW 84.01 g/mol, J.T. Baker Cat. #3509-01 or equivalent
10× Phosphate Buffered Saline with 0.5% tween-20, Boston BioProducts Cat. #IBB-171
5 N Sodium Hydroxide, J.T. Baker Cat. #5671-02 or equivalent
5 N Hydrochloric Acid, J.T. Baker Cat. #5618-02 or equivalent
SuperBlock in TBS, Thermo Scientific Cat #37535, or equivalent
Sulfuric acid 4N, Ricca Cat. #8322-32 (2N=1 M), or equivalent
K-Blue TMB Substrate, Neogen Cat. #308177 or equivalent
0.22 μM CA Sterile filter units, Corning or equivalent
Abcam Sample Diluent, Abcam Cat. #GR3347356-3; ab193972
Rabbit-Anti-CHO-PLA2 coating polyclonal antibody, 1 mg/mL, store at nominal −80° C.
Biotinylated Rabbit-Anti-CHO-PLA2 polyclonal antibody, 1 mg/mL, store at nominal −80° C.
Recombinant PLA2 standard, [PLA-2G15 (cg) (34-412)]-6His, 1.05 mg/mL, store at nominal −80° C.
Neutravidin-HRP conjugate, Thermo Scientific Cat. #31030 or equivalent, aliquot, store at nominal 4° C.
Risankizumab Assay Control, risankizumab Bulk Drug Substance 145 mg/mL, store at nominal −80° C.

5. Preparation of Reagents and Solutions

NOTE: Reverse pipetting was used throughout the assay. The coating buffer and substrate were used cold (taken from nominal 4° C. right before use).

5.1 50 mM Sodium Bicarbonate, pH 9.4±0.1 (Coating Buffer):

To a 1 L beaker add 900 mL of Milli-Q water.

Add 4.20 g±0.01 g Sodium Bicarbonate.

Stir until completely dissolved.

Adjust pH to 9.4±0.1 with 5 N NaOH and 5 N HCl.

Transfer to a 1 L volumetric flask and bring to volume with Milli-Q water.

Mix by inversion until homogeneous.

Filter through a sterile filter unit (0.22 μm).

Store at nominal 4° C. for up to 7 days from the date of preparation.

5.2 Plate Wash Buffer (1×PBS+0.05% tween-20):

To a 1 L graduated cylinder, add 100 mL of 10× phosphate buffered saline with 0.5% tween-20 to 900 mL of Milli-Q water.

Stir until homogeneous.

Filter through a 0.22 μm sterile filter unit.

Store at room temperature for up to 6 months.

5.3 Coating antibody mixture: rabbit anti-CHO PLA2 polyclonal antibody (1 mg/mL), affinity purified:

NOTE: Antibody stocks stored at nominal −80° C. in vials. Prepare aliquots. Take out one aliquot per plate immediately before use. 50 mM coating buffer (step 5.1) was taken from nominal 4° C. right before use. Mixture was applied to plates while cold.

Immediately before use: Dilute coating antibody to a final concentration of 3.0 μg/mL in cold 50 mM Sodium Bicarbonate as follows.

For example: add 36 μL of coating antibody to 11964 μL of cold coating buffer. Mix gently by inversion.

5.4 Rabbit anti-CHO PLA2 biotinylated polyclonal antibody (1 mg/mL)

NOTE: Stocks stored at nominal −80° C. in vials. Prepare aliquots. Take out one aliquot per plate at time of use.

Immediately before use: Dilute biotinylated antibody to a final concentration of 0.20 μg/mL in SuperBlock in TBS as follows.

For example: Prepare Dilution A by diluting 10 μL of biotinylated antibody in 90 μL of SuperBlock in TBS. Mix gently by inversion. Prepare Dilution B by further diluting 24 μL of Dilution A in 11976 μL of SuperBlock in TBS for a final dilution factor of 1:5000.

5.5 Neutravidin-HRP Conjugate (1 mg/mL)

NOTE: Stocks stored at nominal 4° C. Take out one aliquot per plate at time of use and warm to room temperature.

Immediately before use, pipet up and down gently to mix the conjugate. Dilute neutravidin-HRP conjugate to a final concentration of 0.2 μg/mL. Vortex gently to mix.

For example: Prepare Dilution A by diluting 10 μL of HRP conjugate into 90 μL of SuperBlock in TBS. Mix gently by inversion. Prepare Dilution B by further diluting 24 μL of Dilution A into 11976 μL of SuperBlock in TBS.

6. Preparation of Standards and Spike

NOTE: Stocks stored at nominal −80° C. in single use aliquots.

6.1 Recombinant PLA2 Standard, [PLA-2G15(cg)(34-412)]-6His (1.05 mg/mL)

6.1.1 Thaw an aliquot at room temperature. Perform serial dilutions in Abcam sample diluent to a concentration of 21 ng/mL. Serial dilutions to prepare a standard curve are shown in the table below using Abcam sample diluent in polypropylene tubes.

TABLE 24

Recombinant PLA2 Standard Dilution Scheme

| Conc. (ng/ml) | Vol. μL of X ng/mL solution | Vol. of Abcam Sample Diluent (μL) | Serial Dilution From |
|---|---|---|---|
| 1050000 | stock | — | stock |
| 105000 | 10 uL from stock | 90 μL | 10X from stock |
| 10500 | 10 uL from 105000 | 90 μL | 10X from 105000 |
| 1050 | 20 uL from 10500 | 180 μL | 10X from 10500 |
| 105 | 150 uL from 1050 | 1350 μL | 10X from 1050 |
| 21.000, standard 1 (A) | 1200 uL from 105 | 4800 μL | 5X from 105 |
| 10.500, standard 2 (B) | 3000 uL from A | 3000 μL | 2X from A |
| 5.250, standard 3 (C) | 3000 uL from B | 3000 μL | 2X from B |
| 2.625, standard 4 (D) | 3000 uL from C | 3000 μL | 2X from C |
| 1.313, standard 5 (E) | 3000 uL from 0.256 ng/ml | 3000 μL | 2X from D |
| 0.656, standard 6 (F) | 3000 uL from E | 3000 μL | 2X from E |
| 0.328, standard 7 (G) | 3000 uL from F | 3000 μL | 2X from F |

6.1.2 Pipet standards gently up an down to mix.

6.1.3 Transfer to polypropylene microtubes.

6.1.4 Load triplicates of each standard at 100 μL per well onto the 96-well microtiter plate.

6.2 Preparation of Spike

In a polypropylene microtube, prepare a high level of PLA2 spike 10.5 ng/mL by diluting 21.000 ng/mL standard (standard 1 in step 6.1.1) 2× with Abcam sample diluent. Perform a single dilution.

For example: dilute 400 μL of 21.000 ng/mL (standard 1) in 400 μL Abcam sample diluent for a final concentration of 10.5 ng/mL.

In a polypropylene microtube, prepare an intermediate level of PLA2 spike 5.25 ng/mL by diluting 10.5 ng/mL standard (standard 2 in step 6.1.1) 2× with Abcam sample diluent. Perform a single dilution.

In a polypropylene microtube, prepare an intermediate level of PLA2 spike 1.313 ng/mL by diluting 2.625 ng/mL standard (standard 4 in step 6.1.1) 2× with Abcam sample diluent. Perform a single dilution.

Load triplicates of the spike at 100 μL per well onto the 96-well microtiter plate.

7. Preparation of Samples 7.1 In polypropylene tubes, dilute risankizumab Process 1 BDS to 2.81 mg/mL in Abcam sample diluent (Step 4). Perform pre-dilutions with sufficient volume for serial dilutions to be plated in triplicates for 100 μL/well.

NOTE: Use the dilution scheme below to prepare spiked samples (step 8) and risankizumab Process 1 BDS nominal test dilutions.

TABLE 25

For example, predilution:

| Conc (mg/mL) | Vol. μL of X mg/mL solution | Vol. μL of Sample diluent | Serial Dilution From |
|---|---|---|---|
| 90 | Stock sample | N/A | N/A |
| 9 | 100 μL of 90 mg/mL | 900 | 10X from 90 mg/mL |
| 2.81 | 281.25 μL of 9 mg/mL | 618.75 | 3.2 X from 9 mg/mL |

7.2 In polypropylene microtubes, further dilute risankizumab Process 1 BDS using sample diluent to 0.18 mg/mL (Dilution 1~4 assayed by PLA2 ELISA).

TABLE 26

For example:

| Conc (mg/mL) | Vol. μL of X mg/mL solution | Vol. μL of diluent | Serial Dilution From |
|---|---|---|---|
| 2.81 | Step 7.1 | N/A | N/A |
| 1.41 (Dilution 1) | 400 | 400 | 2X from 2.81 mg/mL |
| 0.70 (Dilution 2) | 400 | 400 | 2X from 1.41 mg/mL |
| 0.35 (Dilution 3) | 400 | 400 | 2X from 0.70 mg/mL |
| 0.18 (Dilution 4) | 400 | 400 | 2X from 0.35 mg/mL |

7.3 In polypropylene microtubes, dilute risankizumab Process 2 BDS 150 mg/mL to 9.38 mg/mL using sample diluent.

NOTE: Use the dilution scheme below to prepare spiked samples (step 8) and nominal test dilutions of risankizumab Process 2 BDS samples.

TABLE 27

For example, predilution:

| Conc (mg/mL) | Vol. μL of X mg/mL solution | Vol. μL of diluent | Serial Dilution From |
|---|---|---|---|
| 150 | Stock sample | N/A | N/A |
| 9.38 | 56.25 μL of 150 mg/mL | 843.75 | 16 X from 150 mg/mL |

7.4 In polypropylene microtubes, further dilute Process 2 BDS 150 mg/mL (9.38 mg/mL) solution to 0.59 mg/mL using Abcam sample diluent (Dilution 1~4 assayed by PLA2 ELISA).

TABLE 28

For example:

| Conc (mg/mL) | Vol. μL of X ug/mL solution | Vol. μL of diluent | Serial Dilution From |
|---|---|---|---|
| 9.38 | Step 7.3 | N/A | N/A |
| 4.69 (Dilution 1) | 400 μL of 9.38 mg/mL | 400 | 2X from 9.38 mg/mL |
| 2.34 (Dilution 2) | 400 μL of 4.69 mg/mL | 400 | 2X from 4.69 mg/mL |

TABLE 28-continued

| For example: | | | |
|---|---|---|---|
| Conc (mg/mL) | Vol. µL of X ug/mL solution | Vol. µL of diluent | Serial Dilution From |
| 1.17 (Dilution 3) | 400 µL of 2.34 mg/mL | 400 | 2X from 2.34 mg/mL |
| 0.59 (Dilution 4) | 400 µL of 1.17 mg/mL | 400 | 2X from 1.17 mg/mL |

7.5 In polypropylene microtubes, dilute risankizumab Process 3 BDS 150 mg/mL to 37.5 mg/mL.

NOTE: Use the dilution scheme below for spiking samples in step 8 and to nominal dilution of risankizumab Process 3 BDS samples

TABLE 29

| For example, predilution: | | | |
|---|---|---|---|
| Conc (mg/mL) | Vol. µL of X mg/mL solution | Vol. µL of diluent | Serial Dilution From |
| 150 | Stock sample | N/A | N/A |
| 37.5 | 200 µL of 150 mg/mL | 600 | 4X from 150 mg/mL |

7.6 In polypropylene microtubes, further dilute the 37.5 mg/mL risankizumab Process 3 BDS solution to 2.34 mg/mL using sample diluent (Dilution 1~4 assayed by PLA2 ELISA)

TABLE 30

| For example: | | | |
|---|---|---|---|
| Conc (mg/mL) | Vol. µL of X mg/ml solution | Vol. µL of diluent | Serial Dilution From |
| 37.5 | Step 7.5 | N/A | N/A |
| 18.75 (Dilution 1) | 400 µL of 37.5 mg/mL | 400 | 2X from 37.5 mg/mL |
| 9.38 (Dilution 2) | 400 µL of 18.75 mg/mL | 400 | 2X from 18.75 mg/mL |
| 4.69 (Dilution 3) | 400 µL of 9.38 mg/mL | 400 | 2X from 9.38 mg/mL |
| 2.34 (Dilution 4) | 400 µL of 4.69 mg/mL | 400 | 2X from 4.69 mg/mL |

7.7 In polypropylene microtubes, dilute risankizumab Process 4 BDS 150 mg/mL to 20 mg/mL.

NOTE: Use the dilution scheme below to prepare spiked samples (step 8) and nominal test dilutions of risankizumab Process 4 BDS samples.

TABLE 31

| For example, predilution: | | | |
|---|---|---|---|
| Conc (mg/mL) | Vol. µL of X mg/mL solution | Vol. µL of diluent | Serial Dilution From |
| 150 | Spike 4 µL of 1.05 µg/mL PLA2 standard into 200 µL of risankizumab Process 3 BDS sample | | |
| 20 | 120 µL of 150 mg/mL | 780 | 7.5 X from 150 mg/mL |

7.8 In polypropylene microtubes, further dilute the 20 mg/mL risankizumab Process 4 BDS solution to 1.25 mg/mL using sample diluent (Dilution 1~4 assayed by PLA2 ELISA)

TABLE 32

| For example: | | | |
|---|---|---|---|
| Conc (mg/mL) | Vol. µL of X mg/ml solution | Vol. µL of diluent | Serial Dilution From |
| 20 | Step 7.7 | N/A | N/A |
| 10 (Dilution 1) | 400 µL of 37.5 mg/mL | 400 | 2X from 20 mg/mL |
| 5 (Dilution 2) | 400 µL of 18.75 mg/mL | 400 | 2X from 10 mg/mL |
| 2.5 (Dilution 3) | 400 µL of 9.38 mg/mL | 400 | 2X from 5 mg/mL |
| 1.25 (Dilution 4) | 400 µL of 4.69 mg/mL | 400 | 2X from 2.5 mg/mL |

7.9 Load triplicate wells for each of the nominal test solutions (Dilution 1~4 from steps 7.2, 7.4, 7.6, 7.8) on the plate at 100 µL/well.

8. Preparation of Spiked Samples 8.1 In polypropylene microtubes, mix 400 µL of Abcam sample diluent with the same volume 400 µL of prediluted risankizumab BDS samples (step 7.1, 7.3, 7.5 and 7.7) as the non-spiked risankizumab BDS sample.

8.2 In polypropylene microtubes, mix 400 µL of 21 ng/mL PLA2 standard solution (standard 1) with the same volume 400 µL prediluted risankizumab BDS samples (steps 7.1, 7.3, and 7.5 and 7.7). These were tested as spiked sample at high level of PLA2.

8.3 In polypropylene microtubes, mix 400 µL of 10.5 ng/mL PLA2 standard solution (standard 2) with the same volume 400 µL prediluted risankizumab BDS samples (steps 7.1, 7.3, and 7.5 and 7.7). These were tested as spiked sample at intermediate level of PLA2.

8.4 In polypropylene microtubes, mix 400 µL of 2.625 ng/mL PLA2 standard solution (standard 4) with the same volume 400 µL prediluted risankizumab BDS samples (steps 7.1, 7.3, and 7.5 and 7.7). These were tested as spiked sample at low level of PLA2.

8.5 The final test concentrations of the spiked samples were the same as the nonspiked sample preparations (Dilutions 1-4)+5.250 ng/mL (spike diluted 2× in sample from 10.500 ng/mL).

8.6 Load triplicate wells for each spiked sample solution on the plate at 100 µL/well for the non-spiked samples and (low, intermediate, and high level of PLA2) standard-spiked samples.

9. Preparation of Risankizumab Sample Control 9.1 A control range must be set for every new control stock solution before use in routine testing.

9.2 The control was risankizumab bulk drug substance 145 mg/mL.

9.3 Control Stock: Prepare 50 µL aliquots of a batch of risankizumab bulk drug substance and store at nominal −80° C.

Working Control: Thaw an aliquot of control at room temperature. In polypropylene tubes, dilute the control to 7.25 mg/mL with Abcam sample diluent. Transfer the 7.25 mg/mL solution to polypropylene microtubes and load into 3 wells of the plate at 100 µL per well. A single dilution was appropriate. Record result in PA control logbook rounded to the nearest 0.1 ng/mg.

TABLE 33

| For example: | | | |
|---|---|---|---|
| Conc (mg/mL) | Vol. µL of X mg/mL solution | Vol. µL of diluent | Serial Dilution From |
| 145 | From step 9.2 | N/A | N/A |
| 7.25 (Dilution 1) | 20 | 380 | 20X from 145 mg/mL |

10. Preparation of Assay Control 10.1 Prepare PLA2 standard assay control at 5.25 ng/mL, dilute using 600 µL of Abcam sample diluent mixed with 200 µL 21 ng/ml PLA2 standard solution (Standard 1 in step 6.1.1)

10.2 Load triplicate wells using 5.25 ng/mL PLA2 standard solution as the assay control at 100 µL/well.

11. Procedure 11.1 Plate Washing Instructions

Fill plate wash bottle with plate wash buffer ((1×PBS+0.05% tween-20, refer to step 5.2). Prime plate washer. Check the following parameters.

Parameters should be set to: Plate Type: 1

For each Cycle (a total of 4 cycles): Volume: 350 µL

Soak Time: 10 seconds

Asp. Time: 4 seconds

For BioTek Elx405 plate washer parameters should be set to:

Method: 4 Cycles

Soak/Shake: Yes

Soak Duration: 010 sec

Shake before soak: No

Prime after soak: No

DISP: Dispense Volume: 350 µL/well

Dispense Flow Rate: 05

Dispense Height: 120 (15.240 mm)

Horizontal DISP POS: 0 mm

Bottom Wash First: No

Prime Before Start: No

ASPR: Aspirate Height: 029 (3.683 mm)

Horizontal ASPR POS: −30 (−1.372 mm)

Aspiration Rate: 03 (4 mm/sec)

Aspirate Delay: 0004 Msec

Crosswise ASPR: Yes

Crosswise On: All

Crosswise Height: 024 (3.048 mm)

Crosswise Horizontal POS: 30 (1.372 mm)

Final Aspiration: Yes

Final Aspiration Delay: 0000 sec

After each day of use, prime washer with at least 4 L of Milli-Q water to remove plate wash buffer.

Prime 1 L of warmed 1% Tergazyme through washer, followed by at least 4 L of Milli-Q water to remove Tergazyme. Store washer dry.

11.2 Assay Procedure: A checklist can be used as a guide by checking off steps as they were completed. Additionally, record all equipment used during the assay.

NOTE: Reverse pipetting was used throughout the assay. The coating buffer and substrate were used cold. Samples, standards, spikes, spiked samples, and control must be diluted in polypropylene tubes (smallest size possible depending on volume) and transferred to polypropylene microtubes to load on plate. Dilutions may also be prepared in polypropylene microtubes if volume allows.

11.2.1 Coat plates with 100 L/well of coating antibody (step 5.3). Tap the side of the plate until the coating solution covers the bottom of the wells uniformly, cover with sealing tape and incubate at nominal 4° C. for 16 hours with shaking at 180 rpm on orbital plate shaker (or equivalent).

11.2.2 After incubation, remove plate and blocking buffer (SuperBlock in PBS) from refrigerator and allow to equilibrate to ambient temperature.

11.2.3 Aspirate liquid from plate and tap plate firmly on Kimwipes to remove excess buffer.

11.2.4 Block plate by adding 300 µL/well of SuperBlock in TBS to each well. Incubate at 37° C. for 1 hour shaking at 200 rpm on orbital plate shaker.

11.2.5 Prepare standards, sample, controls, spike, and spiked samples during blocking incubation (refer to steps 6 through 9). Transfer volumes to the polypropylene microtubes. Rearrange tubes to match plate map.

11.2.6 Wash plate using 350 µL/well for 4 wash cycles with the plate washer using Plate Wash Buffer (step 5.2) at the plate washer setting listed in step 11.1. Blot plate firmly on Kimwipes.

11.2.7 Using an 8-channel pipette, add 100 µ/well of standards, samples, control, spike, and spiked samples into triplicate wells of the plate. Add 100 µL/well of Abcam sample diluent into all empty wells of the plate to serve as blanks. Cover with sealing tape and incubate at 37° C. for 1 hour while shaking at 200 rpm on the orbital plate shaker (or equivalent). Fill out a template to use as a guide when loading plate.

11.2.8 Wash plate using 350 µL/well for 4 wash cycles with the plate washer using Plate Wash Buffer (step 5.2) at plate washer setting at step 11.1. Blot plate firmly on Kimwipes.

11.2.9 Add 100 µL/well of biotinylated antibody (step 5.4) to each well. Cover with sealing tape and incubate plate for 1 hour at 37° C. while shaking at 200 rpm on orbital plate shaker (or equivalent).

11.2.10 Wash plate using 350 µL/well for 4 wash cycles with the plate washer using Plate Wash Buffer (step 5.2) at plate washer setting listed in step 11.1. Blot plate firmly on Kimwipes.

11.2.11 Add 100 µL/well of neutravidin-HRP (Step 5.5) to each well. Cover with sealing tape and incubate plate for 1 hour at 37° C. while shaking at 200 rpm on orbital plate shaker (or equivalent).

11.2.12 Wash plate using 350 µL/well for 4 wash cycles with the plate washer using Plate Wash Buffer (step 5.2) at plate washer setting listed in step 11.1. Blot plate firmly on Kimwipes.

11.2.13 Add 100 µL/well of K-Blue substrate to each well. Cover with sealing tape and incubate for 10 minutes at room temperature (25° C.±2° C.) without shaking.

11.2.14 Stop the reaction by adding 100 µL/well of 2M (4N) Sulfuric Acid to each well.

11.2.15 Read plate at 450 nanometers using the plate reader.

11.2.16 Plate Reader Set-Up

Turn on computer, monitor, and plate reader.

Log onto the computer. Double click on the Softmax Pro icon and select OPEN under the file pull-down menu.

Create a new SoftMax file.

Verify the parameters, Determination of Residual Phospholipase A2 Concentration by ELISA Protocol Parameters.

Set up the template, entering concentrations for standards. Do not enter dilution factors for samples, control, spike, or spiked samples. Assign the wells containing diluent (refer to step 11.2.7) as blanks to be subtracted from all wells.

12. Data Analysis and Calculations

NOTE: Only samples, spikes, spiked samples, and control, with optical densities falling within the practical quantitation limit (0.328 ng/mL-21.000 ng/mL standard) of the standard curve and meeting the % CV or the % difference criteria stated below, were accepted. If sample OD's fall below the 0.328 ng/mL standard, the result should be reported as less than 0.328 ng/mL. This value should be divided by the diluted risankizumab sample concentration to report value in ng/mg. If the sample is high in PLA2 concentration causing the non-spiked and/or the spiked sample to be above standard curve, report value as >21.000 ng/mL. This value should be divided by the diluted risankizumab sample concentration to report value in ng/mg.

NOTE: If one sample dilution has a mean OD value that is ≥the mean OD value of the 0.328 ng/mL standard and the other dilution has a mean OD value that is <the mean OD value of the 0.328 ng/mL standard, report result using the value of the dilution that has the mean OD value that is the ≥0.328 ng/mL standard mean OD value, as long as % difference between this ng/mL value and the 0.328 ng/mL value is ≤30%. If the % difference is >30%, repeat the sample.

12.1 Standard Curve 12.1.1 Standard concentrations should be entered into the protocol template. A 4-parameter logistic curve fit was used.

12.1.2 Coefficient of determination must be ≥0.99 and the % CV between triplicate wells must be ≤20%. If these criteria are not met:

12.1.2.1 One standard (1 level, 3 wells) may be dropped. If the 0.328 ng/mL is dropped, only samples and spiked samples with optical densities falling within the 0.656 ng/mL and 21.000 ng/mL (the remaining standard curve points) optical densities are acceptable.

12.1.2.2 Additionally, for the triplicates of each standard level, if a single well is clearly contaminated or shows low binding, it may be dropped. If a well is dropped from a standard level, the remaining replicates must have a % difference≤20%.

12.1.2.3 The % CV for the lowest standard, which shows OD values close to the background (blanks) of the plate, should be ≤30%. If one well is dropped, the % difference for the remaining replicates must be ≤35%. If the lowest standard is dropped, only samples and spiked samples with optical densities falling within the remaining standard curve level optical densities are acceptable.

12.1.2.4 Calculate % difference as follows:

$$\% \text{ Difference} = (\text{Abs.}(OD1 - OD2)/\text{mean value}) \times 100\%.$$

The assay must be repeated if the standards do not meet the above criteria.

Report % CV and/or % difference value and standard curve coefficient of determination results.

12.2 Samples

% CV should be ≤20% between triplicate wells. Report % CV between triplicate wells. One well from each sample dilution may be dropped. The remaining replicates must have a % difference of ≤20%. Note: If non-spiked sample OD is below the 0.328 ng/mL standard OD the % difference criteria does not apply to the non-spiked results. Refer to calculation in step 12.1.2.4. Refer to second note at the beginning of section 12 for instructions when one sample dilution is ≥0.328 ng/mL (LOQ) and the second dilution is ≤0.328 ng/mL.

Report "Non-spiked Sample Result" for each dilution in ng/mL. These values were used in spike recovery calculations.

Calculate the mean "Non-spiked Sample Result (ng/mL)" and the % difference between dilutions. Refer to calculation in step 12.1.2.4. The % difference between dilutions must be ≤20%. Report results.

Calculate the PLA2 Concentration in ng/mg from the mean (ng/mL) value as follows:

$$CHO \text{ Residual } PLA2 \text{ (ng/mg)} = \frac{\text{Mean "Non-spiked Sample Result (ng/mL)"}}{\text{Diluted Sample Concentration (mg/ml)}}$$

Record result.

12.3 Spikes

% CV should be ≤20% between triplicate wells. Record % CV. One well from the spike may be dropped. The remaining wells must have a % difference≤20%. Refer to the calculation in step 12.1.2.4.

Report PLA2 concentration in ng/mL. This result was used in spike recovery calculations.

The resulting concentration for the spike (ng/mL) must be ±20% of the theoretical spike concentration. Record result and indicate Pass or Fail. If the spike result is not within 20% of the theoretical, the assay must be repeated.

$$\frac{\text{Mean Spike Concentration (ng/mL)}}{5.250 \text{ ng/mL}} \times 100 = \text{must be } 100\% \pm 20\%$$

Spiked Samples

% CV should be ≤20% between triplicate wells. Record % CV. One well from each spiked sample dilution may be dropped. The remaining replicates must have a % difference of ≤20%. Refer to calculation in step 12.1.2.4.

Report "Spiked sample result" for each dilution in ng/mL. Record % difference (see step 12.1.2.4 for formula) between duplicate dilutions. The % difference between dilutions should be ≤25%. These results were used in spike recovery calculations.

Calculate % spike recovery for each dilution set using the formula below:

$$\% \text{ Spike Recovery} = \frac{\text{Spiked sample value} - \text{Non-spiked sample value}}{\text{Spike value}} \times 100$$

NOTE: (1) If non-spiked sample value's OD falls below 0.328 ng/mL standard (LOQ) consider value as zero in % spike recovery calculation.

% Spike recovery must be 100%±50% (50%-150%) for each dilution for each sample. Record results and Pass/Fail.

12.5 Control 12.5.1% CV should be ≤20% between triplicate wells. Record % CV result. One well from the control may be dropped. The remaining replicates must have a % difference of ≤20%. Refer to calculation in step 12.1.2.4.

12.5.2 Record PLA2 concentration in ng/mL.

Calculate PLA2 concentration in ng/mg as follows:

$$\text{Residual } PLA2\ (\text{ng/mg}) = \frac{\text{Assay Control result in ng/mL (step 12.5.2)}}{\text{Diluted risankizumab control concentration (mg/mL)}}$$

Report results appropriately and in the control logbook (ng/mg). The assay must be repeated if the control is out of the established range.

12.6 Blanks

If any blank wells show significant contamination, mask the well(s).

12.7 Assay Range

The assay range has been determined to be 0.328 ng/mL to 21.000 ng/mL.

13. Protocols for Preparation of the Recombinant PLA2, Polyclonal Rabbit Anti-CHO PLA2 Antibody, and Purification of the PLA2 Antibody 13.1 Production of PLA2G15 antigen A DNA sequence encoding PLA2G15 from *Cricetulus griseus* (Chinese hamster) (UNIPROT G3HKV9; amino acids 1-412) was synthesized and cloned into pHybE (U.S. Pat. No. 8,187,836 B2) vector followed by an in-frame hexahistidine tag (SEQ ID NO: 15). The pHybE expression vector utilizes an EF-1α promoter and an OriP origin of replication derived from Epstein-Barr virus (EBV).

This plasmid was transfected into CHO-3E7 cells (NRC Canada) grown in BalanCD CHO medium (Irvine Scientific) at 3.3×10e6 cells/ml using the transfection reagent Polyethylenimine Max (PEI Max, Polysciences Inc) at a PEI:DNA ratio of 8:1. The transfected cell culture was fed with 4% 1×CHO4 feed (Irvine Scientific), 5% Transfectory supplement (Irvine Scientific) and 2.5 g/L glucose at 24 h post-transfection. On day 7 post-transfection, the transfected cell culture was cleared by centrifugation followed by filtration through Sartopore-2 0.45+0.2 mm filter (Sartorius).

Cleared medium was loaded on a 5 ml HisTrap Excel column (Cytiva) equilibrated with PBS, pH 7.4. The column was washed with 25 mm imidazole in PBS, pH 7.4 and bound protein was eluted with 500 mM imidazole in PBS, pH 7.4. Eluted protein was concentrated using Centricon Plus-70 centrifugal filter devices (Millipore) with 30 kDa molecular weight cut-off, and further purified by SEC on a 26/60 Superdex 200 column (Cytiva) equilibrated and run with PBS, pH 7.4. Fractions containing PLA2G15 were pooled, concentration measured by absorbance at 280 nm, and samples analyzed by SEC, SDS-PAGE, and mass spectrometry. Purified [PLA2G15(cg) (34-412)]-6His stored in aliquots at −80° C.

13.2. Generation of Polyclonal Rabbit Anti-CHO PLA2 Antibody

Polyclonal rabbit anti-CHO PLA2 antibody can be generated by immunizing rabbits (e.g., New Zealand white rabbits) with the PLA2G15 antigen described above.

The antigen can be used with adjuvants (e.g., Freund's Adjuvant) to enhance the immune response for polyclonal antibody production.

The antigen can be injected intramuscularly, intradermally, or subcutaneously into the animal.

Booster immunizations can be given, for example at 1 to 8 weeks after the priming immunization and continued at 1-4 week intervals.

Polyclonal antibody production in the rabbits can be assessed by taking serum samples prior to the priming immunization and following each of the priming immunization and booster immunizations.

When the antibody titer has reached an acceptable level, the production of polyclonal antibodies can be ended.

Animals are bled and serum is collected from whole blood.

13.3. Affinity Purification of Polyclonal Rabbit Anti-CHO PLA2 Antibody

PBS equilibrated PLA2-coupled CnBr-Sepharose beads (#17-0430-01) was added to 740 ml anti-PLA2 serum and incubated rotating at 4° C. for 2 days.

Beads were drained using an EconoPac column or similar, and flow through was collected and kept for control purposes.

Beads were washed with ~200 ml TTBS and ~75 ml Gentle elution Buffer and 200 ml TTBS, and eluted with about ~50 ml volumes of IgG elution buffer (Pierce #21009).

The eluates were neutralize with 10% v/v 2M Tris-HCl pH 7.5 (predispensed into collection tubes). Protein peak were be measured with 1:5 water-diluted Bradford solution predispensed into 96 well plate (200 ul Bradford/well, add 20 ul elution).

PLA2-coupled CNBr-Sepharose beads were neutralized with 10 bed volumes of PBS, and add back to flow through from the beads draining step (using an EconoPac) to second round incubation over weekend at 4° C.

The eluates were dialyzed three times against PBS exchange buffer on Big Tuna (Unchained Labs) (50 ml elution was subjected to 96% exchange to PBS on Big Tuna. After the first round, 25 ml were taken out, mixed, concentration was measured, the pool was aliquoted 96× with 250 ul/aliquot. The other 25 ml were transferred to a new Big Tuna filter plate and subjected to new round to 96% exchange to PBS with final 2-fold concentration then biotinylated)

PLBL2 ELISA

1. Principle 96-well microtiter plates (Nunc Maxisorp Cat. #439454; VWR Cat. #62409-002) were coated with polyclonal anti-PLBL2 antibodies (2 mg/mL). Plates were then incubated with SuperBlock in PBS (Thermo Scientific Cat #37515) to block non-specific sites. Recombinant PLBL2 standards ([PLBL-2(cg) (38-585)]-6His, 1.27 mg/mL) and drug substance were then added to the plates. Plates were incubated to allow for the residual PLBL2 present in the standards and samples to bind to the polyclonal anti-PLBL2 antibodies. Plates were washed to remove unbound material and biotinylated anti-PLBL2 polyclonal antibodies (1 mg/mL) were added to the plates. Plates were incubated to allow for the biotinylated antibodies to bind to the residual PLBL2 antigens bound to the anti-PLBL2 antibodies. Plates were washed to remove unbound material and streptavidin-poly-HRP (enzyme labeled horse radish peroxidase; Thermo Scientific Cat. #21140) was added to the plates. Plates were incubated to allow for the streptavidin-poly-HRP to bind to the bound biotinylated antibodies. Plates were washed to remove unbound material and K Blue TMB substrate (Neogen Cat. #308177) was added to the plates. The chromogenic substrate was oxidized by the bound enzyme conjugated antibody, producing a blue color. Reaction was stopped with 4N (2M) Sulfuric Acid (Ricca Cat. #8310-32), changing color to yellow. Color intensity was directly proportional to the amount of residual PLBL2 antigen bound in the wells. Plates were read at 450 nanometers using the plate reader.

2. Safety

Standard laboratory safety precautions.

3. Equipment

Molecular Devices Plate Reader or equivalent
Tecan's 96 W Plate Washer or equivalent
Adjustable pipettes with tips, Rainin or equivalent
8 or 12 channel pipette with tips, Rainin or equivalent
Titer plate shaker, Lab-line or equivalent, room temperature
Incubator/Shaker, Lab-line Environ plate shaker or equivalent, room temperature
pH Meter
Balance 4. Materials 96-well microtiter plates, Nunc Maxisorp Cat. #439454 (VWR Cat. #62409-002) or equivalent
ELISA plate sealing tape—Corning Cat. #430454 or equivalent
Polypropylene tubes
Opaque microtiter plate covers
Milli-Q Water, MPS-66 or equivalent
Sodium Bicarbonate, $NaHCO_3$FW 84.01 g/mol, J.T. Baker Cat. #3509-01 or equivalent
Tween-20, J.T. Baker Cat. #X251-07 or equivalent
5 N Sodium Hydroxide, J.T. Baker Cat. #5671-02 or equivalent
5 N Hydrochloric Acid, J.T. Baker Cat. #5618-02 or equivalent
Sodium Chloride, NaCl FW 58.44 g/mol, Sigma Cat. #S3014 or equivalent
Sodium Phosphate Dibasic, 7-Hydrate, Crystals Na2HPO4*7H2O, FW 268.07, J.T. Baker Cat. #3817-01 or equivalent
SuperBlock in PBS, Thermo Scientific Cat #37515, or equivalent
Sulfuric acid 4N, Ricca Cat. #8310-32 (2N=1 M), or equivalent
K-Blue TMB Substrate, Neogen Cat. #308177 or equivalent
0.22 μM CA Sterile filter units, Corning or equivalent
Plate wash buffer, 1×PBS+0.05% tween-20, MPS-40, store at room temperature
Anti-id-PLBL2 polyclonal coating antibody, 2 mg/mL, store at nominal −80° C.
Biotinylated anti-PLBL2 polyclonal detection antibody, 1 mg/mL, store at nominal −80° C.
Recombinant PLBL2 Standard, [PLBL-2(cg) (38-585)]-6His, 1.27 mg/mL, store at nominal −80° C.
Streptavidin-Poly-HRP conjugate, Thermo Scientific Cat. #21140 or equivalent, aliquot, store at nominal 4° C.
PLBL2 Assay Control, risankizumab Ultrafiltration/Diafiltration (UF/DF) retentate 10 mg/mL, Lot #91400096, aliquot, store at nominal −80° C.

5. Preparation of Reagents and Solutions

NOTE: Reverse pipetting was used throughout the assay. The coating buffer and substrate were used cold (taken from nominal 4° C. right before use).

5.1 50 mM Sodium Bicarbonate, pH 9.4±0.1 (Coating Buffer):

To a 1 L beaker add 900 mL of Milli-Q water.

Add 4.20 g±0.01 g Sodium Bicarbonate.

Stir until completely dissolved.

Adjust pH to 9.4±0.1 with 5 N NaOH and 5 N HCl.

Transfer to a 1 L volumetric flask and bring to volume with Milli-Q water.

Mix by inversion until homogeneous.

Filter through a sterile filter unit (0.22 μm).

Store at nominal 4° C. for up to 7 days from the date of preparation.

5.2 10× Phosphate Buffered Saline (PBS), MPS-73:

To a glass beaker add 800 mL of Milli-Q water.

Add 80.0 g of NaCl to a final concentration of 80.0 g/L or 1.37 M.

Add 2.00 g of KCl to a final concentration of 2.00 g/L or 0.0268 M.

Add 27.88 g of $Na_2HPO_4 \cdot 7\ H_2O$ to a final concentration of 27.88 g/L or 0.1040 M.

Add 2.40 g of $KH_2PO_4$ to a final concentration of 2.40 g/L or 0.0176 M.

Bring to 1000 mL with Milli-Q Water.

Stir until homogeneous.

Check pH and adjust, if necessary, to 6.8-6.9 with 5 N HCl.

Stir until homogeneous.

Sterilize at 123° C. for 30 minutes.

Store at room temperature for up to 12 months.

5.3 Plate Wash Buffer/Assay Diluent/MPS-40 (1×PBS+0.05% tween-20):

To a 1 L graduated cylinder, add 100 mL of MPS-73 (step 5.2) to 900 mL of Milli-Q water.

Add 0.5 mL of tween-20 to the solution.

Stir until homogeneous.

Check pH and adjust, if necessary, to 7.40±0.05 with 5 N HCl.

Stir until homogeneous.

Filter through a 0.22 μm sterile filter unit.

Store at room temperature for up to 6 months.

5.4 Coating antibody mixture: anti-id PLBL2 polyclonal antibody (2 mg/mL), affinity purified:

NOTE: Antibody stocks stored at nominal −80° C. in vials. Prepare aliquots. Take out one aliquot per plate immediately before use. 50 mM coating buffer (step 5.1) was taken from nominal 4° C. right before use. Mixture was applied to plates while cold.

Immediately before use: Dilute coating antibody to a final concentration of 1 μg/mL in cold 50 mM Sodium Bicarbonate as follows.

For example: add 6 μL of coating antibody to 11994 μL of cold coating buffer. Mix gently by inversion.

5.5 Anti-PLBL2 polyclonal antibody-biotin conjugated (1 mg/mL)

NOTE: Stocks stored at nominal −80° C. in vials. Prepare aliquots. Take out one aliquot per plate at time of use.

Immediately before use: Dilute biotinylated antibody to a final concentration of 0.80 μg/mL in MPS-40 (step 5.3) as follows.

For example: dilute 10 μL of biotinylated antibody in 12490 μL of MPS-40. Mix gently by inversion.

5.6 Streptavidin-Poly-HRP Conjugate (0.5 mg/mL)

NOTE: Stocks stored at nominal 4° C. Take out one aliquot per plate at time of use and warm to room temperature Immediately before use, pipet up and down gently to mix the conjugate. Dilute streptavidin-poly-HRP conjugate to a final concentration of 0.083 μg/mL. Vortex gently to mix.

For example: Dilute 10 μL of HRP conjugate into 990 μL of MPS-40 (Dilution A). Then further dilute HRP conjugate by adding 200 μL of Dilution A into 11800 μL of MPS-40 (Dilution B).

6. Preparation of Standards and Spike

NOTE: Stocks stored at nominal −80° C. in single use aliquots.

6.1 Recombinant PLBL2 Standard, [PLBL-2(cg) (38-585)]-6His (1.27 mg/mL)

6.1.1 Thaw an aliquot at room temperature. Perform serial dilutions in MPS-40 (step 5.3) to a concentration of 4 ng/mL. Serial dilutions to prepare a standard curve are shown in the table below using MPS-40 in polypropylene tubes.

TABLE 34

Recombinant PLBL2 Standard Dilution Scheme

| Conc. (ng/mL) | Vol. μL of X ng/ml solution | Vol. of MPS-40 (μL) | Serial Dilution From |
|---|---|---|---|
| 1270000 | stock | — | stock |
| 12700 | 10 μL from stock | 990 μL | 100X from stock |
| 127 | 10 μL from 12700 | 990 μL | 100X from 12700 |
| 4.000, standard 1 (A) | 200 μL from 127 | 6150 μL | 31.75X from 127 |
| 1.600, standard 2 (B) | 2000 μL from 4.000 | 3000 μL | 2.5X from 4.000 ng/mL |
| 0.640, standard 3 (C) | 2000 μL from 1.600 ng/mL | 3000 μL | 2.5X from 1.600 ng/mL |
| 0.256, standard 4 (D) | 2000 μL from 0.640 ng/mL | 3000 μL | 2.5X from 0.640 ng/mL |
| 0.102, standard 5 (E) | 2000 μL from 0.256 ng/mL | 3000 μL | 2.5X from 0.256 ng/mL |
| 0.041, standard 6 (F) | 2000 μL from 0.102 ng/mL | 3000 μL | 2.5X from 0.102 ng/mL |
| 0.016, standard 7 (G) | 2000 μL from 0.041 ng/mL | 3000 μL | 2.5X from 0.041 ng/mL |

6.1.3 Transfer to polypropylene microtubes.

6.1.4 Load triplicates of each standard at 100 μL per well onto the 96-well microtiter plate.

6.2 Preparation of Spike 6.2.1 In a polypropylene microtube, prepare a 0.320 ng/mL recombinant PLBL2 spike from the 0.640 ng/mL standard (standard 3) prepared above (step 6.1.1) by diluting it 2× with MPS-40 (step 5.3). Perform a single dilution.

6.2.2 For example: dilute 300 μL of 0.640 ng/mL (standard 3) in 300 μL MPS-40 for a final concentration of 0.320 ng/mL.

6.2.3 Load triplicates of the spike at 100 μL per well onto the 96-well microtiter plate.

6.2.4 Use the 0.640 ng/mL standard (standard 3) from step 6.1.1 for spiking sample.

7. Preparation of Samples 7.1 In polypropylene tubes, dilute BDS to 0.045 mg/mL in MPS-40 (step 5.3). Perform pre-dilutions with sufficient volume for serial dilutions to be plated in triplicates at 100 μL per well.

NOTE: Use the dilution scheme below to prepare spiked samples (step 8) and BDS nominal test dilutions.

TABLE 35

For example, predilution:

| Conc (mg/mL) | Vol. μL of X mg/mL solution | Vol. μL of diluent | Serial Dilution From |
|---|---|---|---|
| 89.38 | Stock sample | N/A | N/A |
| 0.8938 | 10 | 990 | 100X from 89.38 mg/mL |
| 0.1788 | 200 | 800 | 5X from 0.8938 mg/mL |

7.2 In polypropylene microtubes, further dilute the 0.1788 mg/mL solution to 0.01117 mg/mL in MPS-40 (step 5.3).

TABLE 36

For example:

| Conc (mg/mL) | Vol. μL of X mg/mL solution | Vol. μL of diluent | Serial Dilution From |
|---|---|---|---|
| 0.1788 | Step 7.1 | N/A | N/A |
| 0.08938 (Dilution 1) | 400 | 400 | 2X from 0.1788 mg/mL |
| 0.04469 (Dilution 2) | 400 | 400 | 2X from 0.08938 mg/mL |
| 0.02235 (Dilution 3) | 400 | 400 | 2X from 0.04469 mg/mL |
| 0.01117 (Dilution 4) | 400 | 400 | 2X from 0.02235 mg/mL |

7.3 Risankizumab clarified harvest follows a similar dilution scheme as the risankizumab BDS where the final plated serial dilutions were 1000×, 2000×, 4000×, and 8000×.

NOTE: Use the dilution scheme below to prepare spiked samples (step 8) and clarified harvest nominal test dilutions.

TABLE 37

For example, predilution:

| Conc (mg/mL) | Vol. μL of X mg/mL solution | Vol. μL of diluent | Serial Dilution From |
|---|---|---|---|
| 0.49 | Stock sample | N/A | N/A |
| 0.0049 | 10 | 990 | 100X from 0.49 mg/mL |
| 0.00098 | 200 | 800 | 5X from 0.0049 mg/mL |

7.4 In polypropylene microtubes, further dilute the 0.00098 mg/mL (0.98 μg/mL) solution to 0.061 μg/mL in MPS-40 (step 5.3).

TABLE 38

For example:

| Conc (μg/mL) | Vol. μL of X μg/mL solution | Vol. μL of diluent | Serial Dilution From |
|---|---|---|---|
| 0.98 | Step 7.3 | N/A | N/A |
| 0.49 (Dilution 1) | 400 | 400 | 2X from 0.98 μg/mL |
| 0.25 (Dilution 2) | 400 | 400 | 2X from 0.49 μg/mL |
| 0.13 (Dilution 3) | 400 | 400 | 2X from 0.25 μg/mL |
| 0.061 (Dilution 4) | 400 | 400 | 2X from 0.13 μg/mL |

7.5 Risankizumab protein A eluate followed a similar dilution scheme as the risankizumab BDS where the final plated serial dilutions were 1000×, 2000×, 4000×, and 8000×.

NOTE: Use the dilution scheme below for spiking samples in step 8 and to prepare protein A eluate nominal test dilutions.

TABLE 39

For example, predilution:

| Conc (mg/mL) | Vol. μL of X mg/mL solution | Vol. μL of diluent | Serial Dilution From |
|---|---|---|---|
| 8.23 | Stock sample | N/A | N/A |
| 0.0823 | 10 | 990 | 100X from 8.23 mg/mL |
| 0.0165 | 200 | 800 | 5X from 0.0823 mg/mL |

7.6 In polypropylene microtubes, further dilute the 0.0165 mg/mL solution to 0.00103 mg/mL in MPS-40 (step 5.3).

TABLE 40

For example:

| Conc (mg/mL) | Vol. μL of X mg/mL solution | Vol. μL of diluent | Serial Dilution From |
|---|---|---|---|
| 0.0165 | Step 7.5 | N/A | N/A |
| 0.00823 (Dilution 1) | 400 | 400 | 2X from 0.01646 mg/mL |
| 0.00412 (Dilution 2) | 400 | 400 | 2X from 0.00823 mg/mL |
| 0.00206 (Dilution 3) | 400 | 400 | 2X from 0.00416 mg/mL |
| 0.00103 (Dilution 4) | 400 | 400 | 2X from 0.00206 mg/mL |

7.7 Load triplicate wells for each of the nominal test solutions on the plate at 100 μL per well for a total of 36 wells.

8. Preparation of Spiked Samples 8.1 In polypropylene microtubes, add 400 μL of the 0.640 ng/mL standard (standard 3) to an equivalent number of fresh microtubes as the nonspiked sample test dilutions.

8.2 From steps 7.1, 7.3, and 7.5, transfer 400 μL of the 500× predilutions (i.e., 0.1788 mg/mL BDS, 0.00098 mg/mL Clarified Harvest, and 0.0165 mg/mL Protein A Eluate respectively) into fresh microtubes containing 400 μL of 0.640 ng/mL spike. These were tested as Spiked Dilution 1.

8.3 Dilute Dilutions 1, 2, and 3 from each of the non-spiked sample preparations (steps 7.2, 7.4, and 7.6) 2× by adding 400 μL of sample to fresh microtubes containing 400 μL of 0.640 ng/mL spike. These were tested as Spiked Dilutions 2-4.

For example: Spiking risankizumab BDS 89.38 mg/mL to final test dilutions 1000×, 2000×, 4000×, 8000×.

TABLE 41

| Conc (mg/mL) | Vol. μL of X mg/mL solution | Vol. μL of 0.320 ng/ml spike | Serial Dilution From |
|---|---|---|---|
| 0.1788 | Step 7.1 | N/A | N/A |
| 0.08938 (Dilution 1) | 400 | 400 | 2X from 0.1788 mg/mL |
| 0.04469 (Dilution 2) | 400 | 400 | 2X from 0.08938 mg/mL |
| 0.02235 (Dilution 3) | 400 | 400 | 2X from 0.02235 mg/mL |
| 0.01117 (Dilution 4) | 400 | 400 | 2X from 0.01117 mg/mL |

8.4 The final test concentrations of the spiked samples were the same as the nonspiked sample preparations (Dilutions 1-4)+0.320 ng/mL (spike diluted 2× in sample from 0.640 ng/mL).

8.5 Load triplicate wells for each spiked sample solution on the plate at 100 μL per well for a total of 36 wells.

9. Preparation of Control 9.1 A control range must be set for every new control stock solution before use in routine testing.

The control was risankizumab UF/DF retentate 10 mg/mL.

9.2 Control Stock: Prepare 500 μL aliquots of a batch of risankizumab UF/DF retentate and store at nominal −80° C.

9.3 Working Control: Thaw an aliquot of control at room temperature. In polypropylene tubes, dilute the control to 1 mg/mL with MPS-40 (step 5.3). Transfer the 1 mg/mL solution to polypropylene microtubes and load into 3 wells of the plate at 100 μL per well. A single dilution was appropriate. Record result in PA control logbook rounded to the nearest 0.1 pg/mg.

TABLE 42

For example:

| Conc (mg/mL) | Vol. μL of X mg/mL solution | Vol. μL of diluent | Serial Dilution From |
|---|---|---|---|
| 10 | From step 9.2 | N/A | N/A |
| 1 (Dilution 1) | 40 | 360 | 10X from 10 mg/mL |

10. Procedure 10.1 Plate Washing Instructions

Fill plate wash bottle with plate wash buffer (refer to step 5.3, MPS-40). Prime plate washer. Check the following parameters.

Parameters should be set to: Plate Type: 1

For each Cycle (a total of 4 cycles): Volume: 300 μL

Soak Time: 10 seconds

Asp. Time: 4 seconds

For BioTek Elx405 plate washer parameters should be set to:

Method: 4 Cycles

Soak/Shake: Yes

Soak Duration: 010 sec

Shake before soak: No

Prime after soak: No

DISP: Dispense Volume: 300 μL/well

Dispense Flow Rate: 05

Dispense Height: 120 (15.240 mm)

Horizontal DISP POS: 0 mm

Bottom Wash First: No

Prime Before Start: No

ASPR: Aspirate Height: 029 (3.683 mm)
Horizontal ASPR POS: −30 (−1.372 mm)
Aspiration Rate: 03 (4 mm/sec)
Aspirate Delay: 0004 Msec
Crosswise ASPR: Yes
Crosswise On: All
Crosswise Height: 024 (3.048 mm)
Crosswise Horizontal POS: 30 (1.372 mm)
Final Aspiration: Yes
Final Aspiration Delay: 0000 sec After each day of use, prime washer with at least 4 L of Milli-Q water to remove plate wash buffer.

Prime 1 L of warmed 1% Tergazyme through washer, followed by at least 4 L of Milli-Q water to remove Tergazyme. Store washer dry.

10.2 Assay Procedure: A checklist can be used as a guide by checking off steps as they were completed. Additionally, record all equipment used during the assay.

NOTE: Reverse pipetting was used throughout the assay. The coating buffer and substrate were used cold. Samples, standards, spikes, spiked samples, and control must be diluted in polypropylene tubes (smallest size possible depending on volume) and transferred to polypropylene microtubes to load on plate. Dilutions may also be prepared in polypropylene microtubes if volume allows.

10.2.1 Coat plates with 100 L/well of coating antibody (step 5.4). Tap the side of the plate until the coating solution covers the bottom of the wells uniformly, cover with sealing tape and incubate at nominal 4° C. for 18±1 hours with shaking at 180 rpm on orbital plate shaker (or equivalent).

10.2.2 After incubation, remove plate and blocking buffer (SuperBlock in PBS) from refrigerator and allow to equilibrate to ambient temperature.

10.2.3 Empty liquid from plate into sink and tap plate firmly on Kimwipes to remove excess buffer.

10.2.4 Block plate by adding 300 μL/well of SuperBlock in PBS to each well. Incubate at room temperature for 1 hour without shaking.

10.2.5 Prepare standards, sample, control, spike, and spiked samples during blocking incubation (refer to steps 6 through 9). Transfer volumes to polypropylene microtubes. Rearrange tubes to match plate map.

10.2.6 Wash plate using 300 μL/well for 4 wash cycles with the plate washer using MPS-40 (step 5.3). Blot plate firmly on Kimwipes.

10.2.7 Using an 8-channel pipette, add 100 μ/well of standards, samples, control, spike, and spiked samples into triplicate wells of the plate. Add 100 μL/well of MPS-40 (step 5.3) into all empty wells of the plate to serve as blanks. Cover with sealing tape and incubate at room temperature (25° C.±2° C.) for 2 hours while shaking at 400 rpm on the orbital plate shaker (or equivalent). Fill out a template to use as a guide when loading plate.

10.2.8 Wash plate using 300 μL/well for 4 wash cycles with the plate washer using MPS-40 (step 5.3). Blot plate firmly on Kimwipes.

10.2.9 Add 100 μL/well of biotinylated antibody (step 5.5) to each well. Cover with sealing tape and an opaque plate cover to protect the reaction from light. Incubate plate for 45 minutes at room temperature (25° C.±2° C.) while shaking at 400 rpm on orbital plate shaker (or equivalent).

10.2.10 Wash plate using 300 μL/well for 4 wash cycles with the plate washer using MPS-40 (step 5.3). Blot plate firmly on Kimwipes.

10.2.11 Add 100 μL/well of Streptavidin-Poly-HRP (Step 5.6) to each well. Cover with sealing tape and an opaque plate cover to protect the reaction from light. Incubate plate for 30 minutes at room temperature (25° C.±2° C.) while shaking at 400 rpm on orbital plate shaker (or equivalent).

10.2.12 Wash plate using 300 μL/well for 4 wash cycles with the plate washer using MPS-40 (step 5.3). Blot plate firmly on Kimwipes.

10.2.13 Add 100 μL/well of K-Blue substrate to each well. Cover with sealing tape and an opaque plate cover to protect the reaction from light. Incubate for 10 minutes at room temperature (25° C.±2° C.) while shaking at 400 rpm on orbital plate shaker (or equivalent).

10.2.14 Stop the reaction by adding 100 μL/well of 2M (4N) Sulfuric Acid to each well.

10.2.15 Read plate at 450 nanometers using the plate reader.

10.2.16 Plate Reader Set-Up

Turn on computer, monitor, and plate reader.

Log onto the computer. Double click on the Softmax Pro icon and select OPEN under the file pull-down menu.

Create a new SoftMax file, set up the parameters and plate maps.

Verify the parameters, Determination of Residual Phospholipase B-Like 2 Concentration by ELISA Protocol Parameters.

Set up the template, entering concentrations for standards. Do not enter dilution factors for samples, control, spike, or spiked samples. Assign the wells containing diluent (refer to step 10.2.7) as blanks to be subtracted from all wells.

11. Data Analysis and Calculations

NOTE: Only samples, spikes, spiked samples, and control, with optical densities falling within the practical quantitation limit (0.041 ng/mL-4 ng/mL standard) of the standard curve and meeting the % CV or the % difference criteria stated below, were accepted. If sample OD's fall below the 0.041 ng/mL standard, the result should be reported as less than 0.041 ng/mL. This value should be divided by the diluted sample concentration and multiplied by 1000 to report value in pg/mg. If the sample is high in PLBL2 concentration causing the non-spiked and/or the spiked sample to be above standard curve, report value as >4 ng/mL. This value should be divided by the diluted sample concentration and multiplied by 1000 to report value in pg/mg. Consider sample value zero for spike recovery calculations when the sample is below the 0.041 ng/mL standard.

NOTE: If one sample dilution has a mean OD value that is ≥the mean OD value of the 0.041 ng/mL standard and the other dilution has a mean OD value that is <the mean OD value of the 0.041 ng/mL standard, report result using the value of the dilution that has the mean OD value that is ≥the 0.041 ng/mL standard mean OD value, as long as % difference between this ng/mL value and the 0.041 ng/mL value is ≤30%. If the % difference is >30%, repeat the sample.

11.1 Standard Curve 11.1.1 Standard concentrations should be entered into the protocol template. A 4-parameter logistic curve fit was used.

11.1.2 Coefficient of determination must be ≥0.99 and the % CV between triplicate wells must be ≤20%. If these criteria are not met:

11.1.2.1 One standard (1 level, 3 wells) may be dropped. If the 0.016 ng/mL was dropped, only samples and spiked samples with optical densities falling within the 0.041 ng/mL and 4 ng/mL (the remaining standard curve points) optical densities are acceptable.

11.1.2.2 Additionally, for the triplicates of each standard level, if a single well was clearly contaminated or shows low binding, it may be dropped. If a well was dropped from a standard level, the remaining replicates must have a % difference≤20%.

11.1.2.3 The % CV for the lowest standard, which shows OD values close to the background (blanks) of the plate, should be ≤30%. If one well is dropped, the % difference for the remaining replicates must be ≤35%. If the lowest standard is dropped, only samples and spiked samples with optical densities falling within the remaining standard curve level optical densities are acceptable.

11.1.2.4 Calculate % difference as follows:

$$\% \text{ Difference} = (\text{Abs.}\,(OD\,1 - OD\,2)/\text{mean value}) \times 100\%.$$

11.1.3 The assay must be repeated if the standards do not meet the above criteria.

11.1.4 Report % CV and/or % difference value and standard curve coefficient of determination results.

11.2 Samples

% CV should be ≤20% between triplicate wells. Report % CV between triplicate wells. One well from each sample dilution may be dropped. The remaining replicates must have a % difference of ≤20%. Note: If non-spiked sample OD is below the 0.041 ng/mL standard OD the % difference criteria does not apply to the non-spiked results. Refer to calculation in step 11.1.2.4. Refer to second note at the beginning of section 11 for instructions when one sample dilution is ≥0.041 ng/mL (LOQ) and the second dilution is <0.041 ng/mL.

Report "Non-spiked Sample Result" for each dilution in ng/mL. These values were used in spike recovery calculations.

Calculate the mean "Non-spiked Sample Result (ng/mL)" and the % difference between dilutions. Refer to calculation in step 11.1.2.4. The % difference between dilutions must be ≤25%. Report results.

Calculate the PLBL2 Concentration in pg/mg from the mean (ng/mL) value as follows:

$$CHO \text{ Residual } PLA2\,(\text{pg/mg}) = \frac{\text{Mean "Non-spiked Sample Result (ng/mL)"} \times 1000}{\text{Diluted Sample Concentration (mg/ml)}}$$

Record result.

11.3 Spikes

% CV should be ≤20% between triplicate wells. Record % CV. One well from the spike may be dropped. The remaining wells must have a % difference≤20%. Refer to the calculation in step 11.1.2.4.

Report PLBL2 concentration in ng/mL. This result was used in spike recovery calculations.

The resulting concentration for the spike (ng/mL) must be ±20% of the theoretical spike concentration. Record result and indicate Pass or Fail. If the spike result is not within 20% of the theoretical, the assay must be repeated.

$$\frac{\text{Mean Spike Concentration (ng/mL)}}{0.320 \text{ ng/mL}} \times 100 = \text{must be } 100\% \pm 20\%$$

11.4 Spiked Samples

% CV should be ≤20% between triplicate wells. Record % CV. One well from each spiked sample dilution may be dropped. The remaining replicates must have a % difference of ≤20%. Refer to calculation in step 11.1.2.4.

Report "Spiked sample result" for each dilution in ng/mL. Record % difference (see step 11.1.2.4 for formula) between duplicate dilutions. The % difference between dilutions should be ≤25%. These results were used in spike recovery calculations.

6) Calculate % spike recovery for each dilution set using the formula below:

$$\% \text{ Spike Recovery} = \frac{\text{Spiked sample value} - \text{Non-spiked sample value}}{\text{Spike value}} \times 100$$

NOTE: (1) If non-spiked sample value's OD falls below 0.041 ng/mL standard (LOQ) consider value as zero in % spike recovery calculation.

% Spike recovery must be 100%±50% (50%-150%) for each dilution for each sample. Record results and Pass/Fail.

11.5 Control

% CV should be ≤20% between triplicate wells. Record % CV result. One well from the control may be dropped. The remaining replicates must have a % difference of ≤20%. Refer to calculation in step 11.1.2.4.

Record PLBL2 concentration in ng/mL.

Calculate PLBL2 concentration in pg/mg as follows:

$$\text{Residual } PLBL2\,(\text{pg/mg}) = \frac{\text{Assay Control result in ng/mL (step 11.5.2)} \times 1000}{\text{Diluted control concentration (mg/mL)}}$$

Report results appropriately and in the control logbook (pg/mg). The assay must be repeated if the control is out of the established range.

11.6 Blanks

If any blank wells show significant contamination, mask the well(s).

11.7 Assay Range

The assay range has been determined to be 0.041 ng/mL to 4.000 ng/mL.

LPL ELISA

1. Principle

A commercial kit was used to perform this assay: Mouse LPL/Lipoprotein Lipase ELISA kit (catalogue number LS-F11957; Lifespan Bioscience (LSBio)). The 96-well plates in the purchased kits came pre-coated with anti-LPL antibodies and blocked with blocking reagent. Mouse-LPL standards (provided with the kit) and risankizumab samples (with serial dilutions using sample diluent provided in the kit) were added to the 96-well plates. The 96-well plates were incubated to allow for the LPL present in the standards and samples to bind to the polyclonal anti-LPL antibodies bound on the plates. The 96-well plates were washed to remove unbound material and biotinylated anti-LPL antibodies (detection reagent A) were added to the plates. Plates were incubated to allow for the biotinylated antibodies to bind to the LPL antigens bound to the anti-LPL antibodies. Plates were washed to remove unbound material and streptavidin-HRP conjugate (enzyme labeled horse radish peroxidase, detection reagent B) was added to the plates. Plates were incubated to allow for the streptavidin-HRP to bind to the bound biotinylated antibodies. Plates were washed to remove unbound material and TMB substrate was added to the plates. The chromogenic substrate TMB was oxidized by the bound enzyme (HRP) conjugated antibody, producing a blue color. The colorimetric reaction was stopped with the provided stop solution, changing color to yellow. The optical density of each well was directly proportional to the amount of CHO LPL antigen bound in the wells. Plates were read at 450 nm within 2 minutes after adding stop solution. Blank subtraction was performed.

2. Safety

Standard laboratory safety precautions.

3. Equipment

Molecular Devices Plate Reader or equivalent
Repeater pipette, Eppendorf or equivalent
Sterile filter unit (0.2 μm)
Adjustable pipettes with tips, Rainin or equivalent
8 or 12 channel pipette with tips, Rainin or equivalent
Titer plate shaker, Wallac Delfia Cat. #1296-004 (1.5 mm shaking orbit) or equivalent, room temperature speed approximately 350 RPM
pH Meter
Balance 4. Materials ELISA sealing tape—Corning Cat. #430454 or equivalent
Polypropylene microtubes
Immunoware microtubes with rack, 1.1 ml, or equivalent
Low protein binding tubes, Eppendorf cat. #022431064 (0.5 mL), 022431081 (1.5 mL), and 022431102 (2.0 mL), and 0030108302 (5.0 mL)
MilliQ Water
0.22 μM CA Sterile filter units, Corning or equivalent
Mouse LPL/Lipoprotein lipase ELISA kit, Lifespan Bioscience Cat. #LS-F11957, each kit contains:
96-well ELISA plate (pre-treated with anti-LPL antibody coating and then blocked with blocking buffer by the vendor)
Mouse LPL standard (lyophilized), 2 vials (depend on the lot number, the lots from 2019 have 2 vials of 4 ng/vial lyophilized stock, the lots form 2021 have two vials, 1 ng/vial lyophilized stock)
Sample diluent (20 mL)
Biotinylated anti-LPL antibody (capturing antibody)—detection reagent A (120 μL)
Assay diluent A (>10 mL)
Streptavidin-HRP conjugate—detection reagent B (120 μL)
Assay diluent B (>10 mL)
Wash Buffer (25× concentration), 30 mL
TMB substrate, 10 ML
Stop solution, 10 mL
Adhesive plate sealer 5. Preparation of Reagents and Solutions NOTE: Reverse pipetting was used throughout assay unless otherwise stated. All buffers were used at room temperature.

5.1 1× Plate Wash Buffer

To a 1 L graduated cylinder, add 30 mL of 25× wash buffer concentrate to 720 mL of MilliQ water. Mix until homogeneous.

Wash buffer was stored at 4° C. once prepared.

5.2 Assay Buffer (LSbio proprietary ingredient)

The sample diluent and assay diluents for biotinylated antibody and Neutravidin-HRP conjugate (assay diluent A and B) provided with the kit was used.

5.3 Substrate

The TMB substrate provided by the kit was used.

5.4 Stop Solution

The Stop Solution provided by the kit was used.

5.5 Detection Reagent A Working Solution

Immediately before use: Dilute detection reagent A at a 1:100 ratio with assay diluent A.

For example: If it is necessary to prepare 11 mL of Detection Reagent A Working Solution, add 110 μL of Detection Reagent A to 10,890 μL of Assay diluent A.

5.6 Detection Reagent B Working Solution

Immediately before use: Dilute Detection Reagent B at a 1:100 ratio with Assay diluent B.

For example: If it is necessary to prepare 11 mL of Detection Reagent B Working Solution, add 110 μL of Detection Reagent B to 10,890 μL of Assay diluent B.

5.7 Assay Control

Prepare a control with an LPL level 62.5 pg/mL that fell within the assay range. Prepare single use aliquots and store at nominal −80° C.

For example: using sample diluent 200 μL mix with 200 μL of LPL standard concentration 125 pg/mL;

6. Preparation of Standards and Spike 6.1 Preparation of standard curve solutions 6.1.1 For the historical lots (2019~2020) reconstitute lyophilized standard using 2 mL sample diluent to prepare LPL stock concentrate at 2000 pg/mL concentration. Allow LPL stock to incubate at room temperature for 10 minutes without vortex or vigorous mixing.

6.1.2 For the most recent lots of the kit (from 2021), to reconstitute lyophilized standard using 1 mL sample diluent to prepare the LPL stock concentration at 1000 pg/mL and incubate at room temperature for 10 mins with vortex or vigorous mixing. 6.1.3 Prepare standard curve dilutions by serially diluting the LPL stock concentrate (2000 pg/mL) using sample diluent to the following concentrations: 1000, 500, 250, 125, 62.5, and 31.25 pg/mL from step 6.1.1. See the table below for an example:

TABLE 43

LPL Standard Dilution Scheme Example

| Standard number | Conc. (pg/mL) | Vol. μL of X pg/mL solution | Vol. of assay buffer (μL) | Serial Dilution From |
|---|---|---|---|---|
| | 2000 (Stock) | N/A | N/A | N/A |
| Standard 1 | 1000 | 500 μL of 2000 pg/mL | 500 μL | 2X from Stock |
| Standard 2 | 500 | 500 μL of 1000 pg/mL | 500 μL | 2X from 1000 pg/mL |
| Standard 3 | 250 | 500 μL of 500 pg/mL | 500 μL | 2X from 500 pg/mL |
| Standard 4 | 125 | 500 μL of 250 pg/mL | 500 μL | 2X from 250 pg/mL |
| Standard 5 | 62.5 | 500 μL of 125 pg/mL | 500 μL | 2X from 125 pg/mL |

TABLE 43-continued

| LPL Standard Dilution Scheme Example | | | | |
|---|---|---|---|---|
| Standard number | Conc. (pg/mL) | Vol. μL of X pg/mL solution | Vol. of assay buffer (μL) | Serial Dilution From |
| Standard 6 | 31.25 | 500 μL of 62.5 pg/mL | 500 μL | 2X from 62.5 pg/mL |

6.1.4 Prepare the standard curved dilutions by serially diluting the LPL stock concentrate 1000 pg/mL using sample diluent to the following concentration, 500, 250, 125, 62.5 and 31.25 pg/mL from step 6.1.2. See the table below for the example.

TABLE 44

| Standard number | Conc. (pg/mL) | Vol. μL of X pg/mL solution | Vol. of assay buffer (μL) | Serial Dilution From |
|---|---|---|---|---|
| Standard 1 | 1000 (Stock) | 500 μL stock | N/A | N/A |
| Standard 2 | 500 | 500 μL of 1000 pg/mL | 500 μL | 2X from Stock |
| Standard 3 | 250 | 500 μL of 500 pg/mL | 500 μL | 2X from 500 pg/mL |
| Standard 4 | 125 | 500 μL of 250 pg/mL | 500 μL | 2X from 250 pg/mL |
| Standard 5 | 62.5 | 500 μL of 125 pg/mL | 500 μL | 2X from 125 pg/mL |
| Standard 6 | 31.25 | 500 μL of 61.25 pg/mL | 500 μL | 2X from 62.5 pg/mL |

Note: Depend on the lot of the commercial kits used for the assay, then use the step 6.1.3 or 6.1.4 to dilute the standard curve with range of the concentrations 1000 pg/mL, 500 pg/mL, 250 pg/mL, 125 pg/mL, 62.5 pg/mL and 31.25 pg/mL.

6.2 Preparation of assay spike

Prepare the high level of LPL assay spike 250 pg/mL standard by diluting the 1000 pg/mL (standard 1 in step 6.1) 4× with sample diluent.

For example: dilute 200 μL of 1000 pg/mL (standard 1) in 600 μL sample diluent for a final concentration of 250 pg/mL.

Prepare the intermediate level of LPL assay spike 125 pg/mL by diluting the 500 pg/mL (standard 2 in step 6.1) 4× with sample diluent.

Prepare the low level of LPL assay spike 31.25 pg/mL by diluting the 125 pg/mL (standard 4 in step 6.1) by diluting it 4× with sample diluent.

Load triplicates of the spike at 100 μL per well onto the 96-well microtiter plate.

6.3 Preparation of samples 6.3.1 Dilute risankizumab Process 4 BDS, 150 mg/mL to the concentration 0.075 mg/mL for the spiked sample preparation and nominal dilution of risankizumab BDS samples

TABLE 45

| For example, predilution | | | |
|---|---|---|---|
| Conc (mg/mL) | Vol. μL of X mg/mL solution | Vol. μL of Sample diluent | Serial Dilution From |
| 150 | Stock sample | N/A | N/A |
| 15 | 20 μL of 150 mg/mL | 180 | 10X from 150 mg/mL |
| 1.5 | 50 μL of 15 mg/mL | 450 | 10 X from 15 mg/mL |
| 0.15 | 300 μL of 1.5 mg/mL | 2700 | 10 X from 1.5 mg/mL |
| 0.075 | 2000 μL of 0.15 mg/mL | 2000 | 2 X from 0.15 mg/mL |

6.4 Preparation of spiked samples 6.4.1 In polypropylene microtubes, mix 200 μL of Abcam sample diluent with the same volume 200 μL of prediluted risankizumab BDS samples (step 6.3.1) as the non-spiked risankizumab BDS sample In polypropylene microtubes, mix 200 μL of (standard 2 from step 6.1) 500 pg/mL standard solution with 200 μL of prediluted risankizumab BDS samples (step 6.3.1) as the high level of PLA2 spiked sample In polypropylene microtubes, mix 200 μL of (standard 3 from step 6.1) 250 pg/mL standard solution with 200 μL of prediluted risankizumab BDS samples (step 6.3.1) as the intermediate level of PLA2-spiked sample In polypropylene microtubes, mix 200 μL of (standard 4 from step 6.1) 125 pg/mL standard solution with 200 μL of prediluted risankizumab BDS samples (step 6.3.1) as the intermediate level of PLA2-spiked sample

7. Procedure 7.1 Assay Procedure: A Checklist can be used as a guide by checking off steps as they were completed. Reverse pipetting was used throughout unless otherwise stated.

7.1.1 Bring all contents of the kit to room temperature (RT) for at least 2 hours.

7.1.2 Prepare standard, non-spiked samples, spiked samples, and control.

7.1.3 Using a multi-channel pipette, pipet 100 L/well of standards, non-spiked samples, spiked samples (if applicable), and control, into triplicate wells of the plate and 100 L/well of assay buffer to all empty wells to serve as blanks. Cover with sealing tape and incubate at 37° C. while shaking at approximately 100 rpm for two hours.

7.1.4 Aspirate liquid from each well and discard into the sink. Tap the plate gently on paper towel or kimwipe to remove liquid residue, followed by NO WASH.

7.1.5 Add 100 L/well Detection Reagent A Working Solution (step 5.5). Cover with sealing tape and incubate at room 37° C. while shaking at approximately 100 rpm for one hour.

7.1.6 Aspirate liquid from each well and discard into the sink. Tap the plate gently on paper towel or kimwipe to remove liquid residue. Wash the plate 3 times with 350 L/well of Wash Buffer in each well. For each wash, allow plate to incubate for 2 minutes before aspirating the wash buffer. Blot plate on paper towels.

7.1.7 Add 100 μL/well Detection Reagent B Working Solution (step 5.6). Cover with sealing tape and incubate at 37° C. while shaking at approximately 100 rpm for one hour.

7.1.8 Aspirate liquid from each well and discard into the sink. Tap the plate gently on paper towel or kimwipe to remove liquid residue. Wash the plate 5 times with 350 L/well of Wash Buffer in each well. For each wash, allow plate to incubate for 2 minutes before aspirating the wash buffer. Blot plate on paper towels.

7.1.9 Add 90 L/well of TMB substrate (step 5.3), cover with sealing tape, protect the plate from the light and incubate at 37° C. without shaking for 10 minutes (start timer as soon as substrate was added to first column).

7.1.10 Stop the reaction by adding 50 L/well Stop Solution (step 5.4).

7.1.11 Read plate at 450 nm within 2 minutes after adding stop solution. Blank subtraction was performed.

8. Data Analysis and Calculations

NOTE: Only samples, and control dilutions, with OD values falling within the 31.25 pg/mL standard (assay LOQ) and 1000 pg/mL (highest standard), and passing spike recovery criteria (if applicable), were accepted. If sample falls below the 31.25 pg/mL standard (<31.25 pg/mL) or the LOQ, result should be reported as less than 31.25 pg/mL or less than the LOQ. This result should then be multiplied by the dilution factor and divided by the initial sample concentration (mg/mL) to report result in pg/mg. If the sample is high in LPL concentration causing the sample to be above the standard curve (1000 pg/mL), then repeat at a dilution high enough to be within the standard curve. If a sample fails spike recovery, repeat diluting more.

TABLE 46

| Assay Acceptance Criteria: | | |
|---|---|---|
| Data | Parameter | Acceptance Criteria |
| Coefficient of Determination | Standard Curve Efficiency | $R^2$ ≥0.99 |
| Assay Control | Accuracy of standard curve | Must be within the established range |
| % CV between Samples, Spiked Samples, and Control Dilution Factor Corrected Results (U/mL) (for results within the assay range) | Precision | % CV must be ≤20% |
| Spiked Samples | Accuracy/ Specificity in Samples | % Spike Recovery: 50% to 150% |

8.1 Standard Curve 8.1.1 Standard concentrations should be entered into the protocol template.

8.1.2 Use the 4-parameter curve fit (4P) to graph the standard curve using each of the response values (OD).

Note: The above 4-parameter fit equation is equivalent to:

$$y = D + \frac{A - D}{1 + \left(\frac{x}{C}\right)^B}$$

8.1.3 The assay must be repeated if the standards do not meet the acceptance criteria.

8.2 Spiked Samples (When applicable.)

8.2.1 For spiked results that were within the assay range (evaluating every well): Multiply the spiked sample results by the dilution factors. Calculate the mean and % CV of the dilution factor corrected spiked sample results. % CV must be </=20% between dilutions. Calculate % spike recovery using the equation below.

$$\% \text{ Spike Recovery} = ((\text{Spiked Sample Result}(\text{pg/mL}) - \text{Non-Spiked Sample Result}(\text{pg/mL})) \div (\text{theoretical Spike (S) in pg/mL}) \times 100$$

8.2.2 Spike recovery based on mean results must be within 50% and 150%.

8.2.3 If this criterion is not met, the sample must be repeated.

8.3 Non-spiked Samples 8.3.1 For sample dilutions within the assay range (evaluating every well): Calculate the mean and % CV for the obtained dilution factor corrected results. The % CV between dilutions must be ≤20%. If this criterion is not met the sample must be repeated.

8.3.2 Using the acceptable results, calculate LPL concentration in ng/mg by dividing the final dilution factor corrected mean result by the initial sample stock concentration.

$$LPL\,(\text{ng/mg}) = \frac{\text{Mean Sample Dilution Factor adjusted pg/mL result}}{\text{Initial sample concentration (mg/mL)}}$$

8.3.3 Record final result to a whole number.

8.4 Control 8.4.1 For control dilutions within the assay range (evaluating every well): Calculate the mean and % CV for the obtained dilution factor corrected results. The % CV between dilutions must be ≤20%. If this criterion is not met the assay must be repeated. Record final result to 1 decimal place in ng/mL. The assay must be repeated if the control is out of the established range.

8.5 Assay Range: The assay range was 31.25 pg/mL to 1000 pg/mL.

Results

PLA2, PLBL2, and LPL levels in various lots of DP1, DP2, DP3, and DP4 were determined and shown in Table 47 below.

TABLE 47

| Hitchhiker protein Levels | | | |
|---|---|---|---|
| Process | PLA2 (ng/mg) | PLBL2 (ng/mg) | LPL (ng/mg) |
| DP1 | 0.29-1.09 | 5.7-16.43 | 0.004-0.019 |
| DP2 | 0.25-1.03 | 0.51-1.34 | 0.019-0.291 |
| DP3 | 0.07-0.27 | 0.003-0.020 | 0.008-0.658 |
| DP4 | <0.009 | <0.0006 | 0.015-0.098 |

As shown in Table 47, the levels of PLBL2 are greatly reduced in DP3 and DP4 compared to DP1 and DP2. For example, there is almost more than 1000-fold reduction of PLBL2 level in DP4 compared to DP1 and DP2.

Similarly, the levels of PLA2 are greatly reduced in DP3 and DP4 compared to DP1 and DP2. DP1 and DP2 have at least 0.25 ng/mg (250 pg/mg) of PLA2.

Example 10: Polysorbate Stability is Increased in Risankizumab Drug Products DP3 and DP4

The stability of polysorbate 20 (PS20) and polysorbate 80 (PS80) was determined by detecting the levels of PS20 or PS80, and free fatty acid (FFA) in samples stored at various temperatures (i.e., 5° C., 25° C., and 40° C.) for 6 months.

Determination of PS20/PS80 Using Charged Aerosol Detector (CAD)

Methods for detecting the levels of PS20 in various drug products are described below. The levels of PS80 in various drug products were determined using the same methods.

1. Principle

The polysorbate 20 content in the 150 mg/mL formulation test samples was determined using a Charged Aerosol Detector (CAD). The detection was based on the nebulization of the analyte in a continuous nitrogen flow. After removal of the mobile phase, a second positive charged nitrogen flow causes formation of charged particles. The released charge was proportional to the quantity of polysorbate 20.

2. Equipment

HPLC System with gradient elution, temperature-controlled autosampler, column oven and degassing unit. Also, stainless steel capillaries (connecting HPLC column and column to the detector).

Corona Veo RS Charged Aerosol Detector (CAD), Thermo Fisher Scientific part #5081.0020

Chromatography Data System (e.g., Empower)

Column: Waters Oasis MAX Column (2.1×20 mm, 30 μm), part #186002052

HPLC vials amber, screw cap, Agilent, catalog #5182-0716 or equivalent

Blue screw caps, Agilent, catalog #5182-0717 or equivalent

Analytical balance pH meter

Stir plate, stir bars, and vortex mixer

Volumetric flask

3. Materials

Ammonium formate, Fisher, LC-MS Grade, catalog #A115-50 or equivalent

Methanol, EMD, LC-MS Grade, catalog #MX0486-6 or equivalent

Isopropyl Alcohol, Fisher, LC-MS Grade, catalog #A461-212 or equivalent

Acetonitrile, Fisher, Optima LC-MS Grade, catalog #A955-212 or equivalent

Formic acid, ThermoScientific, catalog #28905 or equivalent

Polysorbate 20 (PS 20), J.T Baker, catalog #4116-02 or equivalent

Project GB Reference Standard

Purified water (Type 1 grade rated, e.g., Milli-Q, WFI or equivalent)

4. Preparation of Solutions 4.1 Diluted formic acid solution (1:1) for pH adjustment of mobile phase A 4.1.1 In a glass beaker, add 7.5 mL formic acid and 7.5 mL of purified water.

4.1.2 Mix the solution until homogeneous.

4.2 Mobile Phase A (10 mM Ammonium formate pH 3.0/20% isopropyl alcohol)

4.2.1 Add 1400 mL of purified water to a 2 L beaker.

4.2.2 Weigh 1.26 g±0.01 g of ammonium formate and add to the beaker.

4.2.3 Using the diluted formic acid solution from step 4.1, adjust the pH of the solution to 3.0±0.1.

4.2.4 Add 400 mL isopropyl alcohol.

4.2.5 Transfer the solution to a 2 L volumetric flask.

4.2.6 Bring to volume with purified water.

4.2.7 Transfer the solution into an appropriate container.

4.2.8 Mix the solution for approximately 15 minutes.

4.2.9 Check homogeneity of the solution by visual inspection.

4.2.10 Store at room temperature for up to 1 week.

4.3 Mobile Phase B (50% isopropyl alcohol/50% acetonitrile)

4.3.1 Add 500 mL of isopropyl alcohol and 500 mL of acetonitrile to a 1 L glass bottle.

4.3.2 Mix the solution for approximately 15 minutes.

4.3.3 Check homogeneity of the solution by visual inspection.

4.3.4 Store at room temperature for up to 1 month.

4.4 Autosampler Rinse Solution (20% Methanol)

4.4.1 Add 200 mL of methanol and 800 mL of purified water to a 1 L glass bottle.

4.4.2 Mix the solution until homogenous.

4.4.3 Store at room temperature for up to 1 week.

5. Preparation of Standards, Samples, and Blank 5.1 Recommendations for preparation of standards and samples 5.1.1 Precise pipetting of polysorbate 20

Caution should be taken when pipetting the PS20 containing samples, standard and dilutions. It is recommended to equilibrate the pipette tip by pipetting up and down 5 times. Pipetting should be done slowly. It is important to wait for the highly viscous solution to be fully drawn and for the thin solution film to fully leave the pipette tip after pipetting up. For pipetting down, waiting for the solution to fully clear the pipette tip is equally important. Waiting approximately 15 sec in each direction (up/down) might be necessary.

5.1.2 Volume of standard and sample solutions

The volume of calibration standards and diluted sample solutions may deviate from 500 μL. However, the volume must be identical for standards and diluted sample solutions.

5.2 Polysorbate 20 Stock Solution I at 10 mg/mL 5.2.1 Weigh 1.00 g±0.01 g of polysorbate 20 into a 100 mL tared volumetric flask.

5.2.2 Bring to volume with purified water.

5.2.3 Carefully add stir bar and appropriate cap. If the flask is not light protective, wrap the flask in foil.

5.2.4 Mix by stirring for approximately 15 minutes.

5.2.5 Check homogeneity of the solution by visual inspection.

5.2.6 Store at 2-8° C. for up to 1 week.

5.3 Polysorbate 20 Stock Solution II at 0.5 mg/mL 5.3.1 Prior to preparation, allow the polysorbate 20 stock solution I to stir at room temperature for at least 10 minutes. This is only required if solution I is not freshly prepared.

5.3.2 Dilute 2.5 mL of polysorbate stock solution I into a 50 mL volumetric flask.

5.3.3 Bring to volume with purified water.

5.3.4 Mix by stirring for approximately 15 minutes. If the flask is not light protective, wrap the flask in foil.

5.3.5 Check homogeneity of the solution by visual inspection.

5.3.6 Store at 2-8° C. for up to 1 week.

5.4 Calibration Solutions

For the calibration curve, a minimum of 6 calibration standards with different PS 20 concentrations are prepared using the polysorbate 20 Stock Solution II from Section 5.3. An example dilution scheme is shown in the table 48 below. All dilutions are prepared in water. Volumes may be adjusted proportionately ensuring that the targeted PS 20 concentration remains unchanged and the total volume of each preparation is greater than 10 mL.

5.4.1 Prepare a polysorbate 20 standard curve from 0.0125 mg/mL to 0.15 mg/mL. Bring to volume in volumetric flasks with purified water as follows:

TABLE 48

| Sample ID | Concentration of PS 20 [mg/mL] | Volume of PS 20 solution [mL] | Total volume [mL] |
|---|---|---|---|
| CS 1 | 0.0125 | 0.5 of Stock Solution II | 20 |
| CS 2 | 0.025 | 1.0 of Stock Solution II | 20 |
| CS 3 | 0.050 | 2.0 of Stock Solution II | 20 |
| CS 4 | 0.075 | 3.0 of Stock Solution II | 20 |
| CS 5 | 0.10 | 4.0 of Stock Solution II | 20 |
| CS 6 | 0.15 | 6.0 of Stock Solution II | 20 |

5.4.2 Mix by inversion approximately 15 times. If the flask is not light protective, wrap the flask in foil.

5.4.3 Store at 2-8° C. for up to 1 week.

5.4.4 Transfer 500 µL of each calibration standard solution into an amber HPLC vial.

5.5.5 Vortex for approximately 15 seconds.

5.5.6 Invert the sample by turning the sample upside down for approximately 5 seconds and back.

5.5.7 Vortex for approximately 15 seconds.

5.5 Precision standard solution preparation (PrS)

5.5.1 Prepare the PrS. Bring to volume in volumetric flasks with purified water as follows:

TABLE 49

| Sample ID | Concentration of PS 20 [mg/mL] | Volume of PS 20 Stock Solution I for Precision Standard [mL] | Total volume [mL] |
|---|---|---|---|
| PrS | 0.10 | 0.20 | 20 |

5.5.2 Mix by inversion approximately 15 times. If the flask is not light protective, wrap the flask in foil.

5.5.3 Store at 2-8° C. for up to 1 week.

5.5.4 Transfer 500 µL of each calibration standard solution into an amber HPLC vial.

5.5.5 Vortex for approximately 15 seconds.

5.5.6 Invert the sample by turning the sample upside down for approximately 5 seconds and back (once).

5.5.7 Vortex for approximately 15 seconds.

5.6 Samples 5.6.1 Bring samples to room temperature and vortex for approximately 15 seconds.

5.6.2 Dilute samples 1:1 with purified water by taking 250 µL sample and 250 µL purified water in an amber HPLC vial. Air bubbles should be avoided.

5.6.3 Vortex for approximately 15 seconds.

5.6.4 Invert the sample by turning the sample upside down for approximately 5 seconds and back (once).

5.6.5 Vortex for approximately 15 seconds.

6 Storage and Stability of Solutions

TABLE 50

| Name | Storage Conditions | Stability |
|---|---|---|
| PS 20 Stock Solution I & II and PrS Stock Solution | 2-8° C., dark | 7 days |
| PS 20 Calibration Standards | 2-8° C., dark | 7 days |
| PS 20 Precision Standard | 2-8° C., dark | 7 days |
| Diluted Samples | RT | 24 hours |
| Diluted Samples in Autosampler | 2-8° C. | 72 hours |
| Undiluted Samples | −80° C./RT | Up to 3 freeze/thaw cycles |
| Mobile Phase A | RT | 1 week |
| Mobile Phase B | RT | 1 month |

7. Procedure 7.1 HPLC Setup 7.1.1 The CAD detector has to be directly connected to the column. Do not connect to column compartment valve.

7.1.2 Columns, Mobile Phase and Solutions

TABLE 51

| | | |
|---|---|---|
| Column | Waters Oasis MAX 30 µm (2.1 × 20 mm), part #186002052 | |
| HPLC capillaries | The capillary material (connecting HPLC to column and column to detector) has to be stainless steel | |
| Mobile Phase A | 10 mM ammonium formate pH 3.0 and 20% isopropyl alcohol in purified water | |
| Mobile Phase B | 50% isopropyl alcohol, 50% acetonitrile | |
| Maximum recommended column pressure | 415 bar | |
| Flow Rate | 1.0 mL/min | |
| Injection Volume | 10 µL | |
| Column Oven Temperature | 30° C. | |
| Autosampler temperature | 2-8° C. | |
| CAD Veo RS | Signal Output/Data collectionrate | 100 Hz |
| | Temperature | 70° C. ± 2° C. |
| | Filter constant | 5 s |
| | Gas flow mode | analytical |
| Run Time | 25 min | |

7.1.3 Gradient

TABLE 52

| Time (min) | Mobile Phase A (%) | Mobile Phase B (%) | Valve |
|---|---|---|---|
| 0 | 100 | 0) | Waste |
| 13.00 | 100 | 0 | CAD |
| 16.00 | 100 | 0 | CAD |
| 16.10 | 0 | 100 | CAD |
| 21.00 | 0 | 100 | CAD |
| 21.10 | 100 | 0 | CAD |
| 24.50 | 100 | 0 | Waste |
| 25.00 | 100 | 0 | Waste |

7.2 Equilibration and Conditioning of the HPLC and CAD 7.2.1 Turn on the CAD. When the start window of the detector appears, turn on the nitrogen flow and select "Gas on" at the panel of the CAD.

7.2.2 Select "Run mode".

7.2.3 Flush the system with 20% methanol/80% purified water at 1.0 mL/min for approximately 30 minutes. The current should not exceed 10 pA.

7.3 Equilibration of a New and Used Column 7.3.1 Equilibration of a new column 7.3.1.1 When a new column is used for the first time, flush the conditioning solution to waste and not through the detector 7.3.1.2 Flush thoroughly with starting conditions (e.g., 100% mobile phase A, 1.0 mL/min) for approximately 30 minutes.

7.3.1.3 Afterwards, switch the flow to the detector and flush column and detector for approximately 60 minutes with 100% mobile phase A, 1.0 mL/min until a stable baseline of the CAD is reached.

7.3.1.4 Start equilibration with 5 injections of purified water followed by 7 injections of CS5 (0.1 mg/mL polysorbate 20 calibration standard).

7.3.1.5 Perform 3 injections of reference standard (WS01 diluted 1:1).

7.3.1.6 Compare the reference standard chromatograms to the reference chromatogram.

7.3.2 Equilibration of a used column 7.3.2.1 Equilibrate a used column for approximately 60 minutes with 100% mobile phase A at 1.0 mL/min until a stable baseline of the CAD is reached.

7.3.2.2 Perform 5 injections of purified water followed by 3 injections of CS5 (0.1 mg/mL polysorbate 20 calibration standard).

7.3.2.3 Perform 3 injections of reference standard (WS01 diluted 1:1).

7.3.2.4 Compare the reference standard chromatograms to the reference chromatogram.

7.4 System Shut Down and Column Storage 7.4.1 Column storage conditions 8.5.1.1 Flush the column with at least double column volumes of 20% methanol/80% purified water and store the column at room temperature.

7.4.2 System shut-down 8.5.2.1 After each sequence, rinse the detector with 20% methanol/80% purified water for at least 1 hour at a flow rate of 1.0 mL/min, stop the liquid flow and let the CAD dry with nitrogen flow for approximately 1 hour.

8. Calculations 8.1 Evaluation and Integration 8.1.1 Evaluation of the concentration (mg/mL) of polysorbate 20 samples is calculated using a quadratic regression not forced through zero ($2^{nd}$ order polynominal equation).

8.1.2 Dilutions are considered by a factor entered and automatically calculated in the chromatographic system, e.g., CDS, or manually.

8.1.3 The polysorbate 20 peaks are integrated without baseline subtraction.

8.1.4 The CAD is sensitive to changes in mobile phase. Switching from mobile phase A to mobile phase B or back influences the evaporation conditions and leads to a signal. These so-called system peaks might be found in each chromatogram at approximately 16 and 24 minutes plus the system dependent delay volume.

8.2 System Suitability 8.2.1 Coefficient 9.2.1.1 The coefficient of determination for the quadratic fit of the calibration curve must be $R^2$ value≥0.99.

8.2.2 Drift Control (DC)

8.2.2.1 As a drift control, the calibration standard CS5 (0.1 mg/mL) is injected after every 20 samples at most and directly after the last sample.

8.2.2.2 The polysorbate 20 concentration of the drift control standard must be within ±10% of the theoretical value (e.g., 0.09 to 0.11 mg/mL for DC with theoretical concentration of 0.10 mg/mL).

8.2.3 Precision Standard (PrS)

8.2.3.1 For the weight check, inject the precision standard (PrS—0.10 mg/mL polysorbate 20) directly after the last calibration standard injection. The polysorbate 20 concentration of the PrS must be within ±10% of the theoretical value (e.g., 0.09 to 0.11 mg/mL for DC with theoretical concentration of 0.10 mg/mL).

8.2.4 System Consistency 8.2.4.1 To ensure nebulizer temperature consistency through a sequence, the peak area of the peak in water injections is evaluated.

8.2.4.2 The peak area of the peak in the water injections must be within ±30% of the peak area of the corresponding peak in the reference water injection (last water injection before the calibration curve).

Determination of FFAs Using RP-HPLC-UV

Principle

Free Fatty acids appear as degradation products of polysorbate 20 or polysorbate 80 in biopharmaceuticals. In protein formulations polysorbate 20 minimizes adsorption to surfaces, reduces the rate of protein denaturation and increases the drug solubility and stability. Due to the diversity of free fatty acids (FFA) and the absence of chromophores, it cannot be accurately analyzed by standard analytical UV/HPLC techniques without a foregoing derivatization or labeling of the FFAs.

This method was performed using reversed-phase HPLC with UV detection. The free fatty acids were labeled with PDAM (1-Pyrenyldiazomethane) prior analyses. The generated signal was directly proportional to the quantity of the analyte.

Equipment

Equipment of comparable quality may be used instead of the items listed below.

TABLE 53

| Equipment | Manufacturer |
|---|---|
| An HPLC system consisting of at least: | |
| Binary pump or quaternary pump | e.g. Thermo Ultimate 3000 |
| Mobile phase degassing unit | e.g. Thermo Ultimate 3000 |
| Refrigerated Autosampler | e.g. Thermo Ultimate 3000 |
| Column oven | e.g. Thermo Ultimate 3000 |
| UV/Vis Detector | e.g. Thermo Ultimate 3000 |
| Pipettes | e.g. Eppendorf |
| Analytical balance | e.g. Mettler Toledo |
| Oven Incubator | e.g. VWR 1525 |

Materials, Chemicals and Reagents

The following materials, chemicals and reagents were used. Materials, chemicals and reagents of comparable or higher quality may be used instead of the items listed below.

TABLE 54

| Name | Purity/quality | Manufacturer |
|---|---|---|
| Water | For chromatography e.g. Milli-Q-water | Milli-Q-water |
| Acetonitrile | Hypergrade for LC-MS | VWR, P/N JT9853 |
| Methanol | CHROMASOLV LC-MS Grade | Honeywell, P/N 14262 |
| Lauric acid | ≥98% | Sigma Aldrich, P/N R420120 |
| Tridecanoic acid | ≥98% | VWR, P/N: TCT0412 |
| Myristic acid | ≥98% | Sigma Aldrich, P/N R420140 |
| Palmitic acid | ≥98% | Sigma Aldrich, P/N R420160 |
| Stearic acid | ≥98% | Sigma Aldrich, P/N R420180 |
| PDAM | >98% | Invitrogen, P/N: P1405 |
| HPLC vials amber | n.a. | Agilent, P/N 5182-0716 |
| Screw cups | n.a. | Agilent, P/N 5182-0717 |

Preparation and Stability of Solutions

The sample weights and volumes given below can vary as long as the concentration remains unchanged.

Mobile Phase A: Milli-Q-Water

Mobile Phase B: Acetonitrile

Fatty Acid Standards (Lauric Acid, Myristic Acid, Palmitic Acid, and Stearic Acid) Stock Solutions (0.6 mg/mL)

Using Lauric acid as an example, accurately weigh 30 mg±2 mg of lauric acid (M=200.32 g/mol) in a 50 mL volumetric flask and dissolve in 50 mL methanol on a stir bar. A dilution was made by diluting the stock solution to a concentration of 500 nmol/ml with acetonitrile based on the real weighed mass.

Example:

$$c\left[\frac{\text{nmol}}{\text{ml}}\right]=\frac{\frac{m}{M}}{V}=\frac{\frac{30.5\text{ mg}}{200.32\text{ mg/mmol}}}{50\text{ ml}}=0.0030\text{ mmol}=3045.1\text{ nmol}$$

$$F_{dil}=3045.1/500=6.09$$

$$V_{stock}*F_{dil}=V_{500\,nmol/ml}$$

$$200\ \mu\text{l}*6.09=1218\ \mu\text{l}$$

Add 200 μl to 1018 μl ACN.

Mixing the four fatty acid standards with 1:1:1:1 ratio, the concentration of each fatty acid is 125 nmol. Store the solution in the dark at room temperature, e.g. in a brown glass screw bottle.

Internal Standard (IS) Tridecanoic Acid

Accurately weigh 30 mg±2 mg of Tridecanoic (M=214, 348 g/mol) acid in a 50 mL volumetric flask and dissolve in 50 mL methanol on a stir bar. A dilution was made by diluting the stock solution to a concentration of 500 nmol/ml with acetonitrile. Storing the solution in the dark at room temperature, e.g., in a brown glass screw bottle.

NaCl Solution 4M

Prepare 4M NaCl solution by adding e.g., 11.7 g of NaCl into a 50 ml volumetric flask and fill up with purified water.

PDAM Solution

Prepare a 1 mg/ml PDAM solution in ethyl-acetate.

Standard Solution Calibration

The calibration was done with four free fatty acids. Since the free acids were labeled with PDAM in the ratio n/n 1:1, this calibration can be used for the quantification of all other fatty acids. The calibration should cover the range of the theoretical free fatty acid concentration. This means that the PS20 concentration in the sample and the ratio of the FFA's needs to be known. In the case of 0.2 mg/ml (163 nmol/ml) PS2 in the formulation the calibration should cover a range of approx. 1-50 nmol/ml. Preferably a pre-dilution to a concentration of 500 nmol/ml (100 mg/ml) in ACN is done. The table 55 below shows an example for a calibration.

TABLE 55

| Sample ID | Concentration of Each Fatty Acid [nmol/mL] | Volume of Stock Mixed Standard Solution (125 nmol/mL each) [μL] | Volume of IS Stock Solution (500 nmole/mL) [μL] | Volume of Acetonitrile [μL] | Total volume [μL] |
|---|---|---|---|---|---|
| CS 1 | 1 | 8 | 100 | 892 | 1000 |
| CS 2 | 2.5 | 20 | 100 | 880 | 1000 |
| CS 3 | 5 | 40 | 100 | 860 | 1000 |
| CS 4 | 10 | 80 | 100 | 820 | 1000 |
| CS 5 | 20 | 160 | 100 | 740 | 1000 |
| CS 6 | 35 | 280 | 100 | 620 | 1000 |
| CS 7 | 50 | 400 | 100 | 500 | 1000 |

TABLE 56

| Sample ID | Concentration of Tridecanoic Acid [nmol/mL] | Volume of Stock Mixed Standard Solution (125 nmol/mL each) [μL] | Volume of IS Stock Solution (500 nmole/mL) [μL] | Volume of Acetonitrile [μL] | Total volume [μL] |
|---|---|---|---|---|---|
| Int St | 50.0 | 0 | 100 | 900 | 1000 |
| Blank | 0 | 0 | 0 | 1000 | 1000 |

Four copies of Int St and four copies of blank need be prepared.

Sample Preparation 5.1 Aqueous sample 5.1.1 Add 250 μL 4 M NaCl solution to 250 μl sample. Mixing with pipette.

5.1.2 Add 50 μL pre-diluted internal standard (IS at 500 nmol/ml).

5.1.3 Mixing with pipette.

5.1.4 Add 450 μL acetonitrile. Vortex for 10 second, then spin down.

5.1.5 Shake at 500 rpm for 5 min at 25° C.

5.1.6 Keep the sample on the bench for 2 min at room temperature to allow a proper phase separation.

5.2 Prepare derivatization samples 5.2.1 Carefully transfer 2×100 μl of the standard or the upper phase of each sample into two amber HPLC vials separately.

5.2.2 Add 25 μl of PDAM solution (1 mg/ml) in each vial.

5.2.3 Close the vials properly with screw caps.

5.2.4 Shake properly and keep the sample at 40° C. for 18 hours.

5.2.5 Let the sample cooling down and vortex them.

5.2.6 The samples can be analyzed as they are.

Chromatographic Conditions 6.1 HPLC Parameter table

TABLE 57

| Parameters | Type/setting |
|---|---|
| Column | AQUITY UPLC Peptide BEH C18, Column 300Å, 1.7 μm, 2.1 mm × 150 mm Part No. 186003687 |
| Mobile phase A | Purified water e.g. MilliQ-water |
| Mobile phase B | Acetonitrile |
| Maximum column pressure | 1300 bar |
| Flow | 0.5 mL/min |
| Injection volume | 10 μL |
| Column oven temperature | 70° C. |
| Autosampler temperature | 5° C. |
| Run time | 13 min |
| Detection | 241 nm |

6.2 HPLC Gradient table

TABLE 58

| Time [min] | % Mobile Phase B |
|---|---|
| 0 | 70 |
| 2.0 | 70 |
| 13.0 | 100 |
| 15.0 | 100 |
| 15.1 | 70 |
| 19.0 | 70 |

Sample Sequence

Before starting the sequence ensure that the system is properly equilibrated. For this reason, it is advisable to inject Milli-Q water and/or blank until no drift and no signal shift is detected.

Evaluation 8.1 Check the blank injection for background peaks 8.2 Check the baseline of blank after calibration samples for carry over.

8.3 Evaluation of the concentration (mg/mL) of FFA samples is calculated using a linear regression, e.g., fit with chromatography software.

8.4 Please note the dilution factor of samples is usually 2.

Results

The levels of PS20 in DP2, DP3, and DP4 samples stored at 5° C., 25° C., and 40° C. for 6 months were determined. PS20 showed increased stability in DP3 and DP4 compared to DP2 after storage at 5° C., 25° C., and 40° C. for 6 months (FIGS. 15A-15C and FIGS. 17A-17C). Consistent with the increased PS20 stability, the levels of the degradation products FFAs in DP3 and DP4 were lower than those in DP2 after storage at 5° C. and 25° C. for 6 months (FIGS. 16A-16B and FIGS. 18A-18D).

A similar improvement in stability was observed for DP3 and DP4 formulated with surfactant PS80 instead of PS20. Higher levels of PS80 and reduced levels of FFAs were found in DP3 and DP4 compared to that in DP2 after storage at 5° C., 25° C., and 40° C. for 6 months (FIGS. 19A-19C and FIGS. 20A-20F).

Example 11: Generation of PLA2 Knockout Cell Line for Risankizumab Production

The PLA2G15 knock-out CHO cell clone generated in Example 6 still had 20% wild-type sequence based on NGS analysis. Because of this, the risankizumab drug product produced from such cell clone and purified with Process 1 still had residual hitchhiker protein PLA2G15 which led to degradation of PS20 (FIGS. 3A-3D). CHO cell clones with complete depletion of PLA2G15 are therefore generated for risankizumab production.

CHO cell clones expressing risankizumab are used as starting cell source for generating CRISPR/Cas9 mediated PLA2G15 knock-out (KO) clones, using a Ribonucleoprotein (RNP) based approach. The KO pool is allowed to recover after CRISPR/cas9 RNP transfection and is then single cell cloned via limiting dilution plating method. Top clones are selected based on phenotype (growth and productivity) and genotype determined by NGS. PLA2G15 knock-out clones having lower than 1% wild-type sequence present in the NGS preparation are selected for risankizumab production.

It is understood that the foregoing detailed description and accompanying examples are merely illustrative and are not to be taken as limitations upon the scope of the invention, which is defined solely by the appended claims and their equivalents.

Example 12: Glycan Profiling of Risankizumab Process 4 Drug Substances by 2-AB Labeling and HILIC-FL Risankizumab contains one N-glycosylation site in the CH2 domain and the N-glycans were found with CHO expressed risankizumab to be mainly of the complex-biantennary type with core fucosylation with zero (A2FG0) or 1 (A2FG1) galactose residue. N-glycans may impact effector functions. It is known that glycans in the Fc part of the antibody may influence antibody-depended cell-mediated cytotoxicity (ADCC) and complement dependent cytotoxicity (CDC) activity.

N-linked glycosylation analysis of reference standard DS1-RS2, representing the material made with Process 1 and four Process 4 batches (DS4-001, DS4-002, DS4-003, DS4-004) was performed using hydrophilic interaction liquid chromatography followed by fluorescence detection (HILIC-FL) of the 2-aminobenzoic amide (2-AB) labeled N-glycans released from the DS samples using PNGase F.

Figure 21A:
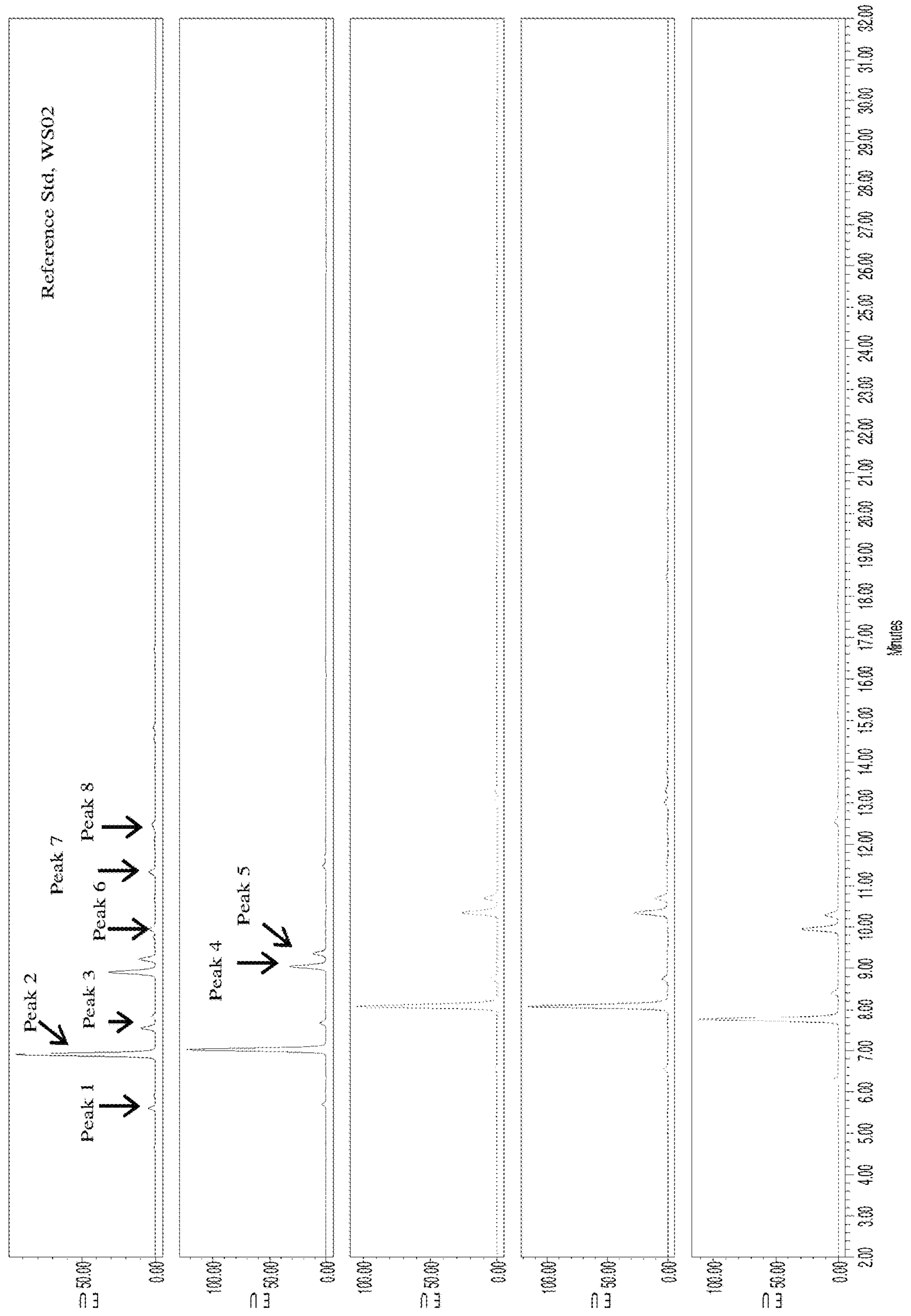
FIG. 21A and FIG. 21B show 2-AB and HILIC-FL chromatograms of Process 4 drug substance (DS) batches and Process 1 reference standard DS1-RS2. Process 4 batch DS4-001 and Process 1 reference standard DS1-RS2 were analyzed side-by-side. The results of reference standard accompanying the other three Process 4 DS batches are not shown. Slight differences in retention time from different runs was observed as expected. The assay performance (relative peak quantitation) is not impacted.
Figure 21B:
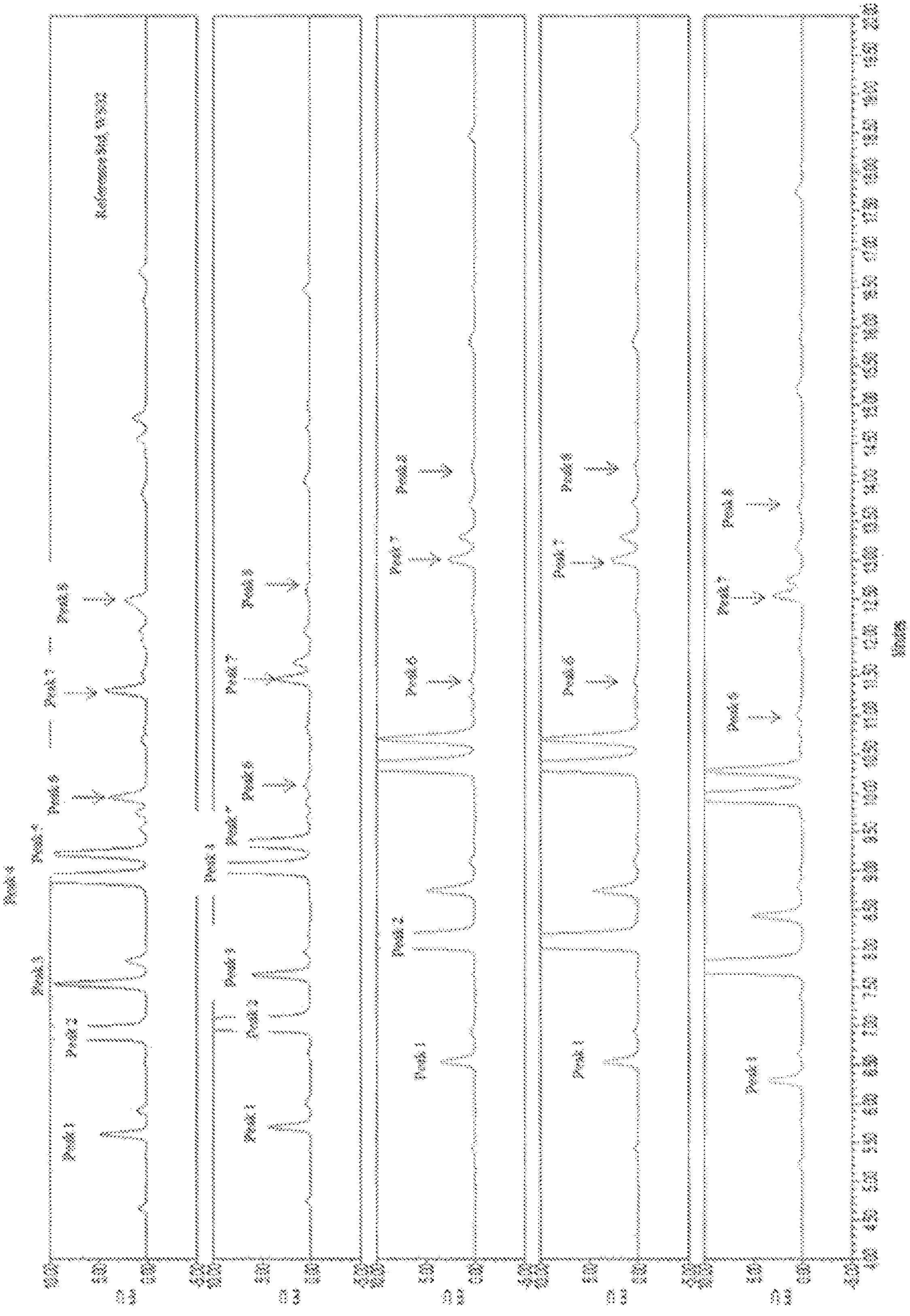

The stacked HILIC-FL chromatograms of the four Process 4 batches with the reference standard DS1-RS2, representative of Process 1, are shown in FIG. 21A. The expanded view is shown in FIG. 21B. The same N-glycan peaks were observed in Process 4 samples and no new N-glycan species was observed in Process 4 batches compared to the Process 1 reference standard DS1-RS2.

The N-glycan levels are summarized in Table 59 and Table 60. Risankizumab Process 4 batches have higher levels of fucosylated biantennary oligosaccharides and lower levels of high mannose species (Man 5, Man 6, and Man 7). Higher levels of fucosylated biantennary oligosaccharide indicates improved product purity in terms of glycoforms.

In summary, the risankizumab Process 4 DS has a higher level of fucosylated biantennary oligosaccharide and a lower level of high mannose than the Process 1 DS.

TABLE 59

2-AB and HILIC-FL Glycan Profiling Results of Risankizumab Process 4 Batches and Process 1 Reference Standard DS1-RS2

| | | | Peak Area Percentage ( %) | | | | |
|---|---|---|---|---|---|---|---|
| Peak | Peak ID | | DS1-RS2 | DS4-001 | DS4-002 | DS4-003 | DS4-004 |
| Peak 1 | G0F-GlcNAc | A1FG0 | 2.3 | 1.9 | 1.9 | 1.8 | 1.9 |
| Peak 2 | G0F | A2FG0 | 50.4 | 61.4 | 62.3 | 63.9 | 61.6 |
| Peak 3 | Man 5 | Man 5 | 5.3 | 3.1 | 3.1 | 2.7 | 3.1 |
| Peak 4 | G1F(a) | A2F[6]G1 | 18.8 | 17.9 | 17.6 | 17.0 | 17.8 |
| Peak 5 | G1F(b) | A2F[3]G1 | 6.5 | 6.6 | 6.5 | 6.4 | 6.5 |
| Peak 6 | Man 6 | Man 6 | 2.6 | 0.5 | 0.5 | 0.4 | 0.5 |
| Peak 7 | G2F | A2FG2 | 2.7 | 2.0 | 1.9 | 1.8 | 2.0 |
| Peak 8 | Man 7 | Man 7 | 2.0 | 0.4 | 0.5 | 0.5 | 0.5 |
| Fucosylated biantennary oligosaccharide (Peaks 1, 2, 4, 5, 7) | | | 80.7 | 89.8 | 90.2 | 90.9 | 89.8 |
| Man 5 + 6 + 7 (Peaks 3, 6, 8) | | | 9.9 | 4.0 | 4.1 | 3.6 | 4.1 |

Note:

Peak 1 A1FG0 A2FG0 with loss of 1 terminal N-acetyl glucosamine

Peak 2 A2FG0 Biantennary N-glycan with core fucosylation and no terminal galactose Peak 3 Man5 Mannose 5 N-glycan Peak 4 A2F[6]G1 Biantennary N-glycan with core fucosylation and 1 terminal galactose Peak 5 A2F[3]G1 Biantennary N-glycan with core fucosylation and 1 terminal galactose Peak 6 Man6 Mannose 6 N-glycan Peak 7 A2FG2 Biantennary N-glycan with core fucosylation and 2 terminal galactoses Peak 8 Man7 Mannose 7 N-glycan

TABLE 60

| Glycan Profiling Results of Risankizumab Process 4 Batches Compared to Process 1 and Process 2 Range | | | | | |
|---|---|---|---|---|---|
| | Range in Process 1, Process 2 | Process 4 | | | |
| Product Quality | (±3SD) | GMP1 | GMP2 | GMP3 | GMP4 |
| % Fucosylated Complex Oligosaccharides | 79.6-84.4 | 89.8 | 90.2 | 90.9 | 89.8 |
| % High mannose glycan | 5.4-13.6 | 4.0 | 4.1 | 3.6 | 4.1 |

Example 13: Glycan Profiling of Risankizumab Process 4 Drug Substances by RapiFluor Labeling and HILIC-FL The glycan profiles of risankizumab DS batches were also analyzed by RapiFluor labeling and HILIC-FL. The glycans were released by enzymatic digestion with PNGase F. The released oligosaccharides were labeled with a fluorescent tag which labels the free reducing end of the glycans. The resulting labeled glycans were separated by HILIC and detected by a fluorescent detector.

Released Glycan Analysis by RapiFluor and HILIC-FL Method

Samples were diluted to 1 mg/mL using water. Samples and reference standard (10 μL each) were transferred to a 96 well plate.

RapiGest buffer was prepared by dissolving one vial (20 mg) of RapiGest in 5× GlycoWorks Rapid Buffer (400 μL) and MilliQ Water (270 μL). RapiGest buffer (10 μL) was added to each sample. The samples were denatured at 90° C. for 3 minutes and allowed to cool for 20 minutes. GlycoWorks Rapid PNGase F was prepared by adding 5× GlycoWorks Rapid Buffer (586.7 μL) to the vial of PNGase F. The PNGase F solution was then added to each sample (10 μL). The samples were then incubated at 55° C. for 5 minutes and allowed to cool for 10 minutes.

Labeling solution was prepared by dissolving one vial of RapiFluor-MS Reagent Powder (55 mg) in DMF (669.4 μL). The Labeling solution was added to each sample (10 μL) and thoroughly mixed with aspiration. The samples incubated for 5 minutes at room temperature to allow for the labelling reaction to complete. Each sample was diluted with acetonitrile (360 μL) in preparation for HILIC SPE.

GlycoWorks HILIC μElution Plate was set up on vacuum manifold. The plate was conditioned with 18.20 Water (200 μL) and 85% Acetonitrile (200 μL). The samples were loaded onto the μElution plate in their entirety (~400 μL). The wells were washed with 1:9:90 Formic Acid: 18.2 Water: Acetonitrile (2×600 μL). The waste tray was replaced with the 96 well collection plate for collection. Each sample was eluted from the plate with 3× applications of elution buffer (30 μL). Each sample was diluted with GlycoWorks Sample Diluent in a HPLC vial (45 μL:155 μL). The vials were then capped and vortexed to ensure mixture. The samples were run on the UPLC for HILIC-FL analysis using the conditions and parameters shown in Table 61.

TABLE 61

| HPLC Conditions for Released Glycan Analysis | | | |
|---|---|---|---|
| Item | Description/Operating conditions | | |
| Mobile Phase A | 100% Acetonitrile | | |
| Mobile Phase B | 100 mM Ammonium Formate, pH 4.5 | | |
| Column | Waters X-Bridge BEH Amide 1.7 μm, 2.1 × 150 mm | | |
| Autosampler Rinse Solution | 50:50 Acetonitrile:Water | | |
| Degas | In-line Degasser | | |
| FLD Settings | Excitation 265 nm, Emission 425 nm | | |
| PMT Gain | 18 | | |
| | Time (minute) | Mobile Phase B (%) | Flow rate (mL/min) |
| Gradient | 0 | 22.50 | 0.7 |
| | 15.5 | 31.63 | 0.7 |
| | 23.0 | 38.65 | 0.7 |
| | 25.0 | 80.00 | 0.4 |
| | 28.0 | 80.00 | 0.4 |
| | 28.1 | 25.00 | 0.7 |
| | 33.0 | 25.00 | 0.7 |

Results

Figure 22:
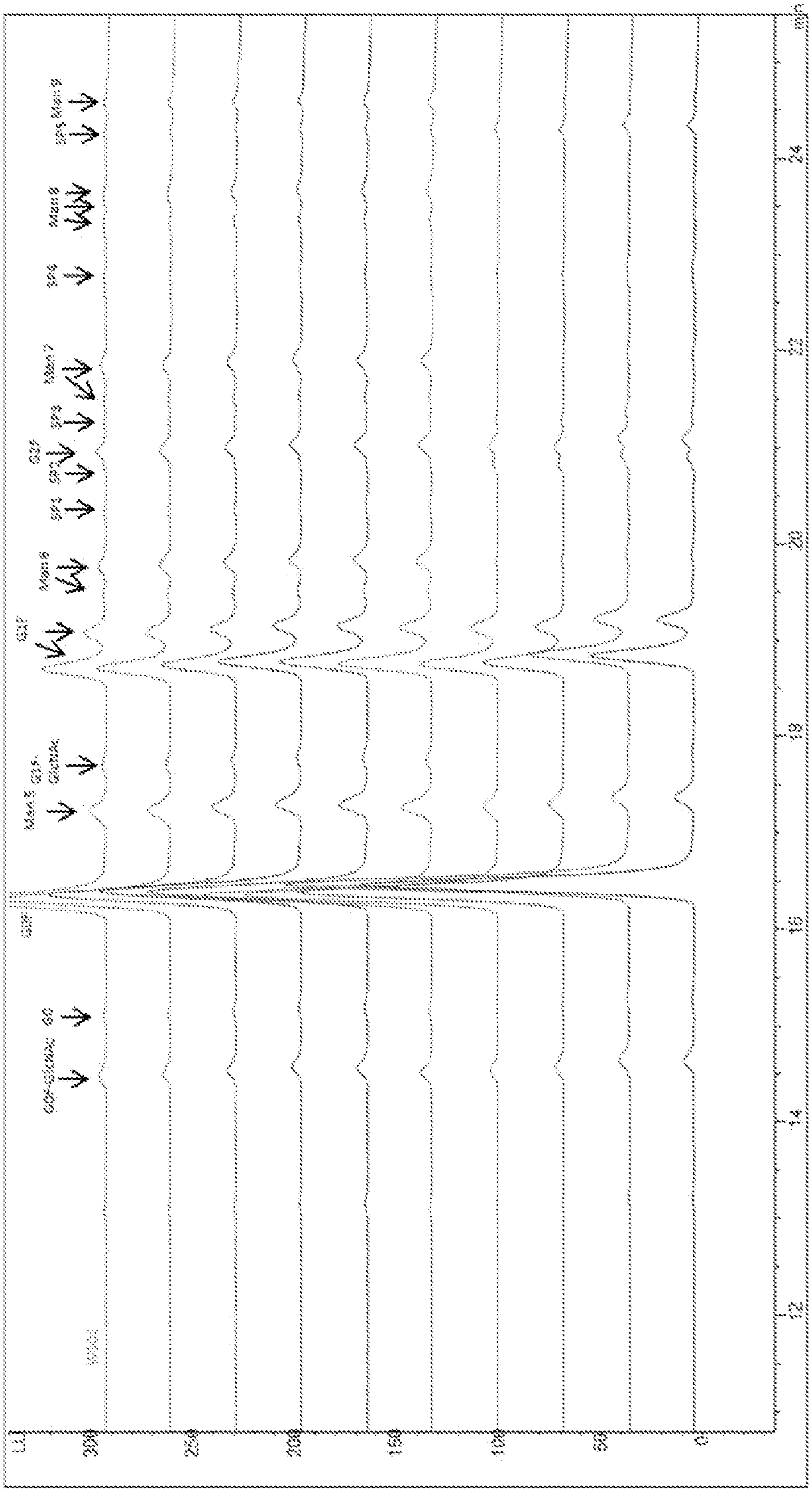
FIG. 22 shows RapiFluor and HILIC-FL chromatograms of Process 1, 2, and 4 DS batches.

The RapiFluor labeling and HILIC-FL chromatograms are shown in FIG. 22 and the relative quantitation of N-glycans are summarized in Table 62 for three Process 1, three Process 2, and four Process 4 DS batches. The RapiFluor HILIC-FL method provides a measurement of total fucosylated complex biantennary oligosaccharides (FBOs), total high mannose glycan (Man5+Man6+Man7) as well as total sialylated N-glycans. A few differences were observed when comparing Process 4 DS with Process 1 and 2 DS:

- Total fucosylated biantennary oligosaccharide level is higher in Process 4 OS (88.0-88.9%) versus Process 1 and 2 OS (76.7-79.5%);
- Total high mannose glycans is lower in Process 4 OS (4.3-4.9%) versus Process 1 and 2 DS (10.3-12.3%);
- Total sialylated glycans is higher in Process 4 DS (3.9%) versus Process 1 and 2 OS (2.1-2.5%)

Risankizumab has been designed with Leu234Aa and Leu235Aa mutations in Fc to diminish its Fc effector binding activity. It was also confirmed that risankizumab does not possess ADCC or COC activity, which is not part of the mechanism of action (MoA) for risankizumab.

Process 4 OS was also observed with lower high mannose glycans, as compared to Process 1 and 2 OS.

It is, therefore, concluded that the Process 4 drug substances have lower levels of high mannose species compared to Process 1 and 2 drug substances in their N-glycosylation demonstrated by both the 2-AB and the RapiFluor and HILIC-FL methods.

TABLE 62

RapiFluor and HILIC-FL Glycan Profiling Results of risankizumab Process 1, 2, and 4 DS Batches

| | Process 1 | | | Process 2 | | | Process 4 | | | |
|---|---|---|---|---|---|---|---|---|---|---|
| Peak ID | DS1-RS1 | DS1-001 | DS1-002 | DS2-001 | DS2-002 | DS2-003 | DS4-001 | DS4-002 | DS4-003 | DS4-004 |
| G0F-GlcNAc | 2.4 | 2.3 | 2.3 | 2.4 | 2.5 | 2.4 | 2.0 | 2.0 | 1.9 | 2.0 |
| G0 | 0.7 | 0.8 | 0.7 | 0.7 | 0.8 | 0.7 | 0.5 | 0.4 | 0.5 | 0.5 |
| G0F | 49.0 | 46.8 | 47.9 | 48.7 | 48.7 | 47.2 | 60.1 | 60.8 | 62.4 | 60.4 |
| Man 5 | 5.7 | 6.4 | 6.3 | 6.3 | 6.5 | 6.5 | 3.6 | 3.6 | 3.2 | 3.7 |
| G1F-GlcNAc | 1.3 | 1.3 | 1.3 | 1.3 | 1.3 | 1.3 | 0.6 | 0.6 | 0.6 | 0.6 |
| G1F(a) | 18.6 | 18.3 | 17.6 | 18.2 | 17.8 | 18.1 | 17.4 | 17.1 | 16.7 | 17.5 |
| G1F(b) | 6.7 | 6.5 | 6.3 | 6.4 | 6.3 | 6.4 | 6.4 | 6.3 | 6.1 | 6.4 |
| Man 6 | 2.5 | 3.2 | 3.2 | 2.9 | 3.1 | 3.1 | 0.7 | 0.6 | 0.6 | 0.6 |
| SP1[a] | 0.7 | 0.7 | 0.6 | 0.6 | 0.6 | 0.6 | 0.4 | 0.4 | 0.4 | 0.4 |
| SP2[b] | 0.4 | 0.3 | 0.4 | 0.3 | 0.3 | 0.3 | 1.0 | 1.1 | 1.2 | 1.1 |
| G2F | 2.8 | 2.9 | 2.6 | 2.8 | 2.7 | 2.8 | 2.1 | 2.0 | 1.8 | 2.1 |
| SP3[b] | 0.5 | 0.3 | 0.4 | 0.4 | 0.4 | 0.4 | 0.7 | 0.7 | 0.7 | 0.7 |
| Man 7 | 2.1 | 2.7 | 2.7 | 2.4 | 2.5 | 2.6 | 0.6 | 0.5 | 0.5 | 0.5 |
| SP4[c] | 0.5 | 0.4 | 0.7 | 0.6 | 0.6 | 0.6 | 0.8 | 0.8 | 0.7 | 0.8 |
| SP5[d] | 0.5 | 0.4 | 0.4 | 0.4 | 0.4 | 0.4 | 0.9 | 0.9 | 0.9 | 0.9 |
| FBO[e] | 79.5 | 76.8 | 76.7 | 78.5 | 78.1 | 76.9 | 88.0 | 88.4 | 88.9 | 88.3 |
| High mannose[f] | 10.3 | 12.3 | 12.2 | 11.6 | 12.0 | 12.2 | 4.9 | 4.7 | 4.3 | 4.8 |
| Sialylated glycans[g] | 2.5 | 2.1 | 2.5 | 2.4 | 2.3 | 2.4 | 3.9 | 3.9 | 3.9 | 3.9 |

[a]SP1: G1F-GlcNAc + sialic acid (SA)
[b]SP2 and SP3: G1F + SA (SP2 and SP3 are isomers)
[c]SP4: G2F + SA
[d]SP5: G2F + 2SA
[e]FBO: fucosylated biantennary oligosaccharide, sum of G0F-GlcNAc, G0F, G1F(a), G1F(b), and G2F peaks.
[f]High mannose: sum of Man 5, Man 6, and Man 7 peaks.
[g]Sialylated glycans: sum of SP1, SP2, SP3, SP4, and SP5 peaks.

Example 14: Fc Aglycosylated Risankizumab Variants in the Process 4 Drug Substances Tryptic peptide map analysis of four risankizumab Process 4 batches, three Process 2 batches, and three Process 1 batches (including the reference standard DS1-RS1) were performed. The quantitation of aglycosylated Fc was performed using Protein Metrics software, which used the peak areas of the extracted ion chromatographic peaks (XIC) of the corresponding m/z of the glycosylated, and correspondingly aglycosylated peptides. The summarized area of the XICs for the glycosylated and aglycosylated HC tryptic peptide were integrated and the percentage of aglycosylation thereof was calculated. The level of aglycosylation of the DS batches are low and highly comparable between the four Process 4 batches, three Process 2 batches, and three Process 1 batches, as shown in Table 63.

TABLE 63

Aglycosylation Levels of Risankizumab Process 1, 2, and 4 DS Batches

| Process | Batch Number | Aglycosylation (%) |
|---|---|---|
| Process 1 | DS1-RS1 | 1.2 |
| | DS1-001 | 1.4 |
| | DS1-002 | 1.4 |
| Process 2 | DS2-001 | 1.6 |
| | DS2-002 | 1.5 |
| | DS2-003 | 1.4 |
| Process 4 | DS4-001 | 0.8 |
| | DS4-002 | 0.9 |
| | DS4-003DS4-003 | 1.4 |
| | DS4-004 | 1.0 |

Example 15: Increased Purity of the Process 4 Drug Substances

The purity of risankizumab is monitored at release via ultra-performance size exclusion chromatography (UP-SEC) and capillary gel electrophoresis under non-reducing conditions (CGE-NR). As described below, Process 4 drug substances (DS) have higher purity as compared to DS produced by Process 1 and 2.

Ultra-Performance Size Exclusion Chromatography (UP SEC)

Figure 23A:
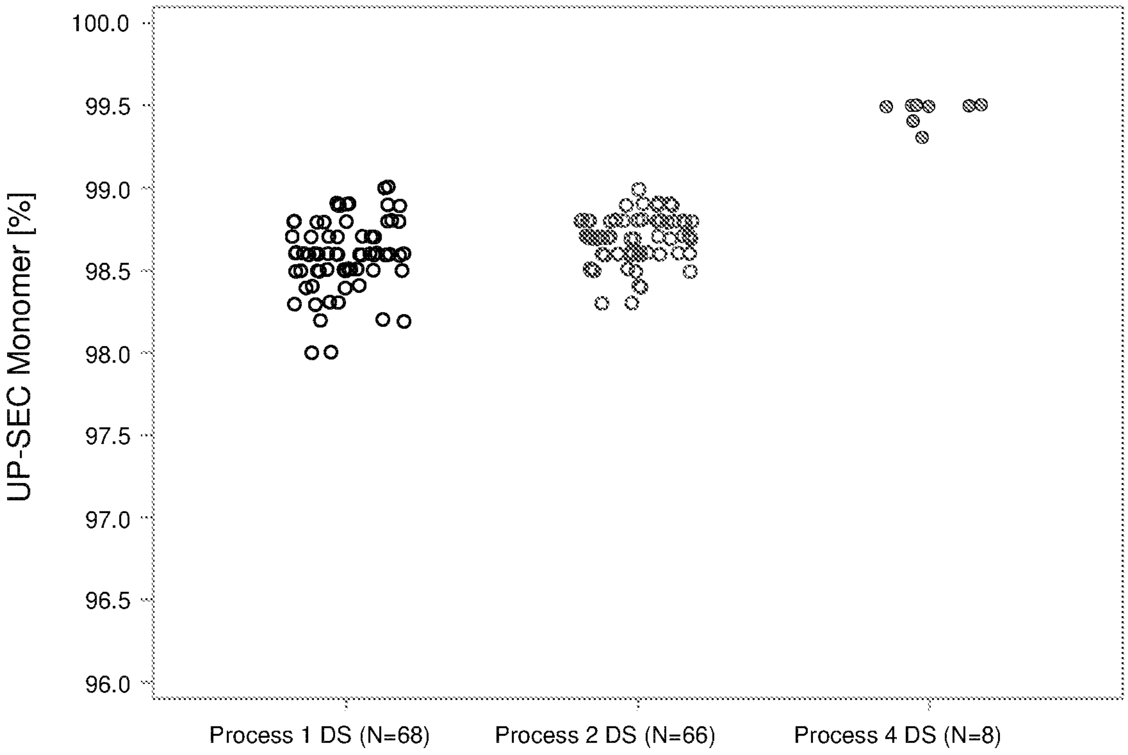
FIG. 23A shows relative distribution of the UP-SEC monomer results for risankizumab Process 1, 2, and 4 DS batches.
Figure 23B:
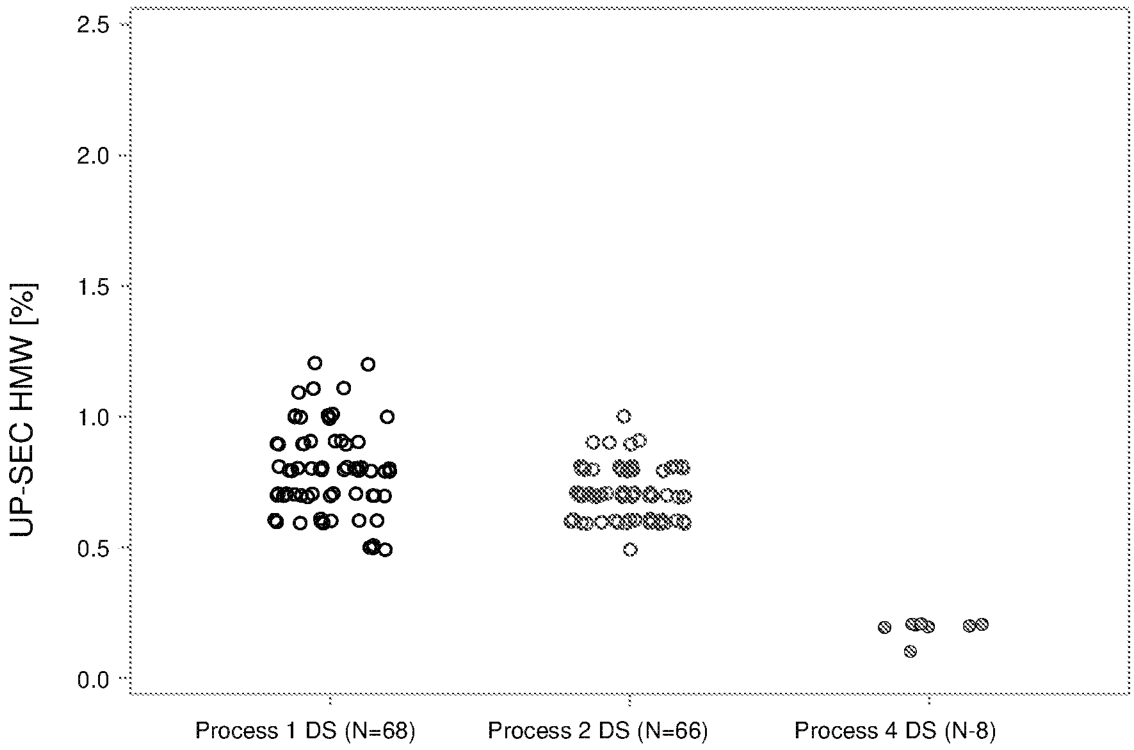
FIG. 23B shows relative distribution of the UP-SEC HMW results for risankizumab Process 1, 2, and 4 DS batches.

FIG. 23A and FIG. 23B show monomer and HMW species levels in DS batches from Process 1, Process 2, and Process 4. Process 4 DS batches have a higher level of purity (monomer) and lower level of HMW than the Process 1 and 2 DS samples. The higher level of purity is a result of the improved process and product related impurity clearance of Process 4.

Figure 23C:
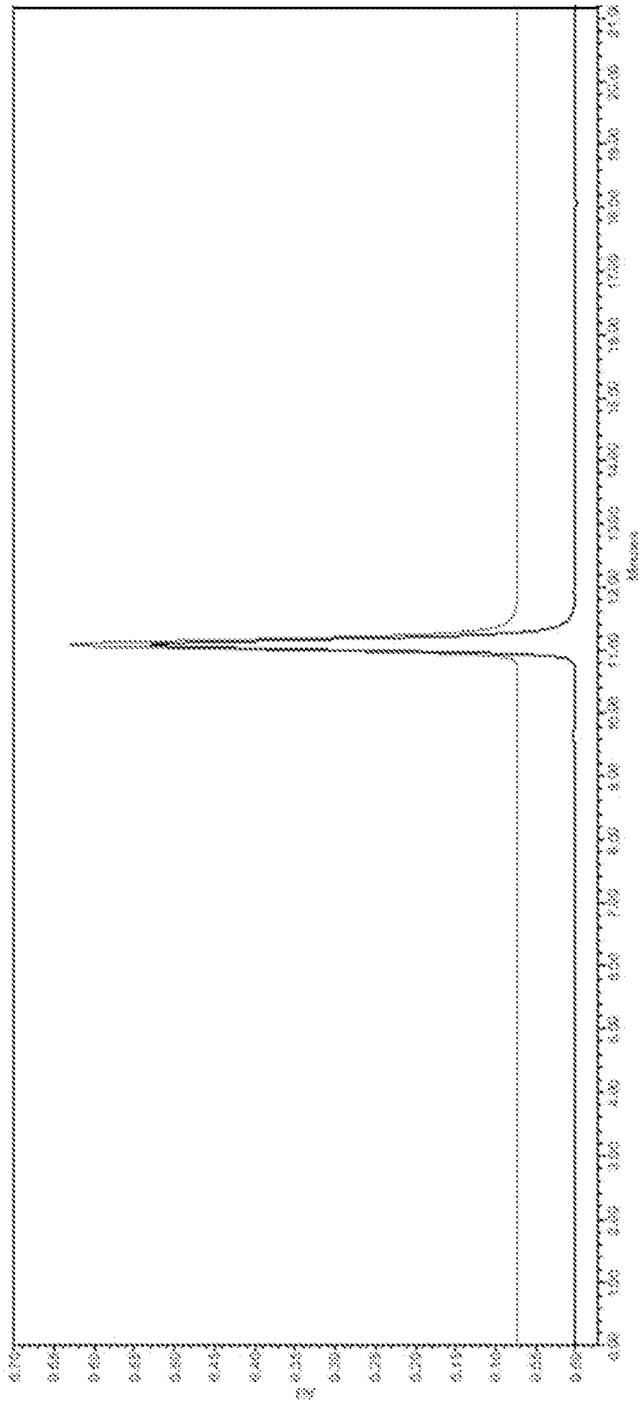
FIG. 23C shows UP-SEC results of risankizumab Process 4 DS batch DS4-005 and Process 1 reference standard DS1-RS2.
Figure 23D:
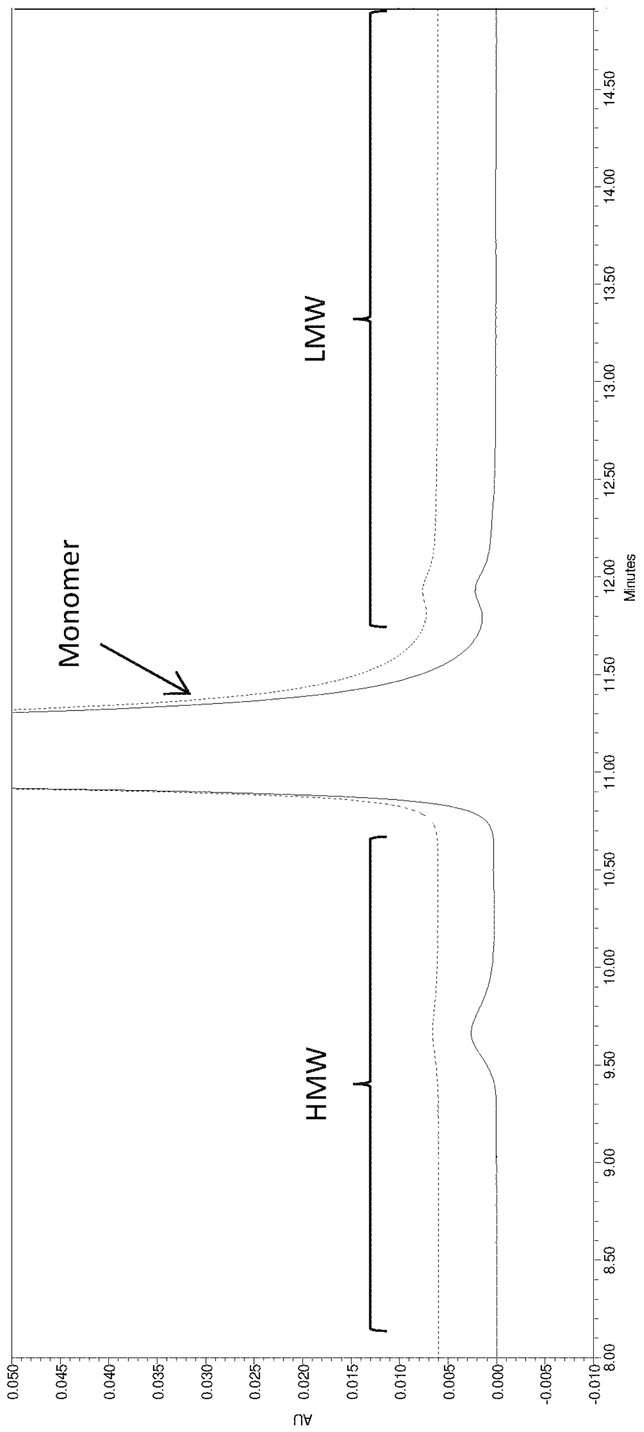
FIG. 23D is an expanded view of FIG. 23C.

Additionally, as demonstrated by the representative chromatograms in FIG. 23C and FIG. 23D, the HMW peak is smaller in Process 4 batch DS4-005 than in Process 1 reference standard DS1-RS2, which is correlated with the higher level of purity (monomer) and lower level of HMW.

Non-Reduced Capillary Gel Electrophoresis (CGE-NR)

Non-reduced capillary gel electrophoresis (CGE-NR) quantitates the size variant distribution of the antibody under denaturing and non-reducing conditions. Purity, represented by the percentage of the main peak, and the level of LMW species are monitored by this method.

Figure 24A:
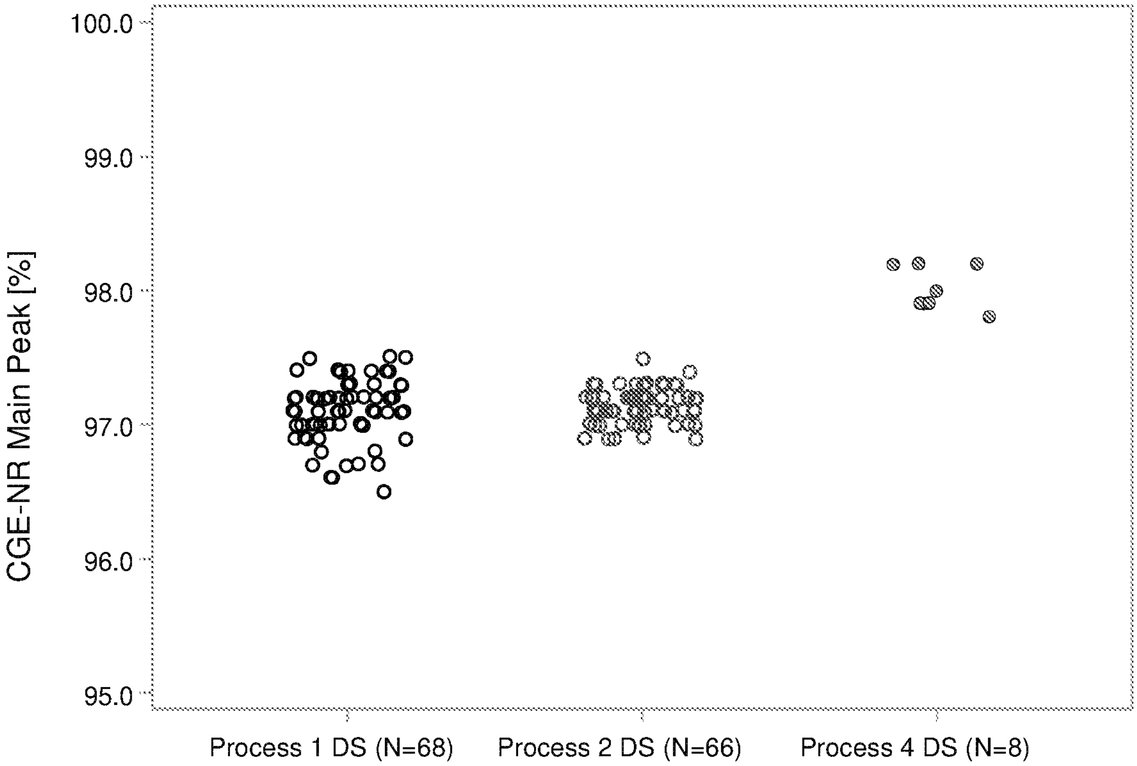
FIG. 24A shows relative distribution of CGE-NR main peak results for risankizumab Process 1, 2, and 4 DS batches.
Figure 24B:
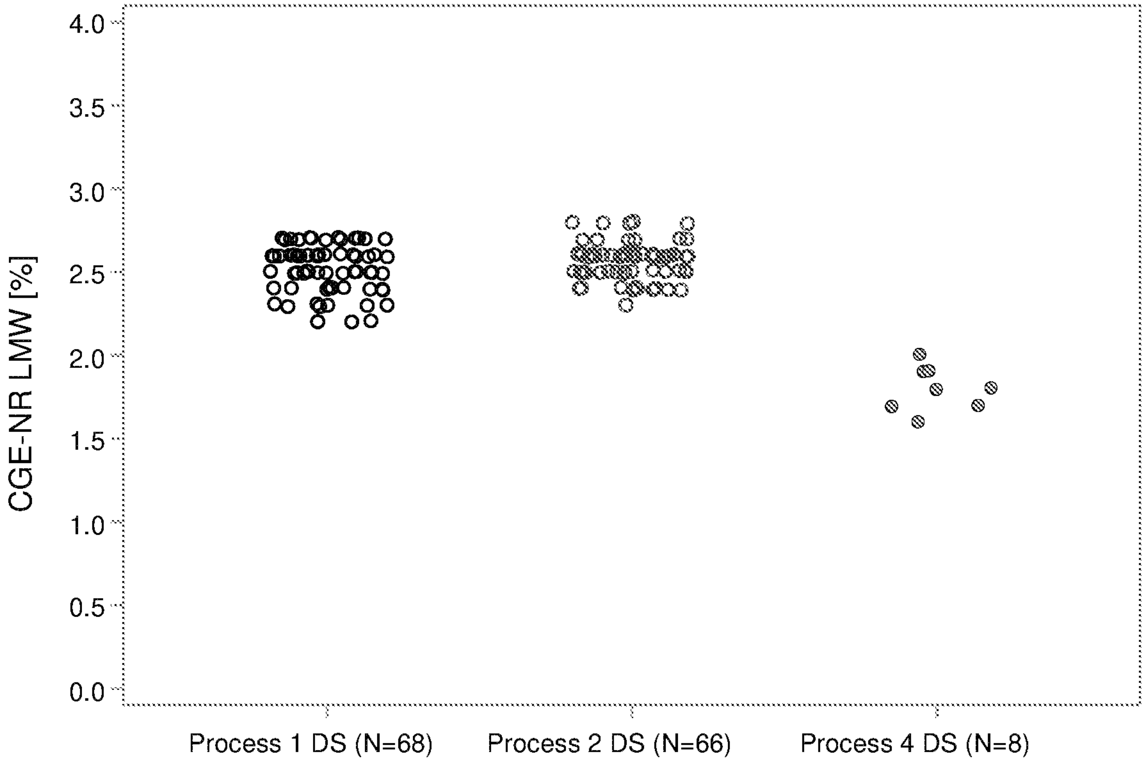
FIG. 24B shows relative distribution of CGE-NR LMW results for risankizumab Process 1, 2, and 4 DS batches.

FIG. 24A and FIG. 24B show purity and LMW species levels in DS batches from Process 1, Process 2, and Process 4. Process 4 DS has a higher level of purity (main peak) and lower level of LMW than the Process 1 and 2 DS's. The higher level of purity and lower level of LMW is a result of the improved process and product related impurity clearance of Process 4.

Figure 24C:
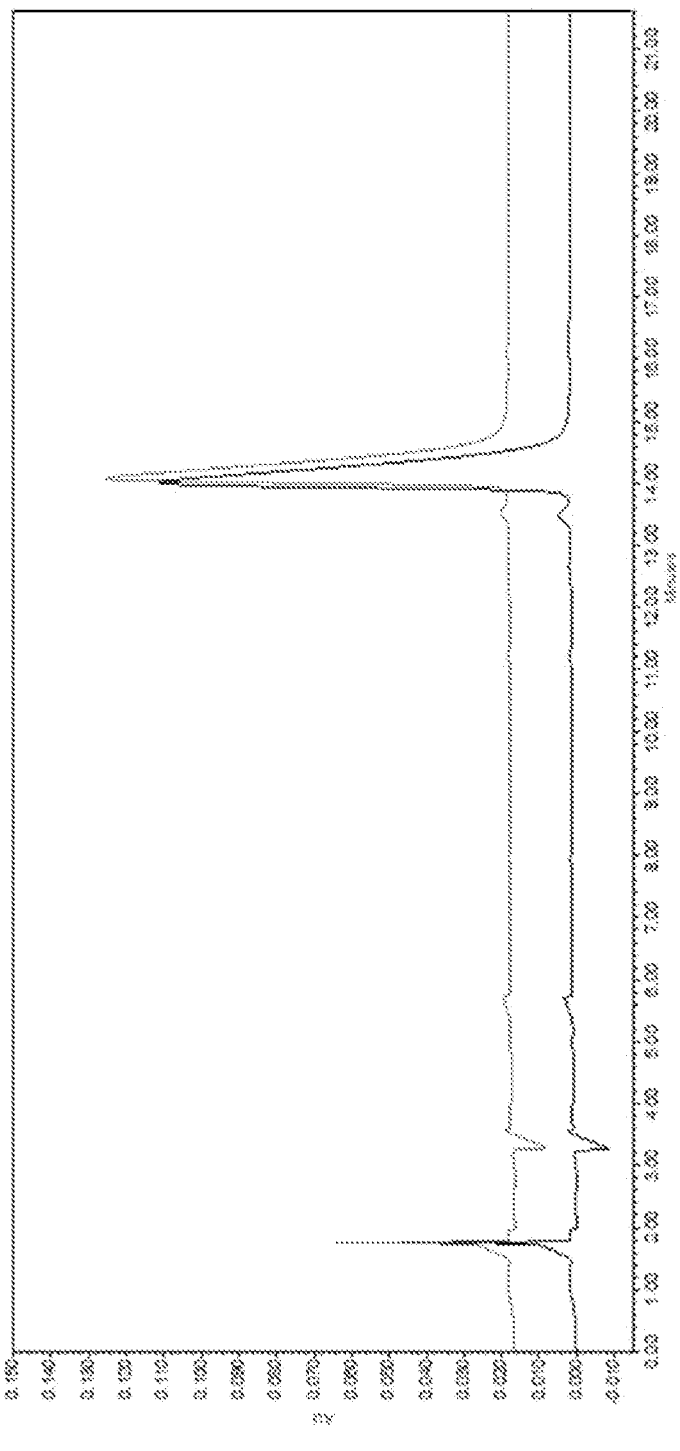
FIG. 24C shows CGE-NR results of risankizumab Process 4 DS batch DS4-005 and Process 1 reference standard DS1-RS2.
Figure 24D:
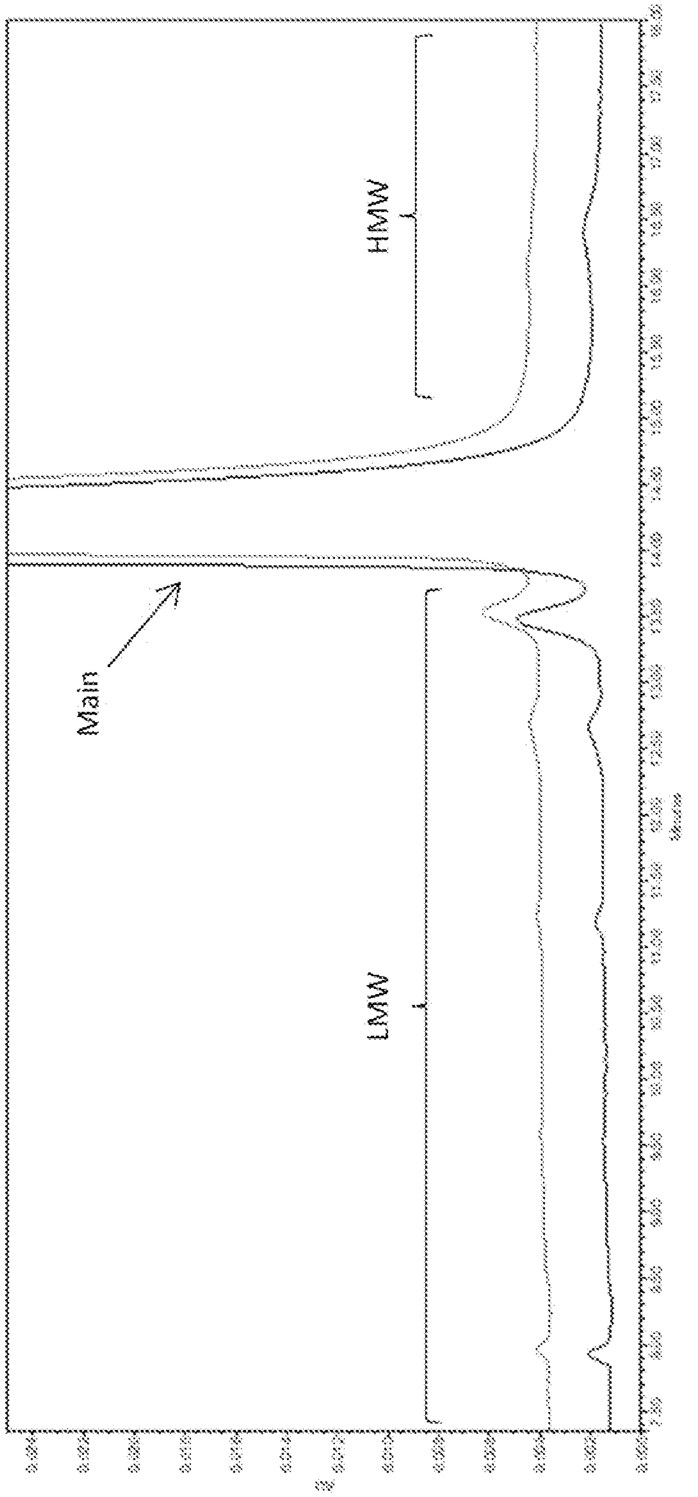
FIG. 24D shows an expanded view of FIG. 24C.

Additionally, as demonstrated by the representative electropherogram of Process 4 DS batch DS4-005 and Process 1 reference standard DS1-RS2 in FIG. 24C and FIG. 24D, the LMW peak is smaller in Process 4 batch DS4-005 than in Process 1 reference standard DS1-RS2, which is correlated with the higher level of purity (main peak) and lower level of LMW.

Example 16: Decreased Immunogenicity of the Low Mannose Compositions

A single-dose, randomized, two-parallel-arm, open-label, multi-center study in healthy adult subjects was carried out. Subjects received a risankizumab 150 mg dose by subcutaneous (SC) injection in the abdomen using a 150 mg/ml formulation in a prefilled syringe (PFS). Arm 1: Risankizumab 150 mg/mL formulation in PFS produced by Process 4 (150 mg×1 SC injection) (test, N=132); Arm 2: Risankizumab 150 mg/mL formulation in PFS produced by Process 2 (150 mg×1 SC injection) (reference, N=130). Serial blood samples for anti-drug antibody (ADA) were collected over a period of 113 days.

Blood samples for ADA assays were collected by venipuncture into labeled evacuated serum collection tubes without gel separators.

The presence of ADA was determined using a validated titer based bridging electrochemiluminescence immunoassay as described below.

Sample Analysis

At the initiation of sample analysis, 54 pre-dose study samples were analyzed, to evaluate the in-study screening false positive rate using the cut points determined during validation. After evaluation of the data, the false positive screening rate was determined to be 1.39%. Based on this false positive screening rate, study specific cut points were set as below:

TABLE 64

| | |
|---|---|
| Screening Cut Point (SCP) (95%) | 1.056 * mean NC |
| Confirmatory Cut Point (CCP) (99%) | 12.594% |
| Titer Cut Point (TCP) (99.9%) | 1.110 * mean NC |

The following reference material and critical reagents were used in analysis.

TABLE 65

| Material/Reagent | Concentration | Storage |
|---|---|---|
| Anti-ID pAb Risankizumab | 1.20 mg/mL | −80° C. |
| Risankizumab | 89.5 mg/mL | −80° C. |
| Bio Risankizumab | 3.30 mg/mL | −80° C. |
| Sulfo Risankizumab | 3.60 mg/mL | −80° C. |

Analysis Method Summary

This is a qualitative assay designed to detect anti-risankizumab antibodies in human serum. Anti-drug antibodies (ADA) against risankizumab in human serum were detected using an electrochemiluminescent (ECL) immunoassay. In this assay, samples, positive controls (PCs), and negative control (NC) were incubated with biotin-risankizumab and Sulfo-tag-risankizumab. Any ADA present in the human serum formed a bridge between the biotin-risankizumab and Sulfo-tag-risankizumab molecules. This complex was bound to a blocked MSD-streptavidin (MSD-SA) plate and detected by a chemiluminescent signal that was generated when voltage was applied. The resulting electrochemiluminescent signal (ECL or relative light units, RLU) was directly proportional to the amount of ADA present in the human serum.

Samples were analyzed in a tiered approach. Samples analyzed in the screening assay having responses equal to or above the plate specific cut point were identified as "potential positive" while those below the cut point were considered "negative." The potential positive samples were analyzed in a confirmatory assay.

The confirmatory assay measured the percent inhibition of ECL immunoassay signals of screened positive samples when spiked with excess risankizumab. The screened positive (reactive) samples spiked with risankizumab were confirmed as positive if the percent inhibition of the spiked to unspiked samples exceeded 12.594%.

ADA incidences were summarized by treatment arms, and ADA titers from treatment-emergent ADA positive subjects were summarized at the respective study visits.

Number of Subjects (Planned and Analyzed):

Arm 1: Planned: 130, Enrolled: 132, Completed: 122, Evaluated for Immunogenicity: 132

Arm 2: Planned 130, Enrolled 130, Completed 127, Evaluated for Immunogenicity: 130

Diagnosis and Main Criteria for Inclusion:

Healthy male and female, and age was between 18 and 60 years old, inclusive. Body weight less than 100 kg at Screening and upon initial confinement. No previous exposure to any anti-IL-12/23 or anti-IL-23 treatment. No intention to perform strenuous exercise to which the subject was unaccustomed within one week prior to administration of study drug or during the study.

Test Product, Dose/Strength/Concentration, Mode of Administration:

Risankizumab 150 mg/mL SC injection

Duration of Treatment:

Subjects received a single dose of risankizumab administered SC.

Criteria for Evaluation

Anti-drug antibody (ADA) incidence was summarized by treatment arms and ADA titers were tabulated for each subject at the respective study visits.

Statistical Methods

ADA incidence was summarized by treatment arms, and ADA titers from treatment-emergent ADA positive subjects were summarized at the respective study visits. The impact of ADA on risankizumab exposure and safety was evaluated by comparing treatment-emergent ADA-positive versus ADA-negative subjects within each group.

Results

A summary of the ADA results following administration of risankizumab is provided in Table 66.

TABLE 66

Incidence of ADA at Baseline and Treatment-Emergent ADA Following Single SC Doses of Risankizumab

| Treatment Group | Baseline ADA Incidence n/N (%) | Treatment-Emergent ADA Incidence n/N (%) | Time to Appearance of ADA[a] (range in days) | Range of ADA Titers in Treatment-Emergent ADA+ Samples |
|---|---|---|---|---|
| Studv Arm 1 150 mg/mL Process 4 formulation | 3/132 (2.3%) | 0/128 (0.0%) | — | — |

TABLE 66-continued

| Incidence of ADA at Baseline and Treatment-Emergent ADA Following Single SC Doses of Risankizumab | | | | |
|---|---|---|---|---|
| Treatment Group | Baseline ADA Incidence n/N (%) | Treatment-Emergent ADA Incidence n/N (%) | Time to Appearance of ADA[a] (range in days) | Range of ADA Titers in Treatment-Emergent ADA+ Samples |
| Study Arm 2 150 mg/mL Process 2 formulation | 1/129 (0.8%) | 6/129 (4.7%) | 15-85 | 79-706 |

[a]Incidence of anti-drug antibody (treatment emergent) to risankizumab was defined when a subject was (1) anti-drug antibody negative or missing assessment at baseline (prior to the first risankizumab dose) and became anti-drug antibody positive at one or more time points post baseline; or (2) anti-drug antibody positive at baseline and showed a 4-fold or greater increase in titer values relative to baseline.

Baseline and treatment-emergent ADA incidence ranged from 0.8% to 2.3% and 0% to 4.7%, respectively, across both treatment groups. There was no incidence of treatment-emergent ADAs in Study Arm 1 for drug substance produced by Process 4. Time of ADA onset ranged from 15 to 85 days for Study Arm 2 (Table 66).

In summary, following a single SC administration of 150 mg risankizumab in healthy subjects, incidence of treatment-emergent ADAs was low with zero ADA positivity for the low mannose composition.

Example 17: Stability Study of Poloxamer in Risankizumab Drug Substances

This example illustrates a laboratory-scale stability study for the utilization of an alternative surfactant, Poloxamer 188 (P188), to the current polysorbate 20 (PS20) excipient in DP2 drug substance (DS) and DP3 DS, stored at 5° C., 25° C., and 40° C. for 6 months. Product quality of the DS was also monitored at the initiation of the study and after the 6-month storage.

P188 showed improved stability to PS20 in DP2 DS and comparable product quality over the 6-month evaluation. In DP3, P188 stability and product quality were comparable to PS20 over the 6-month evaluation.

1.0 Materials and Methods 1.1 Materials

DS from multiple risankizumab batches were used in this study.

To generate DP3 DS containing P188, Poros XS eluate was processed over a HIC column, and the HIC flowthrough and wash pool was buffer exchanged and concentrated, as described in other examples, e.g., in Example 3. The concentrated and buffer-exchange material was then spiked with formulation buffer containing P188.

To generate DP2 DS, Poros XS eluate was buffer exchanged and concentrated as described in other examples, e.g., in Example 1. The concentrated and buffer-exchange material was then spiked with formulation buffer containing either PS20 or P188.

1.2 Methods 1.2.1 Test Methods 1.2.1.1 High-Performance Liquid Chromatography-Charged Aerosol Detector (HPLC-CAD)

PS20 content was measured using the HPLC-CAD method, as described in other examples, e.g., in Example 10. The samples were injected on a Waters Oasis MAX column from Thermo Fisher Scientific (P/N: 5081.0020). The detection was based on the nebulization of the analyte in a continuous nitrogen flow. After removal of the mobile phase, a second positively charged nitrogen flow caused formation of charged particles. The released charge was proportional to the quantity of polysorbate 20. The quantitation was based on prepared external standards.

1.2.1.2 Pluronic F-68 Assay

Poloxamer 188 (Pluronic F-68) content was measured using Pluronic F-68 colorimetric assay.

1.2.1.3 Weak Cation Exchange (WCX-10)

Charge variants, acidic peak group (APG), main peak, and basic peak group (BPG), of risankizumab were separated using a ProPac WCX-10 column.

1.2.1.4 Stability Study Procedures

Samples of DS were aliquoted sterilely into Schott glass 2R vials. The vials were stored at −80° C., 5° C., 25° C., or 40° C. At indicated time intervals, 1-3 samples were removed from their respective storage temperature and placed at −80° C. until analysis. Storage at −80° C. represented the initial or time zero condition, and results from all samples stored exclusively at −80° C. were averaged for the time zero result. Results from 5° C., 25° C., or 40° C. samples in replicate analyses were also averaged. The Time 0, 3-month and 6-month samples from both surfactants were summarized in this Example.

2.0 Results and Discussion

P188 stability was monitored by measuring P188 levels, and PS20 stability was monitored by measuring the PS20 levels. A decrease in P188 or PS20 levels indicates degradation of the surfactant in DS.

Figure 25:
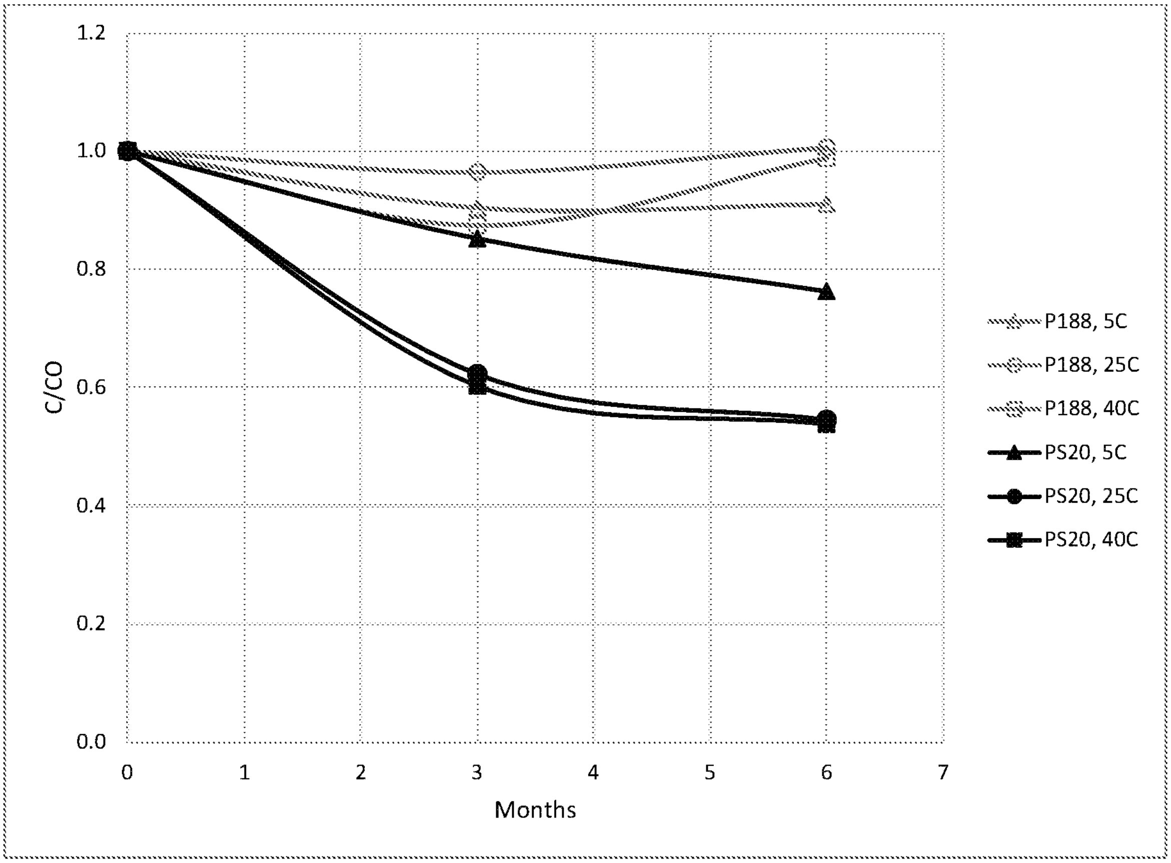
FIG. 25 shows P188 and PS20 levels in DP2 DS.
Figure 26:
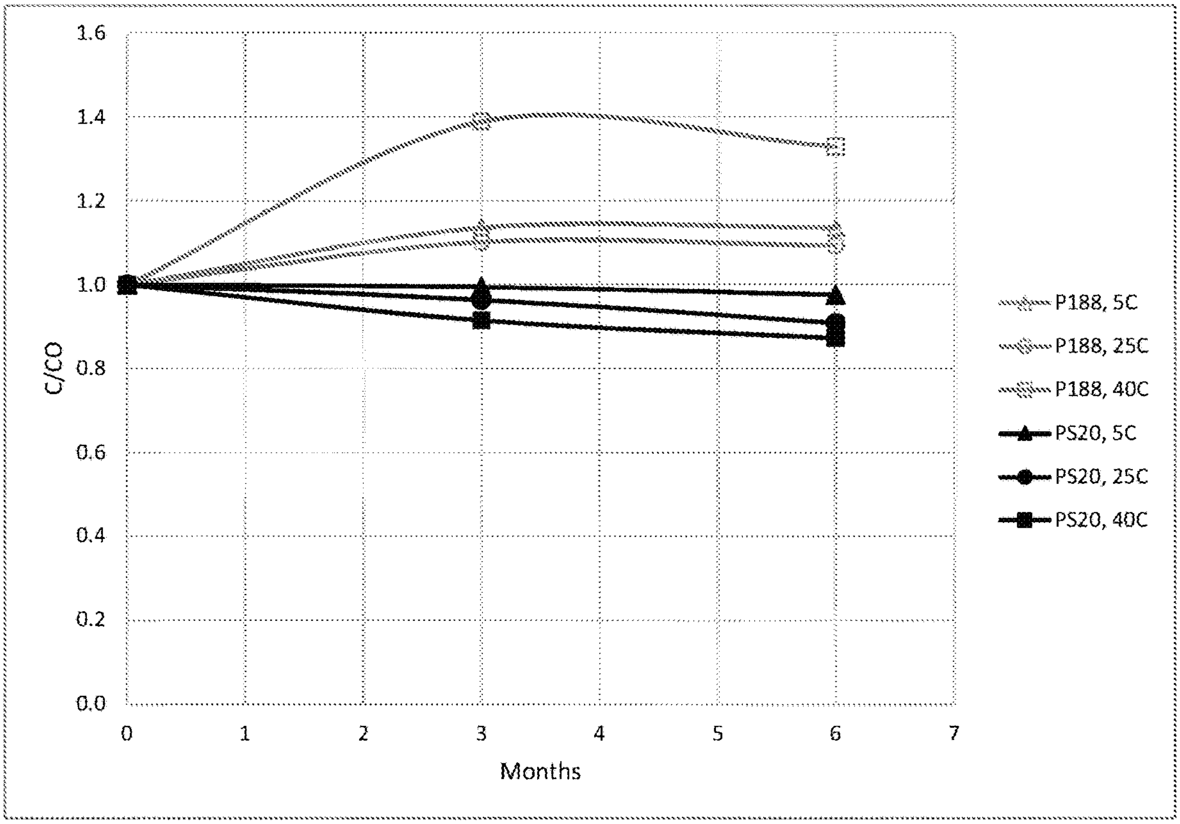
FIG. 26 shows P188 and PS20 levels in DP3 DS.

FIG. 25 shows P188 remained at a constant level in DP2 at all temperatures evaluated, while PS20 levels remained constant only in DP2 at 5° C. during the studied time frame. At 25° C. and 40° C., the PS20 content trended lower by about 50% in DP2 DS over the 6-month study. FIG. 26 shows both P188 and P20 levels remained constant in DP3 DS at all temperatures evaluated.

P188, PS20, HMW, LMW, APG, and BPG data generated from this study is shown in Table 67.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the present disclosure, may be made without departing from the spirit and scope thereof.

TABLE 67

| Tabulated Study Results | | | | | | | | | | | | | | | |
|---|---|---|---|---|---|---|---|---|---|---|---|---|---|---|---|
| | Excipient | P188 | | | | | | | PS20 | | | | | | |
| | Temperature | −80° C. | 5° C. | | 25° C. | | 40° C. | | −80° C. | 5° C. | | 25° C. | | 40° C. | |
| Assay | Time (Month) | 0 | 3 | 6 | 3 | 6 | 3 | 6 | 0 | 3 | 6 | 3 | 6 | 3 | 6 |
| [P188], mg/mL | CMC2.150 | 0.12 | 0.15 | 0.15 | 0.16 | 0.17 | 0.15 | 0.17 | | | | | | | |
| | CMC2.150.HIC | 0.12 | 0.13 | 0.13 | 0.13 | 0.13 | 0.16 | 0.16 | | | | | | | |
| [PS20], mg/mL | CMC2.150 | | | | | | | | 0.21 | 0.18 | 0.15 | 0.13 | 0.11 | 0.12 | 0.11 |
| | CMC2.150.HIC | | | | | | | | 0.25 | 0.24 | 0.22 | 0.24 | 0.21 | 0.22 | 0.20 |
| % HMW | CMC2.150 | | | 1.7 | | 2.7 | | 4.4 | 0.7 | | 1.7 | | 2.5 | | 6.3 |
| | CMC2.150.HIC | | | 1.4 | | 2.3 | | 5.8 | 0.5 | | 1.3 | | 2.2 | | 5.5 |
| % APG | CMC2.150 | | | 25.1 | | 33.8 | | 57.6 | 24.9 | | 25.1 | | 33.2 | | 71.4 |
| | CMC2.150.HIC | | | 24.6 | | 33.3 | | 70.2 | 24.7 | | 24.5 | | 33.3 | | 71.2 |
| % BPG | CMC2.150 | | | 8.5 | | 10.0 | | 10.9 | 7.3 | | 8.2 | | 9.8 | | 10.1 |
| | CMC2.150.HIC | | | 8.3 | | 11.2 | | 11.0 | 6.7 | | 7.8 | | 10.7 | | 10.5 |
| % LMW | CMC2.150 | | | 2.5 | | 4.8 | | 10.0 | 2.9 | | 2.9 | | 4.4 | | 15.1 |
| | CMC2.150.HIC | | | 2.7 | | 4.8 | | 15.2 | 2.5 | | 2.8 | | 4.5 | | 15.5 |

SEQUENCE LISTING

```
Sequence total quantity: 15
SEQ ID NO: 1            moltype = AA  length = 11
FEATURE                 Location/Qualifiers
source                  1..11
                        mol_type = protein
                        organism = synthetic construct
SEQUENCE: 1
KASRDVAIAV A                                                  11

SEQ ID NO: 2            moltype = AA  length = 7
FEATURE                 Location/Qualifiers
source                  1..7
                        mol_type = protein
                        organism = synthetic construct
SEQUENCE: 2
WASTRHT                                                       7

SEQ ID NO: 3            moltype = AA  length = 9
FEATURE                 Location/Qualifiers
source                  1..9
                        mol_type = protein
                        organism = synthetic construct
SEQUENCE: 3
HQYSSYPFT                                                     9

SEQ ID NO: 4            moltype = AA  length = 10
FEATURE                 Location/Qualifiers
source                  1..10
                        mol_type = protein
                        organism = synthetic construct
SEQUENCE: 4
GYTFTDQTIH                                                    10

SEQ ID NO: 5            moltype = AA  length = 17
FEATURE                 Location/Qualifiers
source                  1..17
                        mol_type = protein
                        organism = synthetic construct
SEQUENCE: 5
YIYPRDDSPK YNENFKG                                            17

SEQ ID NO: 6            moltype = AA  length = 11
FEATURE                 Location/Qualifiers
source                  1..11
                        mol_type = protein
                        organism = synthetic construct
SEQUENCE: 6
PDRSGYAWFI Y                                                  11

SEQ ID NO: 7            moltype = AA  length = 107
FEATURE                 Location/Qualifiers
source                  1..107
```

-continued

```
                         mol_type = protein
                         organism = synthetic construct
SEQUENCE: 7
DIQMTQSPSS LSASVGDRVT ITCKASRDVA IAVAWYQQKP GKVPKLLIYW ASTRHTGVPS  60
RFSGSGSRTD FTLTISSLQP EDVADYFCHQ YSSYPFTFGS GTKLEIK                107

SEQ ID NO: 8             moltype = AA  length = 120
FEATURE                  Location/Qualifiers
source                   1..120
                         mol_type = protein
                         organism = synthetic construct
SEQUENCE: 8
QVQLVQSGAE VKKPGSSVKV SCKASGYTFT DQTIHWMRQA PGQGLEWIGY IYPRDDSPKY  60
NENFKGKVTI TADKSTSTAY MELSSLRSED TAVYYCAIPD RSGYAWFIYW GQGTLVTVSS  120

SEQ ID NO: 9             moltype = AA  length = 214
FEATURE                  Location/Qualifiers
source                   1..214
                         mol_type = protein
                         organism = synthetic construct
SEQUENCE: 9
DIQMTQSPSS LSASVGDRVT ITCKASRDVA IAVAWYQQKP GKVPKLLIYW ASTRHTGVPS  60
RFSGSGSRTD FTLTISSLQP EDVADYFCHQ YSSYPFTFGS GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 10            moltype = AA  length = 449
FEATURE                  Location/Qualifiers
source                   1..449
                         mol_type = protein
                         organism = synthetic construct
SEQUENCE: 10
QVQLVQSGAE VKKPGSSVKV SCKASGYTFT DQTIHWMRQA PGQGLEWIGY IYPRDDSPKY  60
NENFKGKVTI TADKSTSTAY MELSSLRSED TAVYYCAIPD RSGYAWFIYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 11            moltype = AA  length = 412
FEATURE                  Location/Qualifiers
source                   1..412
                         mol_type = protein
                         organism = Mus musculus
SEQUENCE: 11
MDRHLCTCRE TQLRSGLLLP LFLLMMLADL TLPAQRHPPV VLVPGDLGNQ LEAKLDKPKV  60
VHYLCSKKTD SYFTLWLNLE LLLPVIIDCW IDNIRLVYNR TSRATQFPDG VDVRVPGFGE  120
TFSMEFLDPS KRNVGSYFYT MVESLVGWGY TRGEDVRGAP YDWRRAPNEN GPYFLALREM  180
IEEMYQMYGG PVVLVAHSMG NVYMLYFLQR QPQVWKDKYI HAFVSLGAPW GGVAKTLRVL  240
ASGDNNRIPV IGPLKIREQQ RSAVSTSWLL PYNHTWSHEK VFVYTPTTNY TLRDYHRFFR  300
DIGFEDGWFM RQDTEGLVEA MTPPGVELHC LYGTGVPTPN SFYYESFPDR DPKICFGDGD  360
GTVNLESVLQ CQAWQSRQEH RVSLQELPGS EHIEMLANAT TLAYLKRVLL EP          412

SEQ ID NO: 12            moltype = AA  length = 236
FEATURE                  Location/Qualifiers
source                   1..236
                         mol_type = protein
                         organism = Mus musculus
SEQUENCE: 12
MDRHLCTCRE TQLRSGLLLP LFLLMMLADL TLPAQRHPPV VLVPGDLGNQ LEAKLDKPKV  60
VHYLCSKKTD SYFTLWLNLE LLLPVIIDCW IDNIRLVYNR TSRATQFPDG VDVRVPGFGE  120
TFSMEFLDPS KRNVGSYFYT MVESLVGWGY TRGEDVRGAP YDWRRAPTAA TSLEGQIYPC  180
LRLTGGALGG RGQDAACPGL RRQQSHSRHW ATEDPGTAAI CRLYQLATAI QPHLVT      236

SEQ ID NO: 13            moltype = AA  length = 412
FEATURE                  Location/Qualifiers
source                   1..412
                         mol_type = protein
                         organism = Cricetulus griseus
SEQUENCE: 13
MDRHHLTCRA TQLRSGLLVP LLLLMMLADL ALSVQRHPPV VLVPGDLGNQ LEAKLDKPKV  60
VHYLCSKRTD SYFTLWLNLE LLLPVIIDCW IDNIRLVYNR TSRATQFPDG VDVRVPGFGE  120
TFSLEFLDPS KRTVGSYFHT MVESLVGWGY TRGEDLRGAP YDWRRAPNEN GPYFLALREM  180
IEEMYQMYGG PVVLVAHSMG NMYTLYFLQR QPQAWKDKYI HAFISLGAPW GGVAKTLRVL  240
ASGDNNRIPV IGPLKIREQQ RSAVSTSWLL PYNHTWSHDK VFVHTPTTNY TLRDYHQFFQ  300
DIRFEDGWFM RQDTEGLVEA MMPPGVELHC LYGTGVPTPD SFYYESFPDR DPKICFGDGD  360
GTVNLESVLQ CQAWQSRQEH KVSLQELPGS EHIEMLANAT TLAYLKRVLF EP          412
```

-continued

```
SEQ ID NO: 14          moltype = AA  length = 212
FEATURE                Location/Qualifiers
source                 1..212
                       mol_type = protein
                       organism = Cricetulus griseus
SEQUENCE: 14
MDRHHLTCRA TQLRSGLLVP LLLLMMLADL ALSVQRHPPV VLVPGDLGNQ LEAKLDKPKV  60
VHYLCSKRTD SYFTLWLNLE LLLPVIIDCW IDNIRLVYNR TSRATQFPDG VDVRVPGFGE  120
TFSLEFLDPS KRTVGSYFHT MVESLVGWGY TRGEDLRGAP YDWRRAPTAT TGLEGQVYPR  180
LHFTGCALGG RGQDPARPGL RRQQSHPCYW AT                                212

SEQ ID NO: 15          moltype = AA  length = 6
FEATURE                Location/Qualifiers
source                 1..6
                       mol_type = protein
                       organism = synthetic construct
SEQUENCE: 15
HHHHHH                                                             6
```

What is claimed is:

1. A composition, comprising a plurality of risankizumab species, wherein the composition comprises risankizumab species with N-glycosylation, and wherein less than about 5.4% of the risankizumab species with N-glycosylation comprise a high mannose N-glycan wherein greater than about 84.4% of the risankizumab species with N-glycosylation comprise fucosylated complex oligosaccharides.

2. The composition of claim 1, wherein, between 15 days and 85 days following subcutaneous administration of a single dose of 150 mg risankizumab of the composition to each human subject in a population of human subjects, incidence of treatment-emergent anti-drug antibody (ADA) in the population of human subjects is less than about 3.5%.

3. The composition of claim 1, wherein the high mannose N-glycan comprises mannose 5 N-glycan (M5), mannose 6 N-glycan (M6), mannose 7 N-glycan (M7), or a combination thereof.

4. The composition of claim 1, wherein the level of the risankizumab species comprising the high mannose N-glycan is from about 3.6% to about 5.3% of the risankizumab species with N-glycosylation.

5. The composition of claim 3, wherein the high mannose N-glycan comprises M5.

6. The composition of claim 5, wherein the level of the risankizumab species comprising M5 is from about 2.7% to about 5.2% of the risankizumab species with N-glycosylation.

7. The composition of claim 3, wherein the high mannose N-glycan comprises M6.

8. The composition of claim 7, wherein the level of the risankizumab species comprising M6 is from about 0.4% to about 2.5% of the risankizumab species with N-glycosylation.

9. The composition of claim 3, wherein the high mannose N-glycan comprises M7.

10. The composition of claim 9, wherein the level of the risankizumab species comprising M7 is from about 0.4% to about 1.9% of the risankizumab species with N-glycosylation.

11. The composition of claim 1, wherein from about 0.8% to about 1.4% of the risankizumab species are aglycosylated risankizumab species.

12. The composition of claim 1, wherein the risankizumab species were produced in CHO cells.

13. The composition of claim 1, wherein the composition is a pharmaceutical composition.

14. The composition of claim 3, wherein the composition comprises risankizumab species comprising M5, risankizumab species comprising M6, and risankizumab species comprising M7.

15. The composition of claim 14, wherein the level of the risankizumab species comprising M5 is from about 2.7% to about 5.2% of the risankizumab species with N-glycosylation, the level of the risankizumab species comprising M6 is from about 0.4% to about 2.5% of the risankizumab species with N-glycosylation, and the level of the risankizumab species comprising M7 is from about 0.4% to about 1.9% of the risankizumab species with N-glycosylation.

16. The composition of claim 15, wherein the sum of the levels of the risankizumab species comprising M5, the risankizumab species comprising M6, and the risankizumab species comprising M7 is from about 3.6% to about 5.3% of the risankizumab species with N-glycosylation.

17. The composition of claim 1, wherein the fucosylated complex oligosaccharides are fucosylated biantennary oligosaccharides.

18. The composition of claim 17, wherein the fucosylated biantennary oligosaccharides comprise biantennary N-glycan with core fucosylation and no terminal galactose.

19. The composition of claim 1, wherein the level of the risankizumab species comprising the high mannose N-glycan is from about 3.6% to about 5.3% of the risankizumab species with N-glycosylation, and the level of risankizumab species comprising fucosylated complex oligosaccharides is greater than about 84.4% of the risankizumab species with N-glycosylation.

20. The composition of claim 1, wherein the level of the risankizumab species comprising the high mannose N-glycan is from about 3.6% to about 5.3% of the risankizumab species with N-glycosylation, the level of risankizumab species comprising fucosylated complex oligosaccharides is greater than about 84.4% of the risankizumab species with N-glycosylation, and the level of aglycosylated risankizumab species is from about 0.8% to about 1.4% of the risankizumab species.

21. The composition of claim 1, wherein the level of risankizumab species comprising M5 is from about 2.7% to about 5.2% of the risankizumab species with N-glycosylation, the level of risankizumab species comprising M6 is from about 0.4% to about 2.5% of the risankizumab species with N-glycosylation, the level of risankizumab species comprising M7 is from about 0.4% to about 1.9% of the risankizumab species with N-glycosylation, and the level of risankizumab species comprising fucosylated biantennary oligosaccharides is greater than about 84.4% of the risankizumab species with N-glycosylation.

22. The composition of claim 21, wherein the fucosylated biantennary oligosaccharides comprise biantennary N-glycan with core fucosylation and no terminal galactose.

23. The composition of claim 1, wherein the level of risankizumab species comprising M5 is from about 2.7% to about 5.2% of the risankizumab species with N-glycosylation, the level of risankizumab species comprising M6 is from about 0.4% to about 2.5% of the risankizumab species with N-glycosylation, the level of risankizumab species comprising M7 is from about 0.4% to about 1.9% of the risankizumab species with N-glycosylation, the level of risankizumab species comprising fucosylated biantennary oligosaccharides is greater than about 84.4% of the risankizumab species with N-glycosylation, and the level of aglycosylated risankizumab species is from about 0.8% to about 1.4% of the risankizumab species.

24. The composition of claim 23, wherein the fucosylated biantennary oligosaccharides comprise biantennary N-glycan with core fucosylation and no terminal galactose.

* * * * *